(12) United States Patent
Reed

(10) Patent No.: US 7,582,297 B2
(45) Date of Patent: Sep. 1, 2009

(54) METHODS OF TREATING RESPIRATORY CONDITIONS

(75) Inventor: Jennifer Lynne Reed, Clarksburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 628 days.

(21) Appl. No.: 10/823,810

(22) Filed: Apr. 12, 2004

(65) Prior Publication Data

US 2005/0147607 A1    Jul. 7, 2005

Related U.S. Application Data

(60) Provisional application No. 60/477,801, filed on Jun. 10, 2003, provisional application No. 60/462,307, filed on Apr. 11, 2003.

(51) Int. Cl.
*A61K 39/395* (2006.01)
*C07K 16/24* (2006.01)

(52) U.S. Cl. ............ 424/141.1; 424/130.1; 530/388.23; 530/387.1

(58) Field of Classification Search ........................ None
See application file for complete search history.

(56) References Cited

U.S. PATENT DOCUMENTS

| 6,261,559 | B1 * | 7/2001 | Levitt et al. | 424/139.1 |
| 6,645,492 | B2 * | 11/2003 | Levitt et al. | 424/139.1 |
| 2003/0133988 | A1 | 7/2003 | Fearon et al. | |
| 2004/0043032 | A1 | 3/2004 | McKenzie et al. | |
| 2005/0002934 | A1 | 1/2005 | Reed | |

OTHER PUBLICATIONS

Cheng et al., Am. J. Resp. Crit. Care Med. 166: 409-416, 2002.*
Skoner, Pediatrics 109: 381-392, 2002.*
M. Elliott, Phil. R. Soc. Lond. 356: 1885-1893, 2001.*
Hennet et al., J. Immunol.149:932-939, 1992.*

* cited by examiner

*Primary Examiner*—Robert Landsman
*Assistant Examiner*—Gyan Chandra

(57) ABSTRACT

The present invention provides prophylactic an tehrapeutic protocols desinged to prevent, manage, treat, or ameliorate a respiratory condition or one or more symptoms thereof. In particular, the present invention provides methods for preventing, managinge, treating, or ameliorating a respiratory condition or one or symptoms caused by environmental factors or a respiratory infection. The present ivnention encompasses combination therapies, pharamceutical compositions, articles of manufacture, and kits.

22 Claims, 18 Drawing Sheets

QVQLVQSGAEVKKPGASVKVSCKAS<u>GYTFTGYWIE</u>WVRQAPGQGLEWMG<u>EI
LPGSGTTNYNEKFKG</u>RVTMTRDTSTSTVYMELSSLRSEDTAVYYCAR<u>ADYYGS
DYVKFDY</u>WGQGTLVTVSS

FIG. 1A

DIQMTQSPSSLSASVGDRVTITC<u>KASQHVGTHVT</u>WYQQKPGKAPKLLIY<u>STSY
RYS</u>GVPSRFSGSGSGTDFTLTISSLQPEDFATYYC<u>QHFYSYPLT</u>FGGGTKVEIK

FIG. 1B

QVQLVQSGAEVKKPGASVKVSCKAS<u>GYTFTGYWIE</u>WVRQAPGQGLEWMGE
<u>WLPGSGTTNYNEKFKG</u>RVTMTRDTSTSTVYMELSSLRSEDTAVYYCAR<u>ADYY
GSDYVKFDY</u>WGQGTLVTVSS

FIG. 2A

DIQMTQSPSSLSASVGDRVTITC<u>KASQHVGTHVT</u>WYQQKPGKAPKLLIY<u>STSY
RYS</u>GVPSRFSGSGSGTDFTLTISSLQPEDFATYYC<u>QHFYSYPLT</u>FGGGTKVEIK

FIG. 2B

QVQLVQSGAEVKKPGASVKVSCKAS<u>GYTFTYYWIE</u>WVRQAPGQGLEWMG<u>EWL
PGSGTTNYNEKFKG</u>RVTMTRDTSTSTVYMELSSLRSEDTAVYYCAR<u>ADYYGSD
HVKFDY</u>WGQGTLVTVSS

FIG. 3A

DIQMTQSPSSLSASVGDRVTITC<u>LASQHVGTHVT</u>WYQQKPGKAPKLLIY<u>GTSY
RYS</u>GVPSRFSGSGSGTDFTLTISSLQPEDFATYYC<u>QHFYDYPLT</u>FGGGTKVEIK

FIG. 3B

QVQLVQSGAEVKKPGASVKVSCKAS<u>GYTFTGYWIE</u>WVRQAPGQGLEWMG<u>E
WLPGSGTTNYNEKFKG</u>RVTMTRDTSTSTVYMELSSLRSEDTAVYYCAR<u>ADYY
GSDHVKFDY</u>WGQGTLVTVSS

FIG. 4A

DIQMTQSPSSLSASVGDRVTITC<u>KASQHVGTHVT</u>WYQQKPGKAPKLLIY<u>GTSY
RYS</u>GVPSRFSGSGSGTDFTLTISSLQPEDFATYYC<u>QHFYEYPLT</u>FGGGTKVEIK

FIG. 4B

QVQLVQSGAEVKKPGSSVKVSCKAS<u>GGTFSGYWIE</u>WVRQAPGQGLEWMG<u>EI
LPGSGTTNYNEKFKG</u>RVTITADESTSTAYMELSSLRSEDTAVYYCAR<u>ADYYGS
DYVKFDY</u>WGQGTLVTVSS

FIG. 5A

DIQMTQSPSSLSASVGDRVTITC<u>KASQHVGTHVT</u>WYQQKPGKAPKLLIY<u>STSY
RYS</u>GVPSRFSGSGSGTDFTLTISSLQPEDFATYYC<u>QQFYEYPLT</u>FGGGTKVEIK

FIG. 5B

QVQLVQSGAEVKKPGSSVKVSCKAS<u>GGTFSGYWIE</u>WVRQAPGQGLEWMG<u>EI
LPGSGTTNPNEKFKG</u>RVTITADESTSTAYMELSSLRSEDTAVYYCAR<u>ADYYGS
DYVKFDY</u>WGQGTLVTVSS

FIG. 6A

DIQMTQSPSSLSASVGDRVTITC<u>KASQHVGTHVT</u>WYQQKPGKAPKLLIY<u>STSY
RYS</u>GVPSRFSGSGSGTDFTLTISSLQPEDFATYYC<u>QQFYEYPLT</u>FGGGTKVEIK

FIG. 6B

QVQLVQSGAEVKKPGSSVKVSCKAS<u>GGTFSGYWIE</u>WVRQAPGQGLEWMG<u>EI
LPGSGTTNYNEKFKG</u>RVTITADESTSTAYMELSSLRSEDTAVYYCAR<u>ADYYGS
DYVKFDY</u>WGQGTLVTVSS

FIG. 7A

DIQMTQSPSSLSASVGDRVTITC<u>KASQHVGTHVT</u>WYQQKPGKAPKLLIY<u>GTSY
RYS</u>GVPSRFSGSGSGTDFTLTISSLQPEDFATYYC<u>QQFYEYPLT</u>FGGGTKVEIK

FIG. 7B

QVQLVQSGAEVKKPGSSVKVSCKAS<u>GGTFSYYWIE</u>WVRQAPGQGLEWMG<u>EI
LPGSGTTNPNEKFKG</u>RVTITADESTSTAYMELSSLRSEDTAVYYCAR<u>ADYYGS
DYVKFDY</u>WGQGTLVTVSS

FIG. 8A

DIQMTQSPSSLSASVGDRVTITC<u>KASQHVITHVT</u>WYQQKPGKAPKLLIY<u>GTS
YSY</u>SGVPSRFSGSGSGTDFTLTISSLQPEDFATYYC<u>QQFYEYPLT</u>FGGGTKVEIK

FIG. 8B

7F3com-2H2 V$_H$

```
  1    CAGGTGCAG CTGGTGCAG TCTGGGGCT GAGGTGAAG AAGCCTGGG
 46    TCCTCAGTG AAGGTTTCC TGCAAGGCA TCTGGAGGC ACCTTCAGC
 91    TATTACTGG ATAGAGTGG GTGCGACAG GCCCCTGGA CAAGGGCTT
136    GAGTGGATG GGAGAGATT TTACCTGGA AGTGGTACT ACTAACCCG
181    AATGAGAAG TTCAAGGGC AGAGTCACC ATTACCGCG GACGAATCC
226    ACGAGCACA GCCTACATG GAGCTGAGC AGCCTGAGA TCTGAGGAC
271    ACGGCCGTG TATTACTGT GCGAGAGCG GATTACTAC GGTAGTGAT
316    TACGTCAAG TTTGACTAC TGGGGCCAA GGAACCCTG GTCACCGTC
361    TCCTCA
```

Fig. 9A

7F3com-2H2 V$_L$

```
  1    GACATCCAG ATGACCCAG TCTCCATCC TCCCTGTCT GCATCTGTA
 46    GGAGACAGA GTCACCATC ACTTGCAAG GCAAGTCAG CATGTGATT
 91    ACTCATGTA ACCTGGTAT CAGCAGAAA CCAGGGAAA GCCCCTAAG
136    CTCCTGATC TATGGACA TCCTACAGC TACAGTGGG GTCCCATCA
181    AGGTTCAGT GGCAGTGGA TCTGGACA GATTTCACT CTCACCATC
226    AGCAGTCTG CAACCTGAA GATTTTGCA ACTTATTAC TGTCAGCAA
271    TTTTACGAG TATCCTCTC ACGTTCGGC GGAGGGACC AAGGTGGAG
316    ATCAAA
```

Fig. 9B

QVQLVQSGAEVKKPGSSVKVSCKAS<u>GGTFSGYWIE</u>WVRQAPGQGLEWMG<u>EI
LPGSGTTNPNEKFKG</u>RVTITADESTSTAYMELSSLRSEDTAVYYCAR<u>ADYYGS
DYVKFDY</u>WGQGTLVTVSS

FIG. 10A

DIQMTQSPSSLSASVGDRVTITC<u>KASQHVGTHVT</u>WYQQKPGKAPKLLIY<u>GTSY
RYS</u>GVPSRFSGSGSGTDFTLTISSLQPEDFATYYC<u>QQFYEYPLT</u>FGGGTKVEIK

FIG. 10B

QVQLVQSGAEVKKPGSSVKVSCKAS<u>GGTFSYYWIE</u>WVRQAPGQGLEWMG<u>EI
LPGSGTTNPNEKFKG</u>RVTITADESTSTAYMELSSLRSEDTAVYYCAR<u>ADYYGS
DYVKFDY</u>WGQGTLVTVSS

FIG. 11A

DIQMTQSPSSLSASVGDRVTITC<u>KASQHVITHVT</u>WYQQKPGKAPKLLIY<u>GTSY
RYS</u>GVPSRFSGSGSGTDFTLTISSLQPEDFATYYC<u>QQFYEYPLT</u>FGGGTKVEIK

FIG. 11B

Accession No. NM_000590

```
  1 ccgctgtcaa gatgcttctg gccatggtcc ttacctctgc cctgctcctg tgctccgtgg
 61 caggccaggg gtgtccaacc ttggcgggga tcctggacat caacttcctc atcaacaaga
121 tgcaggaaga tccagcttcc aagtgccact gcagtgctaa tgtgaccagt tgtctctgtt
181 tgggcattcc ctctgacaac tgcaccagac catgcttcag tgagagactg tctcagatga
241 ccaataccac catgcaaaca agatacccac tgattttcag tcgggtgaaa aaatcagttg
301 aagtactaaa gaacaacaag tgtccatatt tttcctgtga acagccatgc aaccaaacca
361 cggcaggcaa cgcgctgaca tttctgaaga gtcttctgga aattttccag aaagaaaaga
421 tgagagggat gagaggcaag atatgaagat gaaatattat ttatcctatt tattaaattt
481 aaaaagcttt ctctttaagt tgctacaatt taaaaatcaa gtaagctact ctaaatcagt
541 atcagttgtg attatttgtt taacattgta tgtctttatt ttgaaataaa t
```

FIG. 12

Accession No. A60480

```
  1 mllamvltsa lllcsvagqg cptlagildi nflinkmqed paskchcsan vtsclclgip
 61 sdnctrpcfs erlsqmtntt mqtryplifs rvkksvevlk nnkcpyfsce qpcnqttagn
121 altflkslle ifqkekmrgm rgki
```

Accession No. NP_000584

```
  1 maellasags acswdfprap psfpppaasr gglggtrsfr phrgaesprp grdrdgvrvp
 61 massrcpapr gcrclpgasl awlgtvllll adwvllrtal prifsllvpt alpllrvwav
121 glsrwavlwl gacgvlratv gsksenagaq gwlaalkpla aalglalpgl alfreliswg
181 apgsadstrl lhwgshptaf vvsyaaalpa aalwhklgsl wvpggqggsg npvrrllgcl
241 gsetrrlslf lvlvvlsslg emaipfftgr ltdwilqdgs adtftrnltl msiltiasav
301 lefvgdgiyn ntmghvhshl qgevfgavlr qeteffqqnq tgnimsrvte dtstlsdsls
361 enlslflwyl vrglcllgim lwgsvsltmv tlitlpllfl lpkkvgkwyq llevqvresl
421 akssqvaiea lsamptvrsf aneegeaqkf reklqeiktl nqkeavayav nswttsisgm
481 llkvgilyig gqlvtsgavs sgnlvtfvly qmqftqavev llsiyprvqk avgssekife
541 yldrtprcpp sglltplhle glvqfqdvsf aypnrpdvlv lqgltftlrp gevtalvgpn
601 gsgkstvaal lqnlyqptgg qllldgkplp qyehrylhrq vaavgqepqv fgrslqenia
661 ygltqkptme eitaaavksg ahsfisglpq gydtevdeag sqlsggqrqa valaralirk
721 pcvlilddat saldansqlq veqllyespe rysrsvllit qhlslveqad hilfleggai
781 reggthqqlm ekkgcywamv qapadape
```

Accession No. AAC17735

```
  1 mvltsalllc svagqgcptl agildinfli nkmqedpask chcsanvtsc lclgipsdnc
 61 trpcfserls qmtnttmqtr yplifsrvkk svevlknnkc pyfsceqpcn qttagnaltf
121 lkslleifqk ekmrgmrgki
```

FIG. 13

Accession No. NM_002186

```
   1 agcagctctg taatgcgctt gtggtttcag atgtgggcgg cctgtgtgaa cctgtcgtgc
  61 aaagctcacg tcaccaactg ctgcagttat ctcctgaatc aggctgaggg tctttgctgt
 121 gcacccagag atagttgggt gacaaatcac ctccaggttg gggatgcctc agacttgtga
 181 tgggactggg cagatgcatc tgggaaggct ggaccttgga gagtgaggcc ctgaggcgag
 241 acatgggcac ctggctcctg gcctgcatct gcatctgcac ctgtgtctgc ttgggagtct
 301 ctgtcacagg ggaaggacaa gggccaaggt ctagaacctt cacctgcctc accaacaaca
 361 ttctcaggat cgattgccac tggtctgccc cagagctggg acagggctcc agcccctggc
 421 tcctcttcac cagcaaccag gctcctggcg cacacataa gtgcatcttg cggggcagtg
 481 agtgcaccgt cgtgctgcca cctgaggcag tgctcgtgcc atctgacaat ttcaccatca
 541 ctttccacca ctgcatgtct gggagggagc aggtcagcct ggtggacccg gagtacctgc
 601 cccggagaca cgttaagctg acccgccct ctgacttgca gagcaacatc agttctggcc
 661 actgcatcct gacctggagc atcagtcctg ccttggagcc aatgaccaca cttctcagct
 721 atgagctggc cttcaagaag caggaagagg cctgggagca ggcccagcac agggatcaca
 781 ttgtcgggt gacctggctt atacttgaag cctttgagct ggaccctggc tttatccatg
 841 aggccaggct gcgtgtccag atggccacac tggaggatga tgtggtagag gaggagcgtt
 901 atacaggcca gtggagtgag tggagccagc ctgtgtgctt ccaggctccc cagagacaag
 961 gccctctgat cccaccctgg gggtggccag gcaacaccct tgttgctgtg tccatctttc
1021 tcctgctgac tggcccgacc tacctcctgt tcaagctgtc gcccagggtg aagagaatct
1081 tctaccagaa cgtgccctct ccagcgatgt tcttccagcc cctctacagt gtacacaatg
1141 ggaacttcca gacttggatg ggggcccacg gggccggtgt gctgttgagc caggactgtg
1201 ctggcacccc acagggagcc ttggagccct gcgtccagga ggccactgca ctgctcactt
1261 gtggcccagc gcgtccttgg aaatctgtgg ccctggagga ggaacaggag ggccctggga
1321 ccaggctccc ggggaacctg agctcagagg atgtgctgcc agcagggtgt acggagtgga
1381 gggtacagac gcttgcctat ctgccacagg aggactgggc cccacgtcc ctgactaggc
1441 cggctccccc agactcagag ggcagcagga gcagcagcag cagcagcagc agcaacaaca
1501 acaactactg tgccttgggc tgctatgggg gatggcacct ctcagccctc caggaaaaca
1561 cacagagctc tgggcccatc ccagccctgg cctgtggcct ttcttgtgac catcagggcc
1621 tggagaccca gcaaggagtt gcctgggtgc tggctggtca ctgccagagg cctgggctgc
1681 atgaggacct ccagggcatg ttgctccctt ctgtcctcag caaggctcgg tcctggacat
1741 tctaggtccc tgactcgcca gatgcatcat gtccattttg ggaaaatgga ctgaagtttc
1801 tggagccctt gtctgagact gaacctcctg agaagggcc cctagcagcg gtcagaggtc
1861 ctgtctggat ggaggctgga ggctcccccc tcaaccctc tgctcagtgc ctgtggggag
1921 cagcctctac cctcagcatc ctggccacaa gttcttcctt ccattgtccc ttttctttat
1981 ccctgacctc tctgagaagt ggggtgtggt ctctcagctg ttctgccctc atacccttaa
2041 agggccagcc tgggcccagt ggacacaggt aagcaccat gaccacctgg tgtgacctct
2101 ctgtgcctta ctgaggcacc tttctagaga ttaaaagggg cttgatggct gttaaaaaaa
2161 aaaaaaaaa a
```

FIG. 14A

Accession No. NM_176786

```
   1 agcagctctg taatgcgctt gtggtttcag atgtgggcgg cctgtgtgaa cctgtcgtgc
  61 aaagctcacg tcaccaactg ctgcagttat ctcctgaatc aggctgaggg tctttgctgt
 121 gcacccagag atagttgggt gacaaatcac ctccaggttg gggatgcctc agacttgtga
 181 tgggactggg cagatgcatc tgggaagtaa ctgctgcaag aacggacaga cactgctgca
 241 gagaacttgc cacggtgttt catgctgtgg ctggtggttc caggctgcac gctccattct
 301 aggaaagggg ccctcagccc agtccttgc aggctggacc ttggagagtg aggccctgag
 361 gcgagacatg ggcacctggc tcctggcctg catctgcatc tgcacctgtg tctgcttggg
 421 agtctctgtc acaggggaag gacaagggcc aaggtctaga accttcacct gcctcaccaa
 481 caacattctc aggatcgatt gccactggtc tgccccagag ctgggacagg gctccagccc
 541 ctggctcctc ttcaccaggc tcctggcggc acacataagt gcatcttgcg gggcagtgag
 601 tgcaccgtcg tgctgccacc tgaggcagtg ctcgtgccat ctgacaattt caccatcact
 661 ttccaccact gcatgtctgg gagggagcag gtcagcctgg tggacccgga gtacctgccc
 721 cggagacacg agcaacatca gttctggcca ctgcatcctg acctggagca tcagtcctgc
 781 cttggagcca atgaccacac ttctcagcta tgagctggcc ttcaagaagc aggaagaggc
 841 ctgggagcag gcccagcaca gggatcacat tgtcggggtg acctggctta tacttgaagc
 901 ctttgagctg gaccctggct ttatccatga ggccaggctg cgtgtccaga tggccacact
 961 ggaggatgat gtggtagagg aggagcgtta tacaggccag tggagtgagt ggagccagcc
1021 tgtgtgcttc caggctcccc agagacaagg ccctctgatc ccaccctggg ggtggccagg
1081 caacacccct gttgctgtgt ccatcttttct cctgctgact ggcccgacct acctcctgtt
1141 caagctgtcg cccagacttg gatggggcc cacggggccg gtgtgctgtt gagccaggac
1201 tgtgctggca ccccacaggg agccttggag ccctgcgtcc aggaggccac tgcactgctc
1261 acttgtggcc cagcgcgtcc ttggaaatct gtggccctgg aggaggaaca ggagggccct
1321 gggaccaggc tcccggggaa cctgagctca gaggatgtgc tgccagcagg gtgtacggag
1381 tggagggtac agacgcttgc ctatctgcca caggaggact gggccccac gtccctgact
1441 aggccggctc ccccagactc agagggcagc aggagcagca gcagcagcag cagcagcaac
1501 aacaacaact actgtgcctt gggctgctat gggggatggc acctctcagc cctcccagga
1561 aacacacaga gctctgggcc catcccagcc ctggcctgtg gcctttcttg tgaccatcag
1621 ggcctggaga cccagcaagg agttgcctgg gtgctggctg gtcactgcca gaggcctggg
1681 ctgcatgagg acctccaggg catgttgctc ccttctgtcc tcagcaaggc tcggtcctgg
1741 acattctagg tccctgactc gccagatgca tcatgtccat tttgggaaaa tggactgaag
1801 tttctggagc ccttgtctga gactgaacct cctgagaagg ggccctagc agcggtcaga
1861 ggtcctgtct ggatggaggc tggaggctcc ccctcaacc cctctgctca gtgcctgtgg
1921 ggagcagcct ctaccctcag catcctggcc acaagttctt ccttccattg tccctttct
1981 ttatccctga cctctctgag aagtggggtg tggtctctca gctgttctgc cctcataccc
2041 ttaaagggcc agcctgggcc cagtggacac aggtaaggca ccatgaccac ctggtgtgac
2101 ctctctgtgc cttactgagg caccttctta gagattaaaa ggggcttgat ggctgttaaa
2161 aaaaaaaaa aaaaa
```

FIG. 14B

Accession No. NM_000206

```
   1 gaagagcaag cgccatgttg aagccatcat taccattcac atccctctta ttcctgcagc
  61 tgcccctgct gggagtgggg ctgaacacga caattctgac gcccaatggg aatgaagaca
 121 ccacagctga tttcttcctg accactatgc ccactgactc cctcagtgtt tccactctgc
 181 ccctcccaga ggttcagtgt tttgtgttca atgtcgagta catgaattgc acttggaaca
 241 gcagctctga gccccagcct accaacctca ctctgcatta ttggtacaag aactcggata
 301 atgataaagt ccagaagtgc agccactatc tattctctga agaaatcact tctggctgtc
 361 agttgcaaaa aaaggagatc cacctctacc aaacatttgt tgttcagctc caggacccac
 421 gggaacccag gagacaggcc acacagatgc taaaactgca gaatctggtg atccctgggc
 481 ctccagagaa cctaacactt cacaaactga gtgaatccca gctagaactg aactggaaca
 541 acagattctt gaaccactgt tggagcact tggtgcagta ccggactgac tgggaccaca
 601 gctggactga acaatcagtg gattatagac ataagttctc cttgcctagt gtggatgggc
 661 agaaacgcta cacgtttcgt gttcggagcc gctttaaccc actctgtgga agtgctcagc
 721 attggagtga atggagccac ccaatccact ggggagcaa tacttcaaaa gagaatcctt
 781 tcctgtttgc attggaagcc gtggttatct ctgttggctc catgggattg attatcagcc
 841 ttctctgtgt gtatttctgg ctggaacgga cgatgccccg aattccacc ctgaagaacc
 901 tagaggatct tgttactgaa taccacggga cttttcggc ctggagtggt gtgtctaagg
 961 gactggctga gagtctgcag ccagactaca gtgaacgact ctgcctcgtc agtgagattc
1021 ccccaaaagg aggggccctt ggggaggggc ctgggcctc cccatgcaac cagcatagcc
1081 cctactgggc cccccatgt tacaccctaa agcctgaaac ctgaacccca atcctctgac
1141 agaagaaccc cagggtcctg tagccctaag tggtactaac tttccttcat tcaacccacc
1201 tgcgtctcat actcacctca cccactgtg gctgatttgg aattttgtgc ccccatgtaa
1261 gcacccttc atttggcatt ccccacttga gaattaccct tttgccccga acatgttttt
1321 cttctccctc agtctggccc ttccttttcg caggattctt cctcctccc tctttccctc
1381 ccttcctctt tccatctacc ctccgattgt tcctgaaccg atgagaaata aagtttctgt
1441 tgataatcat c
```

FIG. 14C

Accession No.: NP_002177

```
  1 mglgrciweg wtlesealrr dmgtwllaci cictcvclgv svtgegqgpr srtftcltnn
 61 ilridchwsa pelgqgsspw llftsnqapg gthkcilrgs ectvvlppea vlvpsdnfti
121 tfhhcmsgre qvslvdpeyl prrhvkldpp sdlqsnissg hciltwsisp alepmttlls
181 yelafkkqee aweqaqhrdh ivgvtwlile afeldpgfih earlrvqmat leddvveeer
241 ytgqwsewsq pvcfqapqrq gplippwgwp gntlvavsif llltgptyll fklsprvkri
301 fyqnvpspam ffqplysvhn gnfqtwmgah gagvllsqdc agtpqgalep cvqeatallt
361 cgparpwksv aleeeqegpg trlpgnlsse dvlpagctew rvqtlaylpq edwaptsltr
421 pappdsegsr sssssssssnn nnycalgcyg gwhlsalpgn tqssgpipal acglscdhqg
481 letqqgvawv laghcqrpgl hedlqgmllp svlskarswt f
```

Accession No.: NP_789743

```
  1 mhlgsncckn gqtllqrtch gvsccgwwfq aarsilgkgp saqslagwtl esealrrdmg
 61 twllacicic tcvclgvsvt gegqgprsrt ftcltnnilr idchwsapel gqgsspwllf
121 trllaahisa scgavsapsc chlrqcschl tispslstta clggsrsaww trstcpgdts
181 nissghcilt wsispalepm ttllsyelaf kkqeeaweqa qhrdhivgvt wlileafeld
241 pgfihearlr vqmatleddv veeerytgqw sewsqpvcfq apqrqgplip pwgwpgntlv
301 avsifllltg ptyllfklsp rlgwgptgpv cc
```

Accession No.: NP_000197

```
  1 mlkpslpfts llflqlpllg vglnttiltp ngnedttadf flttmptdsl svstlplpev
 61 qcfvfnveym nctwnsssep qptnltlhyw yknsdndkvq kcshylfsee itsgcqlqkk
121 eihlyqtfvv qlqdpreprr qatqmlklqn lvipwapenl tlhklsesql elnwnnrfln
181 hclehlvqyr tdwdhswteq svdyrhkfsl psvdgqkryt frvrsrfnpl cgsaqhwsew
241 shpihwgsnt skenpflfal eavvisvgsm gliisllcvy fwlertmpri ptlknledlv
301 teyhgnfsaw sgvskglaes lqpdyserlc lvseippkgg algegpgasp cnqhspywap
361 pcytlkpet
```

FIG. 15

```
                        SEQUENCE LISTING

<160> NUMBER OF SEQ ID NOS: 63

<210> SEQ ID NO 1
<211> LENGTH: 10
<212> TYPE: PRT
<213> ORGANISM: Homo sapiens

<400> SEQUENCE: 1

Gly Tyr Thr Phe Thr Gly Tyr Trp Ile Glu
1               5                   10

<210> SEQ ID NO 2
<211> LENGTH: 17
<212> TYPE: PRT
<213> ORGANISM: Homo sapiens

<400> SEQUENCE: 2

Glu Ile Leu Pro Gly Ser Gly Thr Thr Asn Tyr Asn Glu Lys Phe Lys
1               5                   10                  15

Gly

<210> SEQ ID NO 3
<211> LENGTH: 13
<212> TYPE: PRT
<213> ORGANISM: Homo sapiens

<400> SEQUENCE: 3

Ala Asp Tyr Tyr Gly Ser Asp Tyr Val Lys Phe Asp Tyr
1               5                   10
```

```
<210> SEQ ID NO 4
<211> LENGTH: 11
<212> TYPE: PRT
<213> ORGANISM: Homo sapiens

<400> SEQUENCE: 4

Lys Ala Ser Gln His Val Gly Thr His Val Thr
1               5                   10

<210> SEQ ID NO 5
<211> LENGTH: 7
<212> TYPE: PRT
<213> ORGANISM: Homo sapiens

<400> SEQUENCE: 5

Ser Thr Ser Tyr Arg Tyr Ser
1               5

<210> SEQ ID NO 6
<211> LENGTH: 9
<212> TYPE: PRT
<213> ORGANISM: Homo sapiens

<400> SEQUENCE: 6

Gln His Phe Tyr Ser Tyr Pro Leu Thr
1               5

<210> SEQ ID NO 7
<211> LENGTH: 118
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Ser Cys Lys Ala Ser Gly Tyr Thr Phe Thr Gly Tyr Trp
            20                  25                  30

Ile Glu Trp Val Arg Gln Ala Pro Gly Gln Leu Glu Trp Met Gly Glu
        35                  40                  45

Ile Leu Pro Gly Ser Thr Thr Asn Tyr Asn Glu Lys Phe Lys Gly Arg
    50                  55                  60

Val Thr Met Thr Arg Asp Thr Ser Thr Ser Thr Val Tyr Met Glu Leu
65                  70                  75                  80

Ser Ser Leu Arg Ser Glu Asp Thr Ala Val Tyr Tyr Cys Ala Arg Ala
                85                  90                  95

Asp Tyr Tyr Gly Ser Asp Tyr Val Lys Phe Asp Tyr Trp Gly Gln Gly
            100                 105                 110

Thr Leu Val Thr Ser Ser
        115

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln His Val Gly Thr His
            20                  25                  30

Val Thr Trp Tyr Gln Gln Lys Pro Gly Lys Ala Pro Lys Leu Leu Ile
```

```
                 35                  40                  45
Tyr Ser Thr Ser Tyr Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Phe Tyr Ser Tyr Pro Leu
                 85                  90                  95

Thr Phe Gly Gly Gly Thr Lys Val Glu Ile Lys
                100                 105

<210> SEQ ID NO 9
<211> LENGTH: 124
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Trp Ile Glu Trp Val Arg Gln Ala Pro Gly Gln Gly Leu Glu Trp Met
             35                  40                  45

Gly Glu Trp Leu Pro Gly Ser Gly Thr Thr Asn Tyr Asn Glu Lys Phe
         50                  55                  60

Phe Lys Gly Arg Val Thr Met Thr Arg Asp Thr Ser Thr Ser Thr
 65                  70                  75                  80

Val Tyr Met Glu Leu Ser Ser Leu Arg Ser Glu Asp Thr Ala Val Tyr
                 85                  90                  95

Tyr Cys Ala Arg Ala Asp Tyr Tyr Gly Ser Asp Tyr Val Lys Phe Asp
                100                 105                 110

Tyr Trp Gly Gln Gly Thr Leu Val Thr Val Ser Ser
            115                 120

<210> SEQ ID NO 10
<211> LENGTH: 17
<212> TYPE: PRT
<213> ORGANISM: Homo sapiens

<400> SEQUENCE: 10

Glu Trp Leu Pro Gly Ser Gly Thr Thr Asn Tyr Asn Glu Lys Phe Lys
 1               5                  10                  15

Gly

<210> SEQ ID NO 11
<211> LENGTH: 10
<212> TYPE: PRT
<213> ORGANISM: Homo sapiens

<400> SEQUENCE: 11

Gly Tyr Thr Phe Thr Tyr Tyr Trp Ile Glu
 1               5                  10

<210> SEQ ID NO 12
<211> LENGTH: 13
<212> TYPE: PRT
<213> ORGANISM: Homo sapiens

<400> SEQUENCE: 12

Ala Asp Tyr Tyr Gly Ser Asp His Val Lys Phe Asp Tyr
```

-continued

```
1               5                   10
```

<210> SEQ ID NO 13
<211> LENGTH: 11
<212> TYPE: PRT
<213> ORGANISM: Homo sapiens

<400> SEQUENCE: 13

```
Leu Ala Ser Gln His Val Gly Thr His Val Thr
1               5                   10
```

<210> SEQ ID NO 14
<211> LENGTH: 7
<212> TYPE: PRT
<213> ORGANISM: Homo sapiens

<400> SEQUENCE: 14

```
Gly Thr Ser Tyr Arg Tyr Ser
1               5
```

<210> SEQ ID NO 15
<211> LENGTH: 120
<212> TYPE: PRT
<213> ORGANISM: Homo sapiens

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Tyr
                20                  25                  30

Trp Ile Glu Trp Val Arg Gln Ala Pro Gly Gln Gly Leu Glu Trp Met
            35                  40                  45

Glu Trp Leu Pro Gly Ser Gly Thr Thr Asn Tyr Asn Glu Lys Phe Lys
        50                  55                  60

Gly Arg Val Thr Met Thr Arg Asp Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Ala Asp Tyr Tyr Gly Ser Asp His Val Lys Phe Asp Tyr Trp Gly
            100                 105                 110

Gln Thr Leu Val Thr Val Ser Ser
        115                 120
```

<210> SEQ ID NO 16
<211> LENGTH: 107
<212> TYPE: PRT
<213> ORGANISM: Homo sapiens

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln His Val Gly Thr His
                20                  25                  30

Val Thr Trp Tyr Gln Gln Lys Pro Gly Lys Ala Pro Lys Leu Leu Ile
            35                  40                  45

Tyr Gly Thr Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

-continued

Glu Asp Phe Ala Thr Tyr Tyr Cys Gln His Phe Tyr Asp Tyr Pro Leu
            85                  90                  95

Thr Phe Gly Gly Gly Thr Lys Val Glu Ile Lys
            100                 105

<210> SEQ ID NO 17
<211> LENGTH: 120
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Ile Glu Trp Val Arg Gln Ala Pro Gly Gln Gly Leu Glu Trp Met
            35                  40                  45

Gly Glu Trp Leu Pro Gly Ser Gly Thr Thr Asn Tyr Asn Glu Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ala Asp Tyr Tyr Gly Ser Asp His Lys Phe Asp Tyr Trp Gly
            100                 105                 110

Gln Gly Thr Leu Thr Val Ser Ser
        115                 120

<210> SEQ ID NO 18
<211> LENGTH: 107
<212> TYPE: PRT
<213> ORGANISM: Homo sapiens

<400> SEQUENCE: 18

Asp Gln Ile Met Thr Gln Ser Pro Ser Ser Leu Ser Ala Ser Val Gly
1               5                   10                  15

Asp Arg Val Thr Ile Thr Cys Lys Ala Ser Gln His Val Gly Thr His
            20                  25                  30

Val Thr Trp Thr Tyr Gln Gln Lys Pro Gly Lys Ala Pro Lys Leu Leu
            35                  40                  45

Ile Tyr Gly Thr Ser Tyr Arg Tyr Ser Gly Val Pro Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Glu Tyr Pro Leu
            85                  90                  95

Thr Phe Gly Gly Gly Thr Lys Val Glu Ile Lys
            100                 105

<210> SEQ ID NO 19
<211> LENGTH: 10
<212> TYPE: PRT
<213> ORGANISM: Homo sapiens

<400> SEQUENCE: 19

Gly Gly Thr Phe Ser Gly Tyr Trp Ile Glu
1               5                   10

```
<210> SEQ ID NO 20
<211> LENGTH: 9
<212> TYPE: PRT
<213> ORGANISM: Homo sapiens

<400> SEQUENCE: 20

Gln Gln Phe Tyr Glu Tyr Pro Leu Thr
1               5

<210> SEQ ID NO 21
<211> LENGTH: 119
<212> TYPE: PRT
<213> ORGANISM: Homo sapiens

<400> SEQUENCE: 21

Gln Val Gln Leu Val Gln Ser Gly Ala Glu Val Lys Lys Pro Gly Ser
1               5                   10                  15

Ser Val Lys Ser Cys Lys Ala Gly Gly Thr Phe Ser Gly Tyr Trp Ile
            20                  25                  30

Glu Trp Val Arg Gln Ala Pro Gly Gln Gly Leu Glu Trp Met Gly Glu
        35                  40                  45

Ile Leu Pro Gly Ser Gly Thr Thr Asn Tyr Asn Glu Lys Phe Lys Gly
    50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Ala Asp Tyr Tyr Gly Ser Asp Tyr Val Lys Phe Asp Tyr Trp Gly Gln
            100                 105                 110

Thr Leu Val Thr Val Ser Ser
        115

<210> SEQ ID NO 22
<211> LENGTH: 107
<212> TYPE: PRT
<213> ORGANISM: Homo sapiens

<400> SEQUENCE: 22

Asp Ile Gln Met Thr Gln Ser Pro Ser Ser Leu Ser Ala Val Gly Asp
1               5                   10                  15

Arg Val Thr Ile Thr Cys Lys Ala Ser Gln His Val Gly Thr His Val
            20                  25                  30

Thr Trp Tyr Gln Gln Lys Pro Gly Lys Ala Pro Lys Lys Leu Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Glu Pro Leu Thr
                85                  90                  95

Gly Phe Gly Gly Gly Thr Lys Val Ile Glu Lys
            100                 105

<210> SEQ ID NO 23
<211> LENGTH: 121
<212> TYPE: PRT
<213> ORGANISM: Homo sapiens

<400> SEQUENCE: 23
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Trp Ile Glu Glu Val Arg Gln Ala Pro Gly Gln Gly Leu Glu Trp Met
        35                  40                  45

Gly Glu Ile Leu Pro Gly Ser Gly Thr Thr Asn Pro Asn Glu Lys Phe
    50                  55                  60

Lys Gly Arg Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Asp Tyr Tyr Gly Ser Asp Tyr Val Lys Phe Asp Tyr Trp Gly
            100                 105                 110

Gln Gly Thr Leu Val Thr Val Ser Ser
        115                 120
```

<210> SEQ ID NO 24
<211> LENGTH: 107
<212> TYPE: PRT
<213> ORGANISM: Homo sapiens

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln His Val Gly Thr His
            20                  25                  30

Val Thr Trp Tyr Gln Gln Lys Pro Gly Lys Ala Pro Lys Leu Leu Ile
        35                  40                  45

Tyr Ser Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Glu Pro Leu
                85                  90                  95

Thr Phe Gly Gly Gly Thr Lys Val Glu Ile Lys
            100                 105
```

<210> SEQ ID NO 25
<211> LENGTH: 107
<212> TYPE: PRT
<213> ORGANISM: Homo sapiens

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Ser Gln His Val Gly Thr
            20                  25                  30

His Val Thr Trp Tyr Gln Gln Lys Pro Gly Lys Ala Pro Lys Leu Leu
        35                  40                  45

Ile Tyr Gly Thr Ser Tyr Arg Tyr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Phe Tyr Glu Tyr Pro
                85                  90                  95
```

```
Leu Thr Phe Gly Gly Gly Thr Val Glu Ile Lys
            100                 105

<210> SEQ ID NO 26
<211> LENGTH: 10
<212> TYPE: PRT
<213> ORGANISM: Homo sapiens

<400> SEQUENCE: 26

Gly Gly Thr Phe Ser Tyr Tyr Trp Ile Glu
1               5                   10

<210> SEQ ID NO 27
<211> LENGTH: 62
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Tyr Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Thr Thr Asn Pro Asn Glu
    50                  55                  60

<210> SEQ ID NO 28
<211> LENGTH: 107
<212> TYPE: PRT
<213> ORGANISM: Homo sapiens

<400> SEQUENCE: 28

Asp Ile Gln Met Met Thr Gln Ser Pro Ser Ser Leu Ala Ser Val Gly
1               5                   10                  15

Asp Arg Val Thr Ile Thr Cys Lys Ala Ser Gln His Val Ile Thr His
            20                  25                  30

Val Thr Trp Tyr Gln Gln Lys Pro Gly Lys Ala Pro Lys Leu Leu Ile
        35                  40                  45

Tyr Gly Thr Ser Tyr Ser Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Glu Tyr Pro Leu
                85                  90                  95

Thr Phe Gly Gly Gly Thr Lys Val Glu Ile Lys
            100                 105

<210> SEQ ID NO 29
<211> LENGTH: 122
<212> TYPE: PRT
<213> ORGANISM: Homo sapiens

<400> SEQUENCE: 29

Gln Val Gln Leu Val Gln Ser Asx Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Trp Ile Glu Trp Val Arg Gln Ala Pro Gly Gln Gly Leu Glu Trp Met
        35                  40                  45
```

```
Gly Glu Ile Leu Pro Gly Ser Gly Thr Thr Asn Pro Asn Glu Lys Phe
        50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Asp Tyr Tyr Gly Ser Asp Tyr Val Lys Phe Asp Tyr Trp
             100                 105                 110

Gly Gln Gly Thr Leu Val Thr Val Ser Ser
            115                 120

<210> SEQ ID NO 30
<211> LENGTH: 105
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
  1               5                  10                  15

Asp Arg Thr Ile Thr Cys Lys Ala Ser Gln His Val Gly Thr His Val
                 20                  25                  30

Thr Trp Tyr Gln Lys Pro Gly Lys Ala Pro Lys Leu Leu Ile Tyr Gly
             35                  40                  45

Thr Ser Tyr Arg Tyr Ser Gly Val Pro Ser Arg Phe Ser Gly Ser Gly
         50                  55                  60

Ser Gly Thr Asp Phe Thr Leu Thr Ile Ser Ser Leu Gln Pro Glu Asp
 65                  70                  75                  80

Phe Ala Thr Tyr Tyr Cys Gln Gln Phe Tyr Glu Tyr Pro Leu Thr Phe
                 85                  90                  95

Gly Gly Gly Thr Lys Val Glu Ile Lys
            100                 105

<210> SEQ ID NO 31
<211> LENGTH: 127
<212> TYPE: PRT
<213> ORGANISM: Homo sapiens

<400> SEQUENCE: 31

Gln Val Gln Leu Val Gln Ser Gly Ala Glu Val Lys Lys Pro Gly Ser
  1               5                  10                  15

Ser Val Lys Pro Gly Ser Ser Val Lys Ser Cys Lys Ala Ser Gly Gly
                 20                  25                  30

Gly Thr Phe Ser Tyr Tyr Trp Ile Glu Trp Val Arg Gln Ala Pro Gly
             35                  40                  45

Gln Gly Leu Glu Trp Met Gly Glu Ile Leu Pro Gly Ser Gly Thr Thr
         50                  55                  60

Asn Pro His Glu Lys Phe Lys Gly Arg Val Thr Ile Thr Ala Asp Glu
 65                  70                  75                  80

Ser Thr Ser Thr Ala Tyr Met Glu Leu Ser Ser Leu Arg Ser Glu Asp
                 85                  90                  95

Thr Ala Val Tyr Tyr Cys Ala Arg Ala Asp Tyr Tyr Gly Ser Asp Tyr
             100                 105                 110

Val Lys Phe Asp Tyr Trp Gly Gln Gly Thr Leu Val Thr Ser Ser
         115                 120                 125

<210> SEQ ID NO 32
```

```
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln His Val Ile Thr His
            20                  25                  30

Val Thr Trp Tyr Gln Gln Lys Pro Gly Lys Ala Pro Lys Leu Leu Ile
        35                  40                  45

Tyr Gly Thr Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Glu Tyr Pro Leu
                85                  90                  95

Thr Phe Gly Gly Gly Thr Lys Val Glu Ile Lys
                100                 105

<210> SEQ ID NO 33
<211> LENGTH: 25
<212> TYPE: PRT
<213> ORGANISM: Homo sapiens

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 34
<211> LENGTH: 14
<212> TYPE: PRT
<213> ORGANISM: Homo sapiens

<400> SEQUENCE: 34

Trp Val Arg Gln Ala Pro Gly Gln Gly Leu Glu Trp Met Gly
1               5                   10

<210> SEQ ID NO 35
<211> LENGTH: 32
<212> TYPE: PRT
<213> ORGANISM: Homo sapiens

<400> SEQUENCE: 35

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 36
<211> LENGTH: 11
<212> TYPE: PRT
<213> ORGANISM: Homo sapiens

<400> SEQUENCE: 36

Trp Gly Gln Gly Thr Leu Val Thr Val Ser Ser
1               5                   10

<210> SEQ ID NO 37
```

```
<211> LENGTH: 25
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15
Ser Val Lys Val Ser Cys Lys Ala Ser
            20                  25

<210> SEQ ID NO 38
<211> LENGTH: 32
<212> TYPE: PRT
<213> ORGANISM: Homo sapiens

<400> SEQUENCE: 38

Arg Val Thr Ile Thr Ala Asp Glu Ser Thr Ser Thr Ala Tyr Met Glu
1               5                   10                  15
Leu Ser Ser Leu Arg Ser Glu Asp Thr Ala Val Tyr Tyr Cys Ala Arg
            20                  25                  30

<210> SEQ ID NO 39
<211> LENGTH: 23
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 40
<211> LENGTH: 15
<212> TYPE: PRT
<213> ORGANISM: Homo sapiens

<400> SEQUENCE: 40

Trp Tyr Gln Gln Lys Pro Gly Lys Ala Pro Lys Leu Leu Ile Tyr
1               5                   10                  15

<210> SEQ ID NO 41
<211> LENGTH: 32
<212> TYPE: PRT
<213> ORGANISM: Homo sapiens

<400> SEQUENCE: 41

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 42
<211> LENGTH: 10
<212> TYPE: PRT
<213> ORGANISM: Homo sapiens

<400> SEQUENCE: 42

Phe Gly Gly Gly Thr Lys Val Glu Ile Lys
1               5                   10

<210> SEQ ID NO 43
<211> LENGTH: 366
```

```
<212> TYPE: DNA
<213> ORGANISM: Homo sapiens

<400> SEQUENCE: 43
caggtgcagc tggtgcagtc tggggctgag gtgaagaagc ctgggtcctc agtgaaggtt      60
tcctgcaagg catctggagg caccttcagc tattactgga tagagtgggt gcgacaggcc     120
cctggacaag ggcttgagtg gatgggagag attttacctg aagtggtac tactaacccg      180 aatgagaagt tcaagggcag agtcaccatt accgcggacg aatccacgag cacagcctac     240
atggagctga gcagcctgag atctgaggac acggccgtgt attactgtgc gagagcggat     300
tactacggta gtgattacgt caagtttgac tactggggcc aaggaaccct ggtcaccgtc     360
tcctca                                                                 366

<210> SEQ ID NO 44
<211> LENGTH: 30
<212> TYPE: DNA
<213> ORGANISM: Homo sapiens

<400> SEQUENCE: 44
ggaggcacct tcagctatta ctggatagag                                        30

<210> SEQ ID NO 45
<211> LENGTH: 51
<212> TYPE: DNA
<213> ORGANISM: Homo sapiens

<400> SEQUENCE: 45
gagattttac ctggaagtgg tactactaac ccgaatgaga agttcaaggg c                51

<210> SEQ ID NO 46
<211> LENGTH: 39
<212> TYPE: DNA
<213> ORGANISM: Homo sapiens

<400> SEQUENCE: 46
gcggattact acggtagtga ttacgtcaag tttgactac                              39

<210> SEQ ID NO 47
<211> LENGTH: 321
<212> TYPE: DNA
<213> ORGANISM: Homo sapiens

<400> SEQUENCE: 47
gacatccaga tgacccagtc tccatcctcc ctgtctgcat ctgtaggaga cagagtcacc       60
atcacttgca aggcaagtca gcatgtgatt actcatgtaa cctggtatca gcagaaacca     120
gggaaagccc ctaagctcct gatctatggg acatcctaca gctacagtgg ggtcccatca     180
aggttcagtg gcagtggata tgggacagat ttcactctca ccatcagcag tctgcaacct     240
gaagattttg caacttatta ctgtcagcaa ttttacgagt atcctctcac gttcggcgga     300
gggaccaagg tggagatcaa a                                                321

<210> SEQ ID NO 48
<211> LENGTH: 33
<212> TYPE: DNA
<213> ORGANISM: Homo sapiens

<400> SEQUENCE: 48
aaggcaagtc agcatgtgat tactcatgta acc                                    33
```

<210> SEQ ID NO 49
<211> LENGTH: 15
<212> TYPE: DNA
<213> ORGANISM: Homo sapiens

<400> SEQUENCE: 49
gggacatcct acagc                                                         15

<210> SEQ ID NO 50
<211> LENGTH: 27
<212> TYPE: DNA
<213> ORGANISM: Homo sapiens

<400> SEQUENCE: 50
cagcaatttt acgagtatcc tctcacg                                             27

<210> SEQ ID NO 51
<211> LENGTH: 591
<212> TYPE: DNA
<213> ORGANISM: Homo sapiens

<400> SEQUENCE: 51
ccgctgtcaa gatgcttctg gccatggtcc ttacctctgc cctgctcctg tgctccgtgg         60
caggccaggg gtgtccaacc ttggcgggga tcctggacat caacttcctc atcaacaaga       120
tgcaggaaga tccagcttcc aagtgccact gcagtgctaa tgtgaccagt tgtctctgtt       180
tgggcattcc ctctgacaac tgcaccagac atgcttcagt gagagactgt gtctcagatga      240 ccaataccac catgcaaaca agatacccac tgattttcag tcgggtgaaa aaatcagttg       300
aagtactaaa gaacaacaag tgtccatatt tttcctgtga acagccatgc aaccaaacca       360
cggcaggcaa cgcgctgaca tttctgaaga gtcttctgga aattttccag aaagaaaaga      420
tgagagggat gagaggcaag atatgaagat gaaatattat ttatcctatt tattaaattt      480
aaaaagcttt ctctttaagt tgctacaatt taaaaatcaa gtaagctact ctaaatcagt      540
atcagttgtg attatttgtt taacattgta tgtctttatt ttgaaataaa t               591

<210> SEQ ID NO 52
<211> LENGTH: 144
<212> TYPE: PRT
<213> ORGANISM: Homo sapiens

<400> SEQUENCE: 52

Met Leu Leu Ala Met Val Leu Thr Ser Ala Leu Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140

<210> SEQ ID NO 53
<211> LENGTH: 808
<212> TYPE: PRT
<213> ORGANISM: Homo sapiens

<400> SEQUENCE: 53

Met Ala Glu Leu Leu Ala Ser Ala Gly Ser Ala Cys Ser Trp Asp Phe
1               5                   10                  15

Pro Arg Ala Pro Pro Ser Phe Pro Pro Ala Ala Ser Arg Gly Gly
            20                  25                  30

Leu Gly Gly Thr Arg Ser Phe Arg Pro His Arg Gly Ala Glu Ser Pro
            35                  40                  45

Arg Pro Gly Arg Asp Arg Asp Gly Val Arg Val Pro Met Ala Ser Ser
    50                  55                  60

Arg Cys Pro Ala Pro Arg Gly Cys Arg Cys Leu Pro Gly Ala Ser Leu
65                  70                  75                  80

Ala Trp Leu Gly Thr Val Leu Leu Leu Ala Asp Trp Val Leu Leu
                85                  90                  95

Arg Thr Ala Leu Pro Arg Ile Phe Ser Leu Leu Val Pro Thr Ala Leu
            100                 105                 110

Pro Leu Leu Arg Val Trp Ala Val Gly Leu Ser Arg Trp Ala Val Leu
            115                 120                 125

Trp Leu Gly Ala Cys Gly Val Leu Arg Ala Thr Val Gly Ser Lys Ser
    130                 135                 140

Glu Asn Ala Gly Ala Gln Gly Trp Leu Ala Ala Leu Lys Pro Leu Ala
145                 150                 155                 160

Ala Ala Leu Gly Leu Ala Leu Pro Gly Leu Ala Leu Phe Arg Glu Leu
                165                 170                 175

Ile Ser Trp Gly Ala Pro Gly Ser Ala Asp Ser Thr Arg Leu Leu His
            180                 185                 190

Trp Gly Ser His Pro Thr Ala Phe Val Val Ser Tyr Ala Ala Ala Leu
        195                 200                 205

Pro Ala Ala Ala Leu Trp His Lys Leu Gly Ser Leu Trp Val Pro Gly
    210                 215                 220

Gly Gln Gly Gly Ser Gly Asn Pro Val Arg Arg Leu Leu Gly Cys Leu
225                 230                 235                 240

Gly Ser Glu Thr Arg Arg Leu Ser Leu Phe Leu Val Leu Val Val Leu
                245                 250                 255

Ser Ser Leu Gly Glu Met Ala Ile Pro Phe Phe Thr Gly Arg Leu Thr
            260                 265                 270

Asp Trp Ile Leu Gln Asp Gly Ser Ala Asp Thr Phe Thr Arg Asn Leu
        275                 280                 285

Thr Leu Met Ser Ile Leu Thr Ile Ala Ser Ala Val Leu Glu Phe Val
    290                 295                 300

Gly Asp Gly Ile Tyr Asn Asn Thr Met Gly His Val His Ser His Leu
305                 310                 315                 320

Gln Gly Glu Val Phe Gly Ala Val Leu Arg Gln Glu Thr Glu Phe Phe
                325                 330                 335

Gln Gln Asn Gln Thr Gly Asn Ile Met Ser Arg Val Thr Glu Asp Thr
            340                 345                 350

Ser Thr Leu Ser Asp Ser Leu Ser Glu Asn Leu Ser Leu Phe Leu Trp

-continued

```
                355                 360                 365
Tyr Leu Val Arg Gly Leu Cys Leu Leu Gly Ile Met Leu Trp Gly Ser
    370                 375                 380
Val Ser Leu Thr Met Val Thr Leu Ile Thr Leu Pro Leu Leu Phe Leu
385                 390                 395                 400
Leu Pro Lys Lys Val Gly Lys Trp Tyr Gln Leu Leu Glu Val Gln Val
                405                 410                 415
Arg Glu Ser Leu Ala Lys Ser Ser Gln Val Ala Ile Glu Ala Leu Ser
                420                 425                 430
Ala Met Pro Thr Val Arg Ser Phe Ala Asn Glu Glu Gly Glu Ala Gln
                435                 440                 445
Lys Phe Arg Glu Lys Leu Gln Glu Ile Lys Thr Leu Asn Gln Lys Glu
                450                 455                 460
Ala Val Ala Tyr Ala Val Asn Ser Trp Thr Thr Ser Ile Ser Gly Met
465                 470                 475                 480
Leu Leu Lys Val Gly Ile Leu Tyr Ile Gly Gly Gln Leu Val Thr Ser
                485                 490                 495
Gly Ala Val Ser Ser Gly Asn Leu Val Thr Phe Val Leu Tyr Gln Met
                500                 505                 510
Gln Phe Thr Gln Ala Val Glu Val Leu Leu Ser Ile Tyr Pro Arg Val
                515                 520                 525
Gln Lys Ala Val Gly Ser Ser Glu Lys Ile Phe Glu Tyr Leu Asp Arg
                530                 535                 540
Thr Pro Arg Cys Pro Pro Ser Gly Leu Leu Thr Pro Leu His Leu Glu
545                 550                 555                 560
Gly Leu Val Gln Phe Gln Asp Val Ser Phe Ala Tyr Pro Asn Arg Pro
                565                 570                 575
Asp Val Leu Val Leu Gln Gly Leu Thr Phe Thr Leu Arg Pro Gly Glu
                580                 585                 590
Val Thr Ala Leu Val Gly Pro Asn Gly Ser Gly Lys Ser Thr Val Ala
                595                 600                 605
Ala Leu Leu Gln Asn Leu Tyr Gln Pro Thr Gly Gly Gln Leu Leu Leu
                610                 615                 620
Asp Gly Lys Pro Leu Pro Gln Tyr Glu His Arg Tyr Leu His Arg Gln
625                 630                 635                 640
Val Ala Ala Val Gly Gln Glu Pro Gln Val Phe Gly Arg Ser Leu Gln
                645                 650                 655
Glu Asn Ile Ala Tyr Gly Leu Thr Gln Lys Pro Thr Met Glu Glu Ile
                660                 665                 670
Thr Ala Ala Ala Val Lys Ser Gly Ala His Ser Phe Ile Ser Gly Leu
                675                 680                 685
Pro Gln Gly Tyr Asp Thr Glu Val Asp Glu Ala Gly Ser Gln Leu Ser
                690                 695                 700
Gly Gly Gln Arg Gln Ala Val Ala Leu Ala Arg Ala Leu Ile Arg Lys
705                 710                 715                 720
Pro Cys Val Leu Ile Leu Asp Asp Ala Thr Ser Ala Leu Asp Ala Asn
                725                 730                 735
Ser Gln Leu Gln Val Glu Gln Leu Leu Tyr Glu Ser Pro Glu Arg Tyr
                740                 745                 750
Ser Arg Ser Val Leu Leu Ile Thr Gln His Leu Ser Leu Val Glu Gln
                755                 760                 765
Ala Asp His Ile Leu Phe Leu Glu Gly Gly Ala Ile Arg Glu Gly Gly
                770                 775                 780
```

```
Thr His Gln Gln Leu Met Glu Lys Lys Gly Cys Tyr Trp Ala Met Val
785                 790                 795                 800

Gln Ala Pro Ala Asp Ala Pro Glu
                805
```

<210> SEQ ID NO 54
<211> LENGTH: 140
<212> TYPE: PRT
<213> ORGANISM: Homo sapiens

<400> SEQUENCE: 54

```
Met Val Leu Thr Ser Ala Leu Leu Leu Cys Ser Val Ala Gly Gln Gly
1               5                   10                  15

Cys Pro Thr Leu Ala Gly Ile Leu Asp Ile Asn Phe Leu Ile Asn Lys
            20                  25                  30

Met Gln Glu Asp Pro Ala Ser Lys Cys His Cys Ser Ala Asn Val Thr
        35                  40                  45

Ser Cys Leu Cys Leu Gly Ile Pro Ser Asp Asn Cys Thr Arg Pro Cys
50                  55                  60

Phe Ser Glu Arg Leu Ser Gln Met Thr Asn Thr Thr Met Gln Thr Arg
65                  70                  75                  80

Tyr Pro Leu Ile Phe Ser Arg Val Lys Lys Ser Val Glu Val Leu Lys
                85                  90                  95

Asn Asn Lys Cys Pro Tyr Phe Ser Cys Glu Gln Pro Cys Asn Gln Thr
            100                 105                 110

Thr Ala Gly Asn Ala Leu Thr Phe Leu Lys Ser Leu Leu Glu Ile Phe
        115                 120                 125

Gln Lys Glu Lys Met Arg Gly Met Arg Gly Lys Ile
    130                 135                 140
```

<210> SEQ ID NO 55
<211> LENGTH: 2171
<212> TYPE: DNA
<213> ORGANISM: Homo sapiens

<400> SEQUENCE: 55

```
agcagctctg taatgcgctt gtggtttcag atgtgggcgg cctgtgtgaa cctgtcgtgc      60
aaagctcacg tcaccaactg ctgcagttat ctcctgaatc aggctgaggg tctttgctgt    120
gcacccagag atagttgggt gacaaatcac ctccaggttg gggatgcctc agacttgtga    180
tgggactggg cagatgcatc tgggaaggct ggaccttgga gagtgaggcc ctgaggcgag    240
acatgggcac ctggctcctg gcctgcatct gcatctgcac ctgtgtctgc ttgggagtct    300
ctgtcacagg ggaaggacaa gggccaaggt ctagaacctt cacctgcctc accaacaaca    360
ttctcaggat cgattgccac tggtctgccc cagagctggg acagggctcc agcccctggc    420
tcctcttcac cagcaaccag gctcctggcg cacacataa gtgcatcttg cggggcagtg    480
agtgcaccgt cgtgctgcca cctgaggcag tgctcgtgcc atctgacaat tcaccatca    540 ctttccacca ctgcatgtct gggagggagc aggtcagcct ggtggacccg gagtacctgc    600
cccggagaca cgttaagctg acccgcccct ctgacttgca gagcaacatc agttctggcc    660
actgcatcct gacctggagc atcagtcctg ccttggagcc aatgaccaca cttctcagct    720
atgagctggc cttcaagaag caggaagagg cctgggagca ggcccagcac agggatcaca    780
ttgtcggggt gacctggctt atacttgaag cctttgagct ggaccctggc tttatccatg    840
aggccaggct gcgtgtccag atggccacac tggaggatga tgtggtagag gaggagcgtt    900
```

```
atacaggcca gtggagtgag tggagccagc ctgtgtgctt ccaggctccc cagagacaag    960
gccctctgat cccaccctgg gggtggccag gcaacaccct tgttgctgtg tccatctttc   1020
tcctgctgac tggcccgacc tacctcctgt tcaagctgtc gcccagggtg aagagaatct   1080
tctaccagaa cgtgccctct ccagcgatgt tcttccagcc cctctacagt gtacacaatg   1140
ggaacttcca gacttggatg ggggcccacg gggccggtgt gctgttgagc caggactgtg   1200
ctggcacccc acagggagcc ttggagccct gcgtccagga ggccactgca ctgctcactt   1260
gtggcccagc gcgtccttgg aaatctgtgg ccctggagga ggaacaggag ggccctggga   1320
ccaggctccc ggggaacctg agctcagagg atgtgctgcc agcagggtgt acggagtgga   1380
gggtacagac gcttgcctat ctgccacagg aggactgggc ccccacgtcc ctgactaggc   1440
cggctccccc agactcagag ggcagcagga gcagcagcag cagcagcagc agcaacaaca   1500
acaactactg tgccttgggc tgctatgggg atggcacct  tcagccctc ccaggaaaca   1560
cacagagctc tgggcccatc ccagccctgg cctgtggcct ttcttgtgac catcagggcc   1620
tggagaccca gcaaggagtt gcctgggtgc tggctggtca ctgccagagg cctgggctgc   1680
atgaggacct ccagggcatg ttgctcccct ctgtcctcag caaggctcgg tcctggacat   1740
tctaggtccc tgactcgcca gatgcatcat gtccattttg ggaaaatgga ctgaagtttc   1800
tggagcccct gtctgagact gaacctcctg agaaggggcc cctagcagcg tcagaggtc    1860
ctgtctggat ggaggctgga ggctcccccc tcaacccctc tgctcagtgc ctgtggggag   1920
cagcctctac cctcagcatc ctggccacaa gttcttcctt ccattgtccc ttttctttat   1980
ccctgacctc tctgagaagt ggggtgtggt ctctcagctg ttctgccctc ataccctta    2040
agggccagcc tgggcccagt ggacacaggt aaggcaccat gaccacctgg tgtgacctct   2100
ctgtgcctta ctgaggcacc tttctagaga ttaaagggg  cttgatggct gttaaaaaaa   2160
aaaaaaaaa a                                                         2171

<210> SEQ ID NO 56
<211> LENGTH: 2175
<212> TYPE: DNA
<213> ORGANISM: Homo sapiens

<400> SEQUENCE: 56
agcagctctg taatgcgctt gtggtttcag atgtgggcgg cctgtgtgaa cctgtcgtgc     60
aaagctcacg tcaccaactg ctgcagttat ctcctgaatc aggctgaggg tctttgctgt   120
gcacccagag atagttgggt gacaaatcac ctccaggttg gggatgcctc agacttgtga   180
tgggactggg cagatgcatc tggaagtaa  ctgctgcaag aacggacaga cactgctgca   240
gagaacttgc cacggtgttt catgctgtgg ctggtggttc caggctgcac gctccattct   300
aggaaagggg ccctcagccc agtcccttgc aggctggacc ttggagagtg aggccctgag   360
gcgagacatg ggcacctggc tcctggcctg catctgcatc tgcacctgtg tctgcttggg   420
agtctctgtc acaggggaag gacaagggcc aaggtctaga accttcacct gcctcaccaa   480
caacattctc aggatcgatt gccactggtc tgccccagag ctgggacagg gctccagccc   540
ctggctcctc ttcaccaggc tcctggcggc acacataagt gcatcttgcg ggcagtgag    600
tgcaccgtcg tgctgccacc tgaggcagtg ctcgtgccat ctgacaattt caccatcact   660
ttccaccact gcatgtctgg gagggagcag gtcagcctgg tggacccgga gtacctgccc   720
cggagacacg agcaacatca gttctggcca ctgcatcctg acctggagca tcagtcctgc   780
```

```
cttggagcca atgaccacac ttctcagcta tgagctggcc ttcaagaagc aggaagaggc    840
ctgggagcag gcccagcaca gggatcacat tgtcggggtg acctggctta tacttgaagc    900 cttttgagctg acccctggct ttatccatga ggccaggctg cgtgtccaga tggccacact    960
ggaggatgat gtggtagagg aggagcgtta tacaggccag tggagtgagt ggagccagcc   1020
tgtgtgcttc caggctcccc agagacaagg ccctctgatc ccaccctggg ggtggccagg   1080
caacaccctt gttgctgtgt ccatctttct cctgctgact ggcccgacct acctcctgtt   1140
caagctgtcg cccagacttg gatggggcc cacgggccg gtgtgctgtt gagccaggac   1200
tgtgctggca ccccacaggg agccttggag ccctgcgtcc aggaggccac tgcactgctc   1260
acttgtggcc cagcgcgtcc ttggaaatct gtggccctgg aggaggaaca ggagggccct   1320
gggaccaggc tcccggggaa cctgagctca aggatgtgc tgccagcagg gtgtacggag   1380
tggagggtac agacgcttgc ctatctgcca caggaggact gggccccac gtccctgact   1440 aggccggctc cccagactc agagggcagc aggagcagca gcagcagcag cagcagcaac   1500
aacaacaact actgtgcctt gggctgctat ggggatggc acctctcagc cctcccagga   1560
aacacacaga gctctgggcc catcccagcc ctggcctgtg gcctttcttg tgaccatcag   1620
ggcctggaga cccagcaagg agttgcctgg gtgctggctg gtcactgcca gaggcctggg   1680
ctgcatgagg acctccaggg catgttgctc ccttctgtcc tcagcaaggc tcggtcctgg   1740
acattctagg tccctgactc gccagatgca tcatgtccat tttgggaaaa tggactgaag   1800
tttctggagc ccttgtctga gactgaacct cctgagaagg ggccctagc agcggtcaga   1860 ggtcctgtct ggatggaggc tggaggctcc cccctcaacc cctctgctca gtgcctgtgg   1920
ggagcagcct ctaccctcag catcctggcc acaagttctt ccttccattg tccctttttct   1980 ttatccctga cctctctgag aagtgggtg tggtctctca gctgttctgc cctcatccc    2040 ttaaagggcc agcctgggcc cagtggacac aggtaaggca ccatgaccac ctggtgtgac   2100
ctctctgtgc cttactgagg caccttttcta gagattaaaa gggcttgat ggctgttaaa   2160 aaaaaaaaaa aaaaa                                                     2175
```

<210> SEQ ID NO 57
<211> LENGTH: 1451
<212> TYPE: DNA
<213> ORGANISM: Homo sapiens

<400> SEQUENCE: 57

```
gaagagcaag cgccatgttg aagccatcat taccattcac atccctctta ttcctgcagc     60
tgcccctgct gggagtgggg ctgaacacga caattctgac gcccaatggg aatgaagaca    120
ccacagctga tttcttcctg accactatgc ccactgactc cctcagtgtt tccactctgc    180
ccctcccaga ggttcagtgt tttgtgttca atgtcgagta catgaattgc acttggaaca    240
gcagctctga gccccagcct accaacctca ctctgcatta ttggtacaag aactcggata    300
atgataaagt ccagaagtgc agccactatc tattctctga gaaatcact tctggctgtc    360 agttgcaaaa aaaggagatc cacctctacc aaacatttgt tgttcagctc caggacccac    420
gggaacccag gagacaggcc acacagatgc taaaactgca gaatctggtg atcccctggg    480
ctccagagaa cctaacactt cacaaactga gtgaatccca gctagaactg aactggaaca    540
acagattctt gaaccactgt ttggagcact ggtgcagta ccggactgac tgggaccaca    600
gctggactga acaatcagtg gattatagac ataaagttctc cttgcctagt gtggatgggc    660
agaaacgcta cacgtttcgt gttcggagcc gctttaaccc actctgtgga agtgctcagc    720
```

```
attggagtga atggagccac ccaatccact gggggagcaa tacttcaaaa gagaatcctt      780
tcctgtttgc attggaagcc gtggttatct ctgttggctc catgggattg attatcagcc      840
ttctctgtgt gtatttctgg ctggaacgga cgatgccccg aattcccacc ctgaagaacc      900
tagaggatct tgttactgaa taccacggga acttttcggc ctggagtggt gtgtctaagg      960
gactggctga gagtctgcag ccagactaca gtgaacgact ctgcctcgtc agtgagattc     1020
ccccaaaagg aggggccctt ggggaggggc ctggggcctc ccatgcaac cagcatagcc      1080 cctactgggc cccccatgt tacaccctaa agcctgaaac ctgaacccca atcctctgac      1140
agaagaaccc cagggtcctg tagccctaag tggtactaac tttccttcat tcaacccacc     1200
tgcgtctcat actcacctca ccccactgtg gctgatttgg aattttgtgc cccatgtaa      1260 gcaccccttc atttggcatt ccccacttga gaattaccct tttgccccga acatgttttt     1320
cttctccctc agtctggccc ttccttttcg caggattctt cctccctccc tctttccctc     1380
ccttcctctt tccatctacc ctccgattgt tcctgaaccg atgagaaata aagtttctgt     1440
tgataatcat c                                                          1451
```

<210> SEQ ID NO 58
<211> LENGTH: 521
<212> TYPE: PRT
<213> ORGANISM: Homo sapiens

<400> SEQUENCE: 58

```
Met Gly Leu Gly Arg Cys Ile Trp Glu Gly Trp Thr Leu Glu Ser Glu
 1               5                  10                  15

Ala Leu Arg Arg Asp Met Gly Thr Trp Leu Ala Cys Ile Cys Ile
            20                  25                  30

Cys Thr Cys Val Cys Leu Gly Val Ser Val Thr Gly Glu Gly Gln Gly
        35                  40                  45

Pro Arg Ser Arg Thr Phe Thr Cys Leu Thr Asn Asn Ile Leu Arg Ile
    50                  55                  60

Asp Cys His Trp Ser Ala Pro Glu Leu Gly Gln Gly Ser Ser Pro Trp
65                  70                  75                  80

Leu Leu Phe Thr Ser Asn Gln Ala Pro Gly Gly Thr His Lys Cys Ile
                85                  90                  95

Leu Arg Gly Ser Glu Cys Thr Val Val Leu Pro Pro Glu Ala Val Leu
            100                 105                 110

Val Pro Ser Asp Asn Phe Thr Ile Thr Phe His His Cys Met Ser Gly
        115                 120                 125

Arg Glu Gln Val Ser Leu Val Asp Pro Glu Tyr Leu Pro Arg Arg His
    130                 135                 140

Val Lys Leu Asp Pro Pro Ser Asp Leu Gln Ser Asn Ile Ser Ser Gly
145                 150                 155                 160

His Cys Ile Leu Thr Trp Ser Ile Ser Pro Ala Leu Glu Pro Met Thr
                165                 170                 175

Thr Leu Leu Ser Tyr Glu Leu Ala Phe Lys Lys Gln Glu Glu Ala Trp
            180                 185                 190

Glu Gln Ala Gln His Arg Asp His Ile Val Gly Val Thr Trp Leu Ile
        195                 200                 205

Leu Glu Ala Phe Glu Leu Asp Pro Gly Phe Ile His Glu Ala Arg Leu
    210                 215                 220

Arg Val Gln Met Ala Thr Leu Glu Asp Asp Val Val Glu Glu Glu Arg
225                 230                 235                 240
```

```
Tyr Thr Gly Gln Trp Ser Glu Trp Ser Gln Pro Val Cys Phe Gln Ala
            245                 250                 255

Pro Gln Arg Gln Gly Pro Leu Ile Pro Pro Trp Gly Trp Pro Gly Asn
            260                 265                 270

Thr Leu Val Ala Val Ser Ile Phe Leu Leu Thr Gly Pro Thr Tyr
            275                 280                 285

Leu Leu Phe Lys Leu Ser Pro Arg Val Lys Arg Ile Phe Tyr Gln Asn
            290                 295                 300

Val Pro Ser Pro Ala Met Phe Phe Gln Pro Leu Tyr Ser Val His Asn
305                 310                 315                 320

Gly Asn Phe Gln Thr Trp Met Gly Ala His Gly Ala Gly Val Leu Leu
            325                 330                 335

Ser Gln Asp Cys Ala Gly Thr Pro Gln Gly Ala Leu Glu Pro Cys Val
            340                 345                 350

Gln Glu Ala Thr Ala Leu Leu Thr Cys Gly Pro Ala Arg Pro Trp Lys
            355                 360                 365

Ser Val Ala Leu Glu Glu Glu Gln Glu Gly Pro Gly Thr Arg Leu Pro
            370                 375                 380

Gly Asn Leu Ser Ser Glu Asp Val Leu Pro Ala Gly Cys Thr Glu Trp
385                 390                 395                 400

Arg Val Gln Thr Leu Ala Tyr Leu Pro Gln Glu Asp Trp Ala Pro Thr
            405                 410                 415

Ser Leu Thr Arg Pro Ala Pro Pro Asp Ser Glu Gly Ser Arg Ser Ser
            420                 425                 430

Ser Ser Ser Ser Ser Asn Asn Asn Asn Tyr Cys Ala Leu Gly Cys
            435                 440                 445

Tyr Gly Gly Trp His Leu Ser Ala Leu Pro Gly Asn Thr Gln Ser Ser
            450                 455                 460

Gly Pro Ile Pro Ala Leu Ala Cys Gly Leu Ser Cys Asp His Gln Gly
465                 470                 475                 480

Leu Glu Thr Gln Gln Gly Val Ala Trp Val Leu Ala Gly His Cys Gln
            485                 490                 495

Arg Pro Gly Leu His Glu Asp Leu Gln Gly Met Leu Leu Pro Ser Val
            500                 505                 510

Leu Ser Lys Ala Arg Ser Trp Thr Phe
            515                 520

<210> SEQ ID NO 59
<211> LENGTH: 332
<212> TYPE: PRT
<213> ORGANISM: Homo sapiens

<400> SEQUENCE: 59

Met His Leu Gly Ser Asn Cys Cys Lys Asn Gly Gln Thr Leu Leu Gln
1               5                   10                  15

Arg Thr Cys His Gly Val Ser Cys Cys Gly Trp Trp Phe Gln Ala Ala
            20                  25                  30

Arg Ser Ile Leu Gly Lys Gly Pro Ser Ala Gln Ser Leu Ala Gly Trp
            35                  40                  45

Thr Leu Glu Ser Glu Ala Leu Arg Arg Asp Met Gly Thr Trp Leu Leu
            50                  55                  60

Ala Cys Ile Cys Ile Cys Thr Cys Val Cys Leu Gly Val Ser Val Thr
65                  70                  75                  80

Gly Glu Gly Gln Gly Pro Arg Ser Arg Thr Phe Thr Cys Leu Thr Asn
```

```
                    85                  90                  95
Asn Ile Leu Arg Ile Asp Cys His Trp Ser Ala Pro Glu Leu Gly Gln
                100                 105                 110
Gly Ser Ser Pro Trp Leu Leu Phe Thr Arg Leu Leu Ala Ala His Ile
            115                 120                 125
Ser Ala Ser Cys Gly Ala Val Ser Ala Pro Ser Cys Cys His Leu Arg
        130                 135                 140
Gln Cys Ser Cys His Leu Thr Ile Ser Pro Ser Leu Ser Thr Thr Ala
145                 150                 155                 160
Cys Leu Gly Gly Ser Arg Ser Ala Trp Trp Thr Arg Ser Thr Cys Pro
                165                 170                 175
Gly Asp Thr Ser Asn Ile Ser Ser Gly His Cys Ile Leu Thr Trp Ser
                180                 185                 190
Ile Ser Pro Ala Leu Glu Pro Met Thr Thr Leu Leu Ser Tyr Glu Leu
            195                 200                 205
Ala Phe Lys Lys Gln Glu Glu Ala Trp Glu Gln Ala Gln His Arg Asp
        210                 215                 220
His Ile Val Gly Val Thr Trp Leu Ile Leu Glu Ala Phe Glu Leu Asp
225                 230                 235                 240
Pro Gly Phe Ile His Glu Ala Arg Leu Arg Val Gln Met Ala Thr Leu
                245                 250                 255
Glu Asp Asp Val Val Glu Glu Arg Tyr Thr Gly Gln Trp Ser Glu
                260                 265                 270
Trp Ser Gln Pro Val Cys Phe Gln Ala Pro Gln Arg Gln Gly Pro Leu
            275                 280                 285
Ile Pro Pro Trp Gly Trp Pro Gly Asn Thr Leu Val Ala Val Ser Ile
        290                 295                 300
Phe Leu Leu Leu Thr Gly Pro Thr Tyr Leu Leu Phe Lys Leu Ser Pro
305                 310                 315                 320
Arg Leu Gly Trp Gly Pro Thr Gly Pro Val Cys Cys
                325                 330

<210> SEQ ID NO 60
<211> LENGTH: 369
<212> TYPE: PRT
<213> ORGANISM: Homo sapiens

<400> SEQUENCE: 60

Met Leu Lys Pro Ser Leu Pro Phe Thr Ser Leu Leu Phe Leu Gln Leu
1               5                   10                  15
Pro Leu Leu Gly Val Gly Leu Asn Thr Thr Ile Leu Thr Pro Asn Gly
            20                  25                  30
Asn Glu Asp Thr Thr Ala Asp Phe Phe Leu Thr Thr Met Pro Thr Asp
        35                  40                  45
Ser Leu Ser Val Ser Thr Leu Pro Leu Pro Glu Val Gln Cys Phe Val
    50                  55                  60
Phe Asn Val Glu Tyr Met Asn Cys Thr Trp Asn Ser Ser Ser Glu Pro
65                  70                  75                  80
Gln Pro Thr Asn Leu Thr Leu His Tyr Trp Tyr Lys Asn Ser Asp Asn
                85                  90                  95
Asp Lys Val Gln Lys Cys Ser His Tyr Leu Phe Ser Glu Glu Ile Thr
                100                 105                 110
Ser Gly Cys Gln Leu Gln Lys Lys Glu Ile His Leu Tyr Gln Thr Phe
            115                 120                 125
```

-continued

```
Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr
```

```
<210> SEQ ID NO 61
<211> LENGTH: 19
<212> TYPE: DNA
<213> ORGANISM: Homo sapiens

<400> SEQUENCE: 61
cgaagcatct tgacagcgg                                                 19

<210> SEQ ID NO 62
<211> LENGTH: 30
<212> TYPE: DNA
<213> ORGANISM: Homo sapiens

<400> SEQUENCE: 62
tccagaagac tcttcagaaa tgtcagcgcg                                     30

<210> SEQ ID NO 63
<211> LENGTH: 30
<212> TYPE: DNA
<213> ORGANISM: Homo sapiens

<400> SEQUENCE: 63
tttatttcaa aataaagaca tacaatgtta                                     30
```

METHODS OF TREATING RESPIRATORY CONDITIONS

This application claims priority to U.S. Provisional Application Ser. No. 60/477,801, filed Jun. 10, 2003, and U.S. Provisional Application Ser. No. 60/462,307, filed Apr. 11, 2003, both of which are incorporated by reference herein in their entireties.

1. FIELD OF THE INVENTION

The present invention provides prophylactic and therapeutic protocols designed to prevent, manage, treat, or ameliorate a respiratory condition or one or more symptoms thereof. In particular, the present invention provides methods for the prevention, management, treatment, or amelioration of a respiratory condition or one or more symptoms thereof, said methods comprising administering to a subject in need thereof an effective amount of one or more agents that modulate the expression and/or activity of interleukin-9 ("IL-9"). The invention also provides combination therapies for the prevention, management, treatment or amelioration of a respiratory condition or one or more symptoms thereof. More specifically, the invention provides methods for the prevention, management, treatment, or amelioration of a respiratory condition or one or more symptoms thereof, said methods comprising administering to a subject in need thereof an effective amount of one or more agents that modulate the expression and/or activity of IL-9 and an effective amount of one or more other agents useful in the prevention, treatment, management, or amelioration of said respiratory condition. The invention further provides pharmaceutical compositions and articles of manufacture for use in the prevention, management, treatment, or amelioration of a respiratory condition or one or more symptoms thereof.

2. BACKGROUND OF THE INVENTION 2.1 Respiratory Conditions
2.1.1 Respiratory Conditions Associated with Environmental Factors
2.1.1.1 Allergies Allergies are disorders of the immune system in which the body reacts to innocuous substances by inducing the generation of large amounts of immunoglobulin E (IgE). In the presence of an allergen, IgE activates mast cells and promotes mast cell proliferation, infiltration, and/or degranulation that results in the release of histamines, leukotrienes, and cytokines which cause rhinitis, hives, redness, itchiness, watery eyes, skin rashes, bronchoconstriction (wheezing), coughing, and difficulty breathing. Common allergens include, but are not limited to, pollens, molds, dust (e.g., dust mites and dust mite waste), animal protein (e.g., dander, urine, oil from the skin), industrial chemicals, foods, medicines, feathers, and insects (e.g., insect stings, cockroaches, and insect waste).

Pollinosis, commonly known as hay fever, is generally induced by wind-borne pollens, including, but not limited to tree pollens (e.g., oak, elm, maple, alder, birch, juniper, and olive), grass pollens (e.g., Bermuda, timothy, sweet vernal, orchard, and Johnson), weed pollens (e.g., Russian thistle, English plantain, and ragweed), and airborne fungal spores. Symptoms of pollinosis include itchy nose, roof of the mouth, pharynx, and eyes, sneezing, runny nose, watery eyes, headaches, anorexia, depression, coughing, insomnia, and wheezing. Common therapies include administration of antihistamines, sympathomimetics, glucocorticoids, and systemic corticosteroids and allergen immunotherapy. Unfortunately, these therapies may cause side effects, such as hypertension and drowsiness or may not be effective.

Anaphylaxis is an acute allergic reaction that results when the allergen reaches the circulation. Common allergens are parenteral enzymes, blood products, β-lactam antibiotics, allergen immunotherapy, and insect stings. Anaphylaxis is characterized by smooth muscle contraction that causes wheezing, vasodilation, pulmonary edema, and obstructive angiodema. If the reaction is prolonged, the subject may develop arrhythmias or cardiogenic shock. In severe cases, the patient may suffer from primary cardiovascular collapse without respiratory symptoms. Long-term immunotherapy is effective for preventing anaphylaxis from insect stings, but is rarely available for patients with drug or serum anaphylaxis. Immediate administration of epinephrine is the most common treatment for anaphylaxis, but may cause side effects including headache, tremulousness, nausea, and arrhythmias. Thus, new therapies for the prevention, treatment, management, and amelioration of allergic reactions are needed.

2.1.1.2 Asthma

About 12 million people in the U.S. have asthma and it is the leading cause of hospitalization for children. *The Merck Manual of Diagnosis and Therapy* (17th ed., 1999).

Asthma is an inflammatory disease of the lung that is characterized by airway hyperresponsiveness ("AHR"), bronchoconstriction (i.e., wheezing), eosinophilic inflammation, mucus hypersecretion, subepithelial fibrosis, and elevated IgE levels. Asthmatic attacks can be triggered by environmental triggers (e.g. acarids, insects, animals (e.g., cats, dogs, rabbits, mice, rats, hamsters, guinea pigs, mice, rats, and birds), fungi, air pollutants (e.g., tobacco smoke), irritant gases, fumes, vapors, aerosols, or chemicals, or pollen), exercise, or cold air. The cause(s) of asthma is unknown. However, it has been speculated that family history of asthma (London et al., 2001, Epidemiology 12(5):577-83), early exposure to allergens, such as dust mites, tobacco smoke, and cockroaches (Melen et al., 2001, 56(7):646-52), and respiratory infections (Wenzel et al., 2002, Am J Med, 112(8):672-33 and Lin et al., 2001, J Microbiol Immuno Infect, 34(4): 259-64) may increase the risk of developing asthma.

Current therapies are mainly aimed at managing asthma and include the administration of β-adrenergic drugs (e.g. epinephrine and isoproterenol), theophylline, anticholinergic drugs (e.g., atropine and ipratorpium bromide), corticosteroids, and leukotriene inhibitors. These therapies are associated with side effects such as drug interactions, dry mouth, blurred vision, growth suppression in children, and osteoporosis in menopausal women. Cromolyn and nedocromil are administered prophylatically to inhibit mediator release from inflammatory cells, reduce airway hyperresponsiveness, and block responses to allergens. However, there are no current therapies available that prevent the development of asthma in subjects at increased risk of developing asthma. Thus, new therapies with fewer side effects and better prophylactic and/or therapeutic efficacy are needed for asthma.

2.1.2 Respiratory Infections

Respiratory infections are common infections of the upper respiratory tract (e.g., nose, ears, sinuses, and throat) and lower respiratory tract (e.g., trachea, bronchial tubes, and lungs). Symptoms of upper respiratory infection include runny or stuffy nose, irritability, restlessness, poor appetite, decreased activity level, coughing, and fever. Viral upper respiratory infections cause and/or are associated with sore throats, colds, croup, and the flu. Examples of viruses that cause upper respiratory tract infections include rhinoviruses and influenza viruses A and B. Common upper respiratory bacterial infections cause and/or associated with, for example, whooping cough and strep throat. An example of a bacteria that causes an upper respiratory tract infection is *Streptococcus*.

Clinical manifestations of a lower respiratory infection include shallow coughing that produces sputum in the lungs, fever, and difficulty breathing. Examples of lower respiratory viral infections are parainfluenza virus infections ("PIV"), respiratory syncytial virus ("RSV"), and bronchiolitis. Examples of bacteria that cause lower respiratory tract infections include *Streptococcus pneumoniae* that causes pneumonococcal pneumonia and *Mycobacterium tuberculosis* that causes tuberculosis. Respiratory infections caused by fungi include systemic candidiasis, blastomycosis crytococcosis, coccidioidomycosis, and aspergillosis. Respiratory infections may be primary or secondary infections.

Current therapies for respiratory infections involve the administration of anti-viral agents, anti-bacterial, and anti-fungal agents for the treatment, prevention, or amelioration of viral, bacterial, and fungal respiratory infections, respectively. Unfortunately, in regard to certain infections, there are no therapies available, infections have been proven to be refractory to therapies, or the occurrence of side effects outweighs the benefits of the administration of a therapy to a subject. The use of anti-bacterial agents for treatment of bacterial respiratory infections may also produce side effects or result in resistant bacterial strains. The administration of anti-fungal agents may cause renal failure or bone marrow dysfunction and may not be effective against fungal infection in patients with suppressed immune systems. Additionally, the infection causing microorganism (e.g., virus, bacterium, or fungus) may be resistant or develop resistance to the administered therapeutic agent or combination of therapeutic agents. In fact, microorganisms that develop resistance to administered therapeutic agents often develop pleiotropic drug or multidrug resistance, that is, resistance to therapeutic agents that act by mechanisms different from the mechanisms of the administered agents. Thus, as a result of drug resistance, many infections prove refractory to a wide array of standard treatment protocols. Therefore, new therapies for the treatment, prevention, management, and/or amelioration of respiratory infections and symptoms thereof are needed.

2.1.2.1 Viral Respiratory Infections
2.1.2.1.1 Parainfluenza Virus Infections

Parainfluenza viral ("PIV") infection results in serious respiratory tract disease in infants and children. (Tao et al., 1999, Vaccine 17: 1100-08). Infectious parainfluenza viral infections account for approximately 20% of all hospitalizations of pediatric patients suffering from respiratory tract infections worldwide. Id.

PIV is a member of the *paramyxovirus* genus of the paramyxoviridae family. PIV is made up of two structural modules: (1) an internal ribonucleoprotein core or nucleocapsid, containing the viral genome, and (2) an outer, roughly spherical lipoprotein envelope. Its genome is a single strand of negative sense RNA, approximately 15,456 nucleotides in length, encoding at least eight polypeptides. These proteins include, but are not limited to, the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins of unknown function. Id.

The parainfluenza nucleocapsid protein (NP, NC, or N) consists of two domains within each protein unit including an amino-terminal domain, comprising about two-thirds of the molecule, which interacts directly with the RNA, and a carboxyl-terminal domain, which lies on the surface of the assembled nucleocapsid. A hinge is thought to exist at the junction of these two domains thereby imparting some flexibility to this protein (see Fields et al. (ed.), 1991, *Fundamental Virology*, 2nd ed., Raven Press, New York, incorporated by reference herein in its entirety). The matrix protein (M), is apparently involved with viral assembly and interacts with both the viral membrane as well as the nucleocapsid proteins. The phosphoprotein (P), which is subject to phosphorylation, is thought to play a regulatory role in transcription and may also be involved in methylation, phosphorylation and polyadenylation. The fusion glycoprotein (F) interacts with the viral membrane and is first produced as an inactive precursor then cleaved post-translationally to produce two disulfide linked polypeptides. The active F protein is also involved in penetration of the parainfluenza virion into host cells by facilitating fusion of the viral envelope with the host cell plasma membrane. Id. The glycoprotein, hemagglutinin-neuraminidase (HN), protrudes from the envelope allowing the virus to contain both hemagglutinin and neuraminidase activities. HN is strongly hydrophobic at its amino terminal which functions to anchor the HN protein into the lipid bilayer. Id. Finally, the large polymerase protein (L) plays an important role in both transcription and replication. Id.

Currently, treatment for PIV comprises treatment of specific symptoms. In most cases, rest, fluids, and a comfortable environment are sufficient therapy for PIV infection. In cases in which fever is high, acetaminophen is recommended over aspirin, especially in children to avoid the risk of Reye's syndrome with influenza. For croup associated with PIV infection, therapies such as humidified air, oxygen, aerosolized racemic epinephrine, and oral dexamethasone (a steroid) are recommended to decrease upper airway swelling and intravenous fluids are administered for dehydration. Therapy for bronchiolitis associated with PIV infection include supportive therapy (e.g., oxygen, humidified air, chest clapping, and postural drainage to remove secretions, rest, and clear fluids) and administration of albuterol or steroids. Antibiotic, anti-viral, and/or antifungal agents may be administered to prevent secondary respiratory infections. See *Merck Manual of Diagnosis and Therapy* (17th ed., 1999).

2.1.2.1.2 Respiratory Syncytial Virus Infections

Respiratory syncytial virus ("RSV") is the leading cause of serious lower respiratory tract disease in infants and children (Feigen et al., eds., 1987, *Textbook of Pediatric Infectious Diseases*, W B Saunders, Philadelphia at pages 1653-1675; New Vaccine Development, Establishing Priorities, Vol. 1, 1985, National Academy Press, Washington D.C. at pages 397-409; and Ruuskanen et al., 1993, Curr. Probl. Pediatr. 23:50-79). The yearly epidemic nature of RSV infection is evident worldwide, but the incidence and severity of RSV disease in a given season vary by region (Hall, C. B., 1993, Contemp. Pediatr. 10:92-110). In temperate regions of the northern hemisphere, it usually begins in late fall and ends in late spring. Primary RSV infection occurs most often in children from 6 weeks to 2 years of age and uncommonly in the first 4 weeks of life during nosocomial epidemics (Hall et al., 1979, New Engl. J. Med. 300:393-396). Children at increased risk from RSV infection include, but are not limited to, pre-term infants (Hall et al., 1979, New Engl. J. Med. 300:393-396) and children with bronchopulmonary dysplasia (Groothuis et al., 1988, Pediatrics 82:199-203), congenital heart disease (MacDonald et al., New Engl. J. Med. 307:397-400), congenital or acquired immunodeficiency (Ogra et al., 1988, Pediatr. Infect. Dis. J. 7:246-249; and Pohl et al., 1992, J. Infect. Dis. 165:166-169), and cystic fibrosis (Abman et al., 1988, J. Pediatr. 113:826-830). The fatality rate in infants with heart or lung disease who are hospitalized with RSV infection is 3%-4% (Navas et al., 1992, J. Pediatr. 121:348-354).

RSV infects adults as well as infants and children. In healthy adults, RSV causes predominantly upper respiratory tract disease. It has recently become evident that some adults, especially the elderly, have symptomatic RSV infections more frequently than had been previously reported (Evans, A. S., eds., 1989, Viral Infections of Humans Epidemiology and Control, 3rd ed., Plenum Medical Book, New York at pages 525-544). Several epidemics also have been reported among nursing home patients and institutionalized young adults (Falsey, A. R., 1991, Infect. Control Hosp. Epidemiol. 12:602-608; and Garvie et al., 1980, Br. Med. J. 281:1253-1254). Finally, RSV may cause serious disease in immunosuppressed persons, particularly bone marrow transplant patients (Hertz et al., 1989, Medicine 68:269-281).

Therapies available for the treatment of established RSV disease are limited. Severe RSV disease of the lower respiratory tract often requires considerable supportive care, including administration of humidified oxygen and respiratory assistance (Fields et al., eds, 1990, Fields Virology, 2nd ed., Vol. 1, Raven Press, New York at pages 1045-1072).

While a vaccine might prevent RSV infection, no vaccine is yet licensed for this indication. A major obstacle to vaccine development is safety. A formalin-inactivated vaccine, though immunogenic, unexpectedly caused a higher and more severe incidence of lower respiratory tract disease due to RSV in immunized infants than in infants immunized with a similarly prepared trivalent parainfluenza vaccine (Kim et al., 1969, Am. J. Epidemiol. 89:422-434; and Kapikian et al., 1969, Am. J. Epidemiol. 89:405-421). Several candidate RSV vaccines have been abandoned and others are under development (Murphy et al., 1994, Virus Res. 32:13-36), but even if safety issues are resolved, vaccine efficacy must also be improved. A number of problems remain to be solved. Immunization would be required in the immediate neonatal period since the peak incidence of lower respiratory tract disease occurs at 2-5 months of age. The immaturity of the neonatal immune response together with high titers of maternally acquired RSV antibody may be expected to reduce vaccine immunogenicity in the neonatal period (Murphy et al., 1988, J. Virol. 62:3907-3910; and Murphy et al., 1991, Vaccine 9:185-189). Finally, primary RSV infection and disease do not protect well against subsequent RSV disease (Henderson et al., 1979, New Engl. J. Med. 300:530-534).

Currently, the only approved approach to prophylaxis of RSV disease is passive immunization. Initial evidence suggesting a protective role for IgG was obtained from observations involving maternal antibody in ferrets (Prince, G. A., Ph.D. diss., University of California, Los Angeles, 1975) and humans (Lambrecht et al., 1976, J. Infect. Dis. 134:211-217; and Glezen et al., 1981, J. Pediatr. 98:708-715). Hemming et al. (Morell et al., eds., 1986, Clinical Use of Intravenous Immunoglobulins, Academic Press, London at pages 285-294) recognized the possible utility of RSV antibody in treatment or prevention of RSV infection during studies involving the pharmacokinetics of an intravenous immune globulin (IVIG) in newborns suspected of having neonatal sepsis. They noted that one infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immune globulin, enriched for RSV neutralizing antibody, to protect cotton rats and primates against RSV infection (Prince et al., 1985, Virus Res. 3:193-206; Prince et al., 1990, J. Virol. 64:3091-3092; Hemming et al., 1985, J. Infect. Dis. 152:1083-1087; Prince et al., 1983, Infect. Immun. 42:81-87; and Prince et al., 1985, J. Virol. 55:517-520). Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

Recent clinical studies have demonstrated the ability of this passively administered RSV hyperimmune globulin (RSV IVIG) to protect at-risk children from severe lower respiratory infection by RSV (Groothius et al., 1993, New Engl. J. Med. 329:1524-1530; and The PREVENT Study Group, 1997, Pediatrics 99:93-99). While this is a major advance in preventing RSV infection, this therapy poses certain limitations in its widespread use. First, RSV IVIG must be infused intravenously over several hours to achieve an effective dose. Second, the concentrations of active material in hyperimmune globulins are insufficient to treat adults at risk or most children with comprised cardiopulmonary function. Third, intravenous infusion necessitates monthly hospital visits during the RSV season. Finally, it may prove difficult to select sufficient donors to produce a hyperimmune globulin for RSV to meet the demand for this product. Currently, only approximately 8% of normal donors have RSV neutralizing antibody titers high enough to qualify for the production of hyperimmune globulin.

One way to improve the specific activity of the immunoglobulin would be to develop one or more highly potent RSV neutralizing monoclonal antibodies (MAbs). Such MAbs should be human or humanized in order to retain favorable pharmacokinetics and to avoid generating a human anti-mouse antibody response, as repeat dosing would be required throughout the RSV season. Two glycoproteins, F and G, on the surface of RSV have been shown to be targets of neutralizing antibodies (Fields et al., 1990, supra; and Murphy et al., 1994, supra). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein may directly neutralize virus or block entry of the virus into the cell or prevent syncytia formation. Although antigenic and structural differences between A and B subtypes have been described for both the G and F proteins, the more significant antigenic differences reside on the G glycoprotein, where amino acid sequences are only 53% homologous and antigenic relatedness is 5% (Walsh et al., 1987, J. Infect. Dis. 155:1198-1204; and Johnson et al., 1987, Proc. Natl. Acad. Sci. USA 84:5625-5629). Conversely, antibodies raised to the F protein show a high degree of cross-reactivity among subtype A and B viruses. Comparison of biological and biochemical properties of 18 different murine MAbs directed to the RSV F protein resulted in the identification of three distinct antigenic sites that are designated A, B, and C. (Beeler and Coelingh, 1989, J. Virol. 7:2941-2950). Neutralization studies were performed against a panel of RSV strains isolated from 1956 to 1985 that demonstrated that epitopes within antigenic sites A and C are highly conserved, while the epitopes of antigenic site B are variable.

A humanized antibody directed to an epitope in the A antigenic site of the F protein of RSV, palivizumab, is approved for intramuscular administration to pediatric patients for prevention of serious lower respiratory tract disease caused by RSV at recommended monthly doses of 15 mg/kg of body weight throughout the RSV season (November through April in the northern hemisphere). Palivizumab is a composite of human (95%) and murine (5%) antibody sequences. See, Johnson et al., 1997, J. Infect. Diseases 176: 1215-1224 and U.S. Pat. No. 5,824,307, the entire contents of which are incorporated herein by reference. The human heavy chain sequence was derived from the constant domains of human $IgG_1$ and the variable framework regions of the VH genes of Cor (Press et al., 1970, Biochem. J. 117:641-660) and Cess (Takashi et al., 1984, Proc. Natl. Acad. Sci. USA 81:194-198). The human light chain sequence was derived from the constant domain of $C_K$ and the variable framework regions of the VL gene K104 with $J_K$-4 (Bentley et al., 1980, Nature 288:5194-5198). The murine sequences derived from a murine monoclonal antibody, Mab 1129 (Beeler et al., 1989, J. Virology 63:2941-2950), in a process which involved the grafting of the murine complementarity determining regions into the human antibody frameworks.

2.1.2.1.3 Avian & Human *Metapneumovirus*

Recently, a new member of the Paramyxoviridae family has been isolated from 28 children with clinical symptoms reminiscent of those caused by human respiratory syncytial virus ("hRSV") infection, ranging from mild upper respiratory tract disease to severe bronchiolitis and pneumonia (Van Den Hoogen et al., 2001, Nature Medicine 7:719-724). The new virus was named human *metapneumovirus* (hMPV) based on sequence homology and gene constellation. The study further showed that by the age of five years virtually all children in the Netherlands have been exposed to hMPV and that the virus has been circulating in humans for at least half a century.

The genomic organization of human *metapneumovirus* is described in van den Hoogen et al., 2002, Virology 295:119-132. Human *metapneumovirus* has recently been isolated from patients in North America (Peret et al., 2002, J. Infect. Diseases 185:1660-1663).

Human *metapneumovirus* is related to avian *metapneumovirus*. For example, the F protein of hMPV is highly homologous to the F protein of avian *pneumovirus* ("APV"). Alignment of the human metapneumoviral F protein with the F protein of an avian *pneumovirus* isolated from Mallard Duck shows 85.6% identity in the ectodomain. Alignment of the human metapneumoviral F protein with the F protein of an avian *pneumovirus* isolated from Turkey (subgroup B) shows 75% identity in the ectodomain. See, e.g., co-owned and co-pending Provisional Application No. 60/358,934, entitled "Recombinant Parainfluenza Virus Expression Systems and Vaccines Comprising Heterologous Antigens Derived from *Metapneumovirus*," filed on Feb. 21, 2002, by Haller and Tang, which is incorporated herein by reference in its entirety.

Respiratory disease caused by an APV was first described in South Africa in the late 1970s (Buys et al., 1980, Turkey 28:36-46) where it had a devastating effect on the turkey industry. The disease in turkeys was characterized by sinusitis and rhinitis and was called turkey rhinotracheitis (TRT). The European isolates of APV have also been strongly implicated as factors in swollen head syndrome (SHS) in chickens (O'Brien, 1985, Vet. Rec. 117:619-620). Originally, the disease appeared in broiler chicken flocks infected with Newcastle disease virus (NDV) and was assumed to be a secondary problem associated with Newcastle disease (ND). Antibody against European APV was detected in affected chickens after the onset of SHS (Cook et al., 1988, Avian Pathol. 17:403-410), thus implicating APV as the cause.

The avian *pneumovirus* is a single stranded, non-segmented RNA virus that belongs to the sub-family Pneumovirinae of the family Paramyxoviridae, genus *metapneumovirus* (Cavanagh and Barrett, 1988, Virus Res. 11:241-256; Ling et al., 1992, J. Gen. Virol. 73:1709-1715; Yu et al., 1992, J. Gen. Virol. 73:1355-1363). The Paramyxoviridae family is divided into two sub-families: the Paramyxovirinae and Pneumovirinae. The subfamily Paramyxovirinae includes, but is not limited to, the genera: *Paramyxovirus*, *Rubulavirus*, and *Morbillivirus*. Recently, the sub-family Pneumovirinae was divided into two genera based on gene order, i.e., *pneumovirus* and *metapneumovirus* (Naylor et al., 1998, J. Gen. Virol., 79:1393-1398; Pringle, 1998, Arch. Virol. 143:1449-1159). The *pneumovirus* genus includes, but is not limited to, human respiratory syncytial virus (hRSV), bovine respiratory syncytial virus (bRSV), ovine respiratory syncytial virus, and mouse *pneumovirus*. The *metapneumovirus* genus includes, but is not limited to, European avian *pneumovirus* (subgroups A and B), which is distinguished from hRSV, the type species for the genus *pneumovirus* (Naylor et al., 1998, J. Gen. Virol., 79:1393-1398; Pringle, 1998, Arch. Virol. 143:1449-1159). The US isolate of APV represents a third subgroup (subgroup C) within *metapneumovirus* genus because it has been found to be antigenically and genetically different from European isolates (Seal, 1998, Virus Res. 58:45-52; Senne et al., 1998, In:Proc. 47th WPDC, California, pp. 67-68).

Electron microscopic examination of negatively stained APV reveals pleomorphic, sometimes spherical, virions ranging from 80 to 200 nm in diameter with long filaments ranging from 1000 to 2000 nm in length (Collins and Gough, 1988, J. Gen. Virol. 69:909-916). The envelope is made of a membrane studded with spikes 13 to 15 nm in length. The nucleocapsid is helical, 14 nm in diameter and has 7 nm pitch. The nucleocapsid diameter is smaller than that of the genera *Paramyxovirus* and *Morbillivirus*, which usually have diameters of about 18 nm.

Avian *pneumovirus* infection is an emerging disease in the USA despite its presence elsewhere in the world in poultry for many years. In May 1996, a highly contagious respiratory disease of turkeys appeared in Colorado, and an APV was subsequently isolated at the National Veterinary Services Laboratory (NVSL) in Ames, Iowa (Senne et al., 1997, Proc. 134th Ann. Mtg., AVMA, pp. 190). Prior to this time, the United States and Canada were considered free of avian *pneumovirus* (Pearson et al., 1993, In:Newly Emerging and Re-emerging Avian Diseases:Applied Research and Practical Applications for Diagnosis and Control, pp. 78-83; Hecker and Myers, 1993, Vet. Rec. 132:172). Early in 1997, the presence of APV was detected serologically in turkeys in Minnesota. By the time the first confirmed diagnosis was made, APV infections had already spread to many farms. The disease is associated with clinical signs in the upper respiratory tract: foamy eyes, nasal discharge and swelling of the sinuses. It is exacerbated by secondary infections. Morbidity in infected birds can be as high as 100%. The mortality can range from 1 to 90% and is highest in six to twelve week old poults.

Avian *pneumovirus* is transmitted by contact. Nasal discharge, movement of affected birds, contaminated water, contaminated equipment; contaminated feed trucks and load-out activities can contribute to the transmission of the virus. Recovered turkeys are thought to be carriers. Because the virus is shown to infect the epithelium of the oviduct of laying turkeys and because APV has been detected in young poults, egg transmission is considered a possibility.

Based upon the recent work with hMPV, hMPV likewise appears to be a significant factor in human, particularly, juvenile respiratory disease.

Thus, theses three viruses, RSV, hMPV, and PIV, cause a significant portion of human respiratory disease. Accordingly, a broad spectrum therapy is needed to reduce the incidence of viral respiratory disease caused by these viruses.

2.1.2.2 Bacterial Respiratory Infections 2.1.2.2.1 Bacterial Pneumonia

There are about 2 million cases of pneumonia each year of which 40,000 to 70,000 result in death. *The Merck Manual of Diagnosis and Therapy* (17th ed. 1999). Although certain viruses and fungi cause pneumonia, most cases of pneumonia in adults are caused by bacteria such as *Streptococcus pneumonia, Staphylococcus aureus, Haemophilus influenzae, Chlmayda pneumoniae, C. psittaci, C. trachomatis, Moraxella (Branhamella) catarrhalis, Legionella pneumophila, Klebsiella penumoniae*, and other gram-negative bacilli. Id.

Pneumonia is usually spread by inhaling droplets small enough to reach the alveoli and aspirating secretions from the upper airways. Id. Alcoholics, institutionalized persons, cigarette smokers, patients with heart failure, patients with chronic obstructive airway disease, the elderly, children, infants, infants born prematurely, patients with compromised immune systems, and patients with dysphagia are at greater risk of developing pneumonia. Id.

Pneumonia is diagnosed based on characteristic symptoms and an infiltrate on chest x-ray. Id. Common symptoms of pneumonia include cough, fever, sputum production, tachypnea, and crackles with bronchial breath sounds. Id. Determination of the specific pathogen causing the pneumonia cannot be made in about 30-50% of patients and specimens may be misleading because of normal flora may contaminate samples through the upper airways. Id. Special culture techniques, special stains, serologic assays, or lung biopsies may be used for diagnosis. Id.

Therapies for the treatment of pneumonia consist of respiratory support, such as oxygen, and antibiotics based on determination of the specific bacteria and/or according to the patient's age, epidemiology, host risk factors, and severity of illness. Id. For example, in cases of Staphylococcal pneumonia, anti-bacterial therapy comprises administration of penicillin (e.g., oxacillin and nafcillin), or cephalosporin (e.g. cephalothin or cefamandol, cefazolin, and cefuroxime). Id. In cases of streptococcal pneumonia, anti-bacterial therapy comprises administration of penicillin, cephalosporins, erythromycin, or clindamycin. Id.

The administration of antibiotics may result in side effects, toxicity, and the development of antibiotic resistant strains. In addition, because the pathogen causing pneumonia is difficult to diagnose, the use of antibiotics may be ineffective since both viruses and fungi also cause pneumonia. Thus, new therapies for the treatment of pneumonia are needed.

2.1.2.2.2 Tuberculosis

*Mycobacterium tuberculosis* infects 1.9 billion and the active disease, tuberculosis ("TB") results in 1.9 million deaths around the world each year. (Dye et al., 1999, JAMA 282:677-686). After a century of steadily declining rates of TB cases in the United States, the downward trend was reversed in the late 1980s as a result of the emergence of a multidrug-resistant strain of *M. tuberculosis*, the HIV epidemic, and influx of immigrants. (Navin et al., 2002, Emerg. Infect. Dis. 8:11).

*M. tuberculosis* is an obligate aerobe, nonmotile rod-shaped bacterium. In classic cases of tuberculosis, *M. tuberculosis* complexes are in the well-aerated upper lobes of the lungs. *M. tuberculosis* are classified as acid-fast bacteria due to the impermeability of the cell wall by certain dyes and stains. The cell wall of *M. tuberculosis*, composed of peptidoglycan and complex lipids, is responsible for the bacterium's resistance to many antibiotics, acidic and alkaline compounds, osmotic lysis, and lethal oxidations, and survival inside macrophages.

TB progresses in five stages. In the first stage, the subject inhales the droplet nuclei containing less than three bacilli. Although alveolar macrophages take up the *M. tuberculosis*, the macrophages are not activated and do not destroy the bacterium. Seven to 21 days after the initial infection, the *M. tuberculosis* multiples within the macrophages until the macrophages burst, which attracts additional macrophages to the site of infection that phagocytose the *M. tuberculosis*, but are not activated and thus do not destroy the *M tuberculosis*. In stage 3, lymphocytes, particularly T-cells, are activated and cytokines, including IFN activate macrophages capable of destroying *M. tuberculosis* are produced. At this stage, the patient is tuberculin-positive and a cell mediated immune response, including activated macrophages releasing lytic enzymes and T cell secreting cytokines, is initiated. Although, some macrophages are activated against the *M. tuberculosis*, the bacteria continue to multiply within inactivated macrophages and begin to grow tubercles which are characterized by semi-solid centers. In stage 4, tubercles may invade the bronchus, other parts of the lung, and the blood supply line and the patient may exhibit secondary lesions in other parts of the body, including the genitourinary system, bones, joints, lymph nodes, and peritoneum. In the final stage, the tubercles liquify inducing increased growth of *M. tuberculosis*. The large bacterium load causes the walls of nearby bronchi to rupture and form cavities that enables the infection to spread quickly to other parts of the lung.

Current therapies available for the treatment of TB comprise an initial two month regime of multiple antibiotics, such as rifampcin, isoniazid, pyranzinamide, ethambutol, or streptomycin. In the next four months, only rifampicin and isoniazid are administered to destroy persisting *M. tuberculosis*. Although proper prescription and patient compliance results in a cure in most cases, the number of deaths from TB has been on the rise as a result from the emergence of new *M. tuberculosis* strains resistant to current antibiotic therapies. (Rattan et al., 1998, Emerging Infectious Diseases, 4(2):195-206). In addition, fatal and severe liver injury has been associated with treatment of latent TB with rifampcin and pyranzinamide. (CDC Morbidity and Mortality Weekly Report, 51(44):998-999).

2.1.2.3 Fungal Respiratory Infections

The number of systemic invasive fungal infections rose sharply in the past decade due to the increase in the at-risk patient population as a result of organ transplants, oncology, human immunodeficiency virus, use of vascular catheters, and misuse of broad spectrum antibiotics. Dodds et al., 2000 Pharmacotherapy 20(11):1335-1355. Seventy percent of fungal-related deaths are caused by *Candida* species, *Aspergillus* species, and *Cryptococcus neoformans*. Yasuda, Calif. Journal of Health-System Pharmacy, May/June 2001, pp. 4-11.

2.1.2.3.1 Systemic Candidiasis

80% of all major systemic fungal infections are due to *Candida* species. *The Merk Manual of Diagnosis and Therapy*, 17th ed., 1999. Invasive candidiasis is most often caused by *Candida albicans, Candida troicalis*, and *Candida glabrata* in immunosuppressd patients. Id. Candidiasis is a defining opportunistic infection of AIDS, infecting the esophagus, trachea, bronchi, and lungs. Id. In HIV-infected patients, candidiasis is usually mucocutaneous and infects the oropharynx, the esophagus, and the vagina. Ampel, April-June 1996, Emerg. Infect. Dis. 2(2):109-116.

*Candida* species are commensals that colonize the normal GI tract and skin. The Merk Manual of Diagnosis and Therapy, Berkow et al. (eds.), 17th ed., 1999. Thus, cultures of *Candidia* from sputum, the mouth, urine, stool, vagina, or skin does not necessarily indicate an invasive, progressive infection. Id. In most cases, diagnosis of candidiasis requires presentation of a characteristic clinical lesion, documentation of histopathologic evidence of tissue invasion, or the exclusion of other causes. Id. Symptoms of systemic candidiasis infection of the respiratory tract are typically nonspecific, including dysphagia, coughing, and fever. Id.

All forms of candidiasis are considered serious, progressive, and potentially fatal. Id. Therapies for the treatment of candidiasis typically include the administration of the combination of the anti-fungal agents amphotericin B and flucytosine. Id. Unfortunately, acute renal failure has been associated with amphotericin B therapy. Dodds, supra. Fluconazole is not as effective as amphotericin B in treating certain species of *Candida*, but is useful as initial therapy in high oral or intravenous doses while species identification is pending. *The Merk Manual of Diagnosis and Therapy*, 17th ed., 1999. Fluconazole, however, has led to increasing treatment failures and anti-fungal resistance. Ampel, supra. Thus, there is a need for novel therapies of systemic candidiasis.

2.1.2.3.2 Aspergillosis

*Aspergillus* includes 132 species and 18 variants among which *Aspergillus fumigatus* is involved in 80% of *Aspergillus*-related diseases. Kurp et al., 1999, Medscape General Medicine 1(3). *Aspergillus fumigatus* is the most common cause of invasive pulmonary aspergillosis that extends rapidly, causing progressive, and ultimately fatal respiratory failure. The *Merk Manual of Diagnosis and Therapy*, 17th ed., 1999. Patients undergoing long-term high-dose corticosteroid therapy, organ transplant patients, patients with hereditary disorders of neutrophil function, and patients infected with AIDS are at risk for aspergillosis.

Clinical manifestations of invasive pulmonary infection by *Aspergillus* include fever, cough, and chest pain. *Aspergillus* colonize preexisting cavity pulmonary lesions in the form of aspergilloma (fungus ball) which is composed of tangled masses hyphae, fibrin exudate, and inflammatory cells encapsulated by fibrous tissue. Id. Aspergillomas usually form and enlarge in pulmonary cavities originally caused by bronchiectasis, neoplasm, TB, and other chronic pulmonary infections. Id. Most aspergillomas do not respond to or require systemic anti-fungal therapy. Id. However, invasive infections often progress rapidly and are fatal, thus aggressive therapy comprising IV amphotericin B or oral itraconazole is required. Id. Unfortunately, high-dose amphotericin B may cause renal failure and itraconazole is effective only in moderately severe cases. Id. Therefore, there is a need for new therapies for the treatment of aspergillosis.

2.1.2.3.3 Cryptococcosis

Cases of cryptococcosis were rare before the HIV epidemic. Ampel, supra. AIDS patients, patients with Hodgkin's or other lymphomas or sarcoidosis, and patients undergoing long-term corticosteroid therapy are at increased risk for cryptococcosis. *The Merk Manual of Diagnosis and Therapy*, 17th ed., 1999. In most cases, cryptococcal infections are self-limited, but AIDS-associated cryptococcal infection may be in the form of a severe, progressive pneumonia with acute dyspnea and primary lesions in the lungs. Id. In cases of progressive disseminated cryptococcosis affecting non-immunocompromised patients, chronic meningitis is most common without clinically evident pulmonary lesions. Id.

Immunocompetent patients do not always require the administration of a therapy to treat localized pulmonary cryptococcosis. However, when such patients are administered a therapy for the treatment of localized pulmonary cryptococcosis, it typically consists of administration of amphotericin B with or without flucytosine. Id. AIDS patients are generally administered an initial therapy consisting of amphotericin B and flucytosine and then oral fluconazole thereafter to treat cryptococcosis. Id. Renal and hematologic function of all patients receiving amphotericin B with or without flucytosine must be evaluated before and during therapy since flucytosine blood levels must be monitored to limit toxicity and administration of flucytosine may not be safe for patients with preexisting renal failure or bone marrow dysfunction. Id. Thus, new therapies for the treatment of cryptococcosis are needed.

2.2 Interleukin-9

Interleukin-9 ("IL-9") is member of the 4-helix bundle cytokine family, which includes IL-2, IL-3, IL-4, IL-5, IL-6, IL-7, IL-15, and IL-23. IL-9 plays a critical role in a number of antigen-induced responses in mice, such as bronchial hyperresponsiveness, epithelial mucin production, eosinophilia, elevated T cells, B cells, mast cells, neutrophils, and other inflammatory cell counts in the bronchial lavage, histologic changes in the lung associated with inflammation, and elevated serum total IgE. See Levitt et al., U.S. Pat. No. 6,261,559, herein incorporated by reference. IL-9 is expressed by activated T cells and mast cells and functions as a T cell growth factor. Further, IL-9 mediates the growth of erythroid progenitors, B cells, mast cells, eosinophils, and fetal thymocytes, acts synergistically with interleukin-3 ("IL-3") to induce mast cell activation and proliferation, and promotes the production of mucin by lung epithelium.

Citation or discussion of a reference herein shall not be construed as an admission that such is prior art to the present invention.

3. SUMMARY OF THE INVENTION

The present invention encompasses treatment protocols that provide better prophylactic or therapeutic profiles than current single agent therapies or combination therapies for respiratory conditions or one or more symptoms thereof. In particular, the invention provides prophylactic and therapeutic protocols for the prevention, treatment, management, or amelioration of a respiratory condition or one or more symptoms thereof comprising the administration of an effective amount of one or more IL-9 antagonists. The invention also encompasses prophylactic and therapeutic protocols for the prevention, treatment, management, or amelioration of a respiratory condition or one or more symptoms thereof comprising the administration of an effective amount of one or more IL-9 antagonists and an amount of at least one other therapy (e.g., prophylactic or therapeutic agent) other than an IL-9 antagonist.

IL-9 antagonists that can be utilized in accordance with the invention include, but are not limited to, proteinaceous agents (e.g., proteins, polypeptides, peptides, fusion proteins, antibodies, and antibody fragments), nucleic acid molecules (e.g., IL-9 antisense nucleic acid molecules, triple helices, double-stranded RNA, or DNA encoding double-stranded RNA that mediates RNAi, or nucleic acid molecules encoding proteinaceous agents), organic molecules, inorganic molecules, small organic molecules, drugs, and small inorganic molecules that block, inhibit, reduce or neutralize a pathologic cellular or humoral phenotype associated with or resulting from IL-9 expression and/or activity (e.g., decreases the secretion of mucin, the differentiation of IL-9 expressing cells into mucin-secreting cells, the secretion of inflammatory agents, the proliferation, migration, and increase in volume of cells (e.g., immune and smooth muscle cells), the secretion of extracellular matrix molecules or matrix metalloproteinases and/or the binding of IL-9 to the IL-9 receptor ("IL-9R")). In a specific embodiment, an IL-9 antagonist is an antibody or fragment thereof that immunospecifically binds to an IL-9 polypeptide. In another embodiment, an IL-9 antagonist is an antibody or fragment thereof that immunospecifically binds to an IL-9R or a subunit thereof. In another embodiment, proteins, polypeptides or peptides (including antibodies and fusion proteins) that are utilized as IL-9 antagonists are derived from the same species as the recipient of the proteins, polypeptides or peptides so as to reduce the likelihood of an immune response to those proteins, polypeptides or peptides. In another embodiment, when the subject is a human, the proteins, polypeptides, or peptides that are utilized as IL-9 antagonists are human or humanized. In yet another embodiment, nucleic acid molecules encoding proteins, polypeptides, or peptides or derivatives, analogs, fragments or variants thereof that function as IL-9 antagonists are utilized in the methods of the invention.

In one embodiment, an IL-9 antagonist reduces the function, activity, and/or expression of a molecule other than an IL-9 polypeptide or IL-9R or a subunit thereof (e.g., a protein involved in IL-9 or IL-9R expression or IL-9R signaling elicited by IL-9). In certain embodiments, an IL-9 antagonist reduces the function, activity, and/or expression of a molecule other than an IL-9 polypeptide or the IL-9R or a subunit thereof by at least 10%, preferably at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline ("PBS") in an in vivo and/or in vitro assay known in the art. In another embodiment, an IL-9 antagonist reduces the function, activity and/or expression of an IL-9 polypeptide, the function, activity and/or expression of the IL-9R or a subunit thereof, and/or the binding of an IL-9 polypeptide to the IL-9R or a subunit thereof. In certain embodiments, an IL-9 antagonist reduces the function, activity and/or expression of an IL-9 polypeptide, the function, activity and/or expression of the IL-9R or a subunit thereof, and/or the binding of an IL-9 polypeptide to the IL-9R or a subunit thereof by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as PBS in an in vivo and/or in vitro assay known in the art.

In certain embodiments, an IL-9 antagonist inhibits or reduces mast cell activation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, an IL-9 antagonist reduces mast cell degranulation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

The IL-9 antagonist utilized in accordance with the invention may inhibit and/or reduce the infiltration of inflammatory cells such as mast cells, T cells, macrophages, B cells, eosinophils, neutrophils, basophils, monocytes, and lymphocytes. In certain embodiments, an IL-9 antagonist inhibits or reduces mast cell infiltration in the upper and/or lower respiratory system by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art. In other embodiments, a IL-9 antagonist inhibits or reduces T cell infiltration, particularly Th2 cell infiltration, in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art.

In other embodiments, an IL-9 antagonist inhibits or reduces macrophage infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art. In other embodiments, an IL-9 antagonist inhibits or reduces B cell infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art.

In other embodiments, an IL-9 antagonist inhibits or reduces eosinophil infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art. In yet other embodiments, an IL-9 antagonist inhibits or reduces neutrophil infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art.

The IL-9 antagonist utilized in accordance with the methods of the invention may inhibit and/or reduce the proliferation of inflammatory cells such as mast cells, T cells, macrophages, B cells, eosinophils, neutrophils, basophils, monocytes, and lymphocytes. In certain embodiments, an IL-9 antagonist inhibits or reduces mast cell proliferation in the upper and/or lower respiratory system by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art. In other embodiments, a IL-9 antagonist inhibits or reduces T cell proliferation, particularly Th2 cell proliferation in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art. In other embodiments, an IL-9 antagonist inhibits or reduces macrophage proliferation in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art.

In other embodiments, an IL-9 antagonist inhibits or reduces B cell proliferation in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art. In other embodiments, an IL-9 antagonist inhibits or reduces eosinophil proliferation in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art. In yet other embodiments, an IL-9 antagonist inhibits or reduces neutrophil proliferation in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vitro and/or an in vivo assay described herein or well-known to one of skill in the art.

The present invention provides methods of preventing, treating, managing, or ameliorating a respiratory condition caused by and/or associated with environmental factors or one or more symptoms thereof, said methods comprising administering to a subject in need thereof an effective amount of one or more IL-9 antagonists alone or in combination with an effective amount of one or more therapies (e.g., one or more prophylactic or therapeutic agents), other than IL-9 antagonists, used or known to be effective in preventing, treating, managing, or ameliorating respiratory conditions or one or more symptoms thereof. Examples of respiratory conditions caused by and/or associated with environmental factors that can be prevented, treated, managed, or ameliorated in accordance with the methods of the invention include, but are not limited to, asthma and allergies. Non-limiting examples of therapies for the prevention, treatment, management, or amelioration of respiratory conditions caused by and/or associated with environmental factors are antihistamines, symphomimetics, glucocorticoids, corticosteroids, β-adrenergic drugs (epinephrine and isoproterenol), theophylline, anticholinergic drugs (e.g., atropine and ipratropium bromide), and leukotriene inhibitors.

The invention also provides methods for preventing, treating, managing, or ameliorating an allergy or one or more symptoms thereof, said methods comprising administering an effective amount of one or more IL-9 antagonists alone or in combination with an effective amount of one or more other therapies for respiratory conditions, in particular allergies. Examples of therapies for allergies include, but are not limited to, the administration of antimediator drugs (e.g., antihistamine), corticosteroids, decongestants, sympathomimetic drugs (e.g., α-adrenergic and β-adrenergic drugs), theophylline and its derivatives, glucocorticoids, adn immunotherapies (e.g., repeated long-term injection of allergen, short course desensitization, and venom immunotherapy. In a specific embodiment, an effective amount of one or more IL-9 antagonists is administered to a subject in combination with an effective amount of one or more anti-IgE antibodies and/or one or more mast cell modulators (e.g., a mast cell protease inhibitor, stem cell factor (c-kit ligand) inhibitor, and c-kit receptor inhibitor) to prevent, treat, manage, or ameliorate an allergy or one or more symptoms thereof. In another specific embodiment, an effective amount of one or more IL-9 antagonists is administered to a subject in combination with an effective amount of VITAXIN™ (MedImmune, Inc.), NUMAX™ (MedImmune, Inc.), palivizumab (MedImmune, Inc.), siplizumab (MedImmune, Inc.), an anti-EphA2 antibody (preferably that elicits EphA2 signaling) (see U.S. Patent Publication No. U.S. 2004/0028685A1, dated Feb. 12, 2004 and U.S. patent application Ser. No. 10/436/783, filed May 12, 2003, which are both incorporated by reference herein in their entireties), an anti-PIV/HMPV antibody, or any combination thereof to prevent, manage, treat, or ameliorate an allergy or one or more symptoms thereof. In a specific embodiment, the invention provides methods of preventing the development of asthma in subjects with allergies, said method comprising administering of an effective amount of one or more IL-9 antagonists with or without an effective amount of one or more therapies, other than IL-9 antagonists.

The invention provides methods for preventing, treating, managing, or ameliorating wheezing, said methods comprising administering an effective amount of one or more IL-9 antagonists alone or in combination with an effective amount of one or more therapies for respiratory conditions, in particular wheezing. Non-limiting examples of therapies for respiratory conditions include immunomodulatory agents, mast cell modulatory agents, anti-inflammatory agents, anti-viral agents, anti-bacterial agents, and anti-fungal agents. In a specific embodiment, an effective amount of one or more IL-9 antagonists is administered to a subject in combination with an effective amount of one or more anti-IgE antibodies and/or one or more mast cell modulators (e.g., a mast cell protease inhibitor, stem cell factor (c-kit ligand) inhibitor, and c-kit receptor inhibitor) to prevent, treat, manage, or ameliorate wheezing. In another embodiment, an effective amount of one or more IL-9 antagonists is administered to a subject in combination with an effective amount VITAXIN™, siplizumab, an anti-EphA2 antibody (preferably that elicits EphA2 signaling) (see U.S. Patent Publication No. U.S. 2004/0028685 A1, dated Feb. 12, 2004 and U.S. patent application Ser. No. 10/436/783, filed May 12, 2003), or any combination thereof to prevent, manage, treat, or ameliorate wheezing or one or more symptoms thereof.

Wheezing may or may not be associated with another respiratory condition. In certain cases, wheezing precedes the onset or development of another respiratory condition. In a specific embodiment, the invention provides methods of preventing, treating, ameliorating, or managing wheezing associated with other respiratory conditions, such as, but not limited to allergies, asthma, viral respiratory infection, fungal respiratory infection, and bacterial respiratory infection, said methods comprising administering to a subject in need thereof an effective amount of one or more IL-9 antagonists alone or in combination with one or more other therapies for such respiratory conditions. In other embodiments, the invention provides methods of preventing the onset, recurrence and/or development of asthma in subjects with wheezing, said method comprising administering to said subject an effective amount of one or more IL-9 antagonists alone or in combination with an effective amount of one or more therapies, other than IL-9 antagonists.

The invention provides methods for preventing, treating, managing, or ameliorating asthma or one or more symptoms thereof, said method comprising administering to a subject in need thereof an effective amount of one or more IL-9 antagonists alone or in combination with an effective amount of one or more therapies for respiratory conditions, in particular asthma. Non-limiting examples of therapies for asthma include adrenergic stimulants (e.g., catecholamines (e.g., epinephrine, isoproterenol, and isoetharine), resorcinols (e.g., metaproterenol, terbutaline, and fenoterol), and saligenins (e.g., salbutamol)), other steroids, immunosuppressant agents (e.g., methotrexate and gold salts), mast cell modulators (e.g., cromolyn sodium (INTAL™) and nedocromil sodium (TILADE™)), and mucolytic agents (e.g., acetylcysteine)). In a specific embodiment, an effective amount of one or more IL-9 antagonists is administered to a subject in combination with an effective amount of VITAXIN™, siplizumab, an anti-EphA2 antibody that elicits EphA2 signaling (see U.S. Patent Publication No. U.S. 2004/0028685A1, dated Feb. 12, 2004 and U.S. patent application Ser. No. 10/436/783, filed May 12, 2003), or any combination thereof to prevent, manage, treat, or ameliorate asthma or one or more symptoms thereof. In another embodiment, the invention provides methods for preventing, treating, managing, or ameliorating asthma or one or more symptoms thereof, said methods comprising administering to a subject in need thereof an effective amount of one or more IL-9 antagonists in combination with one or more leukotriene inhibitors. In accordance with this embodiment, the leukotriene inhibitors is preferably montelukast (SINGULAIR™), zafirlukast (ACCOLATE™), pranlukast (ONON™), or zileuton (ZYFLO™).

In a specific embodiment, the invention provides methods for preventing, treating, managing, or ameliorating one or more symptoms of asthma including, but not limited to elevated IgE levels, mucus hypersecretion, increased mast cell degranulation and infiltration, and increased bronchial hyperresponsiveness, and bronchoconstriction (e.g., wheezing), said methods comprising administering to a subject in need thereof an effective amount of one or more IL-9 antagonists alone or in combination with and effective amount of one or more other therapies (e.g., prophylactic or therapeutic agents) other than IL-9 antagonists for asthma. In another embodiment, the invention provides methods for preventing, treating, managing, or ameliorating asthma-like symptoms in subject with respiratory infections (e.g., RSV, PIV, and hMPV infections), said methods comprising administering to a subject in need thereof an effective amount of one or more IL-9 antagonists alone or in combination with an effective amount of one or more other therapies.

The invention provides methods for preventing, treating, managing, or ameliorating a viral respiratory infection or one or more symptoms thereof, said methods comprising administering to a subject in need thereof an effective amount of one or more IL-9 antagonists alone or in combination with an effective amount of one or more therapies for respiratory conditions, in particular viral respiratory infections. In a specific embodiment, an effective amount of one or more IL-9 antagonists is administered to a subject in combination with an effective amount of one or more anti-viral agents to prevent, treat, manage, and/or ameliorate a viral respiratory infection or one or more symptoms thereof. In another embodiment, an effective amount of one or more IL-9 antagonists is administered in combination with an effective amount of VITAXIN™ (MedImmune, Inc.), NUMAX™ (MedImmune, Inc.), palivizumab (MedImmune, Inc.), siplizumab (MedImmune, Inc.), an anti-EphA2 antibody (preferably that elicits EphA2 signaling) (see U.S. Patent Publication No. U.S. 2004/0028685A1, dated Feb. 12, 2004 and U.S. patent application Ser. No. 10/436/783, filed May 12, 2003), or any combination thereof to prevent, manage, treat, or ameliorate a viral respiratory infection or one or more symptoms thereof. In a specific embodiment, the viral respiratory infection is caused by respiratory syncytial virus ("RSV"), parainfluenza virus ("PIV"), or human *metapneumovirus* ("hMPV").

The invention provides methods for preventing, treating, managing, or ameliorating a bacterial respiratory infection or one or more symptoms thereof, said methods comprising administering to a subject in need thereof an effective amount of one or more IL-9 antagonists alone or in combination with an effective amount of one or more therapies for respiratory conditions, in particular bacterial respiratory infections. In a specific embodiment, an effective amount of one or more IL-9 antagonists is administered to a subject in combination with an effective amount of an anti-bacterial agent (e.g., an antibiotic) to prevent, treat, manage, or ameliorate a bacterial respiratory infection or one or more symptoms thereof. In another embodiment, an effective amount of one or more IL-9 antagonists are administered in combination with an effective amount of VITAXIN™, siplizumab, an anti-EphA2 antibody (preferably that elicits EphA2 signaling) (see U.S. Patent Publication No. U.S. 2004/0028685A1, dated Feb. 12, 2004 and U.S. patent application Ser. No. 10/436/783, filed May 12, 2003), or any combination thereof to prevent, manage, treat, or ameliorate a bacterial respiratory infection or one or more symptoms thereof.

The invention provides methods for preventing, treating, managing, or ameliorating a fungal respiratory infection or one or more symptoms thereof, said methods comprising administering to a subject in need thereof an effective amount of one or more IL-9 antagonists alone or in combination with an effective amount of one or more therapies for respiratory conditions, in particular fungal respiratory infections. In a specific embodiment, an effective amount of one or more IL-9 antagonists is administered to a subject in combination with an effective amount of an anti-fungal agent to prevent, treat, manage, or ameliorate a fungal respiratory infection or one or more symptoms thereof. In another embodiment, an effective amount of one or more IL-9 antagonists is administered to a subject in combination with an effective amount of VITAXIN™, siplizumab, an anti-EphA2 antibody (preferably that elicits EphA2 signaling) (see U.S. Patent Publication No. U.S. 2004/0028685A1, dated Feb. 12, 2004 and U.S. patent application Ser. No. 10/436/783, filed May 12, 2003), or any combination thereof to prevent, manage, treat, or ameliorate a fungal respiratory infection or one or more symptoms thereof.

The invention encompasses methods of preventing, treating, managing, or ameliorating a respiratory condition or one or more symptoms thereof in a patient undergoing therapies for other respiratory conditions. The invention also encompasses methods of preventing, managing, treating, or ameliorating a respiratory condition or one or more symptoms thereof in a patient before any adverse effects or intolerance to therapies other than IL-9 antagonists develop. The invention further encompasses methods of preventing, treating, managing, or ameliorating a respiratory condition or a symptom thereof in refractory patients.

The invention encompasses methods for preventing the development of a respiratory condition in a patient expected to suffer from said respiratory condition or at increased risk of developing said respiratory condition. Such subjects include, but are not limited to, patients with suppressed immune systems (e.g., patients organ-transplant recipients, AIDS patients, patients undergoing chemotherapy, patients with carcinoma of the esophagus with obstruction, patients with tracheobronchial fistula, patients with neurological diseases (e.g., caused by stroke, amyotorphic lateral sclerosis, multiple sclerosis, and myopathies), and patients already suffering from a respiratory condition, particularly a respiratory infection). In a specific embodiment, the patient suffers from bronchopulmonary dysplasia, congenital heart disease, cystic fibrosis, and/or acquired or congenital immunodeficiency. In another specific embodiment, the patient is an infant born prematurely, an infant, a child, an elderly human, or a human in a group home, nursing home, or some other type of institution. The invention also encompasses methods of preventing, managing, treating, or ameliorating a respiratory condition or one or more symptoms thereof in patients who are susceptible to adverse reactions to conventional therapies for respiratory conditions for which no therapies are available.

The invention encompasses compositions for use in the prevention, management, treatment, and/or amelioration of a respiratory condition or one or more symptoms thereof. In a specific embodiment, a composition comprises one or more IL-9 antagonists. In another embodiment, a composition comprises one or more IL-9 antagonists and one or more prophylactic or therapeutic agents other than IL-9 antagonists, said prophylactic or therapeutic agents known to be useful for, or having been or currently being used in the prevention, treatment, management, or amelioration of a respiratory condition or one or more symptoms thereof. In a preferred embodiment, a composition comprises one or more antibodies that immunospecifically binds to an IL-9 polypeptide. In another preferred embodiment, a composition comprises one or more antibodies that immunospecifically bind to an IL-9 polypeptide and one or more prophylactic or therapeutic agents other than IL-9 antagonists, said prophylactic or therapeutic agents known to be useful for, or having been or currently being used in the prevention, treatment, management, or amelioration of a respiratory condition or one or more symptoms thereof. In accordance with these embodiments, the compositions may further comprise a carrier. Non-limiting examples of prophylactic or therapeutic agents include immunomodulatory agents, mast cell modulators, anti-inflammatory agents, anti-viral agents, anti-bacterial agents, and anti-fungal agents.

In a specific embodiment, a pharmaceutical composition comprises a pharmaceutically acceptable carrier, an effective amount of one or more IL-9 antagonists, and optionally, an effective amount of one or more prophylactic or therapeutic agents other than an IL-9 antagonist. In a preferred embodiment, a pharmaceutical composition comprises a pharmaceutically acceptable carrier, an effective amount of one or more antibodies that immunospecifically bind to an IL-9 polypeptide, and optionally, an effective amount of one or more prophylactic or therapeutic agent other than an IL-9 antagonist. In accordance with these embodiments, the pharmaceutical compositions are preferably sterile and in suitable form for the intended method of administration.

The invention provides protocols for the administration of an effective amount of one or more IL-9 antagonists alone or in combination with an effective amount of one or more therapies, other than IL-9 antagonists, for the prevention, treatment, management, or amelioration of a respiratory condition or one or more symptoms thereof to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., prophylactic or therapeutic agents), to avoid or reduce the side effects of one of the therapies (e.g., prophylactic or therapeutic agents), and/or to improve the efficacy of the therapies.

The therapies (e.g., prophylactic or therapeutic agents) of the combination therapies of the invention can be administered to a subject concurrently. The term "concurrently" is not limited to the administration of therapies (e.g., prophylactic or therapeutic agents) at exactly the same time, but rather it is meant that an IL-9 antagonist and another therapy(ies) are administered to a subject in a sequence and within a time interval such that the IL-9 antagonist can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In preferred embodiments, two or more therapies (e.g., prophylactic or therapeutic agents) are administered to a patient within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

The IL-9 antagonists, compositions, or combination therapies of the invention may be administered by any method of administration well-known to one of skill in the art including, but not limited to, parenteral administration (e.g., intradermal, intramuscular, intraperitoneal, intravenous, and subcutaneous administration), epidural administration, topical administration, pulmonary administration, and mucosal administration (e.g., intranasal and oral routes). In a specific embodiment, a prophylactic or therapeutic agent, or a pharmaceutical composition is administered subcutaneously, intramuscularly, topically or intravenously to a subject. In a preferred embodiment, a prophylactic or therapeutic agent, or a pharmaceutical composition is administered orally, intranasally, or by pulmonary administration to a subject. The prophylactic or therapeutic agents or pharmaceutical compositions can be administered systematically or locally.

In one embodiment, an IL-9 antagonist, a composition, or combination therapy of the invention is administered locally to the area in need of treatment to a subject; this may be achieved by, for example, and not by way of limitation, local infusion, by injection, or by means of an implant, said implant being of a porous, non-porous, or gelatinous material, including membranes, such as sialastic membranes, or fibers. In another embodiment, an IL-9 antagonist, a composition, or a combination therapy of the invention is delivered to a subject in a vesicle. In another embodiment, an IL-9 antagonist, a composition, or a combination therapy of the invention is delivered to a subject in a controlled release or sustained release system. In another embodiment, the invention provides methods of preventing, treating, managing, or ameliorating a respiratory condition or one or more symptoms thereof by way of gene therapy, said gene therapy comprising administering to a subject in need thereof nucleic acids encoding an IL-9 antagonist.

The present invention also provides for kits and articles of manufacture comprising in a container an IL-9 antagonist, and optionally in the same container or a different container a therapy, other than an IL-9 antagonist, for the use in the prevention, treatment, management, or amelioration of a respiratory condition or a symptom thereof. The kits or articles of manufacture may further comprise instructions.

3.1 Terminology

As used herein, the term "aberrant" refers to a deviation from the norm, e.g., the average healthy subject and/or a population of average healthy subjects. The term "aberrant expression," as used herein, refers to abnormal expression of a gene product (e.g., RNA, protein, polypeptide, or peptide) by a cell or subject relative to a normal, healthy cell or subject and/or a population of normal, healthy cells or subjects. Such aberrant expression may be the result of the amplification of the gene. In a specific embodiment, the term "aberrant expression" refers to abnormal expression of an IL-9 and/or an IL-9R or subunit thereof gene product by a cell or subject relative to the expression of the gene product by a normal, healthy cell or subject and/or a population of normal, healthy cells or subjects and encompasses the expression of IL-9 and/or an IL-9R or subunit thereof gene product at an unusual location within the cell or subject, the expression of an IL-9 and/or an IL-9R or subunit thereof gene product at an altered level in the cell or subject, the expression of a mutated IL-9 and/or an IL-9R or subunit thereof gene product, or a combination thereof. The term "aberrant activity," as used herein, refers to an increase of activity by a gene product, or the loss of an activity of a gene product in a cell or subject relative to a normal, healthy cell or subject and/or a population of normal, healthy cells or subjects. In specific embodiments, the term "aberrant activity" refers to an IL-9 and/or an IL-9R or subunit thereof activity that deviates from that normally found in a healthy cell or subject and/or a population of normal, healthy cells or subjects (e.g., an increase in IL-9's ability to bind its receptor). Examples of IL-9 activities include, but are not limited to, the phosphorylation of the IL-9R, the activation of Jak3, the activation of MEK, the activation of STAT-1, and the activation of STAT-3.

As used herein, the term "analog" in the context of a proteinaceous agent (e.g., proteins, polypeptides, peptides, and antibodies) refers to a proteinaceous agent that possesses a similar or identical functions as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following:(a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous analog refers to a second organic or inorganic molecule which possess a similar or identical function as a first organic or inorganic molecule and is structurally similar to the first organic or inorganic molecule.

As used herein, the terms "antagonist" and "antagonists" refer to any protein, polypeptide, peptide, peptidomimetic, glycoprotein, antibody, antibody fragment, carbohydrate, nucleic acid, organic molecule, inorganic molecule, large molecule, or small molecule that blocks, inhibits, reduces or neutralizes the function, activity and/or expression of another molecule. In various embodiments, an antagonist reduces the function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

As used herein, the terms "antibody" and "antibodies" refer to monoclonal antibodies, multispecific antibodies, human antibodies, humanized antibodies, camelised antibodies, chimeric antibodies, single-chain Fvs (scFv), single chain antibodies, single domain antibodies, Fab fragments, F(ab) fragments, disulfide-linked Fvs (sdFv), and anti-idiotypic (anti-Id) antibodies, intrabodies, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the terms "anti-IL 9 antibodies," "IL-9 antibodies," "antibodies of the invention," "antibodies of the present invention" and analogous terms refer to the antibodies described in section 5.1.1, infra.

As used herein, the term "control IgG antibody" refers to an IgG antibody or other "control antibody" that does not immunospecifically bind to an IL-9 polypeptide and preferably does not cross-react with an IL-9 polypeptide.

As used herein, the term "cytokine receptor modulator" refers to an agent which modulates the phosphorylation of a cytokine receptor, the activation of a signal transduction pathway associated with a cytokine receptor, and/or the expression of a particular protein such as a cytokine or cytokine receptor. Such an agent may directly or indirectly modulate the phosphorylation of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins and antibodies that immunospecifically binds to a cytokine receptor or a fragment thereof. Further, examples of cytokine receptor modulators include, but are not limited to, peptides, polypeptides (e.g., soluble cytokine receptors), fusion proteins and antibodies that immunospecifically binds to a cytokine or a fragment thereof.

As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses a similar or identical function as the proteinaceous agent from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl, nitryl, or amine group. An organic molecule may also be esterified, alkylated and/or phosphorylated.

As used herein, the term "effective amount" refers to the amount of a therapy (e.g., a prophylactic or therapeutic agent) which is sufficient to reduce or ameliorate the severity and/or duration of a respiratory condition or one or more symptoms thereof, prevent the advancement of a respiratory condition, cause regression of a respiratory condition, prevent the recurrence, development, or onset of one or more symptoms associated with a respiratory condition, or enhance or improve the prophylactic or therapeutic effect(s) of another therapy (e.g., prophylactic or therapeutic agent).

As used herein, the term "elderly human" refers to a human 65 years old or older, preferably 70 years old or older.

As used herein, the term "epitopes" refers to fragments of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide or protein. In a specific embodiment, a fragment of a protein or polypeptide retains at least one function of the protein or polypeptide.

As used herein, the term "functional fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of second, different polypeptide or protein, wherein said polypeptide or protein retains at least one function of the second, different polypeptide or protein. In a specific embodiment, a fragment of a polypeptide or protein retains at least two, three, four, or five functions of the protein or polypeptide. Preferably, a fragment of an antibody that immunospecifically binds to an IL-9 polypeptide retains the ability to immunospecifically bind to an IL-9 polypeptide.

As used herein, the term "fusion protein" refers to a polypeptide or protein that comprises an amino acid sequence of a first protein or polypeptide or functional fragment, analog or derivative thereof, and an amino acid sequence of a heterologous protein, polypeptide, or peptide (i.e., a second protein or polypeptide or fragment, analog or derivative thereof different than the first protein or fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent. For example, two different proteins, polypeptides or peptides with immunomodulatory activity may be fused together to form a fusion protein. In a preferred embodiment, fusion proteins retain or have improved activity relative to the activity of the original protein, polypeptide or peptide prior to being fused to a heterologous protein, polypeptide, or peptide.

As used herein, the term "host cell" includes a particular subject cell transfected or transformed with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "human adult" refers to a human 18 years of age or older.

As used herein, the term "human child" refers to a human between 24 months of age and 18 years of age.

As used herein, the term "human infant" refers to a human less than 24 months, preferably less than 16 months, less than 6 months, less than 3 months, less than 2 months, or less than 1 month of age.

As used herein, the terms "human infant born prematurely," "preterm infant," or "premature infant," or variations thereof refer to a human born at less than 40 weeks of gestational age, preferably less than 35 weeks gestational age, who is less than 6 months old, preferably less than 3 months old, more preferably less than 2 months old, and most preferably less than 1 month old.

As used herein, the term "hybridizes under stringent conditions" describes conditions for hybridization and washing under which nucleotide sequences at least 30% (preferably, 35%, 40%, 45%, 50%, 55%, 60%, 65%, 70%, 75%, 80%, 85%, 90%, 95% or 98%) identical to each other typically remain hybridized to each other. Such stringent conditions are known to those skilled in the art and can be found in *Current Protocols in Molecular Biology*, John Wiley & Sons, N.Y. (1989), 6.3.1-6.3.6.

Generally, stringent conditions are selected to be about 5 to 10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0M sodium ion concentration (or other salts) at pH 7.0 to 8.3 and the temperature is at least about 30° C. for short probes (for example, 10 to 50 nucleotides) and at least 60° C. for long probes (for example, greater than 50 nucleotides). Stringent conditions may also be achieved with the addition of destabilizing agents, for example, formamide. For selective or specific hybridization, a positive signal is at least two times background, preferably 10 times background hybridization.

In one, non-limiting example stringent hybridization conditions are hybridization at 6× sodium chloride/sodium citrate (SSC) at about 45° C., followed by one or more washes in 0.1×SSC, 0.2% SDS at about 68 C. In a preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides.

As used herein, the term "IL-9 polypeptide" refers to IL-9, an analog, derivative or a fragment thereof, including mature and immature forms of IL-9 (see, Van Snick et al., 1989, J. Exp. Med. 169:363-68 and Yang et al., 1989, Blood 74:1880-84, which are both incorporated by reference herein in their entireties), or a fusion protein comprising IL-9, an analog, derivative or a fragment thereof. The IL-9 polypeptide may be from any species. The nucleotide and/or amino acid sequences of IL-9 polypeptides can be found in the literature or public databases, or the nucleotide and/or amino acid sequences can be determined using cloning and sequencing techniques known to one of skill in the art. For example, the nucleotide sequence of human IL-9 can be found in the GenBank database (see, e.g., Accession No. NM_000590; FIG. 12). The amino acid sequence of human IL-9 can be found in the GenBank database (see, e.g., Accession Nos. A60480 and AAC17735; FIG. 13) and in U.S. Provisional Application No. 60/371,683, entitled, "Recombinant Anti-Interleukin-9 antibodies," filed Apr. 12, 2002 (the amino acid sequence of human IL-9 on page 15 is specifically incorporated herein by reference). In a preferred embodiment, an IL-9 polypeptide is human IL-9, an analog, derivative or a fragment thereof.

As used herein, the terms "IL-9 receptor" and "IL-9R" refer to an IL-9 receptor or an analog, derivative, or fragment thereof, or a fusion protein comprising an IL-9 receptor, an analog, derivative, or a fragment thereof. As used herein, the terms "one or more subunits" and "a subunit" in the context of an IL-9R refer to the IL-9R ligand-specific alpha subunit ("IL-9Rα") and/or common $\gamma_c$ chain (also present in IL-2R, IL-4R, IL-7R, and IL-15R complexes) of the functional IL-9R or an analog, derivative, or fragment thereof. In a preferred embodiment, a functional IL-9R mediates a proliferative response in T cells treated with IL-9 as determined by any cell proliferation assay known to those skilled in the art (e.g., a [$^3$H]-thymidine incorporation assay or a hexosaminidase assay) (see, e.g., Renauld et al., 1992, Proc. Natl. Acad. Sci. USA, 89:5690-94 and Bauer et al., 1998, J. Biol. Chem. 273:9255-60, which are both incorporated by reference herein in their entireties). Preferebly, treating a T cell line expressing a functional IL-9R (e.g., TS 1 RA3 cells (R&D Systems) expressing both human and murine IL-9Rα) with IL-9, results in a dose-dependent increase in T cell proliferation, as measured by any cell proliferation assay known to those skilled in the art (see, Renauld et al., 1992, Proc. Natl. Acad. Sci. USA, 89:5690-94 and Bauer et al., 1998, J. Biol. Chem. 273:9255-60). In another preferred embodiment, a functional IL-9R, comprising the $\gamma_c$ and IL-9Rα chains, initiates a signaling cascade through the Janus kinases JAK1 and JAK3, thereby activating homo- and heterodimers of the signal transducer and activator transcription (STAT) factors STAT-1, STAT-3 and STAT-S (see, Bauer et al., 1998, J. Biol. Chem. 273:9255-60). In another preferred embodiment, a functional IL-9R may prevent apoptosis in a mechanism involving STAT-3 and STAT-5, as determined by apoptosis assays known to those skilled in the art (see, Bauer et al., 1998, J. Biol. Chem. 273:9255-60). The IL-9R or one or more subunits thereof may be from any species. The nucleotide and/or amino acid sequences of the IL-9R and the subunits thereof can be found in the literature or in public databases, or the nucleotide and/or amino acid sequences can be determined using cloning and sequencing techniques known to one of skill in the art. For example, the nucleotide sequence of human IL-9R can be found in the GenBank database (see, e.g., Accession Nos. NM_002186, NM_176786, and NM_000206; FIG. 14). The amino acid sequence of human IL-9R can be found in the GenBank database (see, e.g., Accession Nos. NP_002177; NP_789743, and NP_000197; FIG. 15) and in U.S. Provisional Application No. 60/371,683, entitled, "Recombinant Anti-Interleukin-9 Antibodies," filed Apr. 12, 2002 (the amino acid sequence of human IL-9R on page 16 is herein specifically incorporated by reference). In a preferred embodiment, an IL-9R or one or more subunits thereof is a human IL-9R or one or more subunits thereof, an analog, derivative, or a fragment thereof.

As used herein, the term "immunomodulatory agent" and variations thereof including, but not limited to, immunomodulatory agents, immunomodulants or immunomodulatory drugs, refer to an agent that modulates a host's immune system. In a specific embodiment, an immunomodulatory agent is an agent that shifts one aspect of a subject's immune response. In certain embodiments, an immunomodulatory agent is an agent that inhibits or reduces a subject's immune system (i.e., an immunosuppressant agent). In certain other embodiments, an immunomodulatory agent is an agent that activates or increases a subject's immune system (i.e., an immunostimulatory agent). In accordance with the invention, an immunomodulatory agent used in the combination therapies of the invention does not include an IL-9 antagonist. Immunomodulatory agents include, but are not limited to, small molecules, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules.

As used herein, the term "immunospecifically binds to an antigen" and analogous terms refer to peptides, polypeptides, proteins, fusion proteins and antibodies or fragments thereof that specifically bind to an antigen or a fragment and do not specifically bind to other antigens. A peptide, polypeptide, protein, or antibody that immunospecifically binds to an antigen may bind to other peptides, polypeptides, or proteins with lower affinity as determined by, e.g., immunoassays, BIAcore, or other assays known in the art. Antibodies or fragments that immunospecifically bind to an antigen may be cross-reactive with related antigens. Preferably, antibodies or fragments that immunospecifically bind to an antigen do not cross-react with other antigens. An antibody binds specifically to an antigen when it binds to the antigen with higher affinity than to any cross-reactive antigen as determined using experimental techniques, such as radioimmunoassays (RIAs) and enzyme-linked immunosorbent assays (ELISAs). See, e.g., Paul, ed., 1989, Fundamental Immunology, 2nd ed., Raven Press, New York at pages 332-336 for a discussion regarding antibody specificity.

As used herein, the term "immunospecifically binds to an IL-9 polypeptide" and analogous terms refer to peptides, polypeptides, proteins, fusion proteins, and antibodies or fragments thereof that specifically bind to an IL-9 polypeptide and do not specifically bind to other polypeptides. The term "immunospecifically binds to an IL-9R" and analogous terms refer to peptides, polypeptides, proteins, fusion proteins, and antibodies or fragments thereof that specifically bind to an IL-9 receptor or one or more of subunits thereof and do not specifically bind to other receptors. A peptide, polypeptide, protein, or antibody that immunospecifically binds to an IL-9 polypeptide or an IL-9R may bind to other peptides, polypeptides, or proteins with lower affinity as determined by, e.g., immunoassays, BIAcore, or other assays known in the art. Antibodies or fragments that immunospecifically bind to an IL-9 polypeptide or an IL-9R may be cross-reactive with related antigens. Preferably, antibodies or fragments that immunospecifically bind to an IL-9 polypeptide or an IL-9R thereof do not cross-react with other antigens. Antibodies or fragments that immunospecifically bind to an IL-9 polypeptide or an IL-9R can be identified, for example, by immunoassays, BIAcore, or other techniques known to those of skill in the art. An antibody or fragment thereof binds specifically to an IL-9 polypeptide or an IL-9R when it binds to an IL-9 polypeptide or IL-9R with higher affinity than to any cross-reactive antigen as determined using experimental techniques, such as radioimmunoassays (RIAs)

and enzyme-linked immunosorbent assays (ELISAs). See, e.g., Paul, ed., 1989, Fundamental Immunology, 2nd ed., Raven Press, New York at pages 332-336 for a discussion regarding antibody specificity. In a preferred embodiment, an antibody that immunospecifically binds to an IL-9 polypeptide does not bind or cross-react with other antigens. In another embodiment, an antibody that immunospecifically binds to an IL-9 polypeptide that is a fusion protein specifically binds to the portion of the fusion protein that is IL-9.

As used herein, the term "in combination" refers to the use of more than one therapy (e.g., more than one prophylactic agent and/or therapeutic agent). The use of the term "in combination" does not restrict the order in which therapies (e.g., prophylactic and/or therapeutic agents) are administered to a subject with a respiratory condition. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject with a respiratory condition.

As used herein, the term "isolated" in the context of an organic or inorganic molecule (whether it be a small or large molecule), other than a proteinaceous agent or nucleic acid molecule, refers to an organic or inorganic molecule substantially free of a different organic or inorganic molecule. Preferably, an organic or inorganic molecule is 60%, 65%, 70%, 75%, 80%, 85%, 90%, 95%, or 99% free of a second, different organic or inorganic molecule. In a preferred embodiment, an organic and/or inorganic molecule is isolated.

As used herein, the term "isolated" in the context of a proteinaceous agent (e.g., a peptide, polypeptide, fusion protein, or antibody) refers to a proteinaceous agent which is substantially free of cellular material or contaminating proteins from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous protein, polypeptide, peptide, or antibody (also referred to as a "contaminating protein"). When the proteinaceous agent is recombinantly produced, it is also preferably substantially free of culture medium, i.e., culture medium represents less than about 20%, 10%, or 5% of the volume of the proteinaceous agent preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. In a specific embodiment, proteinaceous agents disclosed herein are isolated. In a preferred embodiment, an antibody of the invention is isolated. In a specific embodiment, an "isolated" antibody is purified by a multi-step purification process that comprise three chromatography steps (cation exchange, protein A and anion exchange), a nanofiltration step, and a low pH treatment step (for a detailed description, see Section 6.2, infra).

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized; however, "isolated" excludes members of a library of clones such as a cDNA library. In a preferred embodiment, a nucleic acid molecule encoding an antibody of the invention is isolated. In a preferred embodiment, a nucleic acid molecule encoding an antibody of the invention is isolated.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, the term "mast cell modulator" refers to an agent which modulates the activation of a mast cell, mast cell degranulation, and/or expression of a particular protein such as a cytokine. Such an agent may directly or indirectly modulate the activation of a mast cell, degranulation of the mast cell, and/or the expression of a particular protein such as a cytokine. Non-limiting examples of mast cell modulators include, but are not limited to, small molecules, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides, or peptides), fusion proteins, antibodies, synthetic or natural inorganic molecules, synthetic or natural organic molecule, or mimetic agents which inhibit and/or reduce the expression, function, and/or activity of a stem cell factor, a mast cell protease, a cytokine (such as IL-3, IL-4, and IL-9), a cytokine receptor (such as IL-3R, IL-4R, and IL-9R), and a stem cell receptor. Other non-limiting examples of mast cell modulators include, but are not limited to small molecules, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides, or peptides), fusion proteins, antibodies, synthetic or natural inorganic molecules, synthetic or natural organic molecule, or mimetic agents which inhibit and/or reduce the expression, function and/or activity of IgE. In certain embodiments, a mast cell modulator is an agent that prevents or reduces the activation of additional mast cells following degranulation of mast cells. In other embodiments, a mast cell modulator is an agent that inhibits or reduces mast cell degranulation. In accordance with the invention, a mast cell modulator used in the combination therapies of the invention does not include an IL-9 antagonist.

As used herein, the terms "non-responsive" and refractory" describe patients treated with a currently available therapy (e.g., prophylactic or therapeutic agent) for a respiratory condition which is not clinically adequate to relieve one or more symptoms associated with the respiratory condition. Typically, such patients suffer from severe, persistently active respiratory condition and require additional therapy to ameliorate the symptoms associated with the condition.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing," and "prevention" refer to the inhibition of the recurrence, onset, development or progression of a respiratory condition or the prevention of the recurrence, onset, or development of one or more symptoms of a respiratory condition in a subject resulting from the administration of a therapy (e.g., a prophylactic or therapeutic agent), or the administration of a combination of therapies (e.g., a combination of prophylactic and/or therapeutic agents).

As used herein, the terms "prophylactic agent" and "prophylactic agents" refer to any agent(s) which can be used in the prevention of a respiratory condition or one or more of the symptoms thereof. In certain embodiments, the term "prophylactic agent" refers to an IL-9 antagonist, such as an anti-IL-9 antibody of the invention. In certain other embodiments, the term "prophylactic agent" refers to an agent other than an IL-9 antagonist. Preferably, a prophylactic agent is an agent which is known to be useful to or has been or is currently being used to the prevent or impede the onset, development, progression and/or severity of a respiratory condition or one or more symptoms thereof. Prophylactic agents may be characterized as different agents based upon one or more effects that the agents have in vitro and/or in vivo. For example, a mast cell modulator may also be characterized as an immunomodulatory agent.

As used herein, the term "prophylactically effective amount" refers to the amount of a therapy (e.g., prophylactic agent) which is sufficient to result in the prevention of the development, recurrence, onset or progression of a respiratory condition or one or more symptoms thereof, or to enhance or improve the prophylactic effect(s) of another therapy (e.g., a prophylactic agent).

As used herein, a "prophylactic protocol" refers to a regimen for dosing and timing the administration of one or more therapies (e.g., one or more prophylactic agents) that has a prophylactic effect.

A used herein, a "protocol" includes dosing schedules and dosing regimens. The protocols herein are methods of use and include prophylactic and therapeutic protocols.

As used herein, the phrase "side effects" encompasses unwanted and adverse effects of a prophylactic or therapeutic agent. Side effects are always unwanted, but unwanted effects are not necessarily adverse. An adverse effect from a therapy (e.g., a prophylactic or therapeutic agent) might be harmful, uncomfortable, or risky.

As used herein, the term "respiratory condition" refers to a disruption of normal respiratory function and/or activity of tissues, organs, and cells of the respiratory system (e.g., nose, ears, sinuses, throat, trachea, bronchial tubes, and lungs) caused by or associated with an environmental factor or irritant and/or an infectious agent. Respiratory conditions induced by environmental irritants include, but are not limited to, asthma and allergies. Symptoms of a respiratory condition include, but are not limited to, increased mucus production, coughing, bronchoconstriction (i.e., wheezing), fever, sinus pain, lesions in the lung, inflammation of bronchial tubes, sore throat, and/or elevated IgE levels.

As used herein, the term "small molecules" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such agents.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, such as a cynomolgous monkey, chimpanzee, and a human), and more preferably a human. In a certain embodiment, the subject is a mammal, preferably a human, with a respiratory condition. In another embodiment, the subject is a farm animal (e.g., a horse, pig, or cow) or a pet (e.g., a dog or cat) with a respiratory condition. In another embodiment, the subject is a mammal, preferably a human, at risk of developing a respiratory condition (e.g., an immunocompromised or immunosuppressed mammal). In another embodiment, the subject is not an immunocompromised or immunosuppressed mammal, preferably a human. In another embodiment, the subject is a mammal, preferably a human, with a lymphocyte count that is not under approximately 500 cells/mm$^3$. In another embodiment, the subject is a human infant or a human infant born prematurely. In another embodiment, the subject is a human child or a human adult. In another embodiment, the subject is a human child with bronchopulmonary dysplasia, congenital heart diseases, or cystic fibrosis. In another embodiment, the subject is an elderly human. In yet another embodiment, the subject is a human in an institution or group home, such as, but not limited to, a nursing home.

As used herein, the term "synergistic" refers to a combination of therapies (e.g., prophylactic or therapeutic agents) which is more effective than the additive effects of any two or more single therapies (e.g., one or more prophylactic or therapeutic agents). A synergistic effect of a combination of therapies (e.g., a combination of prophylactic or therapeutic agents) permits the use of lower dosages of one or more of therapies (e.g., one or more prophylactic or therapeutic agents) and/or less frequent administration of said therapies to a subject with a respiratory condition. The ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a respiratory condition. In addition, a synergistic effect can result in improved efficacy of therapies (e.g., prophylactic or therapeutic agents) in the prevention or treatment of a respiratory condition. Finally, the synergistic effect of a combination of therapies (e.g., prophylactic or therapeutic agents) may avoid or reduce adverse or unwanted side effects associated with the use of any single therapy.

As used herein, the term "T cell receptor modulator" refers to an agent which modulates the phosphorylation of a T cell receptor, the activation of a signal transduction pathway associated with a T cell receptor and/or the expression of a particular protein associated with T cell receptor activity such as a cytokine. Such an agent may directly or indirectly modulate the phosphorylation of a T cell receptor, the activation of a signal transduction pathway associated with a T cell receptor, and/or the expression of a particular protein associated with T cell receptor activity such as a cytokine. Examples of T cell receptor modulators include, but are not limited to, peptides, polypeptides, proteins, fusion proteins and antibodies which immunospecifically bind to a T cell receptor or a fragment thereof. Further, examples of T cell receptor modulators include, but are not limited to, proteins, peptides, polypeptides (e.g., soluble T cell receptors), fusion proteins and antibodies that immunospecifically bind to a ligand for a T cell receptor or fragments thereof.

As used herein, the terms "therapeutic agent" and "therapeutic agents" refer to any agent(s) which can be used in the prevention, treatment, management, or amelioration of a respiratory condition or one or more symptoms thereof. In certain embodiments, the term "therapeutic agent" refers to an IL-9 antagonist, preferably an antibody or fragment thereof that immunospecifically binds to an IL-9 polypeptide. In certain other embodiments, the term "therapeutic agent" refers an agent other than an IL-9 antagonist. Preferably, a therapeutic agent is an agent that is known to be useful for, or has been or is currently being used for the prevention, treatment, management, or amelioration of a respiratory condition or one or more symptoms thereof. Therapeutic agents may be characterized as different agents based upon one or more effects the agents have in vivo and/or in vitro, for example, an anti-inflammatory agent may also be characterized as an immunomodulatory agent.

As used herein, the term "therapeutically effective amount" refers to the amount of a therapy (e.g., an IL-9 antagonist, preferably, an antibody or a fragment thereof that immunospecifically binds to an IL-9 polypeptide), that is sufficient to reduce the severity of a respiratory condition, reduce the duration of a respiratory condition, ameliorate one or more symptoms of a respiratory condition, prevent the advancement of a respiratory condition, cause regression of a respiratory condition, or enhance or improve the therapeutic effect(s) of another therapy.

The terms "therapies" and "therapy" can refer to any protocol(s), method(s), and/or agent(s) that can be used in the prevention, treatment, management, or amelioration of a respiratory condition or one or more symptoms thereof. In certain embodiments, the terms "therapy" and "therapy" refer to anti-viral therapy, anti-bacterial therapy, anti-fungal therapy, biological therapy, supportive therapy, and/or other therapies useful in treatment, management, prevention, or amelioration of a respiratory condition or one or more symptoms thereof known to skilled medical personnel.

As used herein, the term "therapeutic protocol" refers to a regimen for dosing and timing the administration of one or more therapies (e.g., therapeutic agents) that has a therapeutic effective.

As used herein, the terms "treat," "treatment," and "treating" refer to the reduction or amelioration of the progression, severity, and/or duration of a respiratory condition or amelioration of one or more symptoms thereof resulting from the administration of one or more therapies (including, but not limited to, the administration of one or more prophylactic or therapeutic agents). In certain embodiments, such terms refer to a reduction in the swelling of organs or tissues, or a reduction in the pain associated with a respiratory condition. In other embodiments, such terms refer to a reduction in the inflammation or constriction of an airway(s) associated with asthma. In other embodiments, such terms refer to a reduction in the replication of an infectious agent, or a reduction in the spread of an infectious agent to other organs or tissues in a subject or to other subjects. In other embodiments, such terms refer to the reduction of the release of inflammatory agents by mast cells, or the reduction of the biological effect of such inflammatory agents. In other embodiments, such terms refer to a reduction of the growth, formation and/or increase in the number of hyperproliferative cells (e.g., cancerous cells). In yet other embodiments, such terms refer to the eradication, removal or control of primary, regional or metastatic cancer (e.g., the minimization or delay of the spread of cancer).

4. BRIEF DESCRIPTION OF THE FIGURES

FIGS. 1A-B show the amino acid sequences of the (A) variable heavy domain (SEQ ID NO.: 7) of 4D4 with the VH CDR1 (SEQ ID NO.: 1), the VH CDR2 (SEQ ID NO.: 2), and the VH CDR3 (SEQ ID NO.: 3) underlined, starting in order from VH CDR1 at the far left; and (B) variable light domain (SEQ ID. NO.: 8) of 4D4, with the VL CDR1 (SEQ ID NO.: 4), the VL CDR2 (SEQ ID NO.: 5), and the VL CDR3 (SEQ ID NO.: 6) underlined, starting in order from VL CDR1 at the far left.

FIGS. 2A-B show the amino acid sequences of the (A) variable heavy domain (SEQ ID NO.: 9) of 4D4H2-1 D11, with the VH CDR1 (SEQ ID NO.: 1), the VH CDR2 (SEQ ID NO.: 10), and the VH CDR3 (SEQ ID NO.: 3) underlined, starting in order from VH CDR1 at the far left; and (B) variable light domain (SEQ ID. NO.: 8) of 4D4H2-1 D11, the VL CDR1 (SEQ ID NO.: 4), the VL CDR2 (SEQ ID NO.: 5), and the VL CDR3 (SEQ ID NO.: 6) underlined, starting in order from VL CDR1 at the far left.

FIGS. 3A-B show the amino acid sequences of the (A) variable heavy domain (SEQ ID NO.: 15) of 4D4com-XF-9, with the VH CDR1 (SEQ ID NO.: 11), the VH CDR2 (SEQ ID NO.: 10), and the VH CDR3 (SEQ ID NO.: 12) underlined, starting in order from VH CDR1 at the far left; and (B) variable light domain (SEQ ID. NO.: 16) of 4D4com-XF-9, the VL CDR1 (SEQ ID NO.: 13), the VL CDR2 (SEQ ID NO.: 14), and the VL CDR3 (SEQ ID NO.: 67) underlined, starting in order from VL CDR1 at the far left.

FIGS. 4A-B show the amino acid sequences of the (A) variable heavy domain (SEQ ID NO.: 17) of 4D4com-2F9, with the VH CDR1 (SEQ ID NO.: 1), the VH CDR2 (SEQ ID NO.: 10), and the VH CDR3 (SEQ ID NO.: 12) underlined, starting in order from VH CDR1 at the far left; and (B) variable light domain (SEQ ID. NO.: 18) of 4D4com-2F9, with the VL CDR1 (SEQ ID NO.: 4), the VL CDR2 (SEQ ID NO.: 14), and the VL CDR3 (SEQ ID NO.: 68) underlined, starting in order from VL CDR1 at the far left.

FIGS. 5A-B show the amino acid sequences of the (A) variable heavy domain (SEQ ID NO.: 21) of 7F3, with the VH CDR1 (SEQ ID NO.: 19), the VH CDR2 (SEQ ID NO.: 2), and the VH CDR3 (SEQ ID NO.: 3) underlined, starting in order from VH CDR1 at the far left; and (B) variable light domain (SEQ ID. NO.: 22) of 7F3, with the VL CDR1 (SEQ ID NO.: 4), the VL CDR2 (SEQ ID NO.: 5), and the VL CDR3 (SEQ ID NO.: 20) underlined, starting in order from VL CDR1 at the far left.

FIGS. 6A-B show the amino acid sequences of the (A) variable heavy domain (SEQ ID NO.: 23) of 71A10, with the VH CDR1 (SEQ ID NO.: 19), the VH CDR2 (SEQ ID NO.: 64), and the VH CDR3 (SEQ ID NO.: 3) underlined, starting in order from VH CDR1 at the far left; and (B) variable light domain (SEQ ID. NO.: 24) of 71A10, the VL CDR1 (SEQ ID NO.: 4), the VL CDR2 (SEQ ID NO.: 5), and the VL CDR3 (SEQ ID NO.: 20) underlined, starting in order from VL CDR1 at the far left.

FIGS. 7A-B show the amino acid sequences of the (A) variable heavy domain (SEQ ID NO.: 21) of 7F3 22D3, with the VH CDR1 (SEQ ID NO.: 19), the VH CDR2 (SEQ ID NO.: 2), and the VH CDR3 (SEQ ID NO.: 3) underlined, starting in order from VH CDR1 at the far left; and (B) variable light domain (SEQ ID. NO.: 25) of 7F3 22D3, with the VL CDR1 (SEQ ID NO.: 4), the VL CDR2 (SEQ ID NO.: 14), and the VL CDR3 (SEQ ID NO.: 20) underlined, starting in order from VL CDR1 at the far left.

FIGS. 8A-B show the amino acid sequences of the (A) variable heavy domain (SEQ ID NO.: 27) of 7F3com-2H2, the VH CDR1 (SEQ ID NO.: 26), with the VH CDR2 (SEQ ID NO.:64), and the VH CDR3 (SEQ ID NO.: 3) are underlined, starting in order from VH CDR1 at the far left; and (B) variable light domain (SEQ ID. NO.: 28) of 7F3com-2H2, the VL CDR1 (SEQ ID NO.: 65), the VL CDR2 (SEQ ID NO.: 66), and the VL CDR3 (SEQ ID NO.: 20) underlined, starting in order from VL CDR1 at the far left.

FIGS. 9A-B show the nucleotide sequences of the (A) variable heavy domain (SEQ ID NO.: 43) of 7F3com-2H2 with the VH CDR1 (SEQ ID NO.: 44), the VH CDR2 (SEQ ID NO.: 45) and the VH CDR3 (SEQ ID NO.: 46) underlined, starting in order from VH CDR1 at the far left; and (B) variable light domain (SEQ ID NO.: 47) of 7F3com-2H2 with the VL CDR1 (SEQ ID NO.: 48), the VL CDR2 (SEQ ID NO.:49), and the VL CDR3 (SEQ ID NO.: 50) underlined, starting in order from VL CDR1 at the far left.

FIGS. 10A-B show the amino acid sequences of the (A) variable heavy domain (SEQ ID NO.: 29) of 7F3com-3H5, with the VH CDR1 (SEQ ID NO.: 19), the VH CDR2 (SEQ ID NO.: 64), and the VH CDR3 (SEQ ID NO.: 3) underlined, starting in order from VH CDR1 at the far left and (B) variable light domain (SEQ ID. NO.: 30) of 7F3com-3H5, with the VL CDR1 (SEQ ID NO.: 4), the VL CDR2 (SEQ ID NO.: 14), and the VL CDR3 (SEQ ID NO.: 20) underlined, starting in order from VL CDR1 at the far left.

FIGS. 11A-B show the amino acid sequences of the (A) variable heavy domain (SEQ ID NO.: 31) of 7F3com-3D4, with the VH CDR1 (SEQ ID NO.: 26), the VH CDR2 (SEQ ID NO.: 64), and the VH CDR3 (SEQ ID NO.: 3) underlined, starting in order from VH CDR1 at the far left and (B) variable light domain (SEQ ID NO.: 32) of 7F3com-3D4, with the VL CDR1 (SEQ ID NO.: 65), the VL CDR2 (SEQ ID NO.: 14), and the VL CDR3 (SEQ ID NO.: 20) underlined, starting in order from VL CDR1 at the far left.

FIG. 12 shows the nucleotide sequence of human IL-9 (SEQ ID NO.: 51) located in the GenBank database (Accession Nos. NM_000590).

FIG. 13 shows the amino acid sequence for human IL-9 located in the GenBank database (Accession Nos. A60480 (SEQ ID NO.: 52), NP_000584 (SEQ ID NO.: 53) and AAC17735 (SEQ ID NO.: 54)).

FIGS. 14A-C shows the nucleotide sequence of human IL-9R subunits found in the GenBank database (Accession Nos. NM_002186 (SEQ ID NO.: 55), NM_176786 (SEQ ID NO.: 56), and NM_000206 (SEQ ID NO.: 57)). (A) Accession No. NM_002186 and (B) Accession No. NM_176786 are the nucleotide sequences of human IL-9R alpha subunit isoform precursors. (C) Accession No. NM_000206 is the nucleotide sequence of the human IL-9R gamma chain.

FIG. 15 shows the amino acid sequence of human IL-9R found in the GenBank database (Accession Nos. NP_002177 (SEQ ID NO.: 58); NP_789743 (SEQ ID NO.: 59), and NP_000197 (SEQ ID NO.: 60)). Accession Nos. NP_002177 and NP_789743 are the amino acid sequences of human IL-9R alpha subunit isoform precursors. NP_000197 is the amino acid sequence of the human IL-9R gamma chain.

Figure 16:
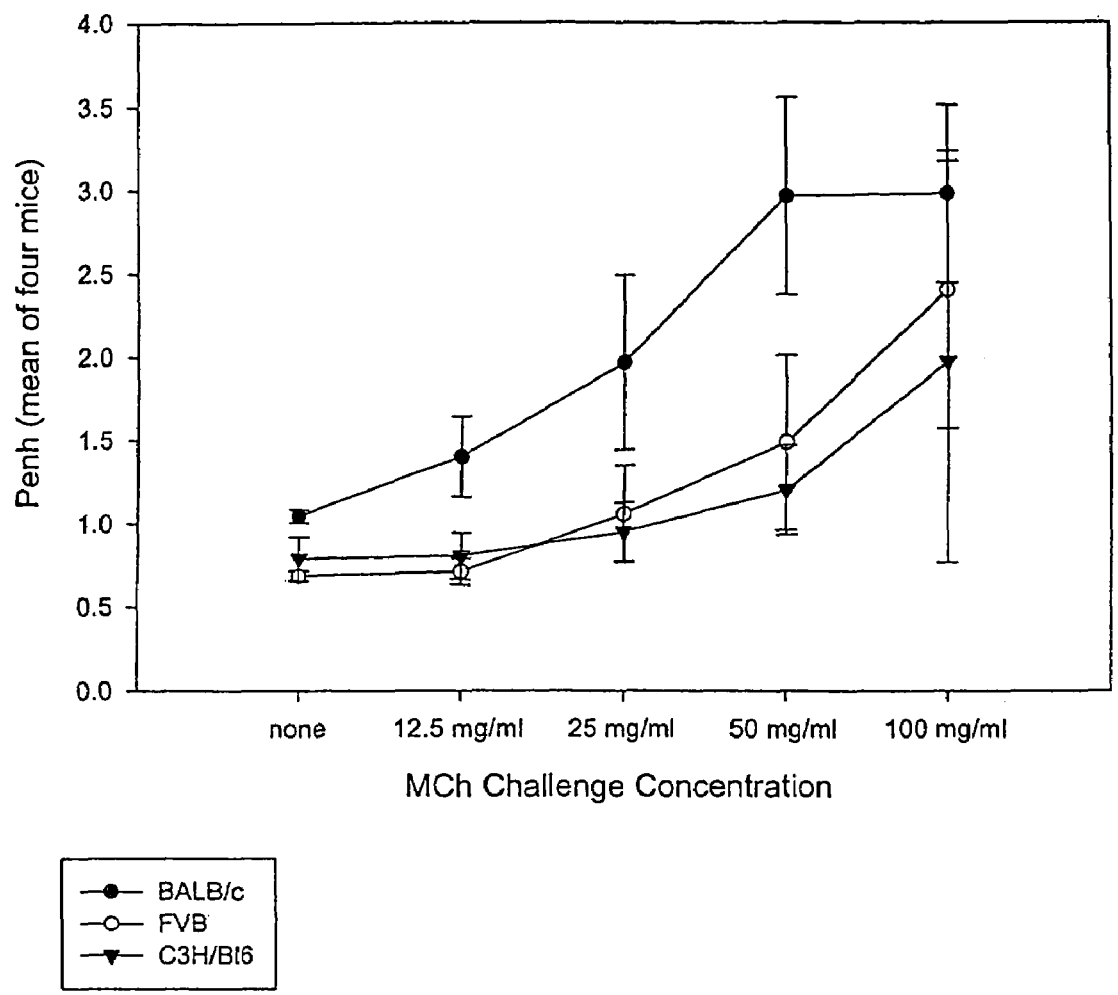

FIG. 16 shows measurement (Penh values) of airway hyperresponsiveness induced by exposure to methylcholine chloride of standard mice strains BLB/c, FVB, and C3H/BI6 with airway.

Figure 17:
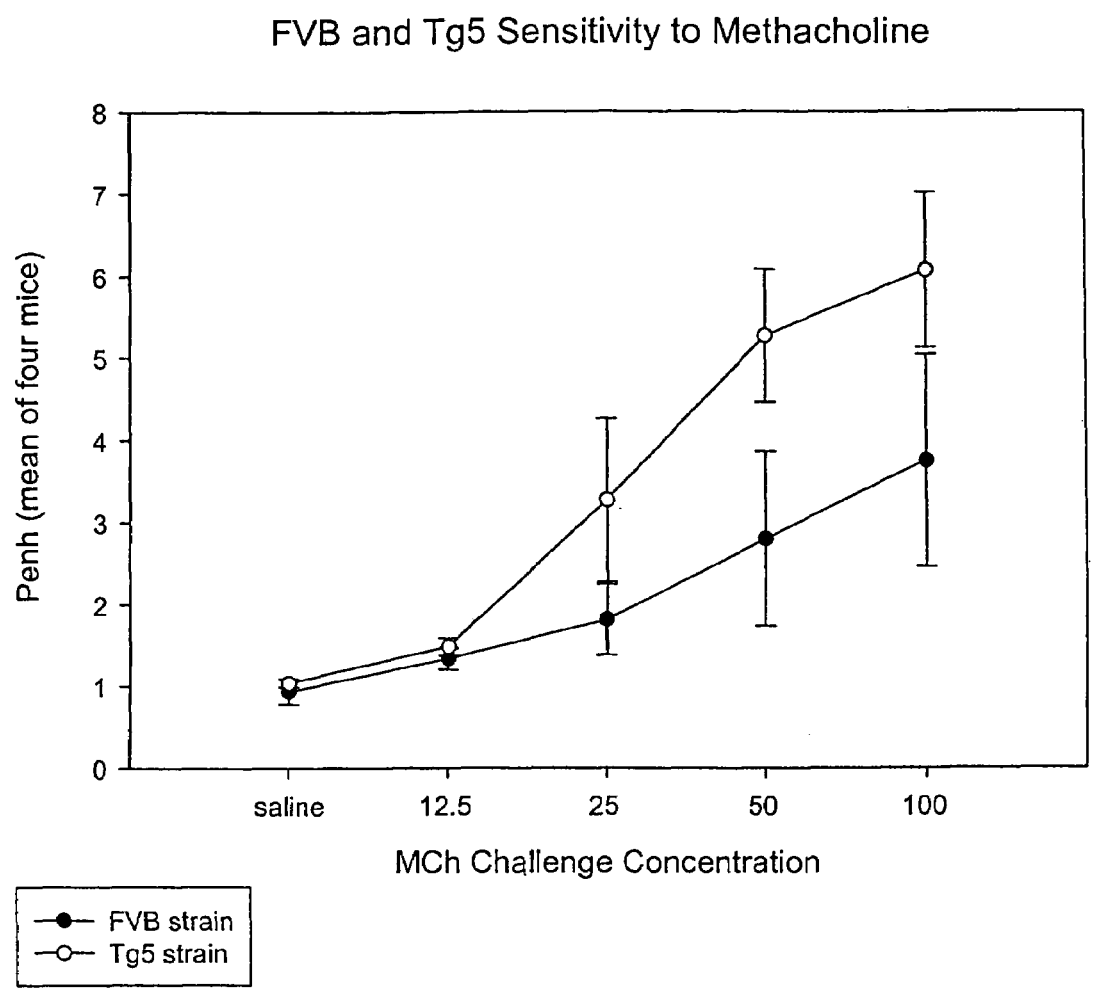

FIG. 17 shows measurement (Penh values) of airway hyperresponsiveness induced by exposure to methylcholine chloride of FVB strain mice and Tg5 strain mice that overexpress IL-9.

Figure 18A:
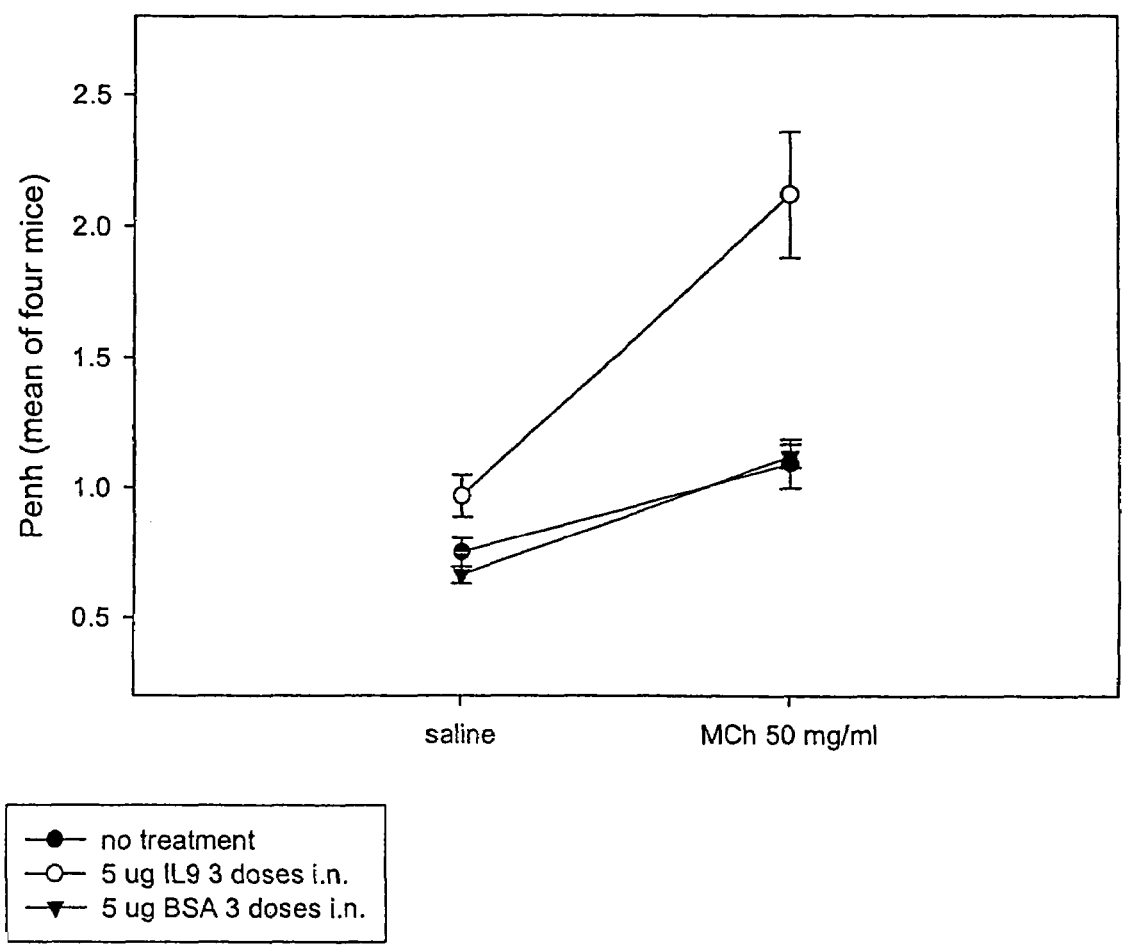
Figure 18B:
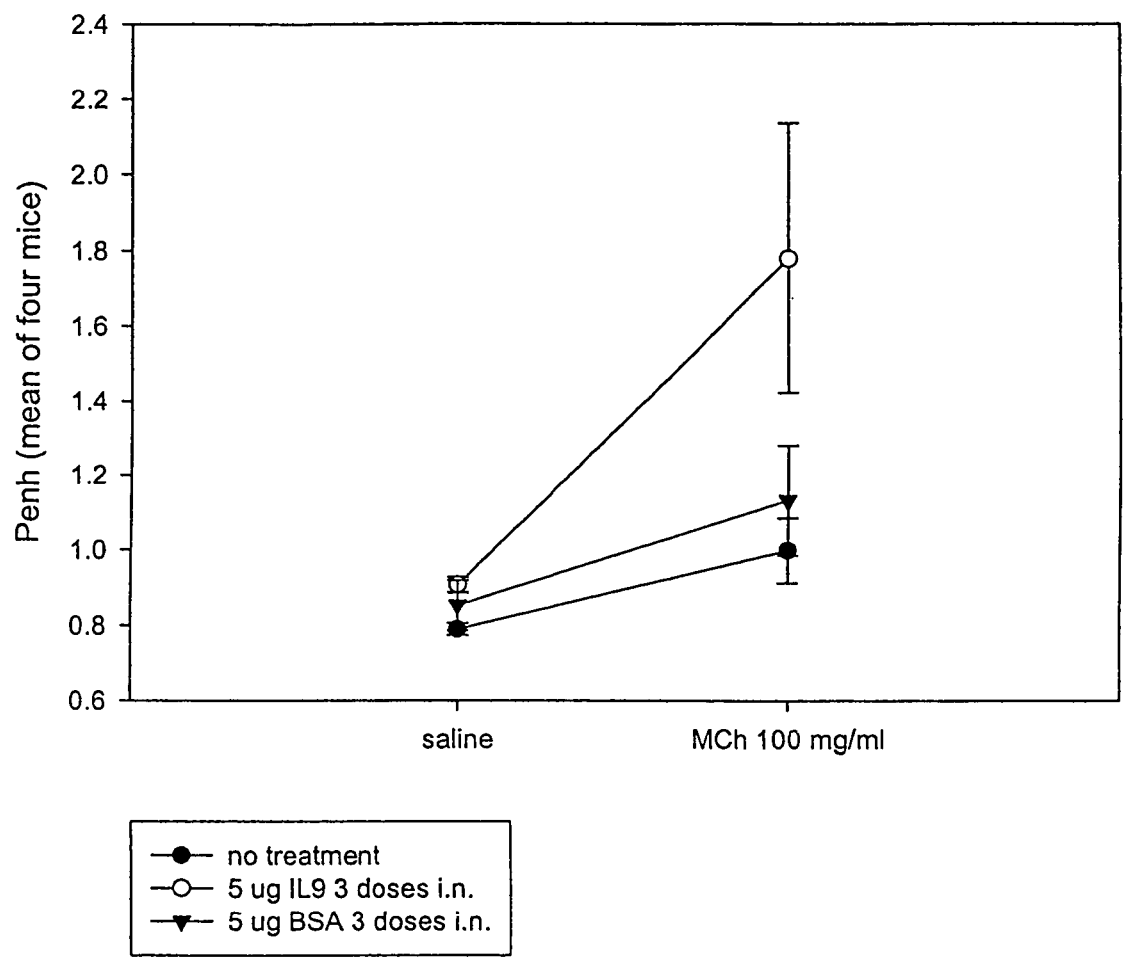

FIGS. 18A-B show measurement (Penh values) of airway hyperresponsiveness induced by exposure to methylcholine chloride in mice locally administered rmuIL-9.

Figure 19:
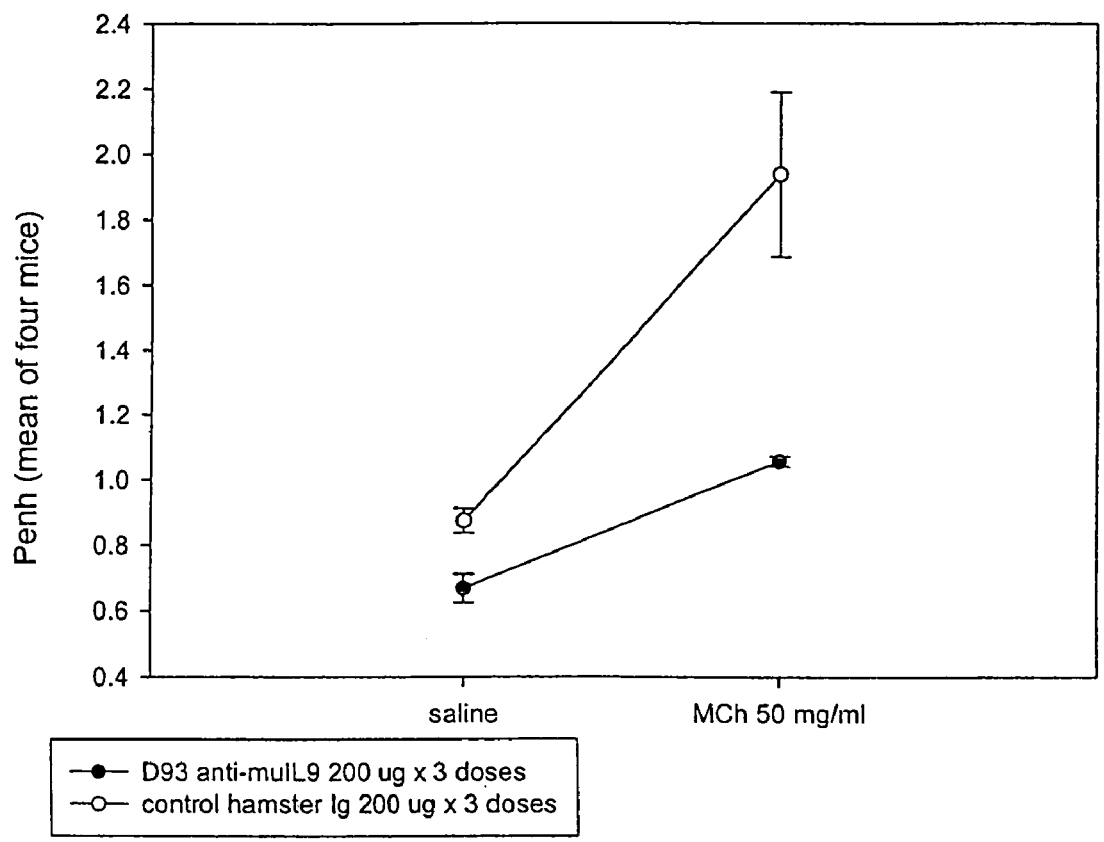

FIG. 19 shows measurement (Penh values) of airway hyperresponsiveness induced by exposure to methylcholine chloride in mice after administration of IL-9 antagonist, D93.

Figure 20:
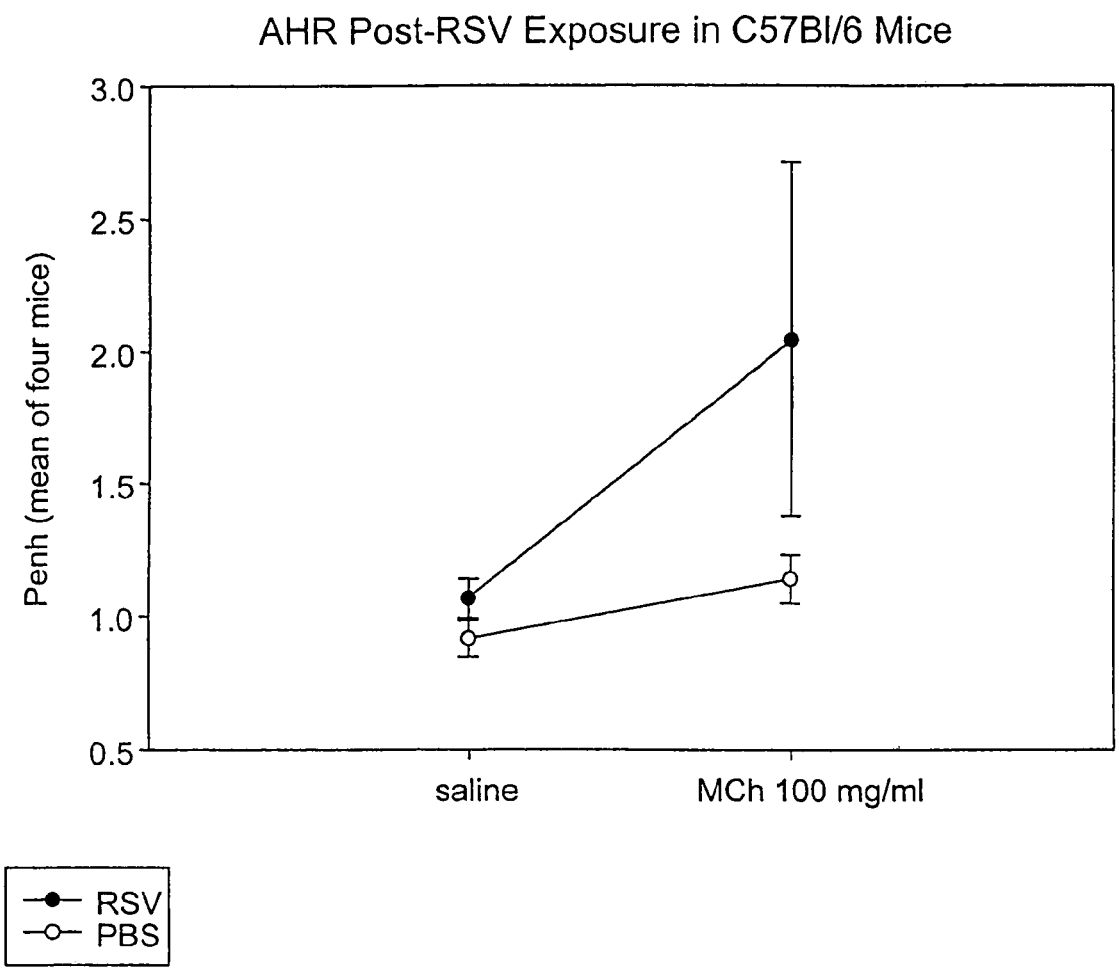

FIG. 20 shows measurement (Penh values) of airway hyperresponsiveness induced by exposure to methylcholinze chloride in mice after inoculation of RSV.

5. DETAILED DESCRIPTION OF THE INVENTION

The present invention encompasses treatment protocols that provide better prophylactic or therapeutic profiles that current single agent therapies or combination therapies for respiratory conditions or one or more symptoms thereof. In particular, the invention provides prophylactic and therapeutic protocols for the prevention, treatment, management, or amelioration of respiratory conditions or one or more symptoms thereof, said protocol comprising administering to a subject in need thereof a prophylactically or therapeutically effective amount of one or more IL-9 antagonists alone or in combination with a prophylactically or therapeutically effective amount of at least one other therapy (e.g., at least one other prophylactic or therapeutic agent) other than an IL-9 antagonist. In a preferred embodiment, the invention provides prophylactic and therapeutic protocols for the prevention treatment, management, or amelioration of respiratory conditions or one or more symptoms thereof, said protocols comprising administering to a subject in need thereof a prophylactically or therapeutically effective amount of an IL-9 antibody alone or in combination with a prophylactically or therapeutically effective amount of at least one other therapy (e.g., at least one other prophylactic or therapeutic agent) other than an IL-9 antibody.

The present invention provides for pharmaceutical compositions, kits, and articles of manufacture comprising one or more IL-9 antagonists for use in the prevention, treatment, management, or amelioration of a respiratory condition or one or more symptoms thereof. The present invention also provides for pharmaceutical compositions, kits, and articles of manufacture comprising one or more IL-9 antagonists and one or more prophylactic or therapeutic agents other than IL-9 antagonists for use in prevention, treatment, management, or amelioration of a respiratory condition or one or more symptoms thereof.

5.1 IL-9 Antagonists

The terms "IL-9 antagonist" or "IL-9 antagonists" as used herein, refer to any agent that blocks, inhibits, reduces, or neutralizes the function, activity and/or expression of an IL-9 polypeptide. An IL-9 antagonist may inhibit a pathologic cellular or humoral phenotype associated with or resulting from IL-9 expression and/or activity (e.g., decreased secretion of mucin, the differentiation of IL-9 expressing cells into a mucin-secreting cell, the secretion of inflammatory agents, the proliferation, migration, and increase in volume of cells (e.g., immune and smooth muscle cells), the secretion of extracellular matrix molecules or matrix metalloproteinases and/or the binding of IL-9 to the IL-9 receptor ("IL-9R")).

IL-9 antagonists include, but are not limited to, proteinaceous agents (e.g., proteins, polypeptides, peptides, fusion proteins, antibodies, and antibody fragments), nucleic acid molecules (e.g., IL-9 antisense nucleic acid molecules, triple helices, double-stranded RNA, or DNA encoding dsRNA that mediates RNAi, or nucleic acid molecules encoding proteinaceous agents), organic molecules, inorganic molecules, small organic molecules, drugs, and small inorganic molecules that block, inhibit, reduce or neutralize a function, an activity and/or the expression of an IL-9 polypeptide, the function, an activity, and/or expression of the IL-9R or a subunit thereof, and/or the binding of an IL-9 polypeptide to the IL-9R or a subunit thereof. In various embodiments, an IL-9 antagonist reduces the function, activity, and/or expression of another molecule other than an IL-9 polypeptide or the IL-9R or a subunit thereof. In other embodiments, an IL-9 antagonist reduces the function, activity, and/or expression of an IL-9 polypeptide, the function, activity, and/or expression of the IL-9R or a subunit thereof, and/or the binding of an IL-9 polypeptide to the IL-9R or a subunit thereof. In particular embodiments, an IL-9 antagonist reduces the function, activity and/or expression of an IL-9 polypeptide, the function, activity, and/or expression of the IL-9R or a subunit thereof, and/or the binding of an IL-9 polypeptide to the IL-9R or a subunit thereof by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as PBS.

In certain embodiments, the IL-9 antagonist that inhibits and/or reduces the expression, activity, and/or function of an IL-9 polypeptide found in the milieu, i.e., not bound to an IL-9R or a subunit thereof. In alternative embodiments, the IL-9 antagonist inhibits and/or reduces the expression, activity, and/or function of an IL-9 polypeptide bound to a soluble IL-9Rα subunit. In another embodiment, the IL-9 antagonist inhibits and/or reduces the expression, activity, and/or function of an IL-9 polypeptide bound to a cellular membrane-bound IL-9R or a subunit thereof.

In one embodiment, antibodies that immunospecifically bind to an IL-9 polypeptide inhibit and/or reduce the interaction between the IL-9 polypeptide and the IL-9 receptor ("IL-9R") or a subunit thereof by approximately 25%, preferably approximately 30%, approximately 35%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo and/or in vitro assay described herein or well-known to one of skill in the art. In an alternative embodiment, antibodies that immunospecifically bind to an IL-9 polypeptide do not inhibit the interaction between an IL-9 polypeptide and the IL-9R or a subunit thereof in an in vivo and/or in vitro assay described herein or well-known to one of skill in the art. In another embodiment, antibodies that immunospecifically bind to an IL-9 polypeptide inhibit the interaction between the IL-9 polypeptide and the IL-9R by less than 20%, less than 15%, less than 10%, or less than 5% relative to a control such as PBS using, for example, an immunoassay such as an ELISA.

In certain embodiments, an IL-9 antagonist does not induce cytokine expression and/or release in an in vivo and/or in vitro assay described herein or well-known to one of skill in the art. In a specific embodiment, an IL-9 antagonist does not induce an increase in the concentration of cytokines such as, e.g., interleukin-4 ("IL-4"), interleukin-5 ("IL-5"), interleukin-10 ("IL-10"), and interleukin-13 ("IL-13") in the serum of a subject administered an IL-9 antagonist. Serum concentrations of cytokines can be measured by any technique well-known to one of skill in the art such as immunoassays, including, e.g., ELISA.

In certain embodiments, an IL-9 antagonist induces cytokine expression and/or release in an in vivo and/or in vitro assay described herein or well-known in the art. In a specific embodiment an IL-9 antagonist induces an increase in the concentration of interleukin-2 ("IL-2"), interleukin-12 ("IL-12), and interferon γ. In another embodiment, an IL-9 antagonist shifts the concentration of Th1 type cytokines and Th2 type cytokines.

In certain embodiments, an IL-9 antagonist induces T-cell anergy in an in vivo and/or in vitro assay described herein or known to one of skill in the art. In alternative embodiments, an IL-9 antagonist does not induce T-cell anergy in an in vivo and/or in vitro assay described herein or known to one of skill in the art. In other embodiments, an IL-9 antagonist elicits a state of antigen-specific unresponsiveness or hyporesponsiveness for at least 30 minutes, at least 1 hour, at least 2 hours, at least 6 hours, at least 12 hours, at least 24 hours, at least 2 days, at least 5 days, at least 7 days, at least 10 days or more in an in vitro assay described herein or well-known to one of skill in the art.

In one embodiment, an IL-9 antagonist reduces and/or inhibits proliferation of inflammatory cells (e.g., mast cells, T cells, B cells, macrophages, neutrophils, basophils, and/or eosinophils) by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In another embodiment, an IL-9 antagonist reduces and/or inhibits infiltration of inflammatory cells into the upper and/or lower respiratory tracts by at least at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet another embodiment, an IL-9 antagonist reduces and/or inhibits infiltration of inflammatory cells into the upper and/or respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and reduces and/or inhibits proliferation of inflammatory cells by at least by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In other embodiments, an IL-9 antagonist inhibits and/or reduces mast cell degranulation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, an IL-9 antagonist inhibits and/or reduces mast cell activation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, the administration of an IL-9 antagonist results in a reduction of mast cell infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, administration of an IL-9 antagonist inhibits and/or reduces mast cell proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, the administration of an IL-9 antagonist inhibits and/or reduces mast cell infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibits and/or reduces mast cell proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, the administration of an IL-9 antagonist results in a reduction of T-cell, particularly Th2 cell, infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known in the art. In other embodiments, administration of an IL-9 antagonist inhibits and/or reduces T-cell proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an assay well-known to one of skill in the art. In yet other embodiments, the administration of an IL-9 antagonist inhibits and/or reduces T cell infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibits and/or reduces T cell proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, an IL-9 antagonist mediates the depletion of peripheral blood T-cells by inducing an increase in apoptosis of T-cells, particularly Th2 cells. In certain embodiements, an IL-9 antagonist induces an increase in apoptosis of T-cells, particularly Th2 cells, and inhibits and/or reduces T cell infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibits and/or reduces T cell proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, the administration of an IL-9 antagonist results in a reduction of macrophage infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, administration of an IL-9 antagonist inhibits and/or reduces macrophage proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, the administration of an IL-9 antagonist inhibits and/or reduces macrophage infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibits and/or reduces macrophages proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, the administration of an IL-9 antagonist results in a reduction of B cell infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in a in vivo assay and/or in vitro assay described herein or well-known to one of skill in the art. In other embodiments, administration of an IL-9 antagonist inhibits and/or reduces B cell proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, the administration of an IL-9 antagonist inhibits and/or reduces B cell infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibits and/or reduces B cell proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, the administration of an IL-9 antagonist results in a reduction of eosinophil infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, administration of an IL-9 antagonist inhibits and/or reduces eosinophil proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, the administration of an IL-9 antagonist inhibits and/or reduces eosinophil infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibits and/or reduces eosinophil proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, administration of an IL-9 antagonist results in a reduction of neutrophil infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative of a control such as PBS in an in vitro and/or in vivo assay described herein or well-known to one of skill in the art. In other embodiments, administration of an IL-9 antagonist inhibits and/or reduces neutrophil proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, the administration of an IL-9 antagonist inhibits and/or reduces neutrophil infiltration in the upper and/or lower respiratory tracts by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibits and/or reduces neutrophil proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, the IL-9 antagonist is not a small organic molecule. In other embodiments, the IL-9 antagonist is not an antisense nucleic acid molecule, triple helix, or double-stranded RNA or DNA encoding the double-stranded RNA that mediates RNAi. In a preferred embodiment, an IL-9 antagonist is an antibody or fragment thereof that immunospecifically binds to an IL-9 polypeptide. In another embodiment, an IL-9 antagonist is an antibody or fragment thereof that immunospecifically binds to an IL-9R or a subunit thereof.

In a preferred embodiment, proteins, polypeptides or peptides (including antibodies and fusion proteins) that are utilized as IL-9 antagonists are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as IL-9 antagonists are human or humanized.

Nucleic acid molecules encoding proteins, polypeptides, or peptides that function as IL-9 antagonists, or proteins, polypeptides, or peptides that function as IL-9 antagonists can be administered to a subject with a respiratory condition in accordance with the methods of the invention. Further, nucleic acid molecules encoding derivatives, analogs, fragments or variants of proteins, polypeptides, or peptides that function as IL-9 antagonists, or derivatives, analogs, fragments or variants of proteins, polypeptides, or peptides that function as IL-9 antagonists can be administered to a subject with a respiratory condition in accordance with the methods of the invention. Preferably, such derivatives, analogs, variants and fragments retain the IL-9 antagonist activity of the full-length wild-type protein, polypeptide, or peptide.

5.1.1 Antibodies

Antibodies that are IL-9 antagonists are well-known in the art. Antibodies that are IL-9 antagonists include, but are not limited to, antibodies that immunospecifically bind to an IL-9 polypeptide, antibodies that immunospecifically bind to an IL-9R, and antibodies that immunospecifically bind to IL-9 bound to its receptor or a subunit thereof. Antibodies that are IL-9 antagonists include, but are not limited to, monoclonal antibodies, bispecific antibodies, multispecific antibodies, human antibodies, humanized antibodies, chimeric antibodies, camelised antibodies, single-chain Fvs (scFv), single chain antibodies, single domain antibodies, Fab fragments, F(ab') fragments, disulfide-linked Fvs (sdFv), and anti-idiotypic (anti-Id) antibodies, and epitope-binding fragments of any of the above. Multispecific antibodies may be specific for different epitopes of, e.g., an IL-9 polypeptide or may be specific for both an IL-9 polypeptide as well as for a heterologous epitope, such as a heterologous polypeptide or solid support material. See, e.g., PCT publications WO 93/17715, WO 92/08802, WO 91/00360, and WO 92/05793; Tutt, et al., J. Immunol. 147:60-69 (1991); U.S. Pat. Nos. 4,474,893, 4,714,681, 4,925,648, 5,573,920, and 5,601,819; and Kostelny et al., J. Immunol. 148:1547-1553 (1992). Antibodies that are IL-9 antagonists include immunoglobulin molecules and immunologically active portions of immunoglobulin molecules, i.e., molecules that contain an antigen binding site that immunospecifically binds to an IL-9 polypeptide. The immunoglobulin molecules of the invention can be of any type (e.g., IgG, IgE, IgM, IgD, IgA, and IgY), class (e.g., $IgG_1$, $IgG_2$, $IgG_3$, $IgG_4$, $IgA_1$, and $IgA_2$) or a subclass of immunoglobulin molecule.

The antibodies that function as IL-9 antagonists may be from any animal origin including birds and mammals (e.g., human, murine, donkey, sheep, rabbit, goat, guinea pig, camel, horse, or chicken). Preferably, the antibodies that function as IL-9 antagonists are human or humanized monoclonal antibodies. As used herein, "human" antibodies include antibodies having the amino acid sequence of a human immunoglobulin and include antibodies isolated form human immunoglobulin libraries or form mice that express antibodies form human genes.

The present invention provides peptides, polypeptides, and/or proteins comprising one or more variable or hypervariable regions of the antibodies described herein. Preferably, peptides, polypeptides, or proteins comprising one or more variable or hypervariable regions or antibodies of the invention further comprise a heterologous amino acid sequence. In certain embodiments, such a heterologous amino acid sequence comprises at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 75 contiguous amino acid residues, at least 100 contiguous amino acid residues or more contiguous amino acid residues. Such peptides, polypeptides and/or proteins may be referred to as fusion proteins.

In a specific embodiment, peptides, polypeptides or proteins comprising one or more variable or hypervariable regions of the antibodies of the invention are 10 amino acid residues, 15 amino acid residues, 20 amino acid residues, 25 amino acid residues, 30 amino acid residues, 35 amino acid residues, 40 amino acid residues, 45 amino acid residues, 50 amino acid residues, 75 amino acid residues, 100 amino acid residues, 125 amino acid residues, or 150 or more amino acid residues in length. In certain embodiments, peptides, polypeptides, or proteins comprising one or more variable or hypervariable regions of an antibody of the invention immunospecifically bind to an IL-9 polypeptide. In other embodiments, peptides, polypeptides, or proteins comprising one or more variable or hypervariable regions of an antibody of the invention do not immunospecifically bind to an IL-9 polypeptide. In certain other embodiments, peptides, polypeptides or proteins comprising one or more variable or hypervariable regions of an antibody of the invention immunospecifically bind an IL-9R or a subunit thereof. In yet other embodiments, peptides, polypeptides, or proteins comprising one or more variable or hypervariable regions of an antibody of the invention do not immunospecifically bind to an IL-9R or a subunit thereof.

5.1.1.1 Antibodies that Immunospecifically Bind to IL-9

It should be recognized that antibodies that antagonize IL-9 are known in the art. Examples of known antibodies that are IL-9 antagonists include, but are not limited to I8431-03, I8431-12, I8431-15A, and I8431-20A (USBiological); SC-7923 (Santa Cruz Biotechnology, Inc.); AF209, BAF209, AB-209-NA, AF409, BAF409, AB-409-NA (R& D Systems); ab9632 and ab9734 (Abcam); and C212 (see, e.g., Faulkner et al., 1998 Infection and Immunity 66(8):3832-3840, Louahed et. al., 1995 J. Immuno. 154:5061-5070; Houssiau et al., J. Immuno. 154:2624-2630; and Gessner et al. Immunobiology 189:419-435). Other examples of antibodies that immunospecifically bind to IL-9 include, but are not limited to, MH9A3 and MH9D1 (MedImmune, Inc., U.S. Application No. 60/371,683, filed on Apr. 12, 2002, which is incorporated herein by reference in its entirety); ML9L1 (MedImmune, Inc., U.S. Application No. 60/371,728, filed on Apr. 12, 2002, which is incorporated herein by reference in its entirety); and D93 (Beckton-Dickinson, Catalog No. 554472). The present invention also encompasses antibodies that immunospecifically bind an IL-9 polypeptide, said antibodies comprising a variable heavy ("VH") domain having an amino acid sequence of the VH domain for 4D4 (FIG. 1A; SEQ ID NO.: 7), 4D4H2-1 D11 (FIG. 2A; SEQ ID NO.: 9), 4D4com-XF-9 (FIG. 3A; SEQ ID NO.: 15), 4D4com-2F9 (FIG. 4A; SEQ ID NO.: 17), 7F3 (FIG. 5A; SEQ ID NO.: 21), 71A10 (FIG. 6A; SEQ ID NO.: 23), 7F3 22D3 (FIG. 7A; SEQ ID NO.: 21), 7F3com-2H2 (FIG. 8A; SEQ ID NO.: 27), 7F3com-3H5 (FIG. 10A; SEQ ID NO.: 29), or 7F3com-3D4 (FIG. 11A; SEQ ID NO.: 31) See U.S. Non-Provisional application Ser. No. 10/823,253 to be filed concurrently herewith, entitled "Recombinant IL-9 antibodies and Uses Thereof," which is incorporated by reference herein in its entirety. In a preferred embodiment, an antibody that immunospecifically binds to an IL-9 polypeptide comprises a VH domain having an amino acid sequence of the VH domain of 7F3com-2H2 (FIG. 8A; SEQ ID NO.: 27). The constant regions for 4D4, 4D4H2-1 D11, 4D4com-XF-9, 4D4com-2F9, 71A10, 7F3 22D3, 7F3com, 7F3com-2H2, 7F3com-3H5, and 7F3com-3D4 are identical to the constant regions of palivizumab (MedImmune, Inc.) $IgG_1$.

The present invention encompasses antibodies that immunospecifically bind to an IL-9 polypeptide, said antibodies comprising a VH CDR having an amino acid sequence of any one of the VH CDRs listed in Table 1, infra. In particular, the invention provides antibodies that immunospecifically bind to an IL-9 polypeptide, said antibodies comprising (or alternatively, consisting of) one, two, three, four, five or more VH CDRs having an amino acid sequence of any of the VH CDRs listed in Table 1, infra. In one embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26. In another embodiment, an antibody that immunospecifically binds to an IL-9 polypeptide comprises a VH CDR2 having the amino acid sequence of SEQ ID NO.: 2 or SEQ ID NO.: 10. In another embodiment, an antibody that immunospecifically binds to an IL-9 polypeptide comprises a VH CDR3 having the amino acid sequence of SEQ ID NO.: 3 or SEQ ID NO.: 12. In another embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26 and a VH CDR2 having the amino acid sequence of SEQ ID NO.: 2 or SEQ ID NO.: 10. In another embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26 and a VH CDR3 having the amino acid sequence of SEQ ID NO.: 3 or SEQ ID NO.: 12. In another embodiment, an antibody that immunospecifically binds to an IL-9 polypeptide comprises a VH CDR2 having the amino acid sequence of SEQ ID NO.: 2 or SEQ ID NO.: 10 and a VH CDR3 having the amino acid sequence of SEQ ID NO.: 3 or SEQ ID NO.: 12. In another embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26, a VH CDR2 having the amino acid sequence of SEQ ID NO.: 2 or SEQ ID NO.: 10, and a VH CDR3 having the amino acid sequence of SEQ ID NO.: 3 or SEQ ID NO.: 12.

The present invention encompasses antibodies that immunospecifically bind to an IL-9 polypeptide, said antibodies comprising a variable light chain ("VL") domain having an amino acid sequence of the VL domain for 4D4 (FIG. 1B; SEQ ID NO.: 8), 4D4H2-1 D11 (FIG. 2B; SEQ ID NO.: 8), 4D4com-XF-9 (FIG. 3B; SEQ ID NO.: 16), 4D4com-2F9 (FIG. 4B; SEQ ID NO.: 18), 7F3 (FIG. 5B; SEQ ID NO.: 22), 71A10 (FIG. 6B; SEQ ID NO.: 24), 7F3 22D3 (FIG. 7B; SEQ ID NO.: 25), 7F3com-2H2 (FIG. 8B; SEQ ID NO.: 28), 7F3com-3H5 (FIG. 10B; SEQ ID NO.: 30), or 7F3com-3D4 (FIG. 11B; SEQ ID NO.: 32). In a preferred embodiment, an antibody that immunospecifically binds to an IL-9 polypeptide comprises a VL domain having an amino acid sequence of the VL domain for 7F3com-2H2 (FIG. 8B; SEQ ID NO:28).

The present invention also provides antibodies that immunospecifically bind to an IL-9 polypeptide, said antibodies comprising a VL CDR having an amino acid sequence of any one of the VL CDRs listed in Table 1, infra. In particular, the invention provides antibodies that immunospecifically bind to an IL-9 polypeptide, said antibodies comprising (or alternatively, consisting of) one, two, three or more VL CDRs having an amino acid sequence of any of the VL CDRs listed in Table 1, infra. In one embodiment, an antibody that immunospecifically binds to an IL-9 polypeptide comprises a VL CDR1 having the amino acid sequence of SEQ ID NO.: 4 or SEQ ID NO.: 13. In another embodiment, an antibody that immunospecifically binds to an IL-9 polypeptide comprises a VL CDR2 having the amino acid sequence of SEQ ID NO.: 5 or SEQ ID NO.: 14. In another embodiment, an antibody that immunospecifically binds to an IL-9 polypeptide comprises a VL CDR3 having the amino acid sequence of SEQ ID NO.: 6 or SEQ ID NO.: 20. In another embodiment, an antibody of that immunospecifically binds to an IL-9 polypeptide comprises a VL CDR1 having the amino acid sequence of SEQ ID NO.: 4 or SEQ ID NO.: 13 and a VL CDR2 having the amino acid sequence of SEQ ID NO.: 5 or SEQ ID NO.: 14. In another embodiment of an antibody that immunospecifically binds to an IL-9 polypeptide comprises a VL CDR1 having the amino acid sequence of SEQ ID NO.: 4 or SEQ ID NO.: 13 and a VL CDR3 having the amino acid sequence of SEQ ID NO.: 6 or SEQ ID NO.: 20. In another embodiment, an antibody that immunospecifically binds to an IL-9 polypeptide comprises a VL CDR2 having the amino acid sequence of SEQ ID NO.: 5 or SEQ ID NO.: 14 and a VL CDR3 having the amino acid sesquence of SEQ ID NO.: 6 or SEQ ID NO.: 20. In another embodiment, an antibody that immunospecifically binds to an IL-9 polypeptide comprises a VL CDR1 having the amino acid sequence of SEQ ID NO.: 4 or SEQ ID NO.: 13, a VL CDR2 having the amino acid sequence of SEQ ID NO.: 5 or SEQ ID NO.: 14, and a VL CDR3 having the amino acid sequence of SEQ ID NO.: 6 or SEQ ID NO.:20, being a part of the antibody.

The present invention provides antibodies that immunospecifically bind to an IL-9 polypeptide, said antibodies comprising a VH domain disclosed herein combined with a VL domain disclosed herein, or other VL domain (e.g., a VL domain disclosed in U.S. provisional application Ser. No. 60/371,683, filed Apr. 12, 2002 and U.S. provisional application Ser. No. 60/371,728, filed Apr. 12, 2002, each of which is incorporated herein by reference in its entirety). The present invention also provides antibodies that immunospecifically bind to an IL-9 polypeptide, said antibodies comprising a VL domain disclosed herein combined with a VH domain disclosed herein, or other VH domain (e.g., a VH domain disclosed in U.S. provisional application Ser. No. 60/371,683, filed Apr. 12, 2002 and U.S. Provisional Application Ser. No. 60/371,728, filed Apr. 12, 2002, both of which are incorporated by reference herein in their entireties).

The present invention provides antibodies that immunospecifically bind to an IL-9 polypeptide, said antibodies comprising (or alternatively, consisting of) a VH CDR listed in Table 1, infra and a VL CDR disclosed in U.S. provisional application Ser. No. 60/371,683, filed Apr. 12, 2002 and U.S. provisional application Ser. No. 60/371,728, filed Apr. 12, 2002. The present invention also provides antibodies that immunospecifically bind to an IL-9 polypeptide, said antibodies comprising (or alternatively, consisting of) a VL CDR listed in Table 1, infra and a VH CDR disclosed in U.S. provisional application Ser. No. 60/371,683, filed Apr. 12, 2002 and U.S. provisional application Ser. No. 60/371,728, filed Apr. 12, 2002. The invention further provides antibodies that immunospecifically bind to an IL-9 polypeptide, said antibodies comprising combinations of VH CDRs and VL CDRs described herein and disclosed in U.S. provisional application Ser. No. 60/371,683, filed Apr. 12, 2002 and U.S. provisional application Ser. No. 60/371,728, filed Apr. 12, 2002.

TABLE 1

Residues that are different between each amino acid sequence encoding the various CDRs appear in bold, underlined font.

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| 4D4 | SEQ. ID NO.: 7 | GYTFTGYWIE (SEQ. ID NO.: 1) | EILPGSGTTN YNEKFKG (SEQ. ID NO.: 2) | ADYYGSDYV KFDY (SEQ. ID NO.:3) | SEQ. ID NO.: 8 | KASQHVGTHVT (SEQ. ID NO.: 4) | STSYRYS (SEQ. ID NO.: 5) | QHFYSYPLT (SEQ. ID NO.: 6) |
| 4D4 H2-1 D11 | SEQ. ID NO.: 9 | GYTFTGYWIE (SEQ. ID NO.: 1) | EWLPGSGTT NYNEKFKG (SEQ. ID NO.: 10) | ADYYGSDYV KFDY (SEQ. ID NO.: 3) | SEQ. ID NO.: 8 | KASQHVGTHVT (SEQ. ID NO.: 4) | STSYRYS (SEQ. ID NO.: 5) | QHFYSYPLT (SEQ. ID NO.: 6) |
| 4D4com-XF-9 | SEQ. ID NO.: 15 | GYTFTYYWIE (SEQ. ID NO.: 11) | EWLPGSGTT NYNEKFKG (SEQ. ID NO.: 10) | ADYYGSDH VKFDY (SEQ. ID NO.: 12) | SEQ. ID NO.: 16 | LASQHVGTHVT (SEQ. ID NO.: 13) | GTSYRYS (SEQ. ID NO.: 14) | QHFYDYPLT (SEQ. ID NO.: 67) |

TABLE 1-continued

Residues that are different between each amino acid sequence encoding the various CDRs appear in bold, underlined font.

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| 4D4com-2F9 | SEQ. ID NO.: 17 | GYTFTGYWIE (SEQ. ID NO.: 1) | EWLPGSGTT NYNEKFKG (SEQ. ID NO.: 10) | ADYYGSDH VKFDY (SEQ. ID NO.: 12) | SEQ. ID NO.: 18 | KASQHVGTHVT (SEQ. ID NO.: 4) | GTSYRYS (SEQ. ID NO.: 14) | QHFYEYPLT (SEQ. ID NO.: 68) |
| 7F3 | SEQ. ID NO.: 21 | GGTFSGYWIE (SEQ. ID NO.: 19) | EILPGSGTTN YNEKFKG (SEQ. ID NO.: 2) | ADYYGSDYV KFDY (SEQ. ID NO.: 3) | SEQ. ID NO.: 22 | KASQHVGTHVT (SEQ. ID NO.: 4) | STSYRYS (SEQ. ID NO.: 5) | QQFYEYPLT (SEQ. ID NO.: 20) |
| 71A10 | SEQ. ID NO.: 23 | GGTFSGYWIE (SEQ. ID NO.: 19) | EILPGSGTTN PNEKFKG (SEQ. ID NO.: 64) | ADYYGSDYV KFDY (SEQ. ID NO.: 3) | SEQ. ID NO.: 24 | KASQHVGTHVT (SEQ. ID NO.: 4) | STSYRYS (SEQ. ID NO.: 5) | QQFYEYPLT (SEQ. ID NO.: 20) |
| 7F3 22D3 | SEQ. ID NO.: 21 | GGTFSGYWIE (SEQ. ID NO.: 19) | EILPGSGTTN YNEKFKG (SEQ. ID NO.: 2) | ADYYGSDYV KFDY (SEQ. ID NO.: 3) | SEQ. ID NO.: 25 | KASQHVGTHVT (SEQ. ID NO.: 4) | GTSYRYS (SEQ. ID NO.: 14) | QQFYEYPLT (SEQ. ID NO.: 20) |
| 7F3com-2H2 | SEQ. ID NO.: 27 | GGTFSYYWIE (SEQ. ID NO.: 26) | EILPGSGTTN PNEKFKG (SEQ. ID NO.: 64) | ADYYGSDYV KFDY (SEQ. ID NO.: 3) | SEQ. ID NO.: 28 | KASQHVITHVT (SEQ. ID NO.: 65) | GTSYSYS (SEQ. ID NO.: 66) | QQFYEYPLT (SEQ. ID NO.: 20) |
| 7F3com-3H5 | SEQ. ID NO.: 29 | GGTFSGYWIE (SEQ. ID NO.: 19) | EILPGSGTTN PNEKFKG (SEQ. ID NO.: 64) | ADYYGSDYV KFDY (SEQ. ID NO.: 3) | SEQ. ID NO.: 30 | KASQHVGTHVT (SEQ ID NO.: 4) | GTSYRYS (SEQ. ID NO.: 14) | QQFYEYPLT (SEQ. ID NO.: 20) |
| 7F3com-3D4 | SEQ. ID NO.: 31 | GGTFSYYWIE (SEQ. ID NO.: 26) | EILPGSGTTN PNEKFKG (SEQ. ID NO.: 64) | ADYYGSDYV KFDY (SEQ. ID NO.: 3) | SEQ. ID NO.: 32 | KASQHVITHVT (SEQ. ID NO.: 65) | GTSYRYS (SEQ. ID NO.: 14) | QQFYEYPLT (SEQ. ID NO.: 20) |

The present invention provides antibodies that immunospecifically bind to an IL-9 polypeptide, said antibodies comprising one or more VH CDRs and one or more VL CDRs listed in Table 1, supra. In particular, the invention provides an antibody that immunospecifically binds to an IL-9 polypeptide, said antibody comprising (or alternatively, consisting of) a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VH CDR3, a VL CDR1, a VL CDR2 and a VL CDR3; a VH CDR1, a VH CDR2, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs listed in Table 1, supra.

In one embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26 and a VL CDR1 having the amino acid sequence of SEQ ID NO.: 4 or SEQ ID NO.: 13. In another embodiment, an antibody that immunospecifically binds to an IL-9 polypeptide comprises a VH CDR1 having the amino acid sequence of SEQ ID NO.: 1, SEQ ID NO.: 1, SEQ ID NO.: 19, or SEQ ID NO.: 26 and a VL CDR2 having the amino acid sequence of SEQ ID NO.: 5 or SEQ ID NO.: 14. In another embodiment, an antibody that immunospecifically binds to an IL-9 polypeptide comprises a VH CDR1 having the amino acid sequence of SEQ ID NO.: 1, SEQ ID NO.: 11, SEQ ID NO.: 19, or SEQ ID NO.: 26 and a VL CDR3 having an amino acid sequence of SEQ ID NO.: 6 or SEQ ID NO.: 20.

In one embodiment, an antibody that immunospecifically binds to an IL-9 polypeptide comprises a VH CDR2 having the amino acid sequence of SEQ ID NO.: 2 or SEQ ID NO.: 10 and a VL CDR1 having the amino acid sequence of SEQ ID NO.: 4 or SEQ ID NO.: 13. In another embodiment, an antibody that immunospecifically binds to an IL-9 polypeptide comprises a VH CDR2 having the amino acid sequence of SEQ ID NO.: 2 or SEQ ID NO.: 10 and a VL CDR2 having the amino acid sequence of SEQ ID NO.: 5 or SEQ ID NO.: 14. In another embodiment, an antibody that immunospecifically binds to an IL-9 polypeptide comprises a VH CDR2 having the amino acid sequence of SEQ ID NO.: 2 or SEQ ID NO.: 10 and a VL CDR3 having an amino acid sequence of SEQ ID NO.: 6 or SEQ ID NO.: 20.

In one embodiment, an antibody that immunospecifically binds to an IL-9 polypeptide comprises a VH CDR3 having the amino acid sequence of SEQ ID NO.: 3 or SEQ ID NO.: 12 and a VL CDR1 having the amino acid sequence of SEQ ID NO.: 4 or SEQ ID NO.: 13. In another embodiment, an antibody that immunospecifically binds to an IL-9 polypeptide comprises a VH CDR3 having the amino acid sequence of SEQ ID NO.: 3 or SEQ ID NO.: 12 and a VL CDR2 having the amino acid sequence of SEQ ID NO.: 5 or SEQ ID NO.: 14. In another embodiment, an antibody that immunospecifically binds to an IL-9 polypeptide comprises a VH CDR3 having the amino acid sequence of SEQ ID NO.: 3 or SEQ ID NO.: 12 and a VL CDR3 having an amino acid sequence of SEQ ID NO.: 6 or SEQ ID NO.: 20.

The present invention provides antibodies that immunospecifically bind to an IL-9 polypeptide, said antibodies encoded by a nucleic acid sequence comprising the nucleotide sequence of 7F3com-2H2 or an antigen-binding fragment thereof. In a specific embodiment, an antibody that immunospecifically binds to an IL-9 polypeptide comprises a VH domain encoded by a nucleic acid sequence having a nucleotide sequence of the VH domain of 7F3com-2H2. In another embodiment, an antibody that immunospecifically binds to an IL-9 polypeptide comprises a VL domain encoded by a nucleic acid sequence having a nucleotide sequence of the VL domain of 7F3com-2H2. In another embodiment, an antibody that immunospecifically binds to an IL-9 polypeptide comprises a VH domain and a VL domain encoded by a nucleic acid sequence having a nucleotide sequence of the VH domain and VL domain of 7F3com-2H2.

In another embodiment, an antibody that immunospecifically binds to an IL-9 polypeptide comprises a VH CDR encoded by a nucleic acid sequence having a nucleotide sequence of a VH CDR of 7F3com-2H2. In another embodiment, an antibody that immunospecifically binds to an IL-9 polypeptide comprises a VL CDR encoded by a nucleic acid sequence having a nucleotide sequence of a VL CDR of 7F3com-2H2. In another embodiment, an antibody that immunospecifically binds to an IL-9 polypeptide comprises a VH CDR and a VL CDR encoded by a nucleic acid sequence having a nucleotide sequence of a VH CDR and a VL CDR of 7F3com-2H2.

The present invention provides for a nucleic acid molecule, generally isolated, encoding an antibody of the present invention that immunospecifically binds to an IL-9 polypeptide. In particular, the invention provides an isolated nucleic acid molecule encoding an antibody that immunospecifically binds to an IL-9 polypeptide, said antibody having the amino acid sequence of 4D4, 4D4H2-1 D11, 4D4com-XF-9, 4D4com-2F9, 7F3, 71A10, 7F3 22D3, 7F3com-2H2, 7F3com-3H5 or 7F3com-3D4, or an antigen-binding fragment thereof. In a preferred embodiment, an isolated nucleic acid molecule encodes an antibody that immunospecifically binds to an IL-9 polypeptide, said antibody having the amino acid sequence of 7F3com-2H2.

The invention provides an isolated nucleic acid molecule encoding an antibody that immunospecifically binds to an IL-9 polypeptide, said antibody comprising (alternatively, consisting of) a VH domain having an amino acid sequence of a VH domain of 4D4, 4D4H2-1 D11, 4D4com-XF-9, 4D4com-2F9, 7F3, 71A10, 7F3 22D3, 7F3com-2H2, 7F3com-3H5, or 7F3com-3D4. In a preferred embodiment, an isolated nucleic acid molecule encodes an antibody that immunospecifically binds to an IL-9 polypeptide, said antibody comprising a VH domain having the amino acid sequence of the VH domain of 7F3com-2H2.

The invention provides an isolated nucleic acid molecule encoding an antibody that immunospecifically binds to an IL-9 polypeptide, said antibody comprising (alternatively, consisting of) a VH CDR having an amino acid sequence of any of the VH CDRs listed in Table 1, supra. In particular, the invention provides an isolated nucleic acid molecule encoding an antibody that immunospecifically binds to an IL-9 polypeptide, said antibody comprising one, two, three, four, five or more VH CDRs having an amino acid sequence of any of the VH CDRs listed in Table 1, supra. In one embodiment, an isolated nucleic acid molecule encodes an antibody that immunospecifically binds to an IL-9 polypeptide, said antibody comprising a VH CDR1 having the amino acid sequence of the VH CDR1 listed in Table 1, supra. In another embodiment, an isolated nucleic acid molecule encodes an antibody that immunospecifically binds to an IL-9 polypeptide, said antibody comprising a VH CDR2 having the amino acid sequence of the VH CDR2 listed in Table 1, supra. In another embodiment, an isolated nucleic acid molecule encodes an antibody that immunospecifically binds to an IL-9 polypeptide, said antibody comprising a VH CDR3 having the amino acid sequence of the VH CDR3 listed in Table 1, supra.

The invention provides an isolated nucleic acid molecule encoding an antibody that immunospecifically binds to an IL-9 polypeptide, said antibody comprising (alternatively, consisting of) a VL domain having an amino acid sequence of a VL domain of 4D4, 4D4H2-1 D11, 4D4com-XF-9, 4D4com-2F9, 7F3, 71A10, 7F3 22D3, 7F3com-2H2, 7F3com-3H5, or 7F3com-3D4. In a preferred embodiment, an isolated nucleic acid molecule encodes an antibody that immunospecifically binds to an IL-9 polypeptide, said antibody comprising a VL domain having the amino acid sequence of the VL domain of 7F3com-2H2.

The invention also provides an isolated nucleic acid molecule encoding an antibody that immunospecifically binds to an IL-9 polypeptide, said antibody comprising (alternatively, consisting of) a VL CDR having an amino acid sequence of any of the VL CDRs listed in Table 1, supra. In particular, the invention provides an isolated nucleic acid molecule encoding an antibody that immunospecifically binds to an IL-9 polypeptide, said antibody comprising one, two, three or more VL CDRs having an amino acid sequence of any of the VL CDRs listed in Table 1, supra. In one embodiment, an isolated nucleic acid molecule encodes an antibody that immunospecifically binds to an IL-9 polypeptide, said antibody comprising a VL CDR1 having the amino acid sequence of the VH CDR1 listed in Table 1, supra. In another embodiment, an isolated nucleic acid molecule encodes an antibody that immunospecifically binds to an IL-9 polypeptide, said antibody comprising a VL CDR2 having the amino acid sequence of the VL CDR2 listed in Table 1, supra. In another embodiment, an isolated nucleic acid molecule encodes an antibody that immunospecifically binds to an IL-9 polypeptide, said antibody comprising a VL CDR3 having the amino acid sequence of the VL CDR3 listed in Table 1, supra.

The present invention provides nucleic acid molecules encoding antibodies that immunospecifically bind to an IL-9 polypeptide, said antibodies comprising one or more VH CDRs and one or more VL CDRs listed in Table 1, supra. In particular, the invention provides an isolated nucleic acid molecule encoding an antibody that immunospecifically binds to an IL-9 polypeptide, said antibody comprising (or alternatively, consisting of) a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2 and a VL CDR1; a VH CDR1, a VH CDR2 and a VL CDR2; a VH CDR1, a VH CDR2 and a VL CDR3; a VH CDR1, a VH CDR3 and a VL CDR1; a VH CDR1, a VH CDR3 and a VL CDR2; a VH CDR1, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR2, a VL CDR2 and a VL CDR3; a VH CDR1, a VH CDR3, a VL CDR1 and a VL CDR2; a VH CDR1, a VH CDR3, a VL CDR1 and a VL CDR3; a VH CDR1, a VH CDR3, a VL CDR2 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs listed in Table 1, supra.

The present invention provides antibodies that immunospecifically bind to an IL-9 polypeptide, said antibodies comprising derivatives of the VH domains, VH CDRs, VL domains, or VL CDRs described herein that immunospecifically bind to an IL-9 polypeptide. Standard techniques known to those of skill in the art can be used to introduce mutations (e.g., deletions, additions, and/or substitutions) in the nucleotide sequence encoding an antibody of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues (i.e., amino acid residues which are not critical for the antibody to immunospecifically bind to an IL-9 polypeptide). A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody can be expressed and the activity of the antibody can be determined.

The present invention provides for antibodies that immunospecifically bind to an IL-9 polypeptide, said antibodies comprising the amino acid sequence of 4D4, 4D4H2-1 D11, 4D4com-XF-9, 4D4com-2F9, 7F3, 71A10, 7F3 22D3, 7F3com-2H2, 7F3com-3H5, or 7F3com-3D4 with one or more amino acid residue substitutions in the variable light (VL) domain and/or variable heavy (VH) domain. The present invention also provides for antibodies that immunospecifically bind to an IL-9 polypeptide, said antibodies comprising the amino acid sequence of 4D4, 4D4H2-1 D11, 4D4com-XF-9, 4D4com-2F9, 7F3, 71A10, 7F3 22D3, 7F3com-2H2, 7F3com-3H5, or 7F3com-3D4 with one or more amino acid residue substitutions in one or more VL CDRs and/or one or more VH CDRs. The present invention also provides for antibodies that immunospecifically bind to an IL-9 polypeptide, said antibodies comprising the amino acid sequence of 4D4, 4D4H2-1 D11, 4D4com-XF-9, 4D4com-2F9, 7F3, 71A10, 7F3 22D3, 7F3com-2H2, 7F3com-3H5, or 7F3com-3D4, or a VH and/or VL domain thereof with one or more amino acid residue substitutions in one or more VH frameworks and/or one or more VL frameworks. The antibody generated by introducing substitutions in the VH domain, VH CDRs, VL domain, VL CDRs and/or frameworks of 4D4, 4D4H2-1 D11, 4D4com-XF-9, 4D4com-2F9, 7F3, 71A10, 7F3 22D3, 7F3com-2H2, 7F3com-3H5, or 7F3com-3D4 can be tested in vitro and/or in vivo, for example, for its ability to bind to an IL-9 polypeptide, or for its ability to inhibit and/or reduce IL-9 mediated cell proliferation, or for its ability to prevent, treat or ameliorate one or more symptoms associated with a respiratory condition.

In a specific embodiment, an antibody that immunospecifically binds to an IL-9 polypeptide comprises a nucleotide sequence that hybridizes to the nucleotide sequence encoding 4D4, 4D4H2-1 D11, 4D4com-XF-9, 4D4com-2F9, 7F3, 71A10, 7F3 22D3, 7F3com-2H2, 7F3com-3H5 or 7F3com-3D4, or an antigen-binding fragment thereof under stringent conditions, e.g., hybridization to filter-bound DNA in 6× sodium chloride/sodium citrate (SSC) at about 45 C followed by one or more washes in 0.2×SSC/0.1% SDS at about 50-65 C, under highly stringent conditions, e.g., hybridization to filter-bound nucleic acid in 6×SSC at about 45 C followed by one or more washes in 0.1×SSC/0.2% SDS at about 68 C, or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In another embodiment, an antibody that immunospecifically binds to an IL-9 polypeptide comprises an amino acid sequence of a VH domain or an amino acid sequence a VL domain encoded by a nucleotide sequence that hybridizes to the nucleotide sequence encoding the VH or VL domains of 4D4, 4D4H2-1 D11, 4D4com-XF-9, 4D4com-2F9, 7F3, 71A10, 7F3 22D3, 7F3com-2H2, 7F3com-3H5 or 7F3com-3D4 under stringent conditions or under other stringent hybridization conditions which are known to those of skill in the art. In another embodiment, an antibody that immunospecifically binds to an IL-9 polypeptide comprises an amino acid sequence of a VH domain and an amino acid sequence of a VL domain encoded by a nucleotide sequence that hybridizes to the nucleotide sequence encoding the VH and VL domains of 4D4, 4D4H2-1 D11, 4D4com-XF-9, 4D4com-2F9, 7F3, 71A10, 7F3 22D3, 7F3com-2H2, 7F3com-3H5 or 7F3com-3D4 under stringent conditions described herein or under other stringent hybridization conditions which are known to those of skill in the art. In another embodiment, an antibody that immunospecifically binds to an IL-9 polypeptide comprises an amino acid sequence of a VH CDR or an amino acid sequence of a VL CDR encoded by a nucleotide sequence that hybridizes to the nucleotide sequence encoding any one of the VH CDRs or VL CDRs listed in Table 1, supra under stringent conditions or under other stringent hybridization conditions which are known to those of skill in the art. In another embodiment, an antibody that immunospecifically binds to an IL-9 polypeptide comprises an amino acid sequence of a VH CDR and an amino acid sequence of a VL CDR encoded by nucleotide sequences that hybridize to the nucleotide sequences encoding any one of the VH CDRs listed in Table 1, supra, and any one of the VL CDRs listed Table 1, supra, under stringent conditions or under other stringent hybridization conditions which are known to those of skill in the art.

In another embodiment, the present invention provides an antibody that immunospecifically binds to an IL-9 polypeptide, said antibody comprising a VH domain and/or VL domain encoded by a nucleotide sequence that hybridizes to the nucleotide sequence of the VH domain and/or VL domain of 7F3com-2H2 (SEQ ID NO.: 43 and SEQ ID NO.: 47, respectively) under stringent conditions. In another embodiment, the present invention provides an antibody that immunospecifically binds to an IL-9 polypeptide, said antibody comprising a VH CDR and/or VL CDR encoded by a nucleotide sequence that hybridizes to the nucleotide sequence of the VH CDR and/or VL CDR of 7F3com-2H2 (FIGS. 9A-B) under stringent conditions.

In a specific embodiment, an antibody that immunospecifically binds to an IL-9 polypeptide comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of 4D4, 4D4H2-1 D11, 4D4com-XF-9, 4D4com-2F9, 7F3, 71A10, 7F3 22D3, 7F3com-2H2, 7F3com-3H5 or 7F3com-3D4, or an antigen-binding fragment thereof. In another embodiment, an antibody that immunospecifically binds to an IL-9 polypeptide comprises an amino acid sequence of a VH domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the VH domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4. In another embodiment, an antibody that immunospecifically binds to an IL-9 polypeptide comprises an amino acid sequence of a VL domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the VL domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4.

In another embodiment, an antibody that immunospecifically binds to an IL-9 polypeptide comprises an amino acid sequence of one or more VL CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of the VL CDRs listed in Table 1, supra. In another embodiment, an antibody that immunospecifically binds to an IL-9 polypeptide comprises an amino acid sequence of one or more VL CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of one of the VL CDRs listed in Table 1, supra.

In another embodiment, the invention provides an antibody that immunospecifically binds to an IL-9 polypeptide, said antibody encoded by a nucleotide sequence that is at least 65%, preferably at least 70%, at least 75%, at least 80%, at least 85%, at least 90%, at least 95%, or at least 99% identical to the nucleotide sequence encoding 7F3com-2H2. In another embodiment, the invention provides an antibody that immunospecifically binds to an IL-9 polypeptide, said antibody comprising a VH domain and/or VL domain encoded by a nucleotide sequence that is at least 65%, preferably at least 70%, at least 75%, at least 80%, at least 85%, at least 90%, at least 95%, or at least 99% identical to the nucleotide sequence of the VH domain and/or VL domain of 7F3com-2H2 (SEQ ID NO.: 43 and SEQ ID NO.: 47, respectively). In another embodiment, the invention provides an antibody that immunospecifically binds to an IL-9 polypeptide, said antibody comprising a VH CDR and/or a VL CDR encoded by a nucleotide sequence that is at last 65%, preferably at least 70%, at least 75%, at least 80%, at least 85%, at least 90%, at least 95%, or at least 99% identical to the nucleotide sequence of the VH CDR and/or VL CDR of 7F3com-2H2 (FIGS. 9A-B).

The present invention encompasses antibodies that compete with an antibody described herein for binding to an IL-9 polypeptide. In particular, the present invention encompasses antibodies that compete with 4D4, 4D4H2-1 D11, 4D4com-XF-9, 4D4com-2F9, 7F3, 71A10, 7F3 22D3, 7F3com-2H2, 7F3com-3H5 or 7F3com-3D4 or an antigen-binding fragment thereof for binding to the IL-9 polypeptide. In a specific embodiment, the invention encompasses an antibody that reduces the binding of 4D4, 4D4H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, 25% to 50%, 45 to 75%, or 75 to 99% relative to a control such as PBS in the competition assay described herein or competition assays well known in the art. In another embodiment, the invention encompasses an antibody that reduces binding of 4D4, 4D4H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 25% to 50%, 45 to 75%, or 75 to 99% relative to a control such as PBS in an ELISA competition assay. In a preferred embodiment, an ELISA competition assay may be performed in the following manner: recombinant IL-9 is prepared in PBS at a concentration of 10 µg/ml. 100 µl of this solution is added to each well of an ELISA 98-well microtiter plate and incubated overnight at 4-8° C. The ELISA plate is washed with PBS supplemented with 0.1% Tween to remove excess recombinant IL-9. Non-specific protein-protein interactions are blocked by adding 100 µl of bovine serum albumin (BSA) prepared in PBS to a final concentration of 1%. After one hour at room temperature, the ELISA plate is washed. Unlabeled competing antibodies are prepared in blocking solution at concentrations ranging from 1 µg/ml to 0.01 µg/ml. Control wells contain either blocking solution only or control antibodies at concentrations ranging from 1 µg/ml to 0.01 µg/ml. Test antibody (e.g., 7F3com-2H2) labeled with horseradish peroxidase is added to competing antibody dilutions at a fixed final concentration of 1 µg/ml. 100 µl of test and competing antibody mixtures are added to the ELISA wells in triplicate and the plate is incubated for 1 hour at room temperature. Residual unbound antibody is washed away. Bound test antibody is detected by adding 100 µl of horseradish peroxidase substrate to each well. The plate is incubated for 30 min. at room temperature, and absorbance is read using an automated plate reader. The average of triplicate wells is calculated. Antibodies which compete well with the test antibody reduce the measured absorbance compared with control wells. In a preferred embodiment, the invention encompasses an antibody that reduces the binding of 7F3com-2H2 to an IL-9 polypeptide by at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 25% to 50%, 45 to 75%, or 75 to 99% relative to a control such as PBS in an ELISA competition assay (described above).

In another embodiment, the invention encompasses an antibody that reduces the binding of an antibody comprising (alternatively, consisting of) an antigen-binding fragment (e.g., a VH domain, a VH CDR, a VL domain or a VL CDR) of 4D4, 4D4H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or more, or 25% to 50%, 45 to 75%, or 75 to 99% relative to a control such as PBS in a competition assay described herein or well-known to one of skill in the art. In another embodiment, the invention encompasses an antibody that reduces the binding of an antibody comprising (alternatively, consisting of) an antigen-binding fragment (e.g., a VH domain, VL domain, a VH CDR, or a VL CDR) of 4D4, 4D4H2-1 D11, 4D4com-XF-9, 4D4com-2F9, 7F3, 71A10, 7F3 22D3, 7F3com-2H2, 7F3com-3H5 or 7F3com-3D4 to an IL-9 polypeptide by at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or more, or 25% to 50%, 45 to 75%, or 75 to 99% relative to a control such as PBS in an ELISA competition assay. In a preferred embodiment, the invention encompasses an antibody that reduces the binding of an antibody comprising (alternatively, consisting of) an antigen-binding fragment of 7F3com-2H2 to an IL-9 polypeptide by at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or more, or 25% to 50%, 45 to 75%, or 75 to 99% relative to a control such as PBS in an ELISA competition assay.

The present invention encompasses polypeptides or proteins comprising (alternatively, consisting of) VH domains that compete with the VH domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4 For binding to an IL-9 polypeptide. The present invention also encompasses polypeptides or proteins comprising (alternatively, consisting of) VL domains that compete with a VL domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4 For binding to an IL-9 polypeptide.

The present invention encompasses polypeptides or proteins comprising (alternatively, consisting of) VH CDRs that compete with a VH CDR listed in Table 1, supra, for binding to an IL-9 polypeptide. The present invention also encompasses polypeptides or proteins comprising (alternatively, consisting of) VL CDRs that compete with a VL CDR listed in Table 1, supra for binding to an IL-9 polypeptide.

The antibodies that immunospecifically bind to an IL-9 polypeptide include derivatives that are modified, i.e., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The present invention also provides antibodies that immunospecifically bind to an IL-9 polypeptide, said antibodies comprising a framework region known to those of skill in the art (e.g., a human or non-human framework). The framework regions may be naturally occurring or consensus framework regions. Preferably, the fragment region of an antibody of the invention is human (see, e.g., Chothia et al., 1998, J. Mol. Biol. 278:457-479 for a listing of human framework regions, which is incorporated herein by reference in its entirety).

The present invention encompasses antibodies that immunospecifically bind to an IL-9 polypeptide, said antibodies comprising the amino acid sequence of 4D4, 4D4H2-1 D 11, 4D4com-XF-9, 4D4com-2F9, 7F3, 71A10, 7F3 22D3, 7F3com-2H2, 7F3com-3H5 or 7F3com-3D4 with mutations (e.g., one or more amino acid substitutions) in the framework regions. In certain embodiments, antibodies that immunospecifically bind to an IL-9 polypeptide comprise the amino acid sequence of 4D4, 4D4H2-1 D11, 4D4com-XF-9, 4D4com-2F9, 7F3, 71A10, 7F3 22D3, 7F3com-2H2, 7F3com-3H5 or 7F3com-3D4 with one or more amino acid residue substitutions in the framework regions of the VH and/or VL domains. Preferably, the amino acid substitutions in the framework region improve binding of the antibody to an IL-9 polypeptide.

In a specific embodiment, antibodies that immunospecifically bind to an IL-9 polypeptide comprise the amino acid sequence of one or more of the CDRs of 4D4, 4D4H2-1 D11, 4D4com-XF-9, 4D4com-2F9, 7F3, 71A10, 7F3 22D3, 7F3com-2H2, 7F3com-3H5 or 7F3com-3D4, a VH framework region 1 having the amino acid sequence of QVQLVQSGAEVKKPGASVKVSCKAS (SEQ ID NO.: 33) or QVQLVQSGAEVK KPGSSVKVSCKAS (SEQ ID NO.: 37), a VH framework region 2 having the amino acid sequence of WVRQAPGQGLEWMG (SEQ ID NO.: 34), a VH framework region 3 region having the amino acid sequence of RVTMTRDTSTSTVYMELSSLRSEDTAVYYCAR (SEQ ID NO.: 35) or RVTITADESTSTAYMELSSLRSEDTAVYYCAR (SEQ ID NO.: 38), and a VH framework region 4 having the amino acid sequence of WGQGTLVTVSS (SEQ ID NO.: 36). In another embodiment, antibodies that immunospecifically bind to an IL-9 polypeptide comprise the amino acid sequence of one or more of the CDRs of 4D4, 4D4H2-1 D11, 4D4com-XF-9, 4D4com-2F9, 7F3, 71A10, 7F3 22D3, 7F3com-2H2, 7F3com-3H5 or 7F3com-3D4, a VL framework region 1 having the amino acid sequence of DIQMTQSPSSLSAS-VGDRVTITC (SEQ ID NO.: 39), a VL framework region 2 having the amino acid sequence of WYQQKPGKAPKLLIY (SEQ ID NO.: 40), a VL framework region 3 region having the amino acid sequence of GVPSRFSGSGSGTDFTLTISS-LQPE DFATYYC (SEQ ID NO.: 41), and a VL framework region 4 region having the amino acid sequence of FGGGT-KVEIK (SEQ ID NO.: 42). In yet another embodiment, antibodies that immunospecifically bind to an IL-9 polypeptide comprise the amino acid sequence of one or more of the CDRs of 4D4, 4D4H2-1 D11, 4D4com-XF-9, 4D4com-2F9, 7F3, 71A10, 7F3 22D3, 7F3com-2H2, 7F3com-3H5 or 7F3com-3D4, a VH framework region 1 having the amino acid sequence of SEQ ID NO.: 33 or SEQ ID NO.: 37, a VH framework region 2 having the amino acid sequence of SEQ ID NO.: 34, a VH framework region 3 having the amino acid sequence of SEQ ID NO.: 35 or SEQ ID NO.: 38, a VH framework region 4 having the amino acid sequence of SEQ ID NO.: 36, a VL framework region 1 having the amino acid sequence of SEQ ID NO.: 39, a VL framework region 2 having the amino acid sequence of SEQ ID NO.: 40, a VL framework region 3 having the amino acid sequence of SEQ ID NO.: 41, and a VL framework region 4 having the amino acid sequence of SEQ ID NO.: 42.

The present invention also encompasses antibodies that immunospecifically bind to an IL-9 polypeptide, said antibodies comprising the amino acid sequence of 4D4, 4D4H2-1 D11, 4D4com-XF-9, 4D4com-2F9, 7F3, 71A10, 7F3 22D3, 7F3com-2H2, 7F3com-3H5 or 7F3com-3D4 with mutations (e.g., one or more amino acid residue substitutions) in the variable and framework regions. Preferably, the amino acid substitutions in the variable and framework regions improve binding of the antibody to an IL-9 polypeptide.

The present invention also provides antibodies of the invention that comprise constant regions known to those of skill in the art. Preferably, the constant regions of an antibody of the invention or fragment thereof are human.

Antibodies that immunospecifically bind to an IL-9 polypeptide expressed by an immune cell (such as, but not limited to, an activated T cell or a mast cell) and function as IL-9 antagonists are well-known in the art. In certain embodiments, antibodies that immunospecifically bind to an IL-9 polypeptide may antagonize IL-9 by modulating an expression, activity, and/or function of inflammatory cells such as T cells, B cells, mast cells, neutrophils, and/or eosinophils. In other embodiments, antibodies that immunospecifically bind to an IL-9 polypeptide may function as IL-9 antagonists by inhibiting and/or reducing the infiltration of inflammatory cells into a tissue, joint, or organ of a subject and/or inhibit and/or reduce epithelial cell hyperplasia.

The invention encompasses antibodies that immunospecifically bind to an IL-9 polypeptide found in the milieu, i.e., not bound to an IL-9R or a subunit thereof. The invention also encompasses antibodies that immunospecifically bind to an IL-9 polypeptide bound to a soluble IL-9Rα subunit. The invention further encompasses antibodies that immunospecifically bind to an IL-9 polypeptide bound to a cellular membrane-bound IL-9R or a subunit thereof.

In one embodiment, an antibody that immunospecifically binds to an IL-9 polypeptide inhibit and/or reduce the interaction between the IL-9 polypeptide and the IL-9 receptor ("IL-9R") or a subunit thereof by approximately 25%, preferably approximately 30%, approximately 35%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS or a control IgG antibody in an in vivo and/or in vitro assay described herein or well-known to one of skill in the art (e.g., an immunoassay such as an ELISA). In an alternative embodiment, an antibody that immunospecifically binds to an IL-9 polypeptide does not inhibit the interaction between an IL-9 polypeptide and the IL-9R or a subunit thereof relative to a control such as PBS or a control IgG antibody in an in vivo and/or in vitro assay described herein or well-known to one of skill in the art (e.g., an immunoassay such as an ELISA). In another embodiment, an antibody that immunospecifically binds to an IL-9 polypeptide inhibits the interaction between the IL-9 polypeptide and the IL-9R by less than 20%, less than 15%, less than 10%, or less than 5% relative to a control such as PBS or a control IgG antibody using, for example, an immunoassay such as an ELISA.

In one embodiment, antibodies that immunospecifically bind to an IL-9 polypeptide inhibit or reduce the interaction between the IL-9 polypeptide and the IL-9 receptor ("IL-9R") or one or more subunits thereof by at least 25%, preferably, at least 30%, at least 35%, at least 45%, at least 50%, at least 55%, at least 60%, at least 65%, at least 70%, at least 75%, at least 80%, at least 85%, at least 90%, at least 95%, or at least 98% relative to a control such as phosphate buffered saline ("PBS") or a control IgG antibody in an in vivo and/or in vitro assay described herein or well-known to one of skill in the art (e.g., a cell proliferation assay using an IL-9 dependent cell line such as an IL-9 dependent mouse T cell line expressing the human IL-9R). In an alternative embodiment, antibodies that immunospecifically bind to an IL-9 polypeptide do not inhibit the interaction between an IL-9 polypeptide and the IL-9R or one or more subunits thereof relative to a control such as PBS or a control IgG antibody in an in vivo and/or in vitro assay described herein or well-known to one of skill in the art (e.g., a cell proliferation assay using an IL-9 dependent cell line such as an IL-9 dependent mouse T cell line expressing the human IL-9R). In another embodiment, antibodies that immunospecifically bind to an IL-9 polypeptide inhibit the interaction between the IL-9 polypeptide and the IL-9R or one or more subunits thereof by less than 20%, less than 15%, less than 10%, or less than 5% relative to a control such as PBS or a control IgG antibody in vivo and/or in vitro assay described herein or well-known to one of skill in the art, (e.g., a cell proliferation assay using an IL-9 dependent cell line such as an IL-9 dependent mouse T cell line expressing the human IL-9R).

The present invention encompasses antibodies that immunospecifically bind to an IL-9 polypeptide and do not induce or reduce cytokine expression and/or release relative to a control such as PBS or a control IgG antibody in an in vivo and/or in vitro assay described herein or well-known to one of skill in the art. In one embodiment, the invention provides antibodies that immunospecifically bind to an IL-9 polypeptide and do not induce an increase in the concentration cytokines such as, e.g., IFN-γ, IL-2, IL-4, IL-5, IL-6, IL-7, IL-10, IL-12, IL-15, and IL-23 in the serum of a subject administered such an antibody relative to the concentration of such cytokines in the serum of a subject administered a control such as PBS or a control IgG antibody. In an alternative embodiment, antibodies that immunospecifically bind to an IL-9 polypeptide induce cytokine expression and/or release relative to a control such as PBS or a control IgG antibody in an in vitro and/or in vivo assay described herein or well-known to one of skill in the art. In a specific embodiment, an antibody that immunospecifically binds to an IL-9 polypeptide induces an increase in the concentration of cytokines such as, e.g., IFN-γ, IL-2, IL-12, and IL-15 in the serum of a subject administered such an antibody relative to the concentration of such cytokines in the serum of a subject administered a control such as PBS or a control IgG antibody. In another specific embodiment, an antibody that immunospecifically binds to an IL-9 polypeptide induces an increase in the concentration of cytokines produced by Th1 cells, such as IFN-γ and IL-12, in a subject administered such an antibody relative to the concentration of such cytokines in the serum of a subject administered a control such as PBS or a control IgG antibody. In another specific embodiment, an antibody that immunospecifically binds to an IL-9 polypeptide induces a decrease in the concentration of cytokines such as, e.g., IL-4, IL-5, IL-10, IL-13, and IL-23 in the serum of a subject administered such an antibody relative to the concentration of such cytokines in the serum of a subject administered a control such as PBS or a control IgG antibody. In another specific embodiment, an antibody that immunospecifically binds to an IL-9 polypeptide induces a decrease in the concentration of cytokines produced by mast cells, such as TNF-α, IL-4, and IL-13, in the serum of a subject administered such an antibody relative to the concentration of such cytokines in the serum of a subject administered a control such as PBS or a control IgG antibody. In yet another specific embodiment, an antibody that immunospecifically binds to an IL-9 polypeptide induces a decrease in the concentration of cytokines produced by Th2 cells, such as IL-4, IL-5, IL-13, and IL-10, in the serum of a subject administered such an antibody relative to the concentration of such cytokines in the serum of a subject administered a control such as PBS or a control IgG antibody. Serum concentrations of a cytokine can be measured by any technique well-known to one of skill in the art such as, e.g., ELISA or Western blot assay.

In one embodiment, antibodies that immunospecifically bind to an IL-9 polypeptide reduce and/or inhibit proliferation of inflammatory cells (e.g., mast cells, T cells, B cells, macrophages, neutrophils, basophils, and/or eosinophils) by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay or $^3$H-thymidine assay). In another embodiment, antibodies that immunospecifically bind to an IL-9 polypeptide reduce and/or inhibit infiltration of inflammatory cells into the upper and/or lower respiratory tracts by at least at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In yet another embodiment, antibodies that immunospecifically bind to an IL-9 polypeptide reduce and/or inhibit infiltration of inflammatory cells into the upper and/or respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known in the art and reduce and/or inhibit proliferation of inflammatory cells by at least by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay or $^3$H-thymidine assay).

In certain embodiments, antibodies that immunospecifically bind to an IL-9 polypeptide reduce mast cell degranulation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (see, e.g., Windmiller and Backer, 2003, *J. Biol. Chem.* 278:11874-78 for examples of mast cell degranulation assays). In other embodiments, antibodies that immunospecifically bind to an IL-9 polypeptide inhibit and/or reduce mast cell activation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In other embodiments, antibodies that immunospecifically bind to an IL-9 polypeptide inhibit and/or reduce the expression and/or release of products of mast cell activation and/or degranulation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described or well-known to one of skill in the art.

In a specific embodiment, antibodies that immunospecifically bind to an IL-9 polypeptide inhibit and/or reduce the expression, activity, serum concentration, and/or release of mast cell proteases, such as chymase and tryptase, by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In a preferred embodiment, mast cell activity may be measured by culturing primary mast cells or a mast cell line in vitro in the presence of 10 ng/ml of IL-9. Baseline levels of protease (e.g., chymase and tryptase) and leukotriene are determined in the supernatant by commercially available ELISA kits. The ability of antibodies to modulate protease or leukotriene levels is assessed by adding an IL-9-reactive antibody or control antibody directly to cell cultures at a concentration of 1 μg/ml. Protease and leukotriene levels are assessed at 24 and 36 hour timepoints. In another specific embodiment, antibodies that immunospecifically bind to an IL-9 polypeptide inhibit and/or reduce the expression, activity, serum concentration, and/or release of mast cell leukotrienes, such as C4, D4, and E4 by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In another specific embodiment, antibodies that immunospecifically bind to an IL-9 polypeptide inhibit and/or reduce the expression, activity, serum concentration, and/or release of mast cell cytokines, such as TNF-α, IL-4, and IL-13 by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., an ELISA or Western blot assay).

In other embodiments, antibodies that immunospecifically bind to an IL-9 polypeptide inhibit and/or reduce mast cell infiltration in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known in the art. In other embodiments, antibodies that immunospecifically bind to an IL-9 polypeptide inhibit and/or reduce mast cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce mast cell infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vitro and/or in vivo assay described herein or well known in the art and inhibit and/or reduce mast cell proliferation at least 25%, at least 30%, at least 35%, at least 40%, at least 50%, at least 55%, at least 60%, at least 65%, at 70%, at least 75%, at least 80%, at least 85%, at least 90%, at least 95%, or at least 98% relative to a control such as PBS or a control IgG antibody in an in vivo and/or in vitro assay described herein or well known to one of skill in the art (e.g., a trypan blue assay, FACS or $^3$H thymidine assay). In a preferred embodiment, reductions in mast cell infiltration may be measured in vivo by sensitizing animals to ovalbumin. Briefly, 100 μg of ovalbumin complexed with aluminum adjuvant is administered subcutaneously on days 1 and 21. Throughout the three-week sensitization procedure, animals are administered an IL-9 reactive antibody or a control antibody at a 10 mg/kg dose every 5 to 7 days. On days 29, 30 and 31, animals are exposed to ovalbumin without adjuvant by aerosol delivery, or alternatively, by intrasal instillation of 100 μl of a 1 μg/ml solution prepared in PBS. On day 31, 6 hours after the last ovalbumin challenge, animals are euthanized and lung tissue is fixed by perfusion with formalin. Mast cell infiltration is assessed histologically by counting mast cells per field in lung epithelial tissue sections. Using this experimental design, mast cell precursors may be differentiated from mast cells in lung epithelium by assessing (for example) whether metachromatic granules are present, and/or by immunohistochemistry using differentiation-dependent cell surface markers (e.g., FcepsilonRI).

In other embodiments, antibodies that immunospecifically bind to an IL-9 polypeptide inhibit and/or reduce infiltration of mast cell precursors in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known in the art. In other embodiments, antibodies that immunospecifically bind to an IL-9 polypeptide inhibit and/or reduce proliferation of mast cell precursors by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce infiltration of mast cell precursors into the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known in the art and inhibit and/or reduce proliferation of mast cell precursors at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In a preferred embodiment, mast cell precursor infiltration may be measured in vivo by the mast cell infiltration assay described supra.

In certain embodiments, antibodies that immunospecifically bind to an IL-9 polypeptide mediate depletion of peripheral blood T-cells by inducing an increase in apoptosis of T-cells, particularly Th2 cells. In a preferred embodiment, Th2 T lymphocyte depletion may be measured in vivo by sensitizing animals with ovalbumin. Briefly, 100 μg of ovalbumin complexed with aluminum adjuvant is administered subcutaneously on days 1 and 21. Throughout the three-week sensitization procedure, animals are administered an IL-9 reactive antibody or a control antibody at a 10 mg/kg dose every 5 to 7 days. On day 28, animals receive a 100 μg boost of ovalbumin protein without adjuvant intravenously. Two days following the intravenous boost, the animals are euthanized. Spleen cells are recovered and analyzed by flow cytometry. Splenic Th2 T lymphocytes, identifiable by cytoplasmic staining for IL-4, should be reduced in animals receiving an IL-9 neutralizing antibody compared with the control antibody recipients. In another embodiment, antibodies that immunospecifically bind to an IL-9 polypeptide mediate inhibit and/or reduce Th1 and Th2 differentiation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., FACS). In certain embodiments, antibodies that immunospecifically bind to an IL-9 polypeptide inhibit and/or reduce T cell infiltration, particularly Th2 cell infiltration, in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay well-known to one of skill in the art. In other embodiments, antibodies that immunospecifically bind to an IL-9 polypeptide inhibits and/or reduce T cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce T cell infiltration, particularly Th2 cell infiltration, in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98%, inhibit and/or reduce T cell proliferation, particularly Th2 cell proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98%, and/or increases apoptosis of T cells relative to a control such as PBS or a control IgG antibody in an in vivo and/or in vitro assay described herein or well-known to one of skill in the art.

In certain embodiments, antibodies that immunospecifically bind to an IL-9 polypeptide reduce macrophage infiltration by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay well-known to one of skill in the art. In a preferred embodiment, reductions in macrophage infiltration may be measured in vivo by sensitizing animals to ovalbumin. Briefly, 100 µg of ovalbumin complexed with aluminum adjuvant is administered subcutaneously on days 1 and 21. Throughout the three-week sensitization procedure, animals are administered IL-9 reactive antibody or control antibody at 10 mg/kg dose every 5 to 7 days. On days 29, 30 and 31, animals are exposed to ovalbumin without adjuvant by aerosol delivery, or alternatively, by intrasal instillation of 100 µl of a 1 µg/ml solution prepared in PBS. On day 31, 6 hours after the last ovalbumin challenge, animals are euthanized and lung tissue is fixed by perfusion with formalin. Macrophage infiltration is assessed by immunocytochemistry by counting CD14 positive cells per field in lung tissue sections. In other embodiments, antibodies that immunospecifically bind to an IL-9 polypeptide inhibit and/or reduce macrophage proliferation by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce macrophage infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art and inhibit and/or reduce macrophage proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art.

In certain embodiments, antibodies that immunospecifically bind to an IL-9 polypeptide reduce B cell infiltration in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art. In a preferred embodiment, reductions in B lymphocyte infiltration may be measured in vivo by systemically sensitizing animals to ovalbumin. Briefly, 100 µg of ovalbumin complexed with aluminum adjuvant is administered subcutaneously on days 1 and 21. Throughout the three-week sensitization procedure, animals are administered an IL-9 reactive antibody or a control antibody at a 10 mg/kg dose every 5 to 7 days. On days 29, 30 and 31, animals are exposed to ovalbumin without adjuvant by aerosol delivery, or alternatively, by intrasal instillation of 100 µl of a 1 µg/ml solution prepared in PBS. On day 31, 6 hours after the last ovalbumin challenge, animals are euthanized and lung tissue is fixed by perfusion with formalin. B lymphocyte infiltration is assessed by immunocytochemistry by counting CD19 positive cells per field in lung tissue sections. In other embodiments, antibodies that immunospecifically bind to an IL-9 polypeptide inhibit and/or reduce B cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce B cell infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art and inhibits and/or reduces B cell proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art.

In certain embodiments, antibodies that immunospecifically bind to an IL-9 polypeptide reduce eosinophil infiltration in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described or well-known to one of skill in the art (see, e.g., Li et al., 2000, *Am. J. Respir. Cell Mol. Biol.* 25:644-51). In other embodiments, antibodies that immunospecifically bind to an IL-9 polypeptide inhibit and/or reduce eosinophil proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art (e.g., a trypan blue assay, FACS or $^3$H thymidine assay). In yet other embodiments, antibodies that immunospecifically bind to an IL-9 polypeptide inhibit and/or reduce eosinophil infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art and inhibits and/or reduces eosinophil proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art.

In other embodiments, antibodies that immunospecifically bind to an IL-9 polypeptide reduce neutrophil infiltration in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In other embodiments, antibodies that immunospecifically bind to an IL-9 polypeptide inhibit and/or reduce neutrophil proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assays described herein or well-known to one of skill in the art (e.g., a trypan blue assay, FACS or $^3$H thymidine assay). In yet other embodiments, antibodies that immunospecifically bind to an IL-9 polypeptide inhibit and/or reduce neutrophil infiltration by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art and inhibits and/or reduces neutrophil proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art.

In a preferred embodiment, an antibody that immunospecifically binds to an IL-9 polypeptide neutralizes or inhibits IL-9 mediated biological effects including, but not limited to inflammatory cell recruitment, epithelia hyperplasia, mucin production of epithelial cells, and mast cell activation, degranulation, proliferation, and/or infiltration.

In a specific embodiment, an antibody that immunospecifically binds to an IL-9 polypeptide acts synergistically with a proteinaceous agent (e.g., a peptide, polypeptide, or protein (including an antibody)) and/or a non-proteinaceous agent that antagonizes the expression, function, and/or activity of IgE to reduce or inhibit the activation, degranulation, proliferation, and/or infiltration of mast cells by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assays described herein or well-known to one of skill in the art.

In another embodiment, an antibody that immunospecifically binds to an IL-9 polypeptide acts synergistically with a proteinaceous agent (e.g., a peptide, polypeptide, protein (including an antibody)) and/or a non-proteinaceous agent that antagonizes the expression, function, and/or activity of a mast cell protease to reduce or inhibit the activation, degranulation, proliferation, and/or infiltration of mast cells by at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well known to one of skill in the art.

In another embodiment, an antibody that immunospecifically binds to an IL-9 polypeptide acts synergistically with a proteinaceous agent (e.g., a peptide, polypeptide, and protein (including an antibody)) or a non-proteinaceous agent that antagonizes the expression, function, and/or activity of a stem cell factor to reduce or inhibit to reduce or inhibit the activation, degranulation, proliferation, and/or infiltration of mast cells by at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% relative to a control such as PBS or a control IgG antibody in an in vivo and/or in vitro assay described herein or well-known to one of skill in the art. In a preferred embodiment, primary mast cells or a mast cell line is cultured in vitro in the presence of 1 ng/ml IL-9 plus 1 ng/ml stem cell factor. Baseline levels of protease (e.g., chymase and tryptase) and leukotriene are determined in the supernatant by commercially available ELISA kits. The ability of antibodies to modulate protease or leukotriene levels is assessed by adding IL-9 reactive antibody or control antibody directly to cell cultures at a concentration of 1 μg/ml. Protease and leukotriene levels are assessed at 24 and 36 hour time points.

The antibodies of the present invention that immunospecifically bind to an IL-9 polypeptide may be monospecific, bispecific, trispecific or of greater multispecificity. Multispecific antibodies may be specific for different epitopes of an IL-9 polypeptide or may be specific for both an IL-9 polypeptide as well as for a heterologous epitope, such as a heterologous polypeptide or solid support material. See, e.g., International publications WO 93/17715, WO 92/08802, WO 91/00360, and WO 92/05793; Tutt, et al., J. Immunol. 147: 60-69 (1991); U.S. Pat. Nos. 4,474,893, 4,714,681, 4,925, 648, 5,573,920, and 5,601,819; and Kostelny et al., J. Immunol. 148:1547-1553 (1992).

The present invention provides for antibodies that have a high binding affinity for an IL-9 polypeptide. In a specific embodiment, an antibody that immunospecifically binds to an IL-9 polypeptide has an association rate constant or $k_{on}$ rate

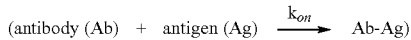

of at least $10^5$ $M^{-1}s^{-1}$, at least $1.5\times10^5$ $M^{-1}s^{-1}$, at least $2\times10^5$ $M^{-1}s^{-1}$, at least $2.5\times10$ $M^{-1}s^{-1}$, at least $5\times10^5$ $M^{-1}s^{-1}$, at least $10^6 M^{-1}s^{-1}$, at least $5\times10^6$ $M^{-1}s^{-1}$, at least $10^7$ $M^{-1}s^{-1}$, at least $5\times10^7$ $M^{-1}s^{-1}$, or at least $10^8$ $M^{-1}s^{-1}$, or $10^5$-$10^8$ $M^{-1}s^{-1}$, $1.5\times10^5$ $M^{-1}s^{-1}$-$1\times10^7$ $M^{-1}s^{-1}$, $2\times10^5$-$1\times10^6 M^{-1}s^{-1}$, or $4.5\times 10^5\times10^7$ $M^{-1}s^{-1}$. In a preferred embodiment, an antibody that immunospecifically binds to an IL-9 polypeptide has a $k_{on}$ of at least $2 \times 10^5$ M$^{-1}$s$^{-1}$, at least $2.5 \times 10^5$ M$^{-1}$s$^{-1}$, at least $5 \times 10^5$ M$^{-1}$s$^{-1}$, at least $10^6$ M$^{-1}$s$^{-1}$, at least $5 \times 10^6$ M$^{-1}$s$^{-1}$, at least $10^7$ M$^{-1}$s$^{-1}$, at least $5 \times 10^7$ M$^{-1}$s$^{-1}$, or at least $10^8$ M$^{-1}$s$^{-1}$ as determined by a BIAcore assay and the antibody neutralizes human IL-9 in the microneutralization assay as described herein. In a preferred embodiment, an antibody that immunospecifically binds to an IL-9 polypeptide has a $k_{on}$ of at most $10^8$ M$^{-1}$s$^-$ at most $10^9$ M$^{-1}$s$^{-1}$, at most $10^{10}$ M$^{-1}$s$^{-1}$, at most $10^{11}$ M$^{-1}$s$^{-1}$, or at most $10^{12}$ M$^{-1}$s$^{-1}$ as determined by a BIAcore assay and the antibody neutralizes human IL-9 in the microneutralization assay as described herein. In accordance with these embodiments, such antibodies may comprise a VH domain and/or a VL domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4 or a VH CDR and/or a VL CDR of 4D4, 4D4H2-1 D11, 4D4com-XF-9, 4D4com-2F9, 7F3, 71A10, 7F3 22D3, 7F3com-2H2, 7F3com-3H5 or 7F3com-3D4.

In another embodiment, an antibody that immunospecifically binds to an IL-9 polypeptide has a $k_{off}$ rate

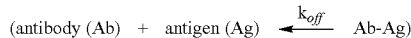

of less than $10^{-3}$ s$^{-1}$, less than $5 \times 10^{-3}$ s$^{-1}$, less than $10^{-4}$ s$^{-1}$, less than $2 \times 10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$, or $10^{-3}$-$10^{-11}$ s$^{-1}$, $10^{-4}$-$10^{-8}$ s$^{-1}$, or $10^{-5}$-$10^{-8}$ s$^{-1}$. In a preferred embodiment, an antibody that immunospecifically binds to an IL-9 polypeptide has a $k_{off}$ of $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$ as determined by a BIAcore assay and the antibody neutralizes human IL-9 in the microneutralization assay described herein. In another preferred embodiment, an antibody that immunospecifically binds to an IL-9 polypeptide has a $k_{off}$ of greater than $10^{-13}$ s$^{-1}$, greater than $10^{-12}$ s$^{-1}$, greater than $10^{-11}$ s$^{-1}$, greater than $10^{-10}$ s$^{-1}$, greater than $10^{-9}$ s$^{-1}$, or greater than $10^{-8}$ s$^{-1}$. In accordance with these embodiments, such antibodies may comprise a VH domain and/or a VL domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4, or a VH CDR and/or a VL CDR of 4D4, 4D4H2-1 D11, 4D4com-XF-9, 4D4com-2F9, 7F3, 71A10, 7F3 22D3, 7F3com-2H2, 7F3com-3H5 or 7F3com-3D4.

In another embodiment, an antibody that immunospecifically binds to an IL-9 polypeptide has an affinity constant or $K_a$ ($k_{on}/k_{off}$) of at least $10^2$ M$^{-1}$, at least $5 \times 10^2$ M$^{-1}$, at least $10^3$ M$^{-1}$, at least $5 \times 10^3$ M$^{-1}$, at least $10^4$ M$^{-1}$, at least $5 \times 10^4$ M$^{-1}$, at least $10^5$ M$^{-1}$, at least $5 \times 10^5$ M$^{-1}$, at least $10^6$ M$^{-1}$, at least $5 \times 10^6$ M$^{-1}$, at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10$ M$^{-1}$, at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$, at least $10^{14}$ M$^{-1}$, at least $5 \times 10^{14}$ M$^{-1}$, at least $10^{15}$ M$^{-1}$, or $10^2$-$5 \times 10^5$ M$^{-1}$, $10^4$-$1 \times 10^{10}$ M$^{-1}$, or $10^5$-$1 \times 10^8$ M$^{-1}$. In another embodiment, an antibody that immunospecifically binds to an IL-9 polypeptide has a $K_a$ of at most $10^{11}$ M$^{-1}$, at most $5 \times 10^{11}$ M$^{-1}$, at most $10^{12}$ M$^{-1}$, at most $5 \times 10^{12}$ M$^{-1}$, at most $10^{13}$ M$^{-1}$, at most $5 \times 10^{13}$ M$^{-1}$, at most $10^{14}$ M$^{-1}$, or at most $5 \times 10^{14}$ M$^{-1}$. In another embodiment, an antibody that immunospecifically binds to an IL-9 polypeptide has a dissociation constant or $K_d$ ($k_{off}/k_{on}$) of less than $10^{-5}$ M, less than $5 \times 10^{-5}$ M, less than $10^{-6}$ M, less than $5 \times 10^{-6}$ M, less than $10^{-7}$ M, less than $5 \times 10^{-7}$ M, less than $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M, less than $5 \times 10^{-14}$ M, less than $10^{-15}$ M, or less than $5 \times 10^{-15}$ M or $10^{-2}$ M-$5 \times 10^{-5}$ M, $10^{-6}$-$10^{-15}$ M, or $10^{-8}$-$10^{-14}$ M. In a preferred embodiment, an antibody that immunospecifically binds to an IL-9 polypeptide has a $K_d$ of less than $10^{-9}$ M, less than $5 \times 10^{-9}$ M, less than $10^{-10}$ M, less than $5 \times 10^{-10}$ M, less than $1 \times 10^{-11}$ M, less than $5 \times 10^{-1}$ M, less than $1 \times 10^{-12}$ M, less than $5 \times 10^{-12}$ M, less than $10^{-13}$ M, less than $5 \times 10^{-13}$ M or less than $1 \times 10^{-14}$ M, or $10^{-9}$ M-$10^{-14}$ M as determined by a BIAcore assay and the antibody neutralizes human IL-9 in the microneutralization assay described herein. In another preferred embodiment, an antibody that immunospecifically binds to an IL-9 polypeptide has a $K_d$ of greater than $10^{-9}$ M, greater than $5 \times 10^{-9}$ M, greater than $10^{-10}$ M, greater than $5 \times 10^{-10}$ M, greater than $10^{-11}$ M, greater than $5 \times 10^{-11}$ M, greater than $10^{-12}$ M, greater than $5 \times 10^{-12}$ M, greater than $6 \times 10^{-12}$ M, greater than $10^{-13}$ M, greater than $5 \times 10^{-13}$ M, greater than $10^{-14}$ M, greater than $5 \times 10^{-14}$ M or greater than $10^{-9}$ M-$10^{-14}$ M. In accordance with these embodiments, such antibodies may comprise a VH domain and/or a VL domain of 4D4, 4D4H2-1 D11, 4D4com-XF-9, 4D4com-2F9, 7F3, 71A10, 7F3 22D3, 7F3com-2H2, 7F3com-3H5 or 7F3com-3D4, or a VH CDR and/or a VL CDR of 4D4, 4D4H2-1 D11, 4D4com-XF-9, 4D4com-2F9, 7F3, 71A10, 7F3 22D3, 7F3com-2H2, 7F3com-3H5 or 7F3com-3D4.

In certain embodiments, the antibodies of the invention do not include antibodies known in the art that immunospecifically bind to an IL-9 polypeptide. Non-limiting examples of known antibodies that immunospecifically bind to an IL-9 polypeptide include 4D4, 4D4H2-1 D11, 4D4com-XF-9, 4D4com-2F9, 7F3, 71A10, 7F3 22D3, 7F3com-2H2, 7F3com-3H5 or 7F3com-3D4.

In specific embodiments, antibodies of the invention bind antigenic epitope-bearing peptides and polypeptides of IL-9, and said antigenic epitope-bearing peptides and polypeptides comprise or consist of an amino acid sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50 contiguous amino acid residues, and, preferably, between about 15 to about 30 contiguous amino acids of IL-9 found in any species. Preferred polypeptides comprising immunogenic or antigenic epitopes are at least 8, at least 10, at least 15, at least 20, at least 25, at least at least 30, or at least 35 amino acid residues in length.

IL-9 epitope-bearing peptides, polypeptides, and fragments thereof may be produced by any conventional means. See, e.g., Houghten, R. A. (1985) "General method for the rapid solid-phase synthesis of large numbers of peptides: specificity of antigen-antibody interaction at the level of individual amino acids," Proc. Natl. Acad. Sci. USA 82:5 13 1-5 135; this "Simultaneous Multiple. Peptide Synthesis (SMPS)" process is further described in U.S. Pat. No. 4,631, 211 to Houghten et al. (1986).

5.1.1.2 Antibodies that Immunospecifically Bind to IL-9R

Antibodies that antagonize IL-9 activity and/or expression by binding to IL-9R are well-known in the art. Examples of known antibodies that immunospecifically bind to IL-9R include, but are not limited to, AH9R2 (IgG2A), AH9R2 (IgG2A), and AH9R7 (IgG2B) (as described in Smedt et al., 2000, J. Immunol. 164:1761-1767, which is incorporated herein by reference in its entirety), MAB290, AF290, BAF290, and 290-R9/CF (R & D Systems), and SC-698, SC-1030, and SC-699 (Santa Cruz Biotechnology, Inc.).

The invention encompasses antibodies that bind to either or both the IL-9R ligand-specific alpha subunit ("IL-9Rα") and/or the common $\gamma_c$ chain also present in IL-2R, IL-4R, IL-7R, and IL-15R complexes. The invention also encompasses antibodies that immunospecifically bind to a soluble IL-9Rα and/or a membrane-bound IL-9Rα such as, for example, IL-9Rα expressed by T cells, B cells, mast cells, neutrophils, and/or eosinophils. The invention also encompasses antibodies that immunospecifically bind to the IL-9R or a subunit thereof bound to an IL-9 polypeptide.

In certain embodiments, antibodies that immunospecifically bind to an IL-9R or one or more subunits thereof modulate an activity and/or function of T cells, B cells, mast cells, neutrophils, and/or eosinophils. In other embodiments, antibodies that immunospecifically bind to an IL-9R or one or more subunits thereof function as IL-9 antagonists by inhibiting or reducing the infiltration of inflammatory cells into a tissue, joint, or organ of a subject and/or inhibit and/or reduce epithelial cell hyperplasia.

In one embodiment, the antibodies that immunospecifically bind to an IL-9R or one or more subunits thereof inhibit and/or reduce the interaction between an IL-9 polypeptide and IL-9R or one or more subunits thereof by approximately 25%, preferably approximately 30%, approximately 35%, approximately 40%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo and/or in vitro assay described herein or well-known to one of skill in the art. In an alternative embodiment, antibodies that immunospecifically bind to an IL-9R or a subunit thereof does not inhibit the interaction between IL-9R or one or more subunits thereof and an IL-9 polypeptide in an in vivo and/or in vitro assay described herein or well-known to one of skill in the art. In another embodiment, antibodies that immunospecifically bind to an IL-9R or one or more subunits thereof inhibit the interaction between the IL-9R or one or more subunits thereof and an IL-9 polypeptide by less than 20%, less than 15%, less than 10%, or less than 5% as determined using, for example, an immunoassay such as an ELISA.

The present invention encompasses antibodies that immunospecifically bind to an IL-9R or one or more subunits thereof and do not induce cytokine expression and/or release in an in vivo and/or in vitro assay described herein or well-known to one of skill in the art. In one embodiment, antibodies that immunospecifically bind to an IL-9R or one or more subunits thereof and do not induce an increase in the concentration cytokines such as, e.g., IL-4, IL-5, IL-6, IL-10, and IL-23 in the serum of a subject administered an antibody that immunospecifically binds to an IL-9R or one or more subunits thereof. In an alternative embodiment, antibodies that immunospecifically bind to an IL-9R or one or more subunits thereof induce cytokine expression and/or release in an in vitro and/or in vivo assay described herein or well-known to one of skill in the art. In a specific embodiment, an antibody that immunospecifically binds to an IL-9R or one or more subunits thereof induces an increase in the concentration of cytokines such as, e.g., IFN-γ, IL-2, IL-7, and IL-15 in the serum of a subject administered an antibody that immunospecifically binds to an IL-9R or one or more subunits thereof. In another specific embodiment, an antibody that immunospecifically binds to an IL-9R or one or more subunits thereof induces an increase in the concentration of cytokines produced by Th1 cells, such as IFN-γ and IL-12, in a subject administered an antibody that immunospecifically binds to an IL-9R or one or more subunits thereof. In an alternative embodiment, antibodies that immunospecifically bind to an IL-9R or one or more subunits thereof reduce or inhibit cytokine expression and/or release in an in vitro and/or an in vivo assay described herein or well-known to one of skill in the art. In a specific embodiment, an antibody that immunospecifically binds to an IL-9R or one or more subunits thereof induces a decrease in the concentration of cytokines such as, e.g., IL-4, IL-5, IL-6, IL-7, IL-10, IL-13, and TNF-α in the serum of a subject administered an antibody that immunospecifically binds to an IL-9R or one or more subunits thereof. In another specific embodiment, an antibody that immunospecifically binds to an IL-9R or one or more subunits thereof induces a decrease in the concentration of cytokines produced by mast cells, such as TNF-α, IL-4, and IL-13, in the serum of a subject administered an antibody that immunospecifically binds to an IL-9R or one or more subunits thereof. In another specific embodiment, an antibody that immunospecifically binds to an IL-9R or one or more subunits thereof induces a decrease in the concentration of cytokines produced by Th2 cells, such as IL-4, IL-5, IL-13, and IL-10, in the serum of a subject administered an antibody that immunospecifically binds to an IL-9R or one or more subunits thereof. Serum concentrations of a cytokine can be measured by any technique well-known to one of skill in the art such as, e.g., ELISA.

In certain embodiments, antibodies that immunospecifically bind to an IL-9R or one or more subunits thereof inhibit or reduce expression and/or release of the products of mast cell activation and/or mast cell degranulation in an in vivo and/or in vitro assay described herein or well-known to one of skill in the art. In an alternative embodiment, antibodies that immunospecifically bind to an IL-9R or one or more subunits thereof induce a decrease in the concentration of the products of mast cell activtion and/or mast cell degranulation in the serum of a subject administered an antibody that immunospecifically binds to an IL-9R or one or more subunits thereof. Non-limiting examples of products of mast cell activation and/or mast cell degranulation are mast cell proteases (e.g., tryptase and chymase), leukotrienes (e.g., C4, D4, and E4) and cytokines (e.g., TNF-α, IL-4, and IL-13). Serum concentrations of products of mast cell degranuation and/or mast cell activation can be measured by any technique well-known to one of skill in the art such as, e.g., ELISA.

In one embodiment, antibodies that immunospecifically bind to an IL-9R or one or more subunits thereof reduce and/or inhibit proliferation of inflammatory cells (e.g., mast cells, T cells, B cells, macrophages, neutrophils, basophils, and/or eosinophils) by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In another embodiment, antibodies that immunospecifically bind to an IL-9R or one or more subunits thereof reduce and/or inhibit infiltration of inflammatory cells into the upper and/or lower respiratory tracts by at least at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet another embodiment, antibodies that immunospecifically bind to an IL-9R or one or more subunits thereof reduce and/or inhibit infiltration of inflammatory cells into the upper and/or respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vivo assay described herein or well known in the art and reduce and/or inhibit proliferation of inflammatory cells by at least by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, antibodies that immunospecifically bind to an IL-9R or one or more subunits thereof reduce mast cell degranulation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, antibodies that immunospecifically bind to an IL-9R or one or more subunits thereof inhibit and/or reduce mast cell activation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, antibodies that immunospecifically bind to an IL-9R or one or more subunits thereof inhibit and/or reduce the expression and/or release of products of mast cell activation and/or degranulation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In a specific embodiment, antibodies that immunospecifically bind to an IL-9R or one or more subunits thereof inhibit and/or reduce the expression, activity, serum concentration, and/or release of mast cell proteases, such as cymase and tryptase, by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In another specific embodiment, antibodies that immunospecifically bind to an IL-9R or one or more subunits thereof inhibit and/or reduce the expression, activity, serum concentration, and/or release of mast cell leukotrienes, such as C4, D4, and E4 by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In another specific embodiment, antibodies that immunospecifically bind to an IL-9R or one or more subunits thereof inhibit and/or reduce the expression, activity, serum concentration, and/or release of mast cell cytokines, such as TNF-α; IL-4, and IL-13 by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In other embodiments, antibodies that immunospecifically bind to an IL-9R or one or more subunits thereof inhibit and/or reduce mast cell infiltration in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known in the art. In other embodiments, antibodies that immunospecifically bind to an IL-9R or one or more subunits thereof inhibit and/or reduce mast cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, antibodies that immunospecifically bind to an IL-9R or one or more subunits thereof inhibit and/or reduce mast cell infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vivo assay described herein or well known in the art and inhibit and/or reduce mast cell proliferation at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In other embodiments, antibodies that immunospecifically bind to an IL-9R or one or more subunits thereof inhibit and/or reduce infiltration of mast cell precursors in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known in the art. In other embodiments, antibodies that immunospecifically bind to an IL-9R or one or more subunits thereof inhibit and/or reduce proliferation of mast cell precursors by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, antibodies that immunospecifically bind to an IL-9R or one or more subunits thereof inhibit and/or reduce infiltration of mast cell precursors into the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vivo assay described herein or well known in the art and inhibit and/or reduce proliferation of mast cell precursors at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, antibodies that immunospecifically bind to an IL-9R or one or more subunits thereof mediate depletion of peripheral blood T-cells by inducing an increase in apoptosis of T-cells, particularly Th2 cells. In another embodiment, antibodies that immunospecifically bind to an IL-9R or one or more subunits thereof mediate inhibit and/or reduce Th1 and Th2 differentiation by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In certain embodiments, antibodies that immunospecifically bind to an IL-9R or one or more subunits thereof inhibit and/or reduce T cell infiltration, particularly Th2 cell infiltration, in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay well-known to one of skill in the art. In other embodiments, antibodies that immunospecifically bind to an IL-9R or one or more subunits thereof inhibits and/or reduce T cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In yet other embodiments, antibodies that immunospecifically bind to an IL-9R or one or more subunits thereof inhibit and/or reduce T cell infiltration, particularly Th2 cell infiltration, in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98%, inhibit and/or reduce T cell proliferation, particularly Th2 cell proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98%, and/or increases apoptosis of T cells relative to a control such as PBS in an in vivo and/or in vitro assay described herein or well-known to one of skill in the art.

In certain embodiments, antibodies that immunospecifically bind to an IL-9R reduce B cell infiltration, in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, antibodies that immunospecifically bind to an IL-9R inhibit and/or reduce B cell proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assays described herein or well-known to one of skill in the art. In other embodiments, antibodies that immunospecifically bind to an IL-9R inhibit and/or reduce B cell infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibit and/or reduce B cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, antibodies that bind to an IL-9R reduce macrophage infiltration, in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein and/or well-known to one of skill in the art. In other embodiments, antibodies that bind to an IL-9R reduce and/or inhibit macrophage proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assays described herein or well-known to one of skill in the art. In other embodiments, antibodies that immunospecifically bind to an IL-9R inhibit and/or reduce macrophage infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibit and/or reduce macrophage proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, antibodies that bind to an IL-9R reduce eosinophil infiltration, in the upper and/or lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, antibodies that bind to an IL-9R reduce and/or inhibit eosinophil proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assays described herein or well-known to one of skill in the art. In other embodiments, antibodies that immunospecifically bind to an IL-9R inhibit and/or reduce eosinophil infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibit and/or reduce eosinophil proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In certain embodiments, antibodies that immunospecifically bind to an IL-9R reduce neutrophil infiltration, in the upper and lower respiratory tracts by at least 25%, preferably at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art. In other embodiments, antibodies that immunospecifically bind to an IL-9R inhibit and/or reduce neutrophil proliferation, by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assays described herein or well-known to one of skill in the art. In other embodiments, antibodies that immunospecifically bind to an IL-9R inhibit and/or reduce neutrophil infiltration in the upper and/or lower respiratory tracts by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art and inhibit and/or reduce neutrophil proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo or in vitro assay described herein or well-known to one of skill in the art.

In a preferred embodiment, an antibody that immunospecifically binds to an IL-9R or one or more subunits thereof neutralizes or inhibits IL-9-mediated biological effects including, but not limited to, inflammatory cell recruitment, epithelial hyperplasia, mucin production of epithelial cells, and mast cell activation, degranulation, proliferation, and/or infiltration.

In a specific embodiment, an antibody that immunospecifically binds to an IL-9R or one or more subunits thereof acts synergistically with a proteinaceous agent (e.g., a peptide, a polypeptide, and a protein (including an antibody)) and/or a non-proteinaceous agent that antagonizes the expression, function, and/or activity of IgE to reduce or inhibit the activation, degranulation, proliferation, and/or infiltration of mast cells by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assays described herein or well-known to one of skill in the art.

In another embodiment, an antibody that immunospecifically binds to an IL-9R or one or more subunits thereof acts synergistically with a proteinaceous agent (e.g., a peptide, a polypeptide, and a protein (including an antibody)) and/or a non-proteinaceous agent that antagonizes the expression, function, and/or activity of a mast cell protease to reduce or inhibit activation, degranulation, proliferation, and/or infiltration of mast cells by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

In another embodiment, an antibody that immunospecifically binds to an IL-9R or one or more subunits thereof acts synergistically with a proteinaceous agent (e.g., a peptide, polypeptide, and protein (including an antibody)) and/or a non-proteinaceous agent that antagonizes the expression, function and/or activity of stem cell factor to reduce or inhibit activation, degranulation, proliferation, and/or infiltration of mast cells by at least 25%, preferably, at least 30%, at least 35%, at least 40%, at least 50%, at least 55%, at least 60%, at least 65%, at least 70%, at least 75%, at least 80%, at least 85%, at least 90%, at least 95%, or at least 98% relative to a control such as PBS in an in vivo and/or in vitro assay described herein or well-known to one of skill in the art.

The present invention provides for antibodies that have a high binding affinity for an IL-9R or one or more subunits thereof. In a specific embodiment, an antibody that immunospecifically binds to an IL-9R or one or more subunits thereof has an association rate constant or $k_{on}$ rate

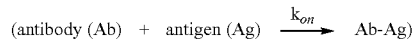

of at least $10^5$ $M^{-1}s^{-1}$, at least $5 \times 10^5 M^{-1}s^{-1}$, at least $10^6$ $M^{-1}s^{-1}$, at least $5 \times 10^6$ $M^{-1}s^{-1}$, at least $10^7$ $M^{-1}s^{-1}$, at least $5 \times 10^7$ $M^{-1}s^{-1}$, or at least $10^8$ $M^{-1}s^{-1}$. In a preferred embodiment, an antibody that immunospecifically binds to an IL-9R or one or more subunits thereof has a $k_{on}$ of at least $2 \times 10^5$ $M^{-1}s^{-1}$, at least $5 \times 10^5$ $M^{-1}s^{-1}$, at least $10^6$ $M^{-1}s^{-1}$, at least $5 \times 10^6$ $M^{-1}s^{-1}$, at least $10^7$ $M^{-1}s^{-1}$, at least $5 \times 10^7$ $M^{-1}s^{-1}$, or at least $10^8$ $M^{-1}s^{-1}$.

In another embodiment, an antibody that immunospecifically binds to an IL-9R or one or more subunits thereof has a $k_{off}$ rate

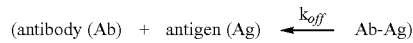

of less than $10^{-1}$ $s^{-1}$, less than $5 \times 10^{-1}$ $s^{-1}$, less than $10^{-2}$ $s^{-1}$, less than $5 \times 10^{-2}$ $s^{-1}$, less than $10^{-3}$ $s^{-1}$, less than $5 \times 10^{-3}$ $s^{-1}$, less than $10^{-4}$ $s^{-1}$, less than $5 \times 10^{-4}$ $s^{-1}$, less than $10^{-5}$ $s^{-1}$, less than $5 \times 10^{-5}$ $s^{-1}$, less than $10^{-6}$ $s^{-1}$, less than $5 \times 10^{-6}$ $s^{-1}$, less than $10^{-7}$ $s^{-1}$, less than $5 \times 10^{-7}$ $s^{-1}$, less than $10^{-8}$ $s^{-1}$, less than $5 \times 10^{-8}$ $s^{-1}$, less than $10^{-9}$ $s^{-1}$, less than $5 \times 10^{-9}$ $s^{-1}$, or less than $10^{-10}$ $s^{-1}$. In a preferred embodiment, an antibody that immunospecifically binds to an IL-9R or one or more subunits thereof has a $k_{on}$ of less than $5 \times 10^{-4}$ $s^{-1}$, less than $10^{-5}$ $s^{-1}$, less than $5 \times 10^{-5}$ $s^{-1}$, less than $10^{-6}$ $s^{-1}$, less than $5 \times 10^{-6}$ $s^{-1}$, less than $10^{-7}$ $s^{-1}$, less than $5 \times 10^{-7}$ $s^{-1}$, less than $10^{-8}$ $s^{-1}$, less than $5 \times 10^{-8}$ $s^{-1}$, less than $10^{-9}$ $s^{-1}$, less than $5 \times 10^{-9}$ $s^{-1}$, or less than $10^{-10}$ $s^{-1}$.

In another embodiment, an antibody that immunospecifically binds to an IL-9R or one or more subunits thereof has an affinity constant or $K_a$ ($k_{on}/k_{off}$) of at least $10^2$ $M^{-1}$, at least $5 \times 10^2$ $M^{-1}$, at least $10^3$ $M^{-1}$, at least $5 \times 10^3$ $M^{-1}$, at least $10^4$ $M^{-1}$, at least $5 \times 10^4$ $M^{-1}$, at least $10^5$ $M^{-1}$, at least $5 \times 10^5$ $M^{-1}$, at least $10^6$ $M^{-1}$, at least $5 \times 10^6$ $M^{-1}$, at least $10^7$ $M^{-1}$, at least $5 \times 10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, at least $5 \times 10^{12}$ $M^{-1}$, at least $10^{13}$ $M^{-1}$, at least $5 \times 10^{13}$ $M^{-1}$, at least $10^{14}$ $M^{-1}$, at least $5 \times 10^{14}$ $M^{-1}$, at least $10^{15}$ $M^{-1}$, or at least $5 \times 10^{15}$ $M^{-1}$. In yet another embodiment, an antibody that immunospecifically binds to an IL-9R or one or more subunits thereof has a dissociation constant or $K_d$ ($k_{off}/k_{on}$) of less than $10^{-2}$ M, less than $5\times10^{-2}$ M, less than $10^{-3}$ M, less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M.

5.1.1.3 Antibodies Having Increased Half-Lives

The present invention provides for antibodies that are IL-9 antagonists which have an extended half-life in vivo. In particular, the present invention provides antibodies that are IL-9 antagonists which have a half-life in a subject, preferably a mammal and most preferably a human, of greater than 3 days, greater than 7 days, greater than 10 days, preferably greater than 15 days, greater than 25 days, greater than 30 days, greater than 35 days, greater than 40 days, greater than 45 days, greater than 2 Months, greater than 3 months, greater than 4 months, or greater than 5 months.

To prolong the serum circulation of antibodies (e.g., monoclonal antibodies, single chain antibodies and Fab fragments) in vivo, for example, inert polymer molecules such as high molecular weight polyethyleneglycol (PEG) can be attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein.

Antibodies having an increased half-life in vivo can also be generated introducing one or more amino acid modifications (i.e., substitutions, insertions or deletions) into an IgG constant domain, or FcRn binding fragment thereof (preferably a Fc or hinge-Fc domain fragment). See, e.g., International Publication No. WO 98/23289; International Publication No. WO 97/34631; International Publication No. WO 02/060919; and U.S. Pat. No. 6,277,375, each of which is incorporated herein by reference in its entirety.

Further, antibodies can be conjugated to albumin in order to make the antibody or antibody fragment more stable in vivo or to increase the half life of the antibody or antibody fragment in vivo. The techniques to produce such an antibody conjugate are well-known in the art, see e.g., International Publication Nos. WO 93/15199, WO 93/15200, and WO 01/77137; and European Patent No. EP 413, 622, all of which are incorporated herein by reference.

5.1.1.4 Antibody Conjugates

The present invention provides antibodies or fragments thereof that are IL-9 antagonists recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)₂ Fragment, a VH domain, a VH CDR, a VL domain or a VL CDR) and a heterologous protein, polypeptide, or peptide. Preferably, the heterologous protein, polypeptide, or peptide that the antibody or antibody fragment is fused to is useful for targeting the antibody to respiratory epithelial cells, mast cells, neutrophils, eosinophils, B cells, macrophages, or activated T cells. For example, an antibody that immunospecifically binds to a cell surface receptor expressed by a particular cell type (e.g., a respiratory epithelial cell, a mast cell, a neutrophil, an eosinophil, a B cell, macrophages, or an activated T cell) may be fused or conjugated to an antibody or fragment of the invention. In a specific embodiment, the IL-9 antagonist is fused or conjugated with an anti-stem cell factor or an anti-kit ligand. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154: 5590-5600; and Vil et al., 1992, Proc. Natl. Acad. Sci. USA 89: 11337-11341 (said references are incorporated herein by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287: 265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that is an IL-9 antagonist may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86: 821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37: 767), and the "flag" tag.

In other embodiments, antibodies of the present invention or fragments thereof conjugated to a diagnostic or detectable agent. Such antibodies can be useful for monitoring or prognosing the onset, development, progression and/or severity of a respiratory condition (e.g., a respiratory infection) as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$s), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and nonradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cis-dichlorodiamine platinum (II) (DDP) cisplatin); anthracyclines (e.g., daunorubicin (formerly daunomycin) and doxorubicin); antibiotics (e.g., dactinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan); kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof) and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-895 If; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate); HMG-CoA reductase inhibitors (e.g., lovastatin, simvastatin, atorvastatin, pravastatin, fluvastatin, statin, cerivastatin, lescol, lupitor, rosuvastatin and atorvastatin); and pharmaceutically acceptable salts, solvates, clathrates, and prodrugs thereof (see, e.g., Rothenberg, M. L., Annals of Oncology 8:837-855 (1997); and Moreau, P., et al., J. Med. Chem. 41:1631-1640 (1998)); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); and tositumomab (BEXXAR®)) and phamaceutically acceptable salts, solvates, clathrates, and prodrugs thereof.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International publication No. WO 97/33899), AIM II (see, International Publication No. WO 97/34911), Fas Ligand (Takahashi et al., 1994, J. Immunol., 6:1567-1574), and VEGF (see, International publication No. WO 99/23105); or a biological response modifier such as, for example, a lymphokine (e.g., interferon gamma ("IFN-γ"), interleukin-1 ("IL-1"), interleukin-2 ("IL-2"), interleukin-6 ("IL-6"), interleukin-12 ("IL-12"), interleukin-23 ("IL-23"), granulocyte macrophage colony stimulating factor ("GM-CSF"), and granulocyte colony stimulating factor ("G-CSF")), or a growth factor (e.g., growth hormone ("GH")). In a specific embodiment, the IL-9 antagonist (e.g., an antibody that is an IL-9 antagonist) is conjugated to a leukotriene antagonist (e.g., montelukast, zafirlukast, pranlukast, and zyleuton).

Moreover, an antibody can be conjugated to therapeutic moieties such as a radioactive metal ion, such as alpha-emiters such as $^{213}$Bi or macrocyclic chelators useful for conjugating radiometal ions, including but not limited to, $^{131}$In, $^{131}$L, $^{131}$Y, $^{131}$Ho, $^{131}$Sm, to polypeptides or any of those listed supra. In certain embodiments, the macrocyclic chelator is 1,4,7,10-tetraazacyclododecane-N,N',N",N'"-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Alternatively, an antibody can be conjugated to a second antibody to form an antibody heteroconjugate as described by Segal in U.S. Pat. No. 4,676,980, which is incorporated herein by reference in its entirety.

The therapeutic moiety or drug conjugated to an IL-9 antagonist or fragment thereof should be chosen to achieve the desired prophylactic or therapeutic effect(s) for a particular respiratory condition in a subject. A clinician or other medical personnel should consider the following when deciding on which therapeutic moiety or drug to conjugate to an IL-9 antagonist or fragment thereof that: the nature of the disease, the severity of the disease, and the condition of the subject.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.1.2 Antisense

The present invention encompasses antisense nucleic acid molecules, i.e., molecules which are complementary to a sense nucleic acid encoding an IL-9 polypeptide or an IL-9R subunit, e.g., complementary to the coding strand of a double stranded cDNA molecule or complementary to an mRNA sequence. Accordingly, an antisense nucleic acid can hydrogen bonded to a sense nucleic acid. The antisense nucleic acid can be complementary to an entire coding strand or to only a portion thereof, e.g., all or part of the protein coding region (or open reading frame). Non-limiting examples of antisense for IL-9 are 5'-cgaagcatcttgacagcgg-3' (SEQ ID NO.:61), 5'-tccagaagac tcttcagaaa tgtcagcgcg-3' (SEQ ID NO.:62), and 5'-tttatttcaa aataaagaca tacaatgtta-3' (SEQ ID NO.:63). An antisense nucleic acid molecule can be antisense to all or part of a non-coding region of the coding strand of a nucleotide sequence encoding a polypeptide of the invention. The non-coding regions include the 5' and 3' sequences which flank the coding region and are not translated into amino acids.

An antisense oligonucleotide can be, for example, about 5, 10, 15, 20, 25, 30, 35, 40, 45, or 50 contiguous nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an IL-9 polypeptide or IL-9R subunit to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. In a specific embodiment, the antisense molecule is modified to bind to the IgE (FCε R I) receptor or one or more subunits thereof on the mast cell. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an anomeric nucleic acid molecule. An anomeric nucleic acid molecule forms specific double-stranded hybrids with complementary RNA in which, contrary to the usual units, the strands run parallel to each other (Gaultier et al. (1987) Nucleic Acids Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

5.1.3 Peptides, Polypeptides, and Fusion Proteins that Compete with or Block IL-9 Binding to IL-9R The present invention encompasses peptides, polypeptides, and fusion proteins that are IL-9 antagonists. In particular, the present invention encompasses peptides, polypeptides, and fusion proteins that mimic an IL-9 polypeptide and compete with or block binding of an IL-9 polypeptide to IL-9R. The invention also encompasses peptides, polypeptides, and fusion proteins of the invention bind to an IL-9R or a subunit thereof and compete with or block the binding of IL-9 polypeptide to IL-9R. In a specific embodiment, a peptide, polypeptide, or fusion protein that inhibits or reduces the interaction between an IL-9 polypeptide and an IL-9R by approximately 25%, preferably approximately 30%, approximately 35%, approximately 40%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo or in vitro assay described herein or well-known to one of skill in the art. One non-limiting example of a polypeptide that competes with or blocks the binding of an IL-9 polypeptide to an IL-9R is soluble IL-9R, such as rhIL-9R described by Hossain et al. (1998 Acta Virol 42(1):47-53). In an alternative embodiment, a peptide, a polypeptide, or a fusion protein that competes with or blocks the binding of an IL-9 polypeptide to an IL-9R does not significantly inhibit and/or reduce the interaction between an IL-9 polypeptide and an IL-9R relative to a control such as PBS in an in vivo or in vitro assay described herein or well-known to one of skill in the art.

In a specific embodiment, a peptide, a polypeptide, or a fusion protein immunospecifically binds to the IL-9Rα receptor and inhibits or reduces the interaction between an IL-9 polypeptide and an IL-9R by approximately 25%, preferably approximately 30%, approximately 35%, approximately 40%, approximately 45%, approximately 50%, approximately 55%, approximately 60%, approximately 65%, approximately 70%, approximately 75%, approximately 80%, approximately 85%, approximately 90%, approximately 95%, or 98% relative to a control such as PBS in an in vivo or in vitro assay described herein or well-known to one of skill in the art. In a specific embodiment, a peptide, a polypeptide, or a fusion protein immunospecifically binds to the IL-9R γ receptor and inhibits or reduces the interaction between an IL-9 polypeptide and an IL-9R by approximately 25%, approximately 30%, approximately 35%, approximately 40%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo or in vitro assay described herein or well-known to one of skill in the art.

In one embodiment, a peptide, a polypeptide, or a fusion protein that immunospecifically binds to an IL-9 polypeptide and competes with or blocks the binding of the IL-9 polypeptide to an IL-9R comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of an IL-9R subunit or a fragment thereof. In another embodiment, a peptide, a polypeptide, or a fusion protein that immunospecifically binds to an IL-9R comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of an IL-9 polypeptide or fragment thereof.

Peptides, polypeptides, and fusion proteins that antagonize IL-9 can be produced by various methods known in the art, see, e.g., the methods described in Nakanishi et al., 1993, Gene 137:51-56; Merrifield, 1963, J. AM. Chem. Soc. 15:2149-2154; Neurath, H., et al., Eds., *The Proteins*, Vol. II, 3d ed., pp. 105-237, Academic Press, New York, N.Y. (1976). For example, a peptide corresponding to a fragment of an IL-9 polypeptide or an IL-9R or one or more subunits thereof which comprises the desired domain can be synthesized by use of a peptide synthesizer. Furthermore, if desired, nonclassical amino acids or chemical amino acid analogs can be introduced as a substitution or addition into an IL-9 polypeptide or IL-9R sequence. Non-classical amino acids include, but are not limited to, D-isomers of the common amino acids, α-amino isobutyric acid, 4-aminobutyric acid, hydroxyproline, sarcosine, citrulline, cysteic acid, t-butylglycine, t-butylalanin, phenylglycine, cyclohexlalanine, β-alanine, and designer amino acids (e.g., β-methyl amino acids, α-methyl amino acids, and Nα-methyl amino acids).

A peptide, a polypeptide, or a fusion protein that antagonizes IL-9 may be isolated and purified by standard methods including chromatography (e.g., ion exchange, affinity, and sizing column chromatography), centrifugation, differential solubility, or by any other standard technique for the purification of peptides, polypeptides, or fusion proteins. The functional properties may be evaluated using any suitable assay described herein or well-known in the art including, but not limited to, competitive and non-competitive assay systems using techniques such as radioimmunoassays, ELISA, "sandwich" immunoassays, immunoradiometric assays, in situ immunoassays (e.g., using colloidal gold, enzyme, or radioisotope labels), western blots, immunofluorescense assays, and immunoelectrophoresis assays.

The production and use of derivatives, analogs, and fragments of peptides, polypeptides, and fusion proteins that antagonize IL-9 Are within the scope of the present invention. In a specific embodiment, the derivative, analog, or fragment is functionally active, i.e., capable of exhibiting one or more functional activities associated with a full-length IL-9 polypeptide and/or IL-9R or a subunit thereof. Derivatives, analogs, and fragments of peptides, polypeptides, and fusion proteins that antagonize IL-9 can be tested for the desired activity by procedures described herein or well-known in the art. In one specific embodiment, peptide libraries can be screened to select a peptide with the desired activity; such screening can be carried out by assaying, e.g., binding to IL-9 polypeptide, binding to IL-9R or one or more subunits thereof or a reduction in the binding of an IL-9 polypeptide to an IL-9R or a subunit thereof.

In particular, derivatives of peptides, polypeptides, and fusion proteins that antagonize IL-9 can be made by altering the sequences of said peptides, polypeptides, and fusion proteins by substitutions, additions, or deletions that provide for functionally equivalent molecules. The derivatives peptides, polypeptides, and fusion proteins that antagonize IL-9 thereof can be made by altering the sequences of said peptides, polypeptides, and fusion proteins by substitutions, additions, or deletions that provide for functionally equivalent molecules. The invention encompasses derivatives including, but not limited to, those containing all or part of the amino acid sequence of a peptide, polypeptide, or fusion protein as the primary amino acid sequence, including altered sequences in which a functionally equivalent amino acid residues are substituted for residues within the sequence resulting in a silent change. For example, one or more amino acid residues within the sequence can be substituted by other amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tryosine, asapragine, and glutamine. The positively charged (basic) amino acids include argininge, lysine, and histidine. The negatively charged (acidic) amino acids include aspartic acid and glutamic acid.

Included within the scope of the invention are peptides, polypeptides, and fusion proteins that antagonize IL-9 which are differentially modified during or after translation, e.g., by glycosylation, acetylation, phosphorylation, amidation, derivatization by known protecting/blocking groups, proteolytic cleavage, linkage to an antibody molecule or other cellular ligand. Any of numerous chemical modification may be carried out by known techniques, including, but not limited to specific chemical cleavage by cyanogen bromide, trypsin, chymotrypsin, papin, V8 protease, $NABH_4$ Acetylation, formylation, oxidation, reduction, and metabolic synthesis in the presence of tunicamycin.

5.1.3.1 Peptide, Polypeptide, and Fusion Protein Conjugate

The present invention also encompasses peptides, polypeptides, and fusion proteins that antagonize IL-9 conjugated or fused to, e.g., a peptide, to facilitate purification. In a specific embodiment, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, a hexa-histidine provides for convenient purification of a polypeptide or peptide. Other peptide tags useful for purification include, but are not limited to, the hemagglutinin ("HA") tag, which corresponds to an epitope derived from the influenza hemagglutinin protein (Wilson et al., 1984, Cell 37:767) and the "flag" tag.

The present invention further encompasses peptides, polypeptides, and fusion proteins that antagonize IL-9 conjugated to a therapeutic moiety. A peptide, a polypeptide, or a fusion protein that antagonize IL-9 May be conjugated to a therapeutic moiety such as cytotoxin, e.g., a cytostatic or cytocidal agent, an agent which has a potential therapeutic benefit, or a radioactive metal ion, e.g., alpha-emitters. A cytotoxin or cytotoxic agent includes any agent that is detrimental to cells. Examples of a cytotoxin or cytotoxic agent include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Other agents which have a potential therapeutic benefit include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, a peptide, a polypeptide, or a fusion protein that antagonize IL-9 may be conjugated to a therapeutic moiety or drug moiety that modifies a given biological response. Agents which have a potential therapeutic benefit or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, IFN-α IFN-β, NGF, PDGF, TPA, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105); or a biological response modifier such as, for example, a lymphokine (e.g., IL-1, IL-2, IL-6, IL-10, GM-CSF, and G-CSF), or a growth factor (e.g., GH)).

5.2 Agents Useful in Combination with IL-9 antagonists

The present invention provides methods for preventing, managing, treating, or ameliorating respiratory conditions comprising administering to a subject in need thereof one or more IL-9 antagonists alone or in combination with one or more therapies (e.g., one or more prophylactic or therapeutic agents) other than an IL-9 antagonist. The present invention also provides compositions comprising one or more IL-9 antagonists and one or more prophylactic or therapeutic agents other than IL-9 antagonists and methods of preventing, managing, treating, or ameliorating a respiratory condition or one or more symptoms thereof utilizing said compositions. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides) antibodies, synthetic or natural inorganic molecules, mimetic agents, and synthetic or natural organic molecules.

Any therapy which is known to be useful, or which has been used or is currently being used for the prevention, management, treatment, or amelioration of a respiratory condition or one or more symptoms thereof can be used in combination with an IL-9 antagonist in accordance with the invention described herein. See, e.g., Gilman et al., *Goodman and Gilman's: The Pharmacological Basis of Therapeutics*, 10th ed., McGraw-Hill, New York, 2001; *The Merck Manual of Diagnosis and Therapy*, Berkow, M. D. et al. (eds.), 17th Ed., Merck Sharp & Dohme Research Laboratories, Rahway, N.J., 1999; *Cecil Textbook of Medicine*, 20th Ed., Bennett and Plum (eds.), W. B. Saunders, Philadelphia, 1996 For information regarding therapies (e.g., prophylactic or therapeutic agents) which have been or are currently being used for preventing, treating, managing, or ameliorating a respiratory condition or one or more symptoms thereof. Examples of such agents include, but are not limited to, immunomodulatory agents, anti-inflammatory agents (e.g., adrenocorticoids, corticosteroids (e.g., beclomethasone, budesonide, flunisolide, fluticasone, triamcinolone, methlyprednisolone, prednisolone, prednisone, hydrocortisone), glucocorticoids, steroids, non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

5.2.1 Immunomodulatory Agents

Any immunomodulatory agent well-known to one of skill in the art may be used in the methods and compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments of the invention, an immunomodulatory agent modulates one aspect of the immune response. In other embodiments, an immunomodulatory agent modulates more than one aspect of the immune response. In a preferred embodiment of the invention, the administration of an immunomodulatory agent to a subject inhibits or reduces one or more aspects of the subject's immune response capabilities. In an alternative embodiment of the invention, the immunomodulatory agent enhances one or more aspects of a subject's immune response. In accordance with the invention, an immunomodulatory agent is not an IL-9 antagonist. In certain embodiments, an immunomodulatory agent is not an anti-inflammatory agent. In other embodiments, an immunomodulatory agent is a chemotherapeutic agent. In yet other embodiments, an immunomodulatory agent is an agent other than a chemotherapeutic agent.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)2 Fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators.

For clarification regarding T cell receptor modulators, cytokine receptor modulators, and mast cell modulators see Section 3.1. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 Antibodies (e.g., an anti-CD5 Ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 Antibodies (e.g., siplizumab (MedImmune, Inc., International Publication Nos. WO 02/098370 and WO 02/069904)), anti-CD11a antibodies (e.g., Xanelim (Genentech)), and anti-B7 Antibodies (e.g., IDEC-114) (IDEC))), CTLA4-immunoglobulin, and LFA-3TIP (Biogen, International Publication No. WO 93/08656 and U.S. Pat. No. 6,162,432).

Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin IL-2, IL-3, IL-4, IL-5, IL-6, IL-7, IL-8, IL-9, IL-10, IL-11, IL-12, IL-13, IL-15, IL-23, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax™ (Protein Design Labs)), anti-IL-3 receptor antibodies, anti-IL-4 receptor antibodies, anti-IL-6 receptor antibodies, anti-IL-10 receptor antibodies, anti-IL-12 receptor antibodies, anti-IL-13 receptor antibodies, anti-IL-15 receptor antibodies, and anti-IL-23 receptor antibodies), anti-cytokine antibodies (e.g., anti-IFN antibodies, anti-TNF-α antibodies, anti-IL-1β, antibodies, anti-IL-3 antibodies, anti-IL-6 antibodies, anti-IL-8 antibodies (e.g., ABX-IL-8 (Abgenix)), anti-IL-12 antibodies, anti-IL-13 antibodies, anti-IL-15 antibodies, and anti-IL-23 antibodies).

In a specific embodiment, a cytokine receptor modulator is IL-3, IL-4, IL-10, or a fragment thereof. In another embodiment, a cytokine receptor modulator is an anti-IL-1β antibody, anti-IL-6 antibody, anti-IL-12 receptor antibody, or anti-TNF-α antibody. In one embodiment, a TNF-α antagonist used in the compositions and methods of the invention is a soluble TNF-α receptor. In a specific embodiment, a TNF-α antagonist used in the compositions and methods of the invention is etanercept (ENBREL™; Immunex) or a fragment, derivative or analog thereof. In another embodiment, a TNF-α antagonist used in the compositions and methods of the invention is an antibody that immunospecifically binds to TNF-α. In a specific embodiment, a TNF-α antagonist used in the compositions and methods of the invention is infliximab (REMICADE®; Centacor) a derivative, analog or antigen-binding fragment thereof. In another embodiment, a cytokine receptor modulator is the extracellular domain of a TNF-α receptor or a fragment thereof. In certain embodiments, a cytokine receptor modulator is not a TNF-α antagonist.

In one embodiment, a cytokine receptor modulator is a mast cell modulator. In an alternative embodiment, a cytokine receptor modulator is not a mast cell modulator. Examples of mast cell modulators include, but are not limited to stem cell factor (c-kit receptor ligand) inhibitors (e.g., mAb 7H6, mAb 8H7A, pAb 1337, FK506, CsA, dexamthasone, and fluconcinonide), c-kit receptor inhibitors (e.g., STI 571 (formerly known as CGP 57148B)), mast cell protease inhibitors (e.g., GW-45, GW-58, wortmannin, LY 294002, calphostin C, cytochalasin D, genistein, KT5926, staurosproine, and lactoferrin), relaxin ("RLX"), IgE antagonists (e.g., antibodies rhuMAb-E25 omalizumab, HMK-12 and 6HD5, and mAB Hu-901), IL-3 antagonists, IL-4 antagonists, IL-10 antagonists, and TGF-beta.

An immunomodulatory agent may be selected to interfere with the interactions between the T helper subsets (TH1 or TH2) and B cells to inhibit neutralizing antibody formation. Antibodies that interfere with or block the interactions necessary for the activation of B cells by TH (T helper) cells, and thus block the production of neutralizing antibodies, are useful as immunomodulatory agents in the methods of the invention. For example, B cell activation by T cells requires certain interactions to occur (Durie et al., Immunol. Today, 15(9): 406-410 (1994)), such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

The CD40 ligand (CD40L)-CD40 interaction is a desirable point to block the immune response because of its broad activity in both T helper cell activation and function as well as the absence of redundancy in its signaling pathway. Thus, in a specific embodiment of the invention, the interaction of CD40L with CD40 is transiently blocked at the time of administration of one or more of the immunomodulatory agents. This can be accomplished by treating with an agent which blocks the CD40 ligand on the TH cell and interferes with the normal binding of CD40 ligand on the T helper cell with the CD40 antigen on the B cell. An antibody to CD40 ligand (anti-CD40L) (available from Bristol-Myers Squibb Co; see, e.g., European patent application 555,880, published Aug. 18, 1993) or a soluble CD40 molecule can be selected and used as an immunomodulatory agent in accordance with the methods of the invention.

An immunomodulatory agent may be selected to inhibit the interaction between TH1 cells and cytotoxic T lymphocytes ("CTLs") to reduce the occurrence of CTL-mediated killing. An immunomodulatory agent may be selected to alter (e.g., inhibit or suppress) the proliferation, differentiation, activity and/or function of the $CD4^+$ and/or $CD8^+$ T cells. For example, antibodies specific for T cells can be used as immunomodulatory agents to deplete, or alter the proliferation, differentiation, activity and/or function of $CD4^+$ and/or $CD8^+$ T cells.

In one embodiment of the invention, an immunomodulatory agent that reduces or depletes T cells, preferably memory T cells, is administered to a subject with a respiratory condition in accordance with the methods of the invention. See, e.g., U.S. Pat. No. 4,658,019. In another embodiment of the invention, an immunomodulatory agent that inactivates $CD8^+$ T cells is administered to a subject with a respiratory condition in accordance with the methods of the invention. In a specific embodiment, anti-CD8 antibodies are used to reduce or deplete $CD8^+$ T cells.

In another embodiment, an immunomodulatory agent which reduces or inhibits one or more biological activities (e.g., the differentiation, proliferation, and/or effector functions) of TH0, TH1, and/or TH2 subsets of $CD4^+$ T helper cells is administered to a subject with a respiratory condition in accordance with the methods of the invention. One example of such an immunomodulatory agent is IL-4. IL-4 enhances antigen-specific activity of TH2 cells at the expense of the TH1 cell function (see, e.g., Yokota et al, 1986 Proc. Natl. Acad. Sci., USA, 83:5894-5898; and U.S. Pat. No. 5,017,691). Other examples of immunomodulatory agents that affect the biological activity (e.g., proliferation, differentiation, and/or effector functions) of T-helper cells (in particular, TH1 and/or TH2 cells) include, but are not limited to, IL-2, IL-4, IL-5, IL-6, IL-10, IL-12, IL-13, IL-15, IL-23, and interferon (IFN)-γ.

In another embodiment, an immunomodulatory agent administered to a subject with a respiratory condition in accordance with the methods of the invention is a cytokine that prevents antigen presentation. In a specific embodiment, an immunomodulatory agent used in the methods of the invention is IL-10. IL-10 also reduces or inhibits macrophage action which involves bacterial elimination.

An immunomodulatory agent may be selected to reduce or inhibit the activation, degranulation, proliferation, and/or infiltration of mast cells. In certain embodiments, the immunomodulatory agent interferes with the interactions between mast cells and mast cell activating agents, including, but not limited to stem cell factors (c-kit ligands), IgE, IL-4, environmental irritants, and infectious agents. In a specific embodiment, the immunomodulatory agent reduces or inhibits the response of mast cells to environmental irritants such as, but not limited to pollen, dust mites, tobacco smoke, and/or pet dander. In another specific embodiment, the immunomodulatory agent reduces or inhibits the response of mast cells to infectious agents, such as viruses, bacteria, and fungi. Examples of mast cell modulators that reduce or inhibit the activation, degranulation, proliferation, and/or infiltration of mast cells include, but are not limited to, stem cell factor (c-kit receptor ligand) inhibitors (e.g., mAb 7H6, mAb 8H7A, and pAb 1337 (see Mendiaz et al., 1996, Eur J Biochem 293(3): 842-849), FK506 and CsA (Ito et al., 1999 Arch Dermatol Res 291(5):275-283), dexamthasone and fluconcinonide (see Finooto et al. J Clin Invest 1997 99(7):1721-1728)), c-kit receptor inhibitors (e.g., STI 571 (formerly known as CGP 57148B) (see Heinrich et al., 2000 Blood 96(3):925-932)), mast cell protease inhibitors (e.g., GW-45 and GW-58 (see see Temkin et al., 2002 J Immunol 169(5):2662-2669), wortmannin, LY 294002, calphostin C, and cytochalasin D (see Vosseller et al., 1997, Mol Biol Cell 1997:909-922), genistein, KT5926, and staurosproine (see Nagai et al. 1995, Biochem Biophys Res Commun 208(2):576-581), and lactoferrin (see He et al., 2003 Biochem Pharmacol 65(6):1007-1015)), relaxin ("RLX") (see Bani et al., 2002 Int Immunopharmacol 2(8):1195-1294), ), IgE antagonists (e.g., antibodies rhuMAb-E25 omalizumab (see Finn et al., 2003 J Allergy Clin Immuno 111(2):278-284; Corren et al., 2003 J Allergy Clin Immuno 111(1):87-90; Busse and Neaville, 2001 Curr Opin Allergy Clin Immuno 1(1):105-108; and Tang and Powell, 2001, Eur J Pediatr 160(12):696-704), HMK-12 and 6HD5 (see Miyajima et al., 2202 Int Arch Allergy Immuno 128(1):24-32), and mAB Hu-901 (see van Neerven et al., 2001 Int Arch Allergy Immuno 124(1-3):400), IL-3 antagonist, IL-4 antagonists, IL-10 antagonists, and TGF-beta (see Metcalfe et al., 1995, Exp Dermatol 4(4 Pt 2):227-230).

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

In accordance with the invention, one or more immunomodulatory agents are administered to a subject with a respiratory condition prior to, subsequent to, or concomitantly with an IL-9 antagonist. Preferably, one or more immunomodulatory agents are administered in combination with an IL-9 antagonist to a subject with a respiratory condition to reduce or inhibit one or more aspects of the immune response as deemed necessary by one of skill in the art. Any technique well-known to one skilled in the art can be used to measure one or more aspects of the immune response in a particular subject, and thereby determine when it is necessary to administer an immunomodulatory agent to said subject. In a preferred embodiment, a mean absolute lymphocyte count of approximately 500 cells/$mm^3$, preferably 600 cells/$mm^3$, 650 cells/$mm^3$, 700 cells/$mm^3$, 750 cells/$mm^3$, 800 cells/$mm^3$, 900 cells/mm³, 1000 cells/mm³, 1100 cells/mm³, or 1200 cells/mm³ is maintained in a subject. In another preferred embodiment, a subject with a respiratory condition is not administered an immunomodulatory agent if their absolute lymphocyte count is 500 cells/mm³ or less, 550 cells/mm³ or less, 600 cells/mm³ or less, 650 cells/mm³ or less, 700 cells/mm³ or less, 750 cells/mm³ or less, or 800 cells/mm³ or less.

In a preferred embodiment, one or more immunomodulatory agents are administered in combination with an IL-9 antagonist to a subject with a respiratory condition so as to transiently reduce or inhibit one or more aspects of the immune response. Such a transient inhibition or reduction of one or more aspects of the immune system can last for hours, days, weeks, or months. Preferably, the transient inhibition or reduction in one or more aspects of the immune response lasts for a few hours (e.g., 2 hours, 4 hours, 6 hours, 8 hours, 12 hours, 14 hours, 16 hours, 18 hours, 24 hours, 36 hours, or 48 hours), a few days (e.g., 3 days, 4 days, 5 days, 6 days, 7 days, or 14 days), or a few weeks (e.g., 3 weeks, 4 weeks, 5 weeks or 6 weeks). The transient reduction or inhibition of one or more aspects of the immune response enhances the prophylactic and/or therapeutic effect(s) of an IL-9 antagonist.

Nucleic acid molecules encoding proteins, polypeptides, or peptides with immunomodulatory activity or proteins, polypeptides, or peptides with immunomodulatory activity can be administered to a subject with a respiratory condition in accordance with the methods of the invention. Further, nucleic acid molecules encoding derivatives, analogs, or fragments of proteins, polypeptides, or peptides with immunomodulatory activity, or derivatives, analogs, or fragments of proteins, polypeptides, or peptides with immunomodulatory activity can be administered to a subject with a respiratory infection in accordance with the methods of the invention. Preferably, such derivatives, analogs, and fragments retain the immunomodulatory activity of the full-length, wild-type protein, polypeptide, or peptide.

Preferably, agents that are commercially available and known to function as immunomodulatory agents are used in the methods of the invention. The immunomodulatory activity of an agent can be determined in vitro and/or in vivo by any technique well-known to one skilled in the art, including, e.g., by CTL assays, proliferation assays, and immunoassays (e.g. ELISAs) for the expression of particular proteins such as co-stimulatory molecules and cytokines.

5.2.2 Anti-inflammatory Agents

Any anti-inflammatory agent, including agents useful in therapies for inflammatory disorders, well-known to one of skill in the art can be used in the compositions and methods of the invention. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), corticosteroids (e.g., methylprednisolone (MEDROL™)), cortisone, hydrocortisone, prednisone (PREDNISONE™ and DELTASONE™), prednisolone (PRELONE™ and PEDIAPRED™), triamcinolone, azulfidine, and inhibitors of eicosanoids (e.g., prostaglandins, thromboxanes, and leukotrienes (see Table 2, infra, for non-limiting examples of leukotriene and typical dosages of such agents)). In another embodiment, VITAXIN™ (MedImmune, Inc.), NUMAX™ (MedImmune, Inc.), palivizumab (MedImmune, Inc.), siplizumab (MedImmune, Inc.), an anti-EphA2 antibody (preferably that elicits EphA2 signaling) (see U.S. Patent Publication No. U.S. 2004/0028685A1, dated Feb. 12, 2004 and U.S. patent application Ser. No. 10/436/783, filed May 12, 2003, which are both incorporated by reference herein in their entireties) may be useful in therapies for inflammatory disorders.

In certain embodiments, the anti-inflammatory agent is an agent useful in the prevention, management, treatment, and/or amelioration of asthma or one or more symptoms thereof. Non-limiting examples of such agents include adrenergic stimulants (e.g., catecholamines (e.g., epinephrine, isoproterenol, and isoetharine), resorcinols (e.g., metaproterenol, terbutaline, and fenoterol), and saligenins (e.g., salbutamol)), adrenocorticoids, blucocorticoids, corticosteroids (e.g., beclomethadonse, budesonide, flunisolide, fluticasone, triamcinolone, methylprednisolone, prednisolone, and prednisone), other steroids, beta2-agonists (e.g., albtuerol, bitolterol, fenoterol, isoetharine, metaproterenol, pirbuterol, salbutamol, terbutaline, formoterol, salmeterol, and albutamol terbutaline), anti-cholinergics (e.g., ipratropium bromide and oxitropium bromide), IL-4 antagonists (including antibodies), IL-5 antagonists (including antibodies), IL-13 antagonists (including antibodies), PDE4-inhibitor, NF-Kappa-β inhibitor, VLA-4 inhibitor, CpG, anti-CD23, selectin antagonists (TBC 1269), mast cell protease inhibitors (e.g., tryptase kinase inhibitors (e.g., GW-45, GW-58, and genisteine), phosphatidylinositide-3' (PI3)-kinase inhibitors (e.g., calphostin C), and other kinase inhibitors (e.g., staurosporine) (see Temkin et al., 2002 J Immunol 169(5):2662-2669; Vosseller et al., 1997 Mol. Biol. Cell 8(5):909-922; and Nagai et al., 1995 Biochem Biophys Res Commun 208(2):576-581)), a C3 receptor antagonists (including antibodies), immunosuppressant agents (e.g., methotrexate and gold salts), mast cell modulator (e.g., cromolyn sodium (INTAL™) and nedocromil sodium (TILADE™)), and mucolytic agents (e.g., acetylcysteine)). In a specific embodiment, the anti-inflammatory agent is a leukotriene inhibitor (e.g., montelukast (SINGULAIR™), zafirlukast (ACCOLATE™), pranlukast (ONON™), or zileuton (ZYFLO™) (see Table 2)).

TABLE 2

Leukotriene Inhibitors for Asthma Therapy

| Leukotriene Inhibitors | Usual Daily Dosage |
| --- | --- |
| Montelukast (SINGULAIR ™) | 4 mg for 2-5 years old<br>5 mg for 6 to 15 years old<br>10 mg for 15 years and older |

TABLE 2-continued

Leukotriene Inhibitors for Asthma Therapy

| Leukotriene Inhibitors | Usual Daily Dosage |
| --- | --- |
| Zafirlukast (ACCOLATE ™) | 10 mg b.i.d. for 5 to 12 years old twice daily |
| | 20 mg b.i.d. for 12 years or older twice daily |
| Pranlukast (ONON ™) | Only avialable in Asia |
| Zyleuton (ZYFLO ™) | 600 mg four times a day for 12 years and older |

In certain embodiments, the anti-inflammatory agent is an agent useful in preventing, treating, managing, or ameliorating allergies or one or more symptoms thereof. Non-limiting examples of such agents include antimediator drugs (e.g., antihistamine, see Table 3 For non-limiting examples of antihistamine and typical dosages of such agents), corticosteroids, decongestants, sympathomimetic drugs (e.g., α-adrenergic and β-adrenergic drugs), TNX901 (Leung et al., 2003, N Engl J Med 348(11):986-993), IgE antagonists (e.g., antibodies rhuMAb-E25 omalizumab (see Finn et al., 2003 J Allergy Clin Immuno 111(2):278-284; Corren et al., 2003 J Allergy Clin Immuno 111(1):87-90; Busse and Neaville, 2001 Curr Opin Allergy Clin Immuno 1(1):105-108; and Tang and Powell, 2001, Eur J Pediatr 160(12):696-704), HMK-12 and 6HD5 (see Miyajima et al., 2202 Int Arch Allergy Immuno 128(1):24-32), and mAB Hu-901 (see van Neerven et al., 2001 Int Arch Allergy Immuno 124(1-3):400), theophylline and its derivatives, glucocorticoids, and immunotherapies (e.g., repeated long-term injection of allergen, short course desensitization, and venom immunotherapy).

TABLE 3

H₁ Antihistamines

| Chemical class and representative drugs | Usual daily dosage |
| --- | --- |
| Ethanolamine | |
| Diphehydramine | 25-50 mg every 4-6 hours |
| Clemastine | 0.34-2.68 mg every 12 hours |
| Ethylenediamine | |
| Tripelennamine | 25-50 mg every 4-6 hours |
| Alkylamine | |
| Brompheniramine | 4 mg every 4-6 hours; or 8-12 mg of SR form every 8-12 hour |
| Chlorpheniramine | 4 mg every 4-6 hours; or 8-12 mg of SR form every 8-12 hour |
| Triprolidine (1.25 mg/5 ml) | 2.5 mg every 4-6 hours |
| Phenothiazine | |
| Promethazine | 25 mg at bedtime |
| Piperazine | |
| Hydroxyzine | 25 mg every 6-8 hours |
| Piperidines | |
| Astemizole (nonsedating) | 10 mg/day |
| Azatadine | 1-2 mg every 12 hours |
| Cetirzine | 10 mg/day |
| Cyproheptadine | 4 mg every 6-8 hour |
| Fexofenadine (nonsedating) | 60 mg every 12 hours |
| Loratidine (nonsedating) | 10 mg every 24 hours |

Anti-inflammatory therapies and their dosages, routes of administration, and recommended usage are known in the art and have been described in such literature as the *Physician's Desk Reference* (57th ed., 2003) and *The Merk Manual* (17th ed., 1999).

5.2.3 Anti-Viral Agents

Any anti-viral agent well-known to one of skill in the art for the treatment, prevention, management, or amelioration of a respiratory condition or a symptom thereof (e.g., viral respiratory infection) can be used in the compositions and methods of the invention. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

In specific embodiments, the anti-viral agent is an antibody agent that is immunospecific for a viral antigen. As used herein, the term "viral antigen" includes, but is not limited to, any viral peptide, polypeptide and protein (e.g., RSV F glycoprotein, RSV G glycoprotein, influenza virus neuraminidase, influenza virus hemagglutinin, and herpes simplex virus glycoprotein (e.g., gB, gC, gD, and gE)) that is capable of eliciting an immune response. Antibodies useful in this invention for prevention, management, treatment, and/or amelioration of a viral infectious disease include, but are not limited to, antibodies against antigens of pathogenic viruses, including as examples and not by limitation: adenovirdiae (e.g., *mastadenovirus* and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory syncytial virus), and metapneumovirus (e.g., avian pneumovirus and human metapneumovirus)), picornaviridae (e.g., enterovirus, rhinovirus, hepatovirus (e.g., human hepatits A virus), *cardiovirus*, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, *lentivirus* (e.g. human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Specific examples of antibodies available useful for the prevention, management, treatment, and/or amelioration of a viral infectious disease include, but are not limited to, PRO542 (Progenics) which is a CD4 Fusion antibody useful for the treatment of HIV infection and palivizumab (MedImmune, Inc.; International Publication No. WO 02/43660) which is a humanized antibody useful for treatment of RSV.

See also U.S. Provisional Application No. 60/388,920, filed Jun. 14, 2002 entitled "Stabilized Anti-Respiratory Syncytial Virus (RSV) Antibody Formulations (NUMAX™)," U.S. patent application Ser. No. 10/461,863, filed Jun. 13, 2003 entitled "Stabilized Anti-Respiratory Syncytial Virus (RSV) Antibody Formulations (NUMAX™)," and International Pub. No. US03/18914, filed Jun. 16, 2003 entitled "Stabilized anti-Respiratory Syncytial Virus (RSV) Antibody Formulations (NUMAX™).

In a specific embodiment, the anti-viral agent used in the compositions and methods of the invention inhibits or reduces a pulmonary or respiratory virus infection, inhibits or reduces the replication of a virus that causes a pulmonary or respiratory infection, or inhibits or reduces the spread of a virus that causes a pulmonary or respiratory infection to other cells or subjects. In another specific embodiment, the anti-viral agent used in the compositions and methods of the invention inhibits or reduces infection by RSV, HMPV, or PIV, inhibits or reduces the replication of RSV, hMPV, or PIV, or inhibits or reduces the spread of RSV, hMPV, or PIV to other cells or subjects. Examples of such agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons. See U.S. Provisional Patent Application 60/398,475 Filed Jul. 25, 2002, entitled "Methods of Treating and Preventing RSV, HMPV, and PIV Using Anti-RSV, Anti-HMPV, and Anti-PIV Antibodies" and U.S. Patent Pub. No. U.S. 2004/0005544 A1, dated Jan. 8, 2004, entitled "Metapneumovirus Strains and Their Use in Vaccine Formulations and as Vectors For Expression of Antigenic Sequences," which are both incorporated herein by reference in their entirety.

In preferred embodiments, the viral infection is RSV and the anti-viral antigen is an antibody that immunospecifically binds to an antigen of RSV. In certain embodiments, the anti-RSV-antigen antibody immunospecifically binds to an RSV antigen of the Group A of RSV. In other embodiments, the anti-RSV-antigen antibody immunospecifically binds to an RSV antigen of the Group B of RSV. In other embodiments, the anti-RSV antigen antibody immunospecifically binds to an antigen of RSV of one Group and cross reacts with the analogous antigen of the other Group. In particular embodiments, the anti-RSV-antigen antibody immunospecifically binds to a RSV nucleoprotein, RSV phosphoprotein, RSV matrix protein, RSV small hydrophobic protein, RSV RNA-dependent RNA polymerase, RSV F protein, and/or RSV G protein. In additional specific embodiments, the anti-RSV-antigen antibody binds to allelic variants of a RSV nucleoprotein, a RSV nucleocapsid protein, a RSV phosphoprotein, a RSV matrix protein, a RSV attachment glycoprotein, a RSV fusion glycoprotein, a RSV nucleocapsid protein, a RSV matrix protein, a RSV small hydrophobic protein, a RSV RNA-dependent RNA polymerase, a RSV F protein, a RSV L protein, a RSV P protein, and/or a RSV G protein.

It should be recognized that antibodies that immunospecifically bind to a RSV antigen are known in the art. For example, palivizumab (SYNAGIS®) is a humanized monoclonal antibody presently used for the prevention of RSV infection in pediatric patients. In a specific embodiment, an antibody to be used with the methods of the present invention is palivizumab or an antibody-binding fragment thereof (e.g., a fragment containing one or more complementarity determining regions (CDRs) and preferably, the variable domain of palivizumab). The amino acid sequence of palivizumab is disclosed, e.g., in Johnson et al., 1997, J. Infectious Disease 176:1215-1224, and U.S. Pat. No. 5,824,307 and International Application Publication NO.: WO 02/43660, entitled "Methods of Administering/Dosing Anti-RSV Antibodies for Prophylaxis and Treatment", by Young et al., which are incorporated herein by reference in their entireties.

One or more antibodies or antigen-binding fragments thereof that bind immunospecifically to a RSV antigen comprise a Fc domain with a higher affinity for the FcRn receptor than the Fc domain of palivizumab can also be used in accordance with the invention. Such antibodies are described in U.S. Pat. Appn. No. 10/020,354, filed Dec. 12, 2001, which is incorporated herein by reference in its entireties. Further, one or more of the anti-RSV-antigen antibodies A4B4; P12F2 P12F4; P11 D4; A1e9; A12A6; A13c4; A17D4; A4B4; 1X-493L1; FR H3-3F4; M3H9; Y10H6; DG; AFFF; AFFF (1); 6H8; L1-7E5; L2-15B10; A13A11; A1H5; A4B4(1); A4B4-F52s; or A4B4L1FR-S28R can be used in accordance with the invention. These antibodies are disclosed in International Application Publication NO.: WO 02/43660, entitled "Methods of Administering/Dosing Anti-RSV Antibodies for Prophylaxis and Treatment", by Young et al., and U.S. Provisional Patent Application 60/398,475 Filed Jul. 25, 2002, entitled "Methods of Treating and Preventing RSV, HMPV, and PIV Using Anti-RSV, Anti-HMPV, and Anti-PIV Antibodies" which are incorporated herein by reference in their entireties.

In certain embodiments, the anti-RSV-antigen antibodies are the anti-RSV-antigen antibodies of or are prepared by the methods of U.S. application Ser. No. 09/724,531, filed Nov. 28, 2000; Ser. No. 09/996,288, filed Nov. 28, 2001; and U.S. Pat. Publication No. U.S. 2003/0091584 A1, published May 15, 2003, all entitled "Methods of Administering/Dosing Anti-RSV Antibodies for Prophylaxis and Treatment", by Young et al., which are incorporated by reference herein in their entireties. Methods and composition for stabilized antibody formulations that can be used in the methods of the present invention are disclosed in U.S. Provisional Application No. 60/388,921, filed Jun. 14, 2002, and 60/388,920, filed Jun. 14, 2002, which are incorporated by reference herein in their entireties.

Anti-viral therapies and their dosages, routes of administration and recommended usage are known in the art and have been described in such literature as the *Physician's Desk Reference* (57th ed., 2003). Additional information on respiratory viral infections is available in *Cecil Textbook of Medicine* (18th ed., 1988).

5.2.4 Anti-Bacterial Agents

Anti-bacterial agents and therapies well-known to one of skill in the art for the prevention, treatment, management, or amelioration of a respiratory condition or one or more symptoms thereof (e.g., a bacterial respiratory infection) can be used in the compositions and methods of the invention. Non-limiting examples of anti-bacterial agents include proteins, polypeptides, peptides, fusion proteins, antibodies, nucleic acid molecules, organic molecules, inorganic molecules, and small molecules that inhibit and/or reduce a bacterial infection, inhibit and/or reduce the replication of bacteria, or inhibit and/or reduce the spread of bacteria to other cells or subjects. Specific examples of anti-bacterial agents include, but are not limited to, antibiotics such as penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine.

In certain embodiments, the anti-bacterial agent is an agent that inhibits or reduces a pulmonary or respiratory bacterial infection, inhibits or reduces the replication of a bacteria that causes a pulmonary or respiratory infection, or inhibits or reduces the spread of a bacteria that causes a pulmonary or respiratory infection to other cells or subjects. In cases in which the pulmonary or respiratory bacterial infection is a mycoplasma infection (e.g., pharyngitis, tracheobronchitis, and pneumonia), the anti-bacterial agent is preferably a tetracycline, erythromycin, or spectinomycin. In cases in which the pulmonary or respiratory bacterial infection is tuberculosis, the anti-bacterial agent is preferably rifampcin, isonaizid, pyranzinamide, ethambutol, and streptomycin. In cases in which the pulmonary or respiratory bacterial infection is pneumonia caused by an aerobic gram negative bacilli (GNB), the anti-bacterial agent is preferably penicillin, first, second, or third generation cephalosporin (e.g., cefaclor, cefadroxil, cephalexin, or cephazolin), erythomycin, clindamycin, an aminoglycoside (e.g., gentamicin, tobramycin, or amikacine), or a monolactam (e.g., aztreonam). In cases in which the respiratory infection is recurrent aspiration pneumonia, the anti-bacterial agent is preferably penicillin, an aminoglycoside, or a second or third generation cephalosporin.

Anti-bacterial therapies and their dosages, routes of administration and recommended usage are known in the art and have been described in such literature as the *Physician's Desk Reference* (57th ed., 2003), *Cecil Textbook of Medicine* (18th ed., 1988), and *The Merk Manual of Diagnosis and Therapy* (17th ed. 1999).

5.2.5 Anti-Fungal Agents

Anti-fungal agents and therapies well known to one of skill in the art for prevention, management, treatment, and/or amelioration of a respiratory condition or one or more symptoms thereof (e.g., a fungal respiratory infection) can be used in the compositions and methods of the invention. Non-limiting examples of anti-fungal agents include proteins, polypeptides, peptides, fusion proteins, antibodies, nucleic acid molecules, organic molecules, inorganic molecules, and small molecules that inhibit and/or reduce fungal infection, inhibit and/or reduce the replication of fungi, or inhibit and/or reduce the spread of fungi to other subjects. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®)), and itraconazole (SPORANOX®)), polyene (e.g., nystatin, amphotericin B (FUNGIZONE®), amphotericin B lipid complex ("ABLC")(ABELCET®), amphotericin B colloidal dispersion ("ABCD")(AMPHOTEC®), liposomal amphotericin B (AMBISONE®)), potassium iodide (KI), pyrimidine (e.g., flucytosine (ANCOBON®)), and voriconazole (VFEND®). See, e.g., Table 4 For a list of specific anti-fungal agents and their recommended dosages.

In certain embodiments, the anti-fungal agent is an agent that inhibits or reduces a respiratory fungal infection, inhibits or reduces the replication of a fungus that causes a pulmonary or respiratory infection, or inhibits or reduces the spread of a fungus that causes a pulmonary or respiratory infection to other subjects. In cases in which the pulmonary or respiratory fungal infection is *Blastomyces dermatitidis*, the anti-fungal agent is preferably itraconazole, amphotericin B, fluconazole, or ketoconazole. In cases in which the pulmonary or respiratory fungal infection is pulmonary aspergilloma, the anti-fungal agent is preferably amphotericin B, liposomal amphotericin B, itraconazole, or fluconazole. In cases in which the pulmonary or respiratory fungal infection is histoplasmosis, the anti-fungal agent is preferably amphotericin B, itraconazole, fluconazole, or ketoconazole. In cases in which the pulmonary or respiratory fungal infection is coccidioidomycosis, the anti-fungal agent is preferably fluconazole or amphotericin B. In cases in which the pulmonary or respiratory fungal infection is cryptococcosis, the anti-fungal agent is preferably amphotericin B, fluconazole, or combination of the two agents. In cases in which the pulmonary or respiratory fungal infection is *chromomycosis*, the anti-fungal agent is preferably itraconazole, fluconazole, or flucytosine. In cases in which the pulmonary or respiratory fungal infection is mucormycosis, the anti-fungal agent is preferably amphotericin B or liposomal amphotericin B. In cases in which the pulmonary or respiratory fungal infection is pseudoallescheriasis, the anti-fungal agent is preferably itraconazole ore miconazole.

Anti-fungal therapies and their dosages, routes of administration, and recommended usage are known in the art and have been described in such literature as Dodds et al., 2000 Pharmacotherapy 20(11) 1335-1355, *the Physician's Desk Reference* (57th ed., 2003) and the *Merk Manual of Diagnosis and Therapy* (17th ed., 1999).

TABLE 4

Anti-fungal Agents

| Anti-fungal Agent | Dosage |
| --- | --- |
| Amphotericin B | |
| ABELCET ® (lipid complex injection) | 5 mg/kg/day |
| AMBISOME ® (liposome for injection) | 3-5 mg/kg/day |
| AMPHOTEC ® (complex for injection) | 3-4 mg/kg/day |
| Caspofungin acetate (CANCIDAS ®) | 70 mg on day one followed by 50 mg/day |
| Fluconazole (DIFLUCAN ®) | up to 400 mg/day (adults) up to 12 mg/kg/day (children) |
| Itraconazole (SPORANOX ®) | 200-400 mg/day |
| Flucytosine (ANCOBON ®) | 50-150 mg/kg/day in divided dose every 6 hours |
| Liposomal nystatin | 1-4 mg/kg |
| Ketoconazole (NIZORAL ®) | 200 mg single daily dose up to 400 mg/day in two divided doses (adults) 3.3-6.6 mg/kg/day for children 2 years old and older |
| Voriconazole (VFEND ®) | 6 mg/kg i.v. loading dose every 12 hours for two doses, followed by maintenance dose of 4 mg/kg i.v. every 12 hours, then oral maintenance dose of 200-100 mg tablet |

5.3 Uses of IL-9 antagonists

The present invention is directed to therapies which involve administering one or more IL-9 antagonists and compositions comprising said antagonists to a subject, preferably a human subject, for preventing, treating, managing, or ameliorating a respiratory condition or one or more symptoms thereof. In one embodiment, the invention provides a method of preventing, treating, managing, or ameliorating a respiratory disorder or one or more symptoms thereof (e.g., an allergy, wheezing, and asthma), said method comprising administering to a subject in need thereof a dose of a prophylactically or therapeutically effective amount of one or more IL-9 antagonists. In another embodiment, the invention provides a method of preventing, treating, managing, or ameliorating a respiratory infection or one or more symptoms thereof, said method comprising administering a prophylactically or therapeutic effective amount of one or more IL-9 antagonists.

In a specific embodiment, the invention provides a method for preventing, managing, treating, or ameliorating a respiratory condition associated or characterized by elevated IgE levels, mucus hypersecretion, increased mast cell degranulation and/or infiltration, increased bronchial hyperresponsiveness and/or bronchoconstriction (i.e., wheezing), said method comprising administering to a subject in need thereof a prophylactically or therapeutically effective amount of one or more IL-9 antagonists. In another embodiment, the invention provides a method for preventing, managing, treating, or ameliorating an asthma-like symptom associated with a respiratory infection, such as, but not limited to PIV, RSV, and hMPV, said method comprising administering to a subject in need thereof a prophylactically or therapeutically effective amount of one or more IL-9 antagonists.

The invention also provides methods of preventing, treating, managing, or ameliorating a respiratory condition or one or more symptoms thereof, said methods comprising administering to a subject in need thereof one or more IL-9 antagonists and one or more therapies (e.g., one or more prophylactic or therapeutic agents) that are currently being used, have been used, or are known to be useful in the prevention, management, treatment, and/or amelioration of said respiratory condition or one or more symptoms associated therewith. In a specific embodiment, the invention provides a method for preventing, treating, managing, or ameliorating a respiratory condition associated with or characterized by IgE levels, mucus hypersecretion, infiltration, increased bronchial hyperresponsiveness, and/or bronchoconstriction (i.e., wheezing), said method comprising administering to a subject in need thereof an effective amount of one or more IL-9 antagonists and an effective amount of one or more therapies (e.g., one or more prophylactic or therapeutic agents) that are currently being used, have been used, or are known to be useful in the prevention, management, treatment, and/or amelioration of said respiratory condition or one or more symptoms thereof. In another embodiment, the invention provides a method for preventing, managing, treating, or ameliorating an asthma-like symptom associated with a respiratory infection, such as but not limited to, PIV, RSV, hMPV, said method comprising administering to a subject in need thereof an effective amount of one or more IL-9 antagonists and an effective amount of one or more therapies (e.g., one or more prophylactic or therapeutic agents) that are currently being used, have been used, or are known to be useful in the prevention, management, treatment, and/or amelioration of said respiratory condition or one or more symptoms thereof.

The components (e.g., prophylactic or therapeutic agents) of the combination therapies of the invention can be administered sequentially or concurrently. In a specific embodiment, the combination therapies of the invention comprise one or more IL-9 antagonists and at least one other therapy (e.g., at least one other prophylactic or therapeutic agent) which has a different mechanism of action than said antagonists. In another embodiment, the combination therapies of the invention comprise one or more IL-9 antagonists and at least one other therapy (e.g., at least one other prophylactic agent) which has the same mechanism of action as said antagonists. In certain embodiments, the combination therapies of the present invention improve the prophylactic or therapeutic effect(s) of one or more antagonists by functioning together with the antagonists to have an additive or synergistic effect. In certain embodiments, the combination therapies of the present invention reduce the side effects associated with the prophylactic or therapeutic agents.

The prophylactic or therapeutic agents of the combination therapies can be administered to a subject, preferably a human subject, in the same pharmaceutical composition. In alternative embodiments, the prophylactic or therapeutic agents of the combination therapies can be administered sequentially or concurrently to a subject in separate pharmaceutical compositions. The prophylactic or therapeutic agents may be administered to a subject by the same or different routes of administration.

In a specific embodiment, a pharmaceutical composition comprising one or more IL-9 antagonists is administered to a subject, preferably a human, to prevent, treat, manage, or ameliorate a respiratory infection or one or more symptoms thereof. In accordance with the invention, pharmaceutical compositions of the invention may also comprise one or more prophylactic or therapeutic agents which are currently being used, have been used, or are known to be useful in the prevention, treatment, management, or amelioration of a respiratory condition or one or more symptoms thereof.

5.3.1 Respiratory Conditions Associated with or Induced by Environmental Factors 5.3.1.1 Allergies The invention provides a method of preventing, treating, managing, or ameliorating allergic reactions or one or more symptoms thereof, said method comprising administering to a subject in need thereof a dose of a prophylactically or therapeutically effective amount of one or more IL-9 antagonists. In another embodiment, the invention provides a method of preventing, treating, managing, or ameliorating allergic reactions or one or more symptoms thereof, said method comprising administering to a subject in need thereof a dose of an effective amount of one or more IL-9 antagonists and a dose of an effective amount of one or more therapies (e.g., prophylactic or therapeutic agents) other than an IL-9 antagonist. Non-limiting examples of such therapies include agents described in section 5.2, supra, in particular the immunomodulatory agents described in section 5.2.1, the anti-inflammatory agents described in section 5.2.2, the anti-viral agents described in section 5.2.3, the anti-bacterial agents described in section 5.2.4, and the anti-fungal agents described in section 5.2.5.

In certain embodiments, an effective amount of one or more IL-9 antagonists is administered in combination with an effective amount of one or more therapies (e.g., one or more prophylactic or therapeutic agents) used for the prevention, treatment, management, or amelioration allergies to a subject in need thereof. Therapies for allergies may comprise the administration of antimediator drugs (e.g., antihistamine (e.g., desloratadine (CLARINEX®), cetirizine hydrochloride (ZYRTEC®), and fexofenadine (ALLEGRA®)), corticosteroids (e.g., budenoside (RHINOCORT AQUA™)), decongestants, sympathomimetic drugs (e.g., α-adrenergic and β-adrenergic drugs), theophylline and its deriviates, glucocorticoids, and immunotherapies (e.g., repeated long-term injection of an allergen, short course desensitization, and venom immunotherapy). In certain embodiments, one or more IL-9 antagonists are administered in combination with one or more supportive measures to a subject in need thereof to prevent, manage, treat, or ameliorate one or more biological effects of exposure to an allergen. Non-limiting examples of supportive measures include humidification of air by ultrasonic nebulizer, aerolized racemic epinephrine, oral dexamethasone, intravenous fluids, intubation, fever reducers (e.g., ibuprofen and acetometaphine), and antibiotic, anti-viral, or anti-fungal therapy (i.e., to prevent or treat secondary respiratory infections).

The invention provides methods of preventing, managing, treating, or ameliorating a biological response to an allergen such as pollen, mold, dust (e.g., dust mites or their waste), animal protein (e.g., dander, urine, or oil), industrial chemicals, foods, medications, feathers, and insects (e.g., insect stings, cockroaches, or insect waste), said methods comprising administering an effective amount of one or more IL-9 antagonists alone or in combination with an effective amount of another therapy. Biological responses to allergens include, but are not limited to, elevated levels of IgE antibodies, elevated nerve growth factor (NGF) levels, increased mast cell proliferation, degranulation and/or infiltration, increased proliferation and/or infiltration of B cells, and increased proliferation and/or infiltration of T cells. The invention also provides methods of preventing, treating, managing, or ameliorating one or more symptoms of an allergic reaction, including, but not limited to, nasal stuffiness, sneezing, nasal itching, nasal discharge, shortness of breath, coughing, wheezing, and/or itchiness, said methods comprising administering an effective amount of one or more IL-9 antagonists alone or in combination with an effective amount of another therapy.

The invention provides methods for preventing the development of asthma in a subject with one or more allergies, said methods comprising administering an effective amount of one or more IL-9 antagonists alone or in combination with an effective amount of another therapy. In a specific embodiment, the subject is a child with allergies.

In a preferred embodiment, an prophylactically or therapeutically effective amount of one or more IL-9 antagonists is administered in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaV Beta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents," and International Publication No. WO 03/075741 A2, dated Sep. 18, 2003 entitled "Methods of Preventing or Treating Disorders by Administering an Integrin αvβ3 Antagonist in Combination With an HMG-CoA Reductase Inhibitor or Bisphosphonate," each of which is incorporated herewith by reference in its entirety) to a subject to prevent, treat, manage or ameliorate an allergy or a symptom thereof. In another preferred embodiment, an effective amount of one or more IL-9 antagonists is administered to a subject allergies in combination with an effective amount of siplizumab (MedImmune, Inc., International Publication No. WO 02/069904, incorporated herewith by reference) to a subject to prevent, treat, manage or ameliorate an allergy or a symptom thereof. In another preferred embodiment, an effective amount of one or more IL-9 antagonists is administered in combination with an effective amount of one or more molecules that either agonize or reduce EphA2 signaling (e.g., one or more anti-EphA2 Antibodies (MedImmune, Inc., International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. Application Ser. No. 10/436,783; and U.S. Appn. No. 60/379, 368, each of which is incorporated herewith by reference)) to a subject to prevent, treat, manage or ameliorate an allergy or a symptom thereof. In yet another preferred embodiment, an effective amount of one or more IL-9 antagonists is administered in combination with an effective amount of VITAXIN™, siplizumab, and/or EphA2 Molecule that agonizes EphA2 or reduces EphA2 expression to a subject to prevent, treat, manage or ameliorate an allergy or a symptom thereof.

In a specific embodiment, an effective amount of one or more IL-9 antagonists is administered in combination with an effective amount of desloratadine (CLARINEX®) to a subject to prevent, treat, manage or ameliorate an allergy or a symptom thereof. In another embodiment, an effective amount of one or more IL-9 antagonists is administered in combination with an effective amount of cetirizine hydrochloride (ZYRTEC®) to a subject to prevent, treat, manage or ameliorate an allergy or a symptom thereof. In another embodiment, an effective amount of one or more IL-9 antagonists is administered in combination with an effective amount of fexofenadine (ALLEGRA®) to a subject to prevent, treat, manage or ameliorate an allergy or a symptom thereof.

In one embodiment, an effective amount of one or more IL-9 antagonists is administered in combination with an effective amount of one or more anti-IgE antibodies to a subject to prevent, treat, manage or ameliorate an allergy or a symptom thereof. In a specific embodiment, an effective amount of one or more IL-9 antagonists is administered with an effective amount of anti-IgE antibody TNX901 to a subject to prevent, treat, manage or ameliorate an allergy or a symptom thereof. In a specific embodiment, an effective amount of one or more IL-9 antagonists is administered with an effective amount of anti-IgE antibody rhuMAb-E25 omalizumab to a subject to prevent, treat, manage or ameliorate an allergy or a symptom thereof. In another embodiment, an effective amount of one or more IL-9 antagonists is administered in combination with an effective amount of anti-IgE antibody HMK-12 to a subject to prevent, treat, manage or ameliorate an allergy or a symptom thereof. In another embodiment, an effective amount of one or more IL-9 antagonists is administered in combination with an effective amount of anti-IgE antibody 6HD5 to a subject to prevent, treat, manage or ameliorate an allergy or a symptom thereof. In another embodiment, an effective amount of one or more IL-9 antagonists is administered in combination with an effective amount of anti-IgE antibody MAb Hu-901 to a subject to prevent, treat, manage or ameliorate an allergy or a symptom thereof.

In one embodiment, an effective amount of one or more IL-9 antagonists is administered in combination with an effective amount of a stem cell factor (c-kit ligand) inhibitor, such as, but not limited to MAb 7H6, MAb 8H7A, pAb 1337, FK506, and CsA to a subject to prevent, treat, manage or ameliorate an allergy or a symptom thereof. In accordance with this embodiment, the stem cell factor inhibitor is preferably administered locally to the affected area. In another embodiment, an effective amount of one or more IL-9 antagonists is administered in combination with an effective amount of one or more c-kit receptor inhibitors, such as, but not limited to STI 571 to a subject to prevent, treat, manage or ameliorate an allergy or a symptom thereof. In accordance with this embodiment, the c-kit ligand inhibitor is preferably administered locally to the affected area.

In one embodiment, an effective amount of one or more IL-9 antagonists is administered in combination with an effective amount of a mast cell protease inhibitor to a subject to prevent, treat, manage or ameliorate an allergy or a symptom thereof. In a specific embodiment, the mast cell protease inhibitor is a tryptase kinase inhibitor, such as, but not limited to GW-45, GW-58, and genisteine. In a specific embodiment, the mast cell protease inhibitor is phosphatidylinositide-3' (PI3)-kinase inhibitors, such as, but not limited to calphostin C. In another embodiment, the mast cell protease inhibitor is a protein kinase inhibitor such as, but not limited to staurosporine. In accordance with these embodiments, the mast cell protease inhibitor is preferably administered locally to the affected area.

The IL-9 antagonists or combination therapies of the invention may be used as the first, second, third, fourth, or fifth therapy to prevent, manage, treat, or ameliorate an allergy or one or more symptom thereof. The invention include methods of preventing, treating, managing, or ameliorating an allergy or one or more symptoms thereof in a patient undergoing therapies for other respiratory conditions. The invention encompasses methods of preventing, managing, treating, or ameliorating an allergy or one or more symptoms thereof in a patient before any adverse effects or intolerance to therapies other than IL-9 antagonists develops. The invention encompasses methods of preventing, treating, managing, or ameliorating an allergy or a symptom thereof in refractory patients. In certain embodiments, a patent with an allergy is refractory to a therapy when one or more biological reactions to an allergen(s) is not prevented, managed, or alleviated. The invention also encompasses methods of preventing, managing, treating, or ameliorating an allergy or a symptom thereof in patients who are susceptible to adverse reactions to conventional therapies. The invention further encompasses methods for preventing an allergic reaction in patients at risk of or expected to suffer an allergic reaction, e.g., patients who will be exposed to allergens because of a social or occupational activity.

The invention encompasses methods for preventing, treating, managing, or ameliorating an allergic reaction or a symptom thereof in a patient who has proven refractory to therapies other than IL-9 antagonists but are no longer on these therapies. In certain embodiments, the patients being managed or treated in accordance with the methods of this invention are patients already being treated with antibiotics, anti-viral therapy, anti-fungals, or other biological therapy/immunotherapy. Among these patients are refractory patients, patients who are too young for conventional therapies, and patients with reoccurring allergic reactions despite management or treatment with existing therapies.

The present invention encompasses methods for preventing, treating, managing, or ameliorating an allergy or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease, patients with broncho-pulmonary dysplasia, patients with congenital heart disease, patients with cystic fibrosis, patients with acquired or congenital heart disease, and patients suffering from a respiratory infection), a person with impaired renal or liver function, the elderly, children, infants, persons with neuropsychiatric disorders or those who take psychotropic drugs, persons with histories of seizures, or persons on medication that would negatively interact with conventional agents used to manage or treat an allergy.

Therapies and dosages, routes of administration, and recommended usage of therapies for preventing, treating, managing, or ameliorating an allergy or one or more symptoms thereof are known in the art and have been described in such literature as the *Physician's Desk Reference* (57th ed., 2003).

5.3.1.2 Wheezing

The invention provides a method of preventing, treating, managing, or ameliorating wheezing, said method comprising administering to a subject in need thereof a dose of an effective amount of one or more IL-9 antagonists. In another embodiment, the invention provides a method of preventing, treating, managing, or ameliorating asthma or one or more symptoms thereof, said method of comprising administering to a subject in need thereof a dose of an effective amount of one or more IL-9 antagonists and a dose of an effective amount of one or more prophylactic or therapeutic agents other than an IL-9 antagonist. Non-limiting examples of such agents include agents described in section 5.2, supra, in particular the immunomodulatory agents described in section 5.2.1, the anti-inflammatory agents described in section 5.2.2, the anti-viral agents described in section 5.2.3, the anti-bacterial agents described in section 5.2.4, and the anti-fungal agents described in section 5.2.5.

In certain embodiments, an effective amount of one or more IL-9 antagonists is administered in combination with an effective amount of one or more therapies (e.g., one or more prophylactic or therapeutic agents) used for preventing, treating, managing, or ameliorating wheezing to a subject in need thereof. In certain embodiments, one or more IL-9 antagonists are administered in combination with one or more supportive measures to a subject in need thereof to prevent, manage, treat, or ameliorate wheezing. Non-limiting examples of supportive measures include humidification of air by ultrasonic nebulizer, aerolized racemic, epinephrine, oral dexamethasone, intravenous fluids, intubation, fever reducers (e.g., ibuprofen and acetometaphine), and antibiotic, anti-viral, or anti-fungal therapy (i.e., to prevent or treat secondary respiratory infections).

The invention provides methods of preventing, managing, treating, or ameliorating wheezing in response to triggers such as, but not limited to, allergens (e.g., pollen, mold, dust (e.g., dust mites or their waste), animal protein (e.g., dander, urine, or oil), industrial chemicals, foods, medications, feathers, and insects (e.g., insect stings, cockroaches, or insect waste), cold air, sudden change in temperature, and exercise. In certain embodiments, the methods of the invention are used to prevent, manage, treat, or ameliorate wheezing associated with another respiratory conditions, such as allergies, asthma, or viral, bacterial, or fungal respiratory infection.

In certain embodiments, the methods of the invention result in a reduction of wheezing by approximately 25%, preferably approximately 30%, approximately 35%, approximately 40%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in in vivo and/or in vitro assay well-known to one skill in the art.

The invention provides methods for preventing the development of asthma in a subject with wheezing, said methods comprising administering an effective amount of one or more IL-9 antagonists alone or in combination with an effective amount of another therapy. In a specific embodiment, the subject is a child with wheezing.

In a preferred embodiment, an effective amount of one or more IL-9 antagonists is administered in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin $\alpha v \beta 13$ Antagonists in Combination With Other Prophylactic or Therapeutic Agents," and International Publication No. WO 03/075741 A2, dated Sep. 18, 2603 entitled "Methods of Preventing or Treating Disorders by Administering an Integrin $\alpha v \beta 3$ Antagonist in Combination With an HMG-CoA Reductase Inhibitor or Bisphosphonate," each of which is incorporated herewith by reference in its entirety) to a subject to prevent, treat, manage, and/or ameliorate wheezing. In another preferred embodiment, an effective amount of one or more IL-9 antagonists is administered to a subject allergies in combination with an effective amount of siplizumab (MedImmune, Inc., International Publication No. WO 02/069904) to a subject to prevent, treat, manage, and/or ameliorate wheezing. In another preferred embodiment, an effective amount of one or more IL-9 antagonists is administered in combination with an effective amount of one or more EphA2 inhibitors (e.g., one or more anti-EphA2 Antibodies that elicit EphA2 signaling (MedImmune, Inc., International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. Appn. No. 10/436,783; and U.S. Appn. No. 60/379, 368, each of which is incorporated herewith by reference)) to a subject to prevent, treat, manage, and/or ameliorate wheezing. In yet another embodiment, an effective amount of one or more IL-9 antagonists is administered in combination with an effective amount of VITAXIN™, siplizumab, and/or EphA2 inhibitor to a subject to prevent, treat, manage, and/or ameliorate wheezing.

In a specific embodiment, an effective amount of one or more IL-9 antagonists is administered in combination with an effective amount of desloratadine (CLARINEX®) to a subject to prevent, treat, manage, and/or ameliorate wheezing. In another embodiment, an effective amount of one or more IL-9 antagonists is administered with an effective amount of cetirizine hydrochloride (ZYRTEC®) to a subject to prevent, treat, manage, and/or ameliorate wheezing. In another embodiment, an effective amount of one or more IL-9 antagonists is administered in combination with an effective amount of fexofenadine (ALELGRA®) to a subject to prevent, treat, manage, and/or ameliorate wheezing.

In one embodiment, an effective amount of one or more IL-9 antagonists is administered in combination with an effective amount of one or more anti-IgE antibodies to a subject to prevent, treat, manage, and/or ameliorate wheezing. In a specific embodiment, an effective amount of one or more IL-9 antagonists is administered in combination with an effective amount of anti-IgE antibody TNX901 to a subject to prevent, treat, manage, and/or ameliorate wheezing. In a specific embodiment, an effective amount of one or more IL-9 antagonists is administered in combination with an effective amount of anti-IgE antibody rhuMAb-E25 omalizumab to a subject to prevent, treat, manage, and/or ameliorate wheezing. In a specific embodiment, an effective amount of one or more IL-9 antagonists is administered in combination with an effective amount of anti-IgE antibody HMK-12 to a subject to prevent, treat, manage, and/or ameliorate wheezing. In a specific embodiment, an effective amount of one or more IL-9 antagonists is administered in combination with an effective amount of anti-IgE antibody 6HD5 to a subject to prevent, treat, manage, and/or ameliorate wheezing. In a specific embodiment, an effective amount of one or more IL-9 antagonists is administered in combination with an effective amount of anti-IgE antibody MAb Hu-901 to a subject to prevent, treat, manage, and/or ameliorate wheezing.

In one embodiment, an effective amount of one or more IL-9 antagonists is administered with an effective amount of a stem cell factor (c-kit ligand) inhibitor, such as, but not limited to MAb 7H6, MAb 8H7A, pAb 1337, FK506, and CsA to a subject to prevent, treat, manage, and/or ameliorate wheezing. In accordance with this embodiment, stem cell factor inhibitor is preferably administered locally to the affected area. In another embodiment, an effective amount of one or more IL-9 antagonists is administered in combination with an effective amount of one or more c-kit receptor inhibitors, such as, but not limited to STI 571 to a subject to prevent, treat, manage, and/or ameliorate wheezing. In accordance with this embodiment, the c-kit ligand inhibitor is preferably administered locally in the affected area.

In one embodiment, an effective amount of one or more IL-9 antagonists is administered in combination with an effective amount of a mast cell protease inhibitor to a subject to prevent, treat, manage, and/or ameliorate wheezing. In another embodiment, the mast cell protease inhibitor is a tryptase kinase inhibitor, such as, but not limited to GW-45, GW-58, and genisteine. In another embodiment, the mast cell protease inhibitor is phosphatidylinositide-3' (PI3)-kinase inhibitors, such as, but not limited to calphostin C. In another embodiment, the mast cell protease inhibitor is a protein kinase inhibitor such as, but not limited to staurosporine. In accordance with these embodiments, the mast cell protease inhibitor is preferably administered locally to the affected area.

The IL-9 antagonists or combination therapies of the invention may be used as the first, second, third, fourth, or fifth therapy to prevent, manage, treat, or ameliorate wheezing. The invention also includes methods of preventing, treating, managing, or ameliorating wheezing in a patient undergoing therapies for other respiratory conditions. The invention encompasses methods of preventing, managing, treating, or ameliorating wheezing in a patient before any adverse effects or intolerance to therapies other than IL-9 antagonists develops. The invention also encompasses methods of preventing, treating, managing, or ameliorating wheezing in refractory patients. In certain embodiments, a patent with wheezing is refractory to a therapy when one or more biological reactions to an inducer such as change in temperature or an allergen(s) is not prevented, treated, managed, or alleviated and wheezing results or continues. The invention also encompasses methods of preventing, managing, treating, or ameliorating wheezing in patients who are susceptible to adverse reactions to conventional therapies. The invention further encompasses methods for preventing wheezing in patients at risk of or expected to suffer wheezing, e.g., patients who will be exposed to triggers of wheezing because of a social or occupational activity.

The invention encompasses methods for preventing, treating, managing, or ameliorating wheezing in a patient who has proven refractory to therapies other than IL-9 antagonists but are no longer on these therapies. In certain embodiments, the patients being managed or treated in accordance with the methods of this invention are patients already being treated with antibiotics, anti-viral therapy, anti-fungals, or other biological therapy/immunotherapy. Among these patients are refractory patients, patients who are too young for conventional therapies, and patients with reoccurring wheezing despite management or treatment with existing therapies.

The present invention encompasses methods for preventing, treating, managing, or ameliorating wheezing as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, patients with immunodeficiency disease, patients with broncho-pulmonary dysplasia, patients with congenital heart disease, patients with cystic fibrosis, patients with acquired or congenital heart disease, and patients suffering from a respiratory infection), a person with impaired renal or liver function, the elderly, children, infants, persons with neuropsychiatric disorders or those who take psychotropic drugs, persons with histories of seizures, or persons on medication that would negatively interact with conventional agents used to prevent, manage, treat, or ameliorate wheezing.

Therapies and dosages, routes of administration, and recommended usage of therapies for preventing, treating, managing, or ameliorating wheezing are known in the art and have been described in such literature as the *Physician's Desk Reference* (57th ed., 2003).

5.3.1.3 Asthma

The invention provides a method of preventing, treating, managing, or ameliorating asthma or one or more symptoms thereof, said method comprising administering to a subject in need thereof a dose of an effective amount of one or more IL-9 antagonists. The invention also provides a method of preventing, treating, managing, or ameliorating asthma or one or more symptoms thereof, said method of comprising administering to a subject in need thereof a dose of an effective amount of one or more IL-9 antagonists and a dose of a prophylactically or therapeutically effective amount of one or more prophylactic or therapeutic agents other than an IL-9 antagonist. Non-limiting examples of such agents include agents described in section 5.2, supra, in particular the immunomodulatory agents described in section 5.2.1, the anti-inflammatory agents described in section 5.2.2, the anti-viral agents described in section 5.2.3, the anti-bacterial agents described in section 5.2.4, and the anti-fungal agents described in section 5.2.5.

In certain embodiments, an effective amount of one or more IL-9 antagonists is administered in combination with an effective amount of one or more therapies used for preventing, treating, managing, or ameliorating asthma. Non-limiting examples of therapies for asthma include anti-cholinergics (e.g., ipratropium bromide and oxitropium bromide), beta-2 antagonists (e.g., albuterol (PROVENTIL® or VENTOLIN®), bitolterol (TOMALATE®), fenoterol, formoterol, isoetharine, metaproterenol, pibuterol (MAXAIR®), salbutamol, salbutamol terbutaline, and salmeterol, terbutlaine (BRETHAIRE®)), corticosteroids (e.g., prednisone, beclomethasone diprpionate (VANCERIL® or BECLOVENT®), triamcinolone acetonide (AZMACORF®), flunisolide (AEROBID®), and fluticasone propionate (FLOVENT®)), leukotriene antagonists (e.g., montelukast, zafirluckast, and zileuton), theophylline (THEO-DUR®, UNIDUR® tablets, and SLO-BID® Gyrocaps), and salmeterol (SEREVENT®), cromolyn, and nedorcomil (INTAL® and TILADE®)), IgE antagonists, IL-4 antagonists (including antibodies), IL-5 antagonists (including antibodies), PDE4 inhibitors, NF-Kappa-B inhibitors, IL-13 antagonists (including antibodies), CpG, CD23 antagonists, selectin antagonist (e.g., TBC 1269), mast cell protease inhibitors (e.g., tryptase kinase inhibitors (e.g., GW-45, GW-58, and genisteine), phosphatidylinositide-3' (PI3)-kinase inhibitors (e.g., calphostin C), and other kinase inhibitors (e.g., staurosporine), C2a receptor antagonists (including antibodies), and supportive respiratory therapy, such as supplemental and mechanical ventilation. In certain embodiments, an effective amount of one or more IL-9 antagonists are administered in combination of one or more supportive measures to a subject to prevent, treat, manage, or ameliorate asthma or one or more symptoms thereof. Non-limiting examples of supportive measures include humidification of air by ultrasonic nebulizer, aerolized racemic epinephrine, oral dexamethasone, intravenous fluids, intubation, fever reducers (e.g., ibuprofen and acetametaphine), and antibiotic, anti-viral, or anti-fungal therapy (i.e., to prevent or treat secondary respiratory infections).

In specific embodiments, the methods of the invention are utilized to prevent, treat, manage, or ameliorate asthma or one or more symptoms thereof induced by environmental triggers such as, but not limited to, acarids (e.g., *Dermatophagoides, D. pteronyssinus, D. farinae, Euroglyphus maynei, Blomia tropicalis*), insects (e.g., cockroaches, *Blatella germanica*), animals (e.g., cats, dogs, rabbits, mice, rats, hamsters, guinea pigs, mice, rats, and birds), fungi (e.g., *Penicillium, Aspergillus,* and *Cladosporium*), air pollutants (e.g., tobacco smoke), irritant gases, fumes, vapors, aerosols, or chemicals, pollen, exercise, or cold air.

In certain embodiments, the invention provides methods for preventing, treating, managing, or ameliorating asthma or one or more symptoms thereof, said methods comprising administrating to a subject in need thereof an effective amount of one or more IL-9 antagonists in combination with an effective amount of one or more leukotriene inhibitors. In a specific embodiment, an effective amount of one or more IL-9 antagonists is administered in combination with an effective amount of a monteleukast (SINGULAIR®) to a subject to prevent, manage, treat, or ameliorate asthma or one or more symptoms thereof. In another embodiment, an effective amount of one or more IL-9 antagonists is administered in combination with an effective amount of zafirlukast (ACCOLATE®) to a subject to prevent, manage, treat, or ameliorate asthma or one or more symptoms thereof. In another embodiment, an effective amount of one or more IL-9 antagonists is administered in combination with an effective amount of pranlukast (ONON®) to a subject to prevent, manage, treat, or ameliorate asthma or one or more symptoms thereof. In yet another embodiment, an effective amount of one or more IL-9 antagonists is administered in combination with an effective amount of zileuton (ZYFLO®) to a subject to prevent, treat, manage, or ameliorate asthma or one or more symptoms thereof.

In a preferred embodiment, an effective amount of one or more IL-9 antagonists is administered to a subject in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents," and International Publication No. WO 03/075741 A2, dated Sep. 18, 2003 entitled "Methods of Preventing or Treating Disorders by Administering an Integrin αvβ3 Antagonist in Combination With an HMG-CoA Reductase Inhibitor or Bisphosphonate," each of which is incorporated herewith by reference in its entirety) to a subject to prevent, treat, manage, and/or ameliorate asthma or one or more symptoms thereof. In another preferred embodiment, an effective amount of one or more IL-9 antagonists is administered to a subject in combination with an effective amount of siplizumab (MedImmune, Inc., International Pub. No. WO 02/069904) to a subject to prevent, treat, manage, and/or ameliorate asthma or one or more symptoms thereof. In another preferred embodiment, an effective amount of one or more IL-9 antagonists is administered in combination with an effective amount of one or more EphA2 inhibitors (e.g., one or more anti-EphA2 antibodies, preferably, that elicit EphA2 signaling (MedImmune, Inc., International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. application Ser. No. 10/436,783; and U.S. Appn. No. 60/379, 368, each of which is incorporated herewith by reference)) to a subject to prevent, treat, manage, and/or ameliorate asthma or one or more symptoms thereof. In yet another preferred embodiment, an effective amount of one or more IL-9 antagonists is administered in combination with an effective amount of VITAXIN™, siplizumab, and/or EphA2 inhibitor to a subject to prevent, treat, manage, and/or ameliorate asthma or one or more symptoms thereof.

The invention encompasses methods of preventing the development of asthma in a patient expected to suffer from, or at risk of developing asthma, e.g., patients with a genetic predisposition for asthma, patients who have or have had one or more respiratory infections, infants, infants born prematurely, children, the elderly, or patients who work with toxic chemicals (i.e., at risk of developing occupational asthma). In specific embodiments, the subjects are children who are at risk of developing asthma, e.g., children who have or have had a respiratory infection, particularly, PIV, RSV, and hMPV, have elevated IgE levels, a family history of asthma, have been exposed to asthma triggers and/or allergens (e.g., animals, cockroach allergens, and tobacco smoke), or have experienced wheezing or bronchial hyperresponsiveness. For a discussion of risk factors for asthma, see, e.g., Klinnert et al., 2001, Pediatrics 108(4): E69; London et al., 2001, Epidemiology, 12(5):577-83; Melen et al., 2001, Allergy, 56(7):464-52; Mochizuki et al., 2001, J Asthma 38(1):1-21; Arruda et al., 2001, Curr Opin Pulm Med, 7(1):14-19; Castro-Rodriguez et al., 2000, Am J Respir Crit Care Med 162: 1403-6; Gold, 2000, Environ Health Perspect 108: 643-51; and Csonka et al., 2000, Pediatr Allergy Immuno, 11(4):225-9.

In one embodiment, an effective amount of one or more IL-9 antagonists is administered with an effective amount of one or more anti-IgE antibodies to a subject to prevent, treat, manage, and/or ameliorate asthma or one or more symptoms thereof. In another embodiment, an effective amount of one or more IL-9 antagonists is administered in combination with an effective amount of anti-IgE antibody TNX901 to a subject to prevent, treat, manage, and/or ameliorate asthma or one or more symptoms thereof. In a specific embodiment, an effective amount of one or more IL-9 antagonists is administered in combination with an effective amount of anti-IgE antibody rhuMAb-E25 omalizumab to a subject to prevent, treat, manage, and/or ameliorate asthma or one or more symptoms thereof. In another embodiment, an effective amount of one or more IL-9 antagonists is administered in combination with an effective amount of anti-IgE antibody HMK-12 to a subject to prevent, treat, manage, and/or ameliorate asthma or one or more symptoms thereof. In another embodiment, an effective amount of one or more IL-9 antagonists is administered in combination with an effective amount of anti-IgE antibody 6HD5 to a subject to prevent, treat, manage, and/or ameliorate asthma or one or more symptoms thereof. In another embodiment, an effective amount of one or more IL-9 antagonists is administered in combination with an effective amount of anti-IgE antibody MAb Hu-901 to a subject to prevent, treat, manage, and/or ameliorate asthma or one or more symptoms thereof.

In one embodiment, an effective amount of one or more IL-9 antagonists is administered in combination with an effective amount of a stem cell factor (c-kit ligand) inhibitor, such as, but not limited to MAb 7H6, MAb 8H7A, pAb 1337, FK506, and CsA to a subject to prevent, treat, manage, and/or ameliorate asthma or one or more symptoms thereof. In accordance with this embodiment, the stem cell factor inhibitor preferably is administered locally to the affected area. In another embodiment, an effective amount of one or more IL-9 antagonists is administered in combination with an effective amount of one or more c-kit receptor inhibitors, such as, but not limited to STI 571 to a subject to prevent, treat, manage, and/or ameliorate asthma or one or more symptoms thereof. In accordance with this embodiment, the c-kit ligand inhibitor is preferably administered locally to the affected area.

In one embodiment, an effective amount of one or more IL-9 antagonists is administered in combination with a mast cell protease inhibitor to a subject to prevent, treat, manage, and/or ameliorate asthma or one or more symptoms thereof. In another embodiment, the mast cell protease inhibitor is a tryptase kinase inhibitor, such as, but not limited to GW-45, GW-58, and genisteine. In another embodiment, the mast cell protease inhibitor is phosphatidylinositide-3' (PI3)-kinase inhibitors, such as, but not limited to calphostin C. In another embodiment, the mast cell protease inhibitor is a protein kinase inhibitor such as, but not limited to staurosporine. In accordance with these embodiments, the mast cell protease inhibitor is preferably administered locally to the affected area.

The IL-9 antagonists or combination therapies of the invention may be used as the first, second, third, fourth, or fifth therapy to prevent, manage, treat, or ameliorate asthma or one or more symptom thereof. The invention also includes methods of preventing, treating, managing, or ameliorating asthma or one or more symptoms thereof in a patient undergoing therapies for other respiratory conditions. The invention encompasses methods of preventing, managing, treating, or ameliorating asthma or one or more symptoms thereof in a patient before any adverse effects or intolerance to therapies other than IL-9 antagonists develops. The invention also encompasses methods of preventing, treating, managing, or ameliorating asthma or a symptom thereof in refractory patients. In certain embodiments, the patient with asthma is refractory to a therapy when one or more biological reactions symptoms of asthma is not prevented, managed, or alleviated. The invention also encompasses methods of preventing, managing, treating, or ameliorating asthma or a symptom thereof in patients who are susceptible to adverse reactions to conventional therapies. The invention further encompasses methods for preventing asthma or one or more symptoms thereof in patients at risk of or expected to suffer an asthmatic attack, e.g., patients who will be exposed to factors that trigger asthmatic attacks because of a social or occupational activity.

The invention encompasses methods for preventing, treating, managing, or ameliorating asthma or a symptom thereof in a patient who has proven refractory to therapies other than IL-9 antagonists but are no longer on these therapies. In certain embodiments, the patients being managed or treated in accordance with the methods of this invention are patients already being treated with antibiotics, anti-viral therapy, anti-fungals, or other biological therapy/immunotherapy. Among these patients are refractory patients, patients who are too young for conventional therapies, and patients with reoccurring asthmatic attacks despite management or treatment with existing therapies.

The present invention encompasses methods for preventing, treating, managing, or ameliorating asthma or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, patients with immunodeficiency disease, patients with broncho-pulmonary dysplasia, patients with congenital heart disease, patients with cystic fibrosis, patients with acquired or congenital heart disease, and patients suffering from a respiratory infection), a person with impaired renal or liver function, the elderly, children, infants, persons with neuropsychiatric disorders or those who take psychotropic drugs, persons with histories of seizures, or persons on medication that would negatively interact with conventional agents used to manage or treat and allergy.

Therapies and dosages, routes of administration, and recommended usage of therapies for preventing, treating, managing, or ameliorating asthma are known in the art and have been described in such literature as the *Physician's Desk Reference* (57th ed., 2003).

5.3.2 Viral Respiratory Infections

The invention provides a method of preventing, treating, managing, or ameliorating a viral respiratory infection or one or more symptoms thereof, said method comprising administering to a subject in need thereof a dose of a prophylactically or therapeutically effective amount of one or more IL-9 antagonists. The invention also provides a method of preventing, treating, managing, or ameliorating a viral respiratory infection or one or more symptoms thereof, said method comprising administering to a subject in need thereof a dose of a prophylactically or therapeutically effective amount of one or more IL-9 antagonists and a dose of a prophylactically or therapeutically effective amount of one or more therapies (e.g., one or more prophylactic or therapeutic agents) other than an IL-9 antagonist. Non-limiting examples of such therapies include the agents described in section 5.2, supra, and in particular, the immunomodulatory agents described in section 5.2.1, the anti-inflammatory agents described in section 5.2.2, the anti-viral agents described in section 5.2.3, the anti-bacterial agents described in section 5.2.4, and the anti-fungal agents described in section 5.2.5.

In certain embodiments, an effective amount of one or more IL-9 antagonists is administered in combination with an effective amount of one or more therapies (e.g., one or more prophylactic or therapeutic agents) currently being used, have been used, or are known to be useful in the prevention, management, treatment, or amelioration of a viral infection to a subject in need thereof. Therapies for a viral infection include, but are not limited to, anti-viral agents such as, but not limited to, amantadine, oseltamivir, ribaviran, palivizumab, and anamivir. In certain embodiments, an effective amount of one or more IL-9 Antagonists is administered in combination with one or more supportive measures to a subject in need thereof to prevent, manage, treat, or ameliorate a viral infection or one or more symptoms thereof. Non-limiting examples of supportive measures include humidification of the air by an ultrasonic nebulizer, aerolized racemic epinephrine, oral dexamethasone, intravenous fluids, intubation, fever reducers (e.g., ibuprofen, acetometaphin), and antibiotic and/or anti-fungal therapy (i.e., to prevent or treat secondary bacterial or fungal infections).

The invention provides methods of preventing, managing, treating, or ameliorating a respiratory condition resulting from or associated with any viral infection, said methods comprising administering an effective amount of one or more IL-9 antagonists alone or in combination with an effective amount of another therapy. Examples of viruses which cause viral infections include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), arenaviruses (e.g., lassa fever virus), paramyxoviruses (e.g., morbillivirus virus, human respiratory syncytial virus, mumps, hMPV, and pneumovirus), adenoviruses, bunyaviruses (e.g., hantavirus), comaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C and PIV), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), and rhabdoviruses (e.g., rabies virus). Biological responses to a viral infection include, but not limited to, elevated levels of antibodies, increased proliferation and/or infiltration of T cells, increased proliferation and/or infiltration of B cells, epithelial hyperplasia, and mucin production. The invention also provides methods of preventing, treating, managing, or ameliorating viral respiratory infections, such as the common cold, viral pharyngitis, viral laryngitis, viral croup, viral bronchitis, influenza, parainfluenza viral diseases ("PIV") (e.g., croup, bronchiolitis, bronchitis, pneumonia), and respiratory syncytial virus ("RSV"), metapneumavirus, and adenovirus diseases (e.g., febrile respiratory disease, croup, bronchitis, pneumonia), said method comprising administering an effective amount of one or more IL-9 antagonists alone or in combination with an effective amount of another therapy.

In one embodiment, the methods of the invention are used to prevent, treat, manage, or ameliorate influenza virus infections, PIV infections, hMPV infections, adenovirus infections, and/or RSV infections, or one or more of symptoms thereof. In a specific embodiment, the invention provides methods for preventing, treating, managing, or ameliorating a RSV respiratory infection or one or more symptoms thereof, said methods comprising administering to a subject in need thereof an effective amount of one or more IL-9 antagonists alone or in combination with an effective amount of one or more anti-viral agents such as, but not limited to, amantadine, rimantadine, oseltamivir, znamivir, ribaviran, RSV-IVIG (i.e., intravenous immune globulin infusion) (RESPI-GAM™), and palivizumab (SYNAGIS™). In another embodiment, the invention provides methods for preventing, treating, managing, or ameliorating a PIV infection or one or more symptoms thereof, said methods comprising administering to a subject in need thereof an effective amount of an effective amount of one or more IL-9 antagonists alone or in combination with one or more anti-viral agents such as, but not limited to, amantadine, rimantadine, oseltamivir, znamivir, and ribaviran. In another embodiment, the invention provides methods for preventing, treating, managing, or ameliorating a hMPV infection or one or more symptoms thereof, said method comprising of administering to a subject in need thereof an effective amount of one or more IL-9 antagonists alone or in combination with an effective amount of one or more anti-viral agents, such as, but not limited to, amantadine, rimantadine, oseltamivir, znamivir, and ribaviran. In a specific embodiment, the invention provides methods for preventing, treating, managing, or ameliorating influenza, said method comprising administering to a subject in need thereof an effective amount of one or more IL-9 antagonists alone or in combination with an effective amount of one or more anti-viral agents such as, but not limited to zanamivir (RELENZA®), oseltamivir (TAMIFLU®), rimantadine, and amantadine (SYMADINE®; SYMMETREL®).

The invention provides methods for preventing the development of asthma in a subject who suffers from or had suffered from a viral respiratory infection, said methods comprising administering an effective amount of one or more IL-9 antagonists alone or in combination with an effective amount of another therapy. In a specific embodiment, the subject is an infant born prematurely, an infant, or a child. In another specific embodiment, the subject suffered from or suffers from RSV infection.

In a specific embodiment, the invention provides methods for preventing, treating, managing, or ameliorating one or more secondary responses to a primary respiratory viral infection, said method comprising of administering to a subject in need thereof an effective amount of one or more IL-9 antagonists alone or in combination with an effective amount of other therapies (e.g., other prophylactic or therapeutic agents). Examples of secondary responses to a primary respiratory viral infection include, but are not limited to, asthma-like responsiveness to mucosal stimula, elevated total respiratory resistance, increased susceptibility to secondary viral, bacterial, and fungal infections, and development of such conditions such as, but not limited to, pneumonia, croup, and febrile bronchitis.

In a specific embodiment, the invention provides methods to prevent, manage, treat, or ameliorate a viral respiratory infection or one or more symptoms thereof, said methods comprising administering to a subject in need thereof an effective amount of one or more IL-9 antagonists in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents," and International Publication No. WO 03/075741 A2, dated Sep. 18, 2003 entitled "Methods of Preventing or Treating Disorders by Administering an Integrin αvβ3 Antagonist in Combination With an HMG-CoA Reductase Inhibitor or Bisphosphonate," each of which is incorporated herewith by reference in its entirety). In another specific embodiment, the invention provides methods to prevent, manage, treat, or ameliorate a viral respiratory infection or one or more symptoms thereof, said methods comprising administering to a subject in need thereof an effective amount of one or more IL-9 antagonists in combination with an effective amount of siplizumab (MedImmune, Inc., International Pub. No. WO 02/069904) to a subject with a viral respiratory infection. In another preferred embodiment, the invention provides methods to prevent, manage, treat, or ameliorate a viral respiratory infection or one or more symptoms thereof, said methods comprising administering to a subject in need thereof an effective amount of one or more IL-9 antagonists in combination with an effective amount of one or more molecules that either agonize or reduce the signaling of EphA2 (e.g., one or more anti-EphA2 antibodies, preferably, that elicit EphA2 signaling (MedImmune, Inc., International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. Application Ser. No. 10/436,783; and U.S. Appn. No. 60/379, 368, each of which is incorporated herewith by reference)) to a subject with a viral respiratory infection. In yet another preferred embodiment, the invention provides methods to prevent, manage, treat, or ameliorate a viral respiratory infection or one or more symptoms thereof, said methods comprising administering to a subject in need thereof an effective amount of one or more IL-9 antagonists in combination with an effective amount of VITAXIN™, siplizumab, and/or EphA2 molecule that antagonizes EphA2 or reduces EphA2 expression to a subject with a viral respiratory infection.

The invention encompasses methods for preventing the development of a viral respiratory infection in a patient expected to suffer from a viral respiratory infection or at increased risk of such an infection, e.g., patients with suppressed immune systems (e.g., organ-transplant recipients, AIDS patients, patients undergoing chemotherapy, the elderly, infants born prematurely, infants, children, patients with carcinoma of the esophagus with obstruction, patients with tracheobronchial fistula, patients with neurological diseases (e.g., caused by stroke, amyotrophic lateral sclerosis, multiple sclerosis, and myopathies), patients with broncho-pulmonary dysplasia, patients with congenital heart disease, patients with cystic fibrosis, patients with acquired or congenital heart disease, and patients already suffering from a respiratory infection). The patients may or may not have been previously treated for a respiratory infection.

The IL-9 antagonists, compositions, or combination therapies of the invention may be used as the first, second, third, fourth, or fifth therapy to prevent, manage, treat, or ameliorate a viral respiratory infection or one or more symptom thereof. The invention also includes methods of preventing, treating, managing, or ameliorating a viral respiratory infection or one or more symptoms thereof in a patient undergoing therapies for other respiratory conditions. The invention encompasses methods of preventing, managing, treating, or ameliorating a viral respiratory infection or one or more symptoms thereof in a patient before any adverse effects or intolerance to therapies other than IL-9 antagonists develops. The invention also encompasses methods of preventing, treating, managing, or ameliorating a viral respiratory infection or a symptom thereof in refractory patients. In certain embodiments, a patient with a viral respiratory infection is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral respiratory infection is refractory when viral replication has not decreased or has increased. The invention also encompasses methods of preventing the onset or reoccurrence of a viral respiratory infection in a patient at risk of developing such an infection. The invention also encompasses methods of preventing, managing, treating, or ameliorating a viral respiratory infection or a symptom thereof in patients who are susceptible to adverse reactions to conventional therapies. The invention further encompasses methods for preventing, treating, managing, or ameliorating viral respiratory infections for which no anti-viral therapy is available.

The invention encompasses methods for preventing, treating, managing, or ameliorating a viral respiratory infection or a symptom thereof in a patient who has proven refractory to therapies other than IL-9 antagonists but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral respiratory infections despite management or treatment with existing therapies.

The present invention encompasses methods for preventing, treating, managing, or ameliorating a viral respiratory infection or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease, patients with broncho-pulmonary dysplasia, patients with congenital heart disease, patients with cystic fibrosis, patients with acquired or congenital heart disease, and patients already suffering from a respiratory infection), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate a viral respiratory infection or one or more symptoms thereof.

Viral infection therapies and their dosages, routes of administration and recommended usage are known in the art and have been described in such literature as the *Physician's Desk Reference* (57th ed., 2003).

5.3.3 Bacterial Respiratory Infections

The invention provides methods for preventing, treating, managing, or ameliorating a bacterial respiratory infection or one or more symptoms thereof, said method comprising administering to a subject in need thereof a dose of an effective amount of one or more IL-9 antagonists. The invention also provides a method of preventing, treating, managing, or ameliorating a bacterial respiratory infection or one or more symptoms thereof, said method comprising administering to a subject in need thereof a dose of an effective amount of a one or more IL-9 antagonists and a dose of an effective amount of one or more therapies (e.g., one or more prophylactic or therapeutic agents) other than an IL-9 antagonist. Non-limiting examples of such agents include the agents described in section 5.2, supra, and in particular, the immunomodulatory agents described in section 5.2.1, the anti-inflammatory agents described in section 5.2.2, the anti-viral agents described in section 5.2.3, the anti-bacterial agents described in section 5.2.4, and the anti-fungal agents described in section 5.2.5.

The invention provides methods to prevent, treat, manage, or ameliorate a bacterial respiratory infection or one or more of the symptoms, said methods comprising administering to a subject in need thereof an effective amount of one or more IL-9 antagonists and an effective amount of one or more therapies used for bacterial respiratory infections. Therapies for bacterial respiratory infections may include, but are not limited to, anti-bacterial agents (e.g., aminoglycosides (e.g., gentamicin, tobramycin, amikacin, netilimicin) aztreonam, celphalosporins (e.g., cefaclor, cefadroxil, cephalexin, cephazolin), clindamycin, erythromycin, penicillin (e.g., penicillin V, crystalline penicillin G, procaine penicillin G), spectinomycin, and tetracycline (e.g., chlortetracycline, doxycycline, oxytetracycine)) or supportive respiratory therapy, such as supplemental and mechanical ventilation. In certain embodiments, an effective amount of one or more IL-9 antagonists is administered in combination with one or more supportive measures to a subject in need thereof to prevent, manage, treat, or ameliorate a bacterial respiratory infection or one or more symptoms thereof. Non-limiting examples of supportive measures include humidification of air by ultrasonic nebulizer, aerolized racemic epinephrine, oral dexamethasone, intravenous fluids, intubation, fever reducers (e.g., ibuprofen, acetometaphin), and more preferably, antibiotic or anti-viral therapy (i.e., to prevent or treat secondary infections).

Any respiratory condition resulting from or associated with a bacterial respiratory infection can be prevented, treated, managed, or ameliorated in accordance with the methods of invention. Examples of bacteria which cause bacterial respiratory infections include, but not limited to, the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, Edwardsiella, *Enterobacter aerogenes, Erwinia* species, *Escherichia coli, Hafnia* species, *Klebsiella* species, *Morganella* species, *Proteus vulgaris, Providencia, Salmonella* species, *Serratia marcescens,* and *Shigella flexneri*), Gardinella family, *Haemophilus influenzae*, Halobacteriaceae family, *Helicobacter* Family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, *Spirillum* Family, Spirosomaceae family, *Staphylococcus* (e.g., methicillin resistant *Staphylococcus aureus* and *Staphylococcus* pyrogenes), *Streptococcus* (e.g., *Streptococcus* enteritidis, *Streptococcus* Fasciae, and *Streptococcus pneumoniae*), Vampirovibr *Helicobacter* Family, and Vampirovibrio family.

The invention provides methods for preventing, managing, treating or ameliorating a biological response to a bacterial respiratory infection such as, but not limited to, inflammatory cell (e.g., mast cell, T cell, B cell, macrophage, neutrophils, and eosinophil) infiltration and proliferation, mucin production, and mast cell degranulation, said methods comprising administering to a subject in need thereof of an effective amount of one or more IL-9 antagonists alone or in combination with an effective amount of one or more other therapies. The invention also provides methods of preventing, treating, managing, or ameliorating respiratory conditions caused by or associated with bacterial infections, such as, but not limited to, pneumonococcal pneumonia, pneumonia caused by aerobic gram-negative bacilli, recurrent aspiration pneumonia, legionellosis, streptococcal disease, infections caused by *Hemophilus*, whooping cough, meningitis, or tuberculosis, said methods comprising administering to a subject in need thereof of an effective amount of one or more IL-9 antagonists alone or in combination with an effective amount of another therapy.

In a specific embodiment, the methods of the invention are utilized to prevent, treat, manage, or ameliorate a bacterial respiratory infection caused by *Pneumonococcus, Mycobacteria*, an aerobic gram-negative bacilli, *Streptococcus*, or *Hemophilus* or one or more symptoms thereof, said method comprising administering to a subject in need thereof an effective amount of one or more IL-9 antagonists alone or in combination with an effective amount of one or more other therapies.

In a specific embodiment, the invention provides methods for preventing, treating, managing, or ameliorating one or more secondary responses to a primary bacterial respiratory infection, said method comprising administering to a subject in need thereof an effective amount of one or more IL-9 antagonists alone or in combination with an effective amount of other therapies (e.g., other prophylactic or therapeutic agents). Examples of secondary responses to a primary bacterial respiratory infection include, but are not limited to, asthma-like responsiveness to mucosal stimula, elevated total respiratory resistance, increased susceptibility to secondary viral, bacterial, and fungal infections, and development of such conditions such as, but not limited to, pneumonia, croup, and febrile bronchitits.

In a specific embodiment, the methods of the invention are used to prevent, manage, treat, or ameliorate a bacterial respiratory infection or one or more symptoms thereof, said methods comprising administering to a subject in need thereof an effective amount of one or more IL-9 antagonists in combination with an effective amount of VITAXIN™ (MedImmune, Inc., International Publication No. WO 00/78815, International Publication No. WO 02/070007 A1, dated Sep. 12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents," and International Publication No. WO 03/075741 A2, dated Sep. 18, 2003 entitled "Methods of Preventing or Treating Disorders by Administering an Integrin αvβ3 Antagonist in Combination With an HMG-CoA Reductase Inhibitor or Bisphosphonate," each of which is incorporated herewith by reference in its entirety). In another embodiment, the invention provides methods to prevent, manage, treat, or ameliorate a bacterial respiratory infection or one or more symptoms thereof, said methods comprising administering to a subject in need thereof an effective amount of one or more IL-9 antagonists in combination with an effective amount of siplizumab (MedImmune, Inc., International Pub. No. WO 02/069904). In another embodiment, the invention provides methods to prevent, manage, treat, or ameliorate a bacterial respiratory infection or one or more symptoms thereof, said methods comprising administering to a subject in need thereof an effective amount of one or more IL-9 antagonists in combination with an effective amount of one or more molecules that either agonize or reduce the signaling of EphA2 (e.g., one or more anti-EphA2 Antibodies, preferably, that elicit EphA2 signaling (MedImmune, Inc., International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. application Ser. No. 10/436,783; and U.S. Appn. No. 60/379,368, each of which is incorporated herewith by reference)). In yet another embodiment, the invention provides methods to prevent, manage, treat, or ameliorate a bacterial respiratory infection or one or more symptoms thereof, said methods comprising administering to a subject in need thereof an effective amount of one or more IL-9 antagonists in combination with an effective amount of VITAXIN™, siplizumab, and/or EphA2 Molecule that agonizes EphA2 or reduces EphA2 expression.

The invention encompasses methods for preventing the development of a bacterial respiratory infection in a patient expected to suffer from a bacterial respiratory infection or at increased risk of such an infection, e.g., patients with suppressed immune systems (e.g., organ-transplant recipients, AIDS patients, patients undergoing chemotherapy, the elderly, infants born prematurely, infants, children, patients with carcinoma of the esophagus with obstruction, patients with tracheobronchial fistula, patients with neurological diseases (e.g., caused by stroke, amyotrophic lateral sclerosis, multiple sclerosis, cystic fibrosis, heart disease, and bronchopulmonary dysplasia, and myopathies), and patients already suffering from a respiratory infection). The patients may or may not have been previously treated for a respiratory infection.

The IL-9 antagonists or combination therapies of the invention may be used as the first, second, third, fourth, or fifth therapy to prevent, manage, treat, or ameliorate a bacterial respiratory infection or one or more symptom thereof. The invention also includes methods of preventing, treating, managing, or ameliorating a bacterial respiratory infection or one or more symptoms thereof in a patient undergoing therapies for other respiratory conditions. The invention encompasses methods of preventing, managing, treating, or ameliorating a bacterial respiratory infection or one or more symptoms thereof in a patient before any adverse effects or intolerance to therapies other than IL-9 antagonists develops. The invention also encompasses methods of preventing, treating, managing, or ameliorating a bacterial respiratory infection or a symptom thereof in refractory patients. In certain embodiments, a patient with a bacterial respiratory infection is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a bacterial respiratory infection is refractory when bacterial replication has not decreased or has increased. The invention also encompasses methods of preventing the onset or reoccurrence of a bacterial respiratory infection in a patient at risk of developing such an infection. The invention also encompasses methods of preventing, managing, treating, or ameliorating a bacterial respiratory infection or a symptom thereof in patients who are susceptible to adverse reactions to conventional therapies. The invention further encompasses methods for preventing, treating, managing, or ameliorating bacterial respiratory infections for which no anti-bacterial therapy is available.

The invention encompasses methods for preventing, treating, managing, or ameliorating a bacterial respiratory infection or a symptom thereof in a patient who has proven refractory to therapies other than IL-9 antagonists but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral respiratory infections despite management or treatment with existing therapies.

The present invention encompasses methods for preventing, treating, managing, or ameliorating a bacterial respiratory infection or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, patients with immunodeficiency disease, patients with cystic fibrosis, heart disease patients, and patients with broncho-pulmonary dysplasia), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate a bacterial respiratory infection or one or more symptoms thereof.

Bacterial infection therapies and their dosages, routes of administration and recommended usage are known in the art and have been described in such literature as the *Physician's Desk Reference* (57th ed., 2003).

5.3.4 Fungal Respiratory Infections

The invention provides a method of preventing, treating, managing, or ameliorating a fungal respiratory infection or one or more symptoms thereof, said method comprising administering to a subject in need thereof a dose of an effective amount of one or more IL-9 antagonists. The invention also provides a method of preventing, treating, managing, or ameliorating a fungal respiratory infection or one or more symptoms thereof, said method comprising administering to a subject in need thereof a dose of an effective amount of one or more IL-9 antagonists and a dose of an effective amount of one or more therapies (e.g., prophylactic or therapeutic agents) other than IL-9 antagonists. Non-limiting examples of such agents include the therapies described in section 5.2, supra, and in particular, the immunomodulatory agents described in section 5.2.1, the anti-inflammatory agents described in section 5.2.2, the anti-viral agents described in section 5.2.3, the anti-bacterial agents described in section 5.2.4, and the anti-fungal agents described in section 5.2.5.

In certain embodiments, an effective amount of one or more IL-9 antagonists is administered in combination with an effective amount of one or more therapies (e.g., one or more prophylactic or therapeutic agents) currently being used, have been used, or are know to be useful in the prevention, management, treatment, or amelioration of a fungal respiratory infection to a subject in need thereof. Therapies for fungal infections include, but are not limited to, anti-fungal agents such as, but not limited to, azole drugs e.g., miconazole, ketoconazole (NIZORAL®), caspofungin acetate (CANCIDAS®), imidazole, triazoles (e.g., fluconazole (DIFLUCAN®)), and itraconazole (SPORANOX®)), polyene (e.g., nystatin, amphotericin B colloidal dispersion ("ABCD") (AMPHOTEC®), liposomal amphotericin B (AMBISONE®)), postassium iodide (KI), pyrimidine (e.g., flucytosine (ANCOBON®)), and voriconazole (VFEND®). In certain embodiments, an effective amount of one or more IL-9 antagonists are administered in combination with one or more supportive measures to a subject in need thereof to prevent, manage, treat, or ameliorate a fungal infection or one or more symptoms thereof. Non-limiting examples of supportive measures include humidification of the air by an ultrasonic nebulizer, aerolized racemic epinephrine, oral desamethasone, intravenous fluids, intubation, fever reducers (e.g., ibuprofen and acetometaphin), and anti-viral or anti-bacterial therapy (i.e., to prevent or treat secondary viral or bacterial infections).

Any type of fungal infection or condition resulting from or associated with a respiratory condition can be prevented, treated, managed, or ameliorated in accordance with the methods of invention. Examples of fungi which cause fungal infections include, but not limited to, *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger,* and *Aspergillus terreus*), *Blastomyces dermatitidis, Candida* species (e.g., *Candida albicans, Candida glabrala, Candida kerr, Candida krusei, Candida parapsilosis, Candida pseudotropicalis, Candida quillermondii, Candida rugosa, Candida stellatoidea,* and *Candida tropicalis*), *Coccidioides immitis, Conidiobolus* species, *Cryptococcus neoforms, Cunninghamella* species, *Histoplasma capsulatum, Mucor pusillus, Paracoccidioides brasiliensis, Pseudallescheria boydii, Pneumocystis carinii, Rhizopus* species (e.g., *Rhizopus arrhizus, Rhizopus oryzae,* and *Rhizopus* Microsporus), *Saccharomyces* species, and *Sporothrix schenckii*. The invention also provides methods for preventing, managing, treating or ameliorating a biological response to a fungal respiratory infection such as, but not limited to, inflammatory cell (e.g., mast cell, T cell, B cell, macrophage, neutrophil, and eosinophil) infiltration and proliferation and mast cell degranulation, said methods comprising administration of an effective amount of one or more IL-9 antagonists alone or in combination with one or more other therapies (e.g., one or more prophylactic or therapeutic antagonists other than an IL-9 antagonist).

In a specific embodiment, the invention provides methods for preventing, treating, managing, or ameliorating one or more secondary responses to a primary fungal respiratory infection, said method comprising of administering to a subject in need thereof an effective amount of one or more IL-9 antagonists alone or in combination with an effective amount of other therapies (e.g., other prophylactic or therapeutic agents). Examples of secondary responses to a primary fungal respiratory infection include, but are not limited to, asthma-like responsiveness to mucosal stimula, elevated total respiratory resistance, increased susceptibility to secondary viral, fungal, and fungal infections, and development of such conditions such as, but not limited to, pneumonia, croup, and febrile bronchitis.

In a specific embodiment, the invention provides methods to prevent, manage, treat, or ameliorate a fungal respiratory infection or one or more symptoms thereof, said methods comprising administering to a subject in need thereof an effective amount of one or more IL-9 antagonists in combination with an effective amount of VITAXIN™ (MedImmune, Inc., International Publication No. WO 00/78815, International Publication No. WO 02/070007 A1, dated Sep.

12, 2002, entitled "Methods of Preventing or Treating Inflammatory or Autoimmune Disorders by Administering Integrin AlphaV Beta3 Antagonists," International Publication No. WO 03/075957 A1, dated Sep. 18, 2003, entitled "The Prevention or Treatment of Cancer Using Integrin AlphaVBeta3 Antagonists in Combination With Other Agents," U.S. Patent Pub. No. U.S. 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents," and International Publication No. WO 03/075741 A2, dated Sep. 18, 2003 entitled "Methods of Preventing or Treating Disorders by Administering an Integrin αvβ3 Antagonist in Combination With an HMG-CoA Reductase Inhibitor or Bisphosphonate," each of which is incorporated herewith by reference in its entirety). In another embodiment, the invention provides methods to prevent, manage, treat, or ameliorate a fungal respiratory infection or one or more symptoms thereof, said methods comprising administering administering to a subject in need thereof an effective amount of one or more IL-9 antagonists in combination with an effective amount of siplizumab (MedImmune, Inc., International Pub. No. WO 02/069904). In another embodiment, the methods of the invention are used to prevent, manage, treat, or ameliorate a fungal respiratory infection or one or more symptoms thereof, said methods comprising administering administering to a subject in need thereof an effective amount of one or more IL-9 antagonists in combination with an effective amount of one or more EphA2 inhibitors (e.g., one or more anti-EphA2 antibodies, preferably, that elicit EphA2 signaling (MedImmune, Inc., International Publication No. WO 02/102974 A4, dated Dec. 27, 2002, entitled "Mutant Proteins, High Potency Inhibitory Antibodies and FIMCH Crystal Structure," International Publication No. 03/094859 A2, dated Nov. 20, 2003, entitled "EphA2 Monoclonal Antibodies and Methods of Use Thereof," U.S. Application Ser. No. 10/436,783; and U.S. Appn. No. 60/379, 368, each of which is incorporated herewith by reference)). In yet another embodiment, the invention provides methods to prevent, manage, treat, or ameliorate a fungal respiratory infection or one or more symptoms thereof, said methods comprising administering administering to a subject in need thereof an effective amount of one or more IL-9 antagonists in combination with an effective amount of VITAXIN™, siplizumab, and/or EphA2.

The invention encompasses methods for preventing the development of a fungal respiratory infection in a patient expected to suffer from a fungal respiratory infection or at increased risk of such an infection, e.g., patients with suppressed immune systems (e.g., organ-transplant recipients, AIDS patients, patients undergoing chemotherapy, the elderly, infants born prematurely, infants, children, patients with carcinoma of the esophagus with obstruction, patients with tracheobronchial fistula, patients with neurological diseases (e.g., caused by stroke, amyotrophic lateral sclerosis, multiple sclerosis, and myopathies), patients with cystic fibrosis, patients with broncho-pulmonary dysplasia, patients with heart disease, and patients already suffering from a respiratory infection). The patients may or may not have been previously treated for a respiratory infection.

The IL-9 antagonists or combination therapies of the invention may be used as the first, second, third, fourth, or fifth therapy to prevent, manage, treat, or ameliorate a fungal respiratory infection or one or more symptom thereof. The invention also includes methods of preventing, treating, managing, or ameliorating n fungal respiratory infection or one or more symptoms thereof in a patient undergoing therapies for other respiratory conditions. The invention encompasses methods of preventing, managing, treating, or ameliorating a fungal respiratory infection or one or more symptoms thereof in a patient before any adverse effects or intolerance to therapies other than IL-9 antagonists develops. The invention also encompasses methods of preventing, treating, managing, or ameliorating a fungal respiratory infection or a symptom thereof in refractory patients. In certain embodiments, a patient with a fungal respiratory infection is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a fungal respiratory infection is refractory when fungal replication has not decreased or has increased. The invention also encompasses methods of preventing the onset or reoccurrence of a fungal respiratory infection in a patient at risk of developing such an infection. The invention also encompasses methods of preventing, managing, treating, or ameliorating a fungal respiratory infection or a symptom thereof in patients who are susceptible to adverse reactions to conventional therapies. The invention further encompasses methods for preventing, treating, managing, or ameliorating fungal respiratory infections for which no anti-fungal therapy is available.

The invention encompasses methods for preventing, treating, managing, or ameliorating a fungal respiratory infection or a symptom thereof in a patient who has proven refractory to therapies other than IL-9 antagonists but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral respiratory infections despite management or treatment with existing therapies.

The present invention encompasses methods for preventing, treating, managing, or ameliorating a fungal respiratory infection or one or more symptoms thereof as an alternative to other conventional therapies. In specific embodiments, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease), patients with cystic fibrosis, patients with broncho-pulmonary dysplasia, patients with heart disease, a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate a fungal respiratory infection or one or more symptoms thereof.

Fungal infection therapies and their dosages, routes of administration and recommended usage are known in the art and have been described in such literature as the *Physician's Desk Reference* (57th ed., 2003).

5.4 Compositions & Methods of Administering Therapies

The invention provides for the prevention, treatment, management, or amelioration of a respiratory condition or one or more symptoms thereof. In a specific embodiment, a composition comprises one or more IL-9 antagonists. In another embodiment, a composition comprises one or more IL-9 antagonists and one or more prophylactic or therapeutic agents other than IL-9 antagonists, said prophylactic or therapeutic agents known to be useful for or having been or currently being used in the prevention, treatment, management, or amelioration of a respiratory condition or one or more symptoms thereof. In another embodiment, a composition comprises one or more antibodies that are IL-9 antagonists. In yet another embodiment, a composition comprises one or more antibodies that are IL-9 antagonists and one or more prophylactic or therapeutic agents other than IL-9 antagonists, said prophylactic or therapeutic agents known to be useful for or having been or currently being used in the prevention, treatment, management, or amelioration of a respiratory condition or one or more symptoms thereof. In accordance with these embodiments, the composition may further comprise of a carrier.

In a specific embodiment, a composition comprises one or more IL-9 antagonists and one or immunomodulatory agents. In another embodiment, the composition comprises one or more IL-9 antagonists and one or more anti-inflammatory agents. In another embodiment, a composition comprises one or more IL-9 antagonists and one or more mast cell modulators (e.g., stem cell factor (c-kit receptor ligand) inhibitors (e.g., mAb 7H6, mAb 8H7A, pAb 1337, FK506, CsA, dexamthasone, and fluconcinonide), c-kit receptor inhibitors (e.g., STI 571 (formerly known as CGP 57148B)), mast cell protease inhibitors (e.g., GW-45, GW-58, wortmannin, LY 294002, calphostin C, cytochalasin D, genistein, KT5926, and staurosproine, and lactoferrin), relaxin ("RLX"), IgE antagonists (e.g., antibodies rhuMAb-E25 omalizumab, HMK-12 and 6HD5, and mAB Hu-901), IL-3 antagonists, IL-4 antagonists, IL-10 antagonists, and TGF-beta). In another embodiment, a composition comprises one or more IL-9 antagonists and one or more anti-viral agents. In another embodiment, a composition comprising one or more IL-9 antagonists and one or more anti-bacterial agents. In another embodiment, a composition comprising one or more IL-9 antagonists and one or more anti-fungal agents. In another embodiment, the composition comprises one or more IL-9 antagonists and any combination of one, two, three, or more of each of the following prophylactic or therapeutic agents: an immunomodulatory agent, an anti-inflammatory agent, a mast cell modulator, an anti-viral agent, an anti-bacterial agent, and an anti-fungal agent. In another embodiment, the composition comprises one or more IL-9 antagonists and VITAXIN™, siplizumab, palivizumab (SYNAGIS®; MedImmune, Inc.), an EphA2 inhibitor, or any combination thereof. In accordance with this embodiment, the composition may also comprise of one or more other prophylactic or therapeutic agent known or used to treat, manage, prevent, or ameliorate a respiratory condition or one or more symptoms thereof.

The compositions of the invention include, but are not limited to, bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention are pharmaceutical compositions and comprise an effective amount of one or more IL-9 antagonists, a pharmaceutically acceptable carrier, and, optionally, an effective amount of another prophylactic or therapeutic agent. See U.S. Provisional Application No. 60/561,845 concurrently filed entitled, "Anti-IL-9 Antibody Formulations and Uses Thereof."

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is contained in or administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer one or more IL-9 antagonists or the combination of one or more IL-9 antagonists and a prophylactic agent or therapeutic agent useful for preventing, managing, treating, or ameliorating a respiratory condition or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262: 4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal adminsitration (e.g., intranasal and oral routes). In addition, pulmonary administration can be employed, e.g., by use of an inhaler or nebulizer, and formulation with an aerosolizing agent. See, e.g., U.S. Pat. Nos.

6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an IL-9 antagonist, combination therapy, or a composition of the invention is administered using Alkermes AIR™ pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®) , or collagen matrices. In one embodiment, an effective amount of one or more IL-9 antagonists is administered locally to the affected area to a subject to prevent, treat, manage, and/or ameliorate a respiratory condition or a symptom thereof. In another embodiment, an effective amount of one or more IL-9 antagonists is administered locally to the affected area in combination with an effective amount of one or more therapies (e.g., one or more prophylactic or therapeutic agents) other than an IL-9 antagonist of a subject to prevent, treat, manage, and/or ameliorate a respiratory condition or one or more symptoms thereof. In another embodiment, an effective amount of a therapy such as a mast cell modulator (e.g., astem cell factor (c-kit receptor ligand) inhibitor (e.g., mAb 7H6, mAb 8H7A, pAb 1337, FK506, CsA, dexamthasone, and fluconcinonide), a c-kit receptor inhibitor (e.g., STI 571 (formerly known as CGP 57148B)) and a mast cell protease inhibitor (e.g., GW-45, GW-58, wortmannin, LY 294002, calphostin C, cytochalasin D, genistein, KT5926, staurosproine, and lactoferrin), and relaxin ("RLX")) is administered locally to the affected area in a subject to prevent, treat, manage, and/or ameliorate a respiratory condition or one or more symptoms thereof.

In yet another embodiment, the prophylactic or therapeutic agent can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In a specific embodiment, an IL-9 antagonist, combination therapy, and/or composition of the invention is administered using Alkermes AIR™ pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. In a preferred embodiment, a phamaceutical composition of the invention is formulated in single dose vials as a sterile liquid that contains 10 mM histidine buffer at pH 6.0 and 150 mM sodium chloride. Each 1.0 mL of solution contains 100 mg of protein, 1.6 mg of histidine and 8.9 mg of sodium chloride in water for optimal stability and solubility. A more detailed description of liquid formulations containing an IL-9 antagonist of the invention is provided in a U.S. provisional application to be concurrently filed herewith, entitled "Anti-IL-9 Antibody Formulations and Uses Thereof." Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompasses administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

Generally, the ingredients of the compositions of the invention are derived from a subject that is the same species origin or species reactivity as recipient of such compositions. Thus, in a preferred embodiment, human or humanized antibodies are administered to a human patient for therapy or prophylaxis.

5.4.1 Gene Therapy

In a specific embodiment, nucleotide sequences comprising nucleic acids encoding an IL-9 antagonist or another prophylactic or therapeutic agent of the invention are administered to treat, prevent, manage, or ameliorate a respiratory condition or one or more symptoms thereof by way of gene therapy. Gene therapy refers to therapy performed by the administration to a subject of an expressed or expressible nucleic acid. In this embodiment of the invention, the nucleic acids produce their encoded IL-9 antagonist or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In one embodiment, the method of the invention comprises administration of a composition comprising nucleic acids encoding IL-9 antagonists or another prophylactic or therapeutic agent of the invention, said nucleic acids being part of an expression vector that expresses the IL-9 antagonist, another prophylactic or therapeutic agent of the invention, or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another embodiment, nucleic acid molecules are used in which the coding sequences of an IL-9 antagonist or another prophylactic or therapeutic agent of the invention and any other desired sequences are flanked by regions that promote homologous recombination at a desired site in the genome, thus providing for intrachromosomal expression of the antibody encoding nucleic acids (Koller and Smithies, 1989, Proc. Natl. Acad. Sci. USA 86: 8932-8935; Zijlstra et al., 1989, Nature 342: 435-438). In specific embodiments, the expressed IL-9 antagonist molecule or other prophylactic or therapeutic agent is a single chain antibody; alternatively, the nucleic acid sequences include sequences encoding both the heavy and light chains, or fragments thereof, of the IL-9 antagonist or another prophylactic or therapeutic agent of the invention.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors). In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., International Publication Nos. WO 92/06180; WO 92/22635; WO92/20316; WO93/14188; and WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In a specific embodiment, viral vectors that contains nucleic acid sequences encoding an IL-9 antagonist, another prophylactic or therapeutic agent of the invention, or fragments thereof are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding the IL-9 antagonist or another prophylactic or therapeutic agent of the invention to be used in gene therapy are cloned into one or more vectors, which facilitates delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the several factors including, but not limited to, the desired effects and the patient state, and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, mast cells, megakaryocytes, granulocytes; various stem or progenitor cells, in particular hematopoietic stem or progenitor cells (e.g., as obtained from bone marrow, umbilical cord blood, peripheral blood, fetal liver, etc.). In a preferred embodiment, the cell used for gene therapy is autologous to the subject.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, 1992, Cell 7 1:973-985; Rheinwald, 1980, Meth. Cell Bio. 21A: 229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.5 Dosage & Frequency of Administration

The amount of a prophylactic or therapeutic agent or a composition of the present invention which will be effective in the treatment, management, prevention, or amelioration of a respiratory condition or one or more symptoms thereof can be determined by standard clinical. The frequency and dosage will vary according to factors specific for each patient depending on the specific therapy or therapies (e.g., the specific therapeutic or prophylactic agent or agents) administered, the severity of the disorder, disease, or condition, the route of administration, as well as age, body, weight, response, and the past medical history of the patient. For example, the dosage of a prophylactic or therapeutic agent or a composition of the invention which will be effective in the treatment, prevention, management, or amelioration of a respiratory condition or one or more symptoms thereof can be determined by administering the composition to an animal model such as, e.g., the animal models disclosed herein or known to those skilled in the art. In addition, in vitro assays may optionally be employed to help identify optimal dosage ranges. Suitable regimens can be selected by one skilled in the art by considering such factors and by following, for example, dosages reported in the literature and recommended in the *Physician's Desk Reference* (57th ed., 2003).

Exemplary doses of a small molecule include milligram or microgram amounts of the small molecule per kilogram of subject or sample weight (e.g., about 1 microgram per kilogram to about 500 Milligrams per kilogram, about 100 micrograms per kilogram to about 5 milligrams per kilogram, or about 1 microgram per kilogram to about 50 micrograms per kilogram).

In embodiments of the invention wherein antibodies, proteins, polypeptides, peptides and fusion proteins are administered to treat, manage, prevent, or ameliorate a respiratory condition or one or more symptoms thereof, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg, or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof may be reduced by enhancing uptake and tissue penetration of the antibodies by modifications such as, for example, lipidation.

In a specific embodiment, the dosage administered to a patient will be calculated using the patient's weight in kilograms (kg) multiplied by the dose to be administered in mg/kg. The required volume (in mL) to be given is then determined by taking the mg dose required divided by the concentration of the antibody or fragment thereof in the formulations (100 mg/mL). The final calculated required volume will be obtained by pooling the contents of as many vials as are necessary into syringe(s) to administer the drug. A maximum volume of 2.0 mL of antibody or fragment thereof in the formulations can be injected per site.

In a specific embodiment, the method of the invention comprises the administration of an IL-9 antagonist or a composition comprising said antagonist to a subject to prevent, treat, manage, or ameliorate a respiratory condition or one or more symptoms thereof in a dosage that is 150 µg/kg or less, preferably 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight. In another embodiment, the dosage of the IL-9 antagonist or composition comprising said antagonist that is administered to prevent, treat, manage, or ameliorate a respiratory condition or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In certain embodiments, a subject is administered one or more doses of an effective amount of one or more IL-9 antagonist, wherein the dose of an effective amount of said IL-9 antagonist prevents at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% of endogenous IL-9 From binding to its receptor. In certain embodiments, a subject is administered one or more doses of an effective amount of one or more IL-9 antagonist, wherein the dose of an effective amount of said IL-9 antagonist reduces and/or inhibits mast cell degranulation at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80 to 85%, at least 85% to 90%, at least 90% to 95%, or at least 95% to 98% relative to a control such as PBS in an in vitro and/or in vivo assay well-known in the art. In certain embodiments, a subject is administered one or more doses of an effective amount of one or more IL-9 antagonist, wherein the dose of an effective amount of said IL-9 antagonist reduces and/or inhibits mast cell activation at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80 to 85%, at least 85% to 90%, at least 90% to 95%, or at least 95% to 98% relative to a control such as PBS in an in vitro and/or in vivo assay well-known in the art. In certain embodiments, a subject is administered one or more doses of an effective amount of one or more IL-9 antagonist, wherein the dose of an effective amount of said IL-9 antagonist reduces and/or inhibits mast cell proliferation at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80 to 85%, at least 85% to 90%, at least 90% to 95%, or at least 95% to 98% relative to a control such as PBS in an in vitro and/or in vivo assay well-known in the art. In certain embodiments, a subject is administered one or more doses of an effective amount of one or more IL-9 antagonist, wherein the dose of an effective amount of said IL-9 antagonist reduces and/or inhibits mast cell infiltration in the upper and/or lower respiratory tracts at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80 to 85%, at least 85% to 90%, at least 90% to 95%, or at least 95% to 98% relative to a control such as PBS in an in vitro and/or in vivo assay well known in the art.

In other embodiments, a subject is administered one or more doses of an effective amount of one or more IL-9 antagonists (preferably, antibodies that immunospecifically bind to IL-9), wherein the dose of an effective amount achieves a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the antagonists. In yet other embodiments, a subject is administered a dose of a prophylactically or therapeutically effective amount of one or more IL-9 antagonists (preferably, one or more antibodies that immunospecifically bind to IL-9) to achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the antagonists and a subsequent dose of a prophylactically or therapeutically effective amount of one or more IL-9 antagonists (preferably, one or more antibodies that immunospecifically bind to IL-9) is administered to maintain a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml. In accordance with these embodiments, a subject may be administered 1, 2, 3, 4, 5, 6, 7, 8, 9, 10, 11, 12 or more subsequent doses.

In a specific embodiment, the invention provides methods of preventing, treating, managing, or treating a respiratory condition or one or more symptoms thereof, said method comprising administering to a subject in need thereof a dose of at least 10 µg, preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 105 µg, at least 110 µg, at least 115 µg, or at least 120 µg of one or more IL-9 antagonists. In another embodiment, the invention provides a method of preventing, treating, managing, or ameliorating a respiratory condition or one or more symptoms thereof, said methods comprising administering to a subject in need thereof a dose of at least 10 µg, preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 105 µg, at least 110 µg, at least 115 µg, or at least 120 µg of one or more IL-9 antagonists once every 3 days, preferably, once every 4 days, once every 5 days, once every 6 days, once every 7 days, once every 8 days, once every 10 days, once every two weeks, once every three weeks, or once a month.

The present invention provides methods of preventing, treating, managing, or preventing a respiratory condition or one or more symptoms thereof, said method comprising: (a) administering to a subject in need thereof one or more doses of a prophylactically or therapeutically effective amount of one or more IL-9 antagonists; and (b) monitoring the plasma level/concentration of the administered IL-9 antagonist or antagonists in said subject after administration of a certain number of doses of the said IL-9 antagonist or antagonists. Moreover, preferably, said certain number of doses is 1, 2, 3, 4, 5, 6, 7, 8, 9, 10, 11, or 12 doses of a prophylactically or therapeutically effective amount one or more IL-9 antagonists.

In a specific embodiment, the invention provides a method of preventing, treating, managing, or ameliorating a respiratory condition or one or more symptoms thereof, said method comprising: (a) administering to a subject in need thereof a dose of at least 10 µg (preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg) of one or more IL-9 antagonists; and (b) administering one or more subsequent doses to said subject when the plasma level of the IL-9 antagonist or antagonists administered in said subject is less than 0.1 µg/ml, preferably less than 0.25 µg/ml, less than 0.5 µg/ml, less than 0.75 µg/ml, or less than 1 µg/ml. In another embodiment, the invention provides a method of preventing, treating, managing, or ameliorating a respiratory condition or one or more symptoms thereof, said method comprising: (a) administering to a subject in need thereof one or more doses of at least 10 µg (preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg) of one or more IL-9 antagonists; (b) monitoring the plasma level of the administered IL-9 antagonist or antagonists in said subject after the administration of a certain number of doses; and (c) administering a subsequent dose of the IL-9 antagonist or antagonists when the plasma level of the administered IL-9 antagonist or antagonists in said subject is less than 0.1 µg/ml, preferably less than 0.25 µg/ml, less than 0.5 µg/ml, less than 0.75 µg/ml, or less than 1 µg/ml. Preferably, said certain number of doses is 1, 2, 3, 4, 5, 6, 7, 8, 9, 10, 11, or 12 doses of an effective amount of one or more IL-9 antagonists.

Therapies (e.g., prophylactic or therapeutic agents), other than IL-9 antagonists, which have been or are currently being used to prevent, treat, manage, or ameliorate a respiratory condition or one or more symptoms thereof can be administered in combination with one or more IL-9 antagonists according to the methods of the invention to treat, manage, prevent, or ameliorate a respiratory condition or one or more symptoms thereof. Preferably, the dosages of prophylactic or therapeutic agents used in combination therapies of the invention are lower than those which have been or are currently being used to prevent, treat, manage, or ameliorate a respiratory condition or one or more symptoms thereof. The recommended dosages of agents currently used for the prevention, treatment, management, or amelioration of a respiratory condition or one or more symptoms thereof can be obtained from any reference in the art including, but not limited to, Hardman et al., eds., 2001, Goodman & Gilman's The Pharmacological Basis Of Basis Of Therapeutics, 10th ed., Mc-Graw-Hill, New York; Physician's Desk Reference (PDR) 57th ed., 2003, Medical Economics Co., Inc., Montvale, N.J., which are incorporated herein by reference in its entirety.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patient visit.

In certain embodiments, one or more IL-9 antagonists and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same IL-9 antagonists may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than an IL-9 antagonist may be repeated and the administration may be separated by at least at least 1 day, 2 days, 3 days, 5 days, 10 days, 15 days, 30 days, 45 days, 2 months, 75 days, 3 months, or at least 6 months.

5.6 Biological Assays 5.6.1 Immunospecificity of the Antibodies of the Invention Antibodies of the present invention or fragments thereof may be characterized in a variety of ways well known to one of skill in the art. In particular, antibodies of the invention or fragments thereof may be assayed for the ability to immunospecifically bind to an IL-9 polypeptide or IL-9R or one or more subunits thereof. Such an assay may be performed in solution (e.g., Houghten, 1992, Bio/Techniques 13:412-421), on beads (Lam, 1991, Nature 354:82-84), on chips (Fodor, 1993, Nature 364: 555-556), on bacteria (U.S. Pat. No. 5,223, 409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Cwirla et al., 1990, Proc. Natl. Acad. Sci. USA 87:6378-6382; and Felici, 1991, J. Mol. Biol. 222: 301-310) (each of these references is incorporated herein in its entirety by reference). Antibodies or fragments thereof that have been identified can then be assayed for specificity and affinity for an IL-9 polypeptide.

The antibodies of the invention or fragments thereof may be assayed for immunospecific binding to a specific antigen (e.g., IL-9 polypeptide or IL-9R or one or more subunits thereof) and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well-known in the art (see, e.g., Ausubel et al., eds., 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, incubating the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. In a preferred embodiment, an ELISA may be performed by coating a high binding 96-well microtiter plate (Costar) with 2 µg/ml of rhu-IL-9 in PBS overnight. Following three washes with PBS, the plate is incubated with three-fold serial dilutions of Fab at 25° C. for 1 hour. Following another three washes of PBS, 1 µg/ml anti-human kappa-alkaline phosphatase-conjugate is added and the plate is incubated for 1 hour at 25° C. Following three washes with PBST, the alkaline phosphatase activity is determined in 50 µl/AMP/PPMP substrate. The reactions are stopped and the absorbance at 560 nm is determined with a VMAX microplate reader. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of an antibody of the present invention or a fragment thereof for a specific antigen (e.g., IL-9 polypeptide or IL-9R or one or more subunits thereof) and the binding off-rates can be determined from the data by scatchard plot analysis. Competition with a second antibody can also be determined using radioimmunoassays. In a specific embodiment, an IL-9 polypeptide is incubated with an antibody that is an IL-9 antagonist conjugated to a labeled compound (e.g., $^3$H or $^{125}$I) in the presence of increasing amounts of an unlabeled second antibody.

In a preferred embodiment, BIAcore kinetic analysis is used to determine the binding on and off rates of antibodies of the invention to an IL-9 polypeptide. BIAcore kinetic analysis comprises analyzing the binding and dissociation of an IL-9 polypeptide from chips with immobilized antibodies of the invention on their surface. A typical BIAcore kinetic study involves the injection of 250 µL of an antibody reagent (mAb, Fab) at varying concentration in HBS buffer containing 0.005% Tween-20 over a sensor chip surface, onto which has been immobilized the antigen. The flow rate is maintained constant at 75 µL/min. Dissociation data is collected for 15 min. or longer as necessary. Following each injection/dissociation cycle, the bound mAb is removed from the antigen surface using brief, 1 min. pulses of dilute acid, typically 10-100 mM HCl, though other regenerants are employed as the circumstances warrant. More specifically, for measurement of the rates of association, $k_{on}$, and dissociation, $k_{off}$, the antigen is directly immobilized onto the sensor chip surface through the use of standard amine coupling chemistries, namely the EDC/NHS method (EDC=N-diethylaminopropyl)-carbodiimide). Briefly, a 5-100 nM solution of the antigen in 10 mM NaOAc, pH4 or pH5 is prepared and passed over the EDC/NHS-activated surface until approximately 30-50 RU's worth of antigen are immobilized. Following this, the unreacted active esters are "capped" off with an injection of 1M Et-NH2. A blank surface, containing no antigen, is prepared under identical immobilization conditions for reference purposes. Once an appropriate surface has been prepared, a suitable dilution series of each one of the antibody reagents is prepared in HBS/Tween-20, and passed over both the antigen and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The antibodies of the invention or fragments thereof can also be assayed for their ability to inhibit the binding of an antigen to its host cell receptor using techniques known to those of skill in the art. For example, cells expressing IL-9 receptor can be contacted with an IL-9 polypeptide in the presence or absence of an antibody or fragment thereof that is an IL-9 antagonist and the ability of the antibody or fragment thereof to inhibit IL-9's binding can measured by, for example, flow cytometry or a scintillation assay. The IL-9 polypeptide or the antibody or antibody fragment can be labeled with a detectable compound such as a radioactive label (e.g., $^{32}$P, $^{35}$s, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between IL-9 and IL-9R. Alternatively, the ability of antibodies or fragments thereof to inhibit IL-9 From binding to IL-9R can be determined in cell-free assays. For example, an IL-9 polypeptide can be contacted with an antibody or fragment thereof that is an IL-9 antagonist and the ability of the antibody or antibody fragment to inhibit the IL-9 polypeptide from binding to IL-9R can be determined. Preferably, the antibody or the antibody fragment that is an IL-9 antagonist is immobilized on a solid support and an IL-9 polypeptide is labeled with a detectable compound. Alternatively, an IL-9 polypeptide is immobilized on a solid support and the antibody or fragment thereof is labeled with a detectable compound. An IL-9 polypeptide may be partially or completely purified (e.g., partially or completely free of other polypeptides) or part of a cell lysate. Further, an IL-9 polypeptide may be a fusion protein comprising IL-9, a derivative, analog or fragment thereof and a domain such as glutathionine-S-transferase. Alternatively, an IL-9 polypeptide can be biotinylated using techniques well known to those of skill in the art (e.g., biotinylation kit, Pierce Chemicals; Rockford, Ill.).

The ability of antibodies or fragments of the invention to inhibit IL-9 From binding to its host cell receptor may be measured by cell proliferation assays. For example, the murine TS1-RA3 T cell line expressing both human and murine IL-9Rα may be grown continuously in growth medium (DMEM) containing rhuIL-9 (25 ng/ml, R & D Systems). Upon withdrawal of rhuIL-9, TS1-RA3 undergoes cell death in 18-24 hours. TS1-RA3 cells are grown in RPMI 1640 (ATCC) medium supplemented with 10% FBS and 25 ng/ml rHu-IL9. Prior to the assay, the cells are washed with media containing no IL-9 and resuspended at $5\times10^5$ cells/ml in media containing 2 ng/ml rhuIL-9. The cells are distributed into a black clear bottom non-binding 96-well microtiter plate (100 µl cells/well) and 100 ml of serially diluted variant Fabs is then added to the plate. The plate is incubated at 72 hours at 37° C., 5% CO2. 20 µl/well of Alamar blue® is added, and the cells are incubated for an additional 4-5 hours. Cell metabolism is quantitated using a fluorimeter with excitation at 555 nm and emission at 590 nm. The ability of antibodies or fragments of the invention to inhibit IL-9 From binding to its host cell receptor may be measured may also be measured by a cell binding assay, such as an IL-9 Binding ELISA assay. For example, each well of a 96-well ELISA plate is coated with 100 µL of IL-9 antibodies or antibody fragments of the invention overnight at 2 to 8° C. The plate is washed three times with PBS/0.5% Tween-20 Buffer, and is blocked for 1 hour at ambient temperature with PBS/0.1% Tween-20 Buffer, 1% (w/v) BSA. After washing the plate, 100 µL of a Reference Standard, samples and controls are loaded onto the assay plate and incubated at ambient temperature for 1 hour. After washing, 100 µL of horseradish peroxidase-labeled (HRP) goat anti-human IgG at a 1:15,000 dilution is added to the assay plate. Following the one-hour incubation, the plate is washed and 100 µL/well of 3,3',5,5'-tetramethylbenzidine (TMB) substrate is added to the plate and incubated at ambient temperature in the dark for 10 minutes. The enzymatic reaction is stopped by the addition of 50 µL/well of 2N sulfuric acid. The absorbance at 450 nm is measured using a microplate reader. Samples are dispositioned as pass/fail based on the parallelism of the sample curve to the Reference Standard curve, and the $ED_{50}$ value of the sample falling in the range of 3.91-31.91 ng/mL.

5.6.2 In Vitro Studies

The IL-9 antagonists, compositions, or combination therapies of the methods of the invention can be tested in vitro and/or in vivo for their ability to modulate the biological activity of immune cells (e.g., T cells, neutrophils, and mast cells), endothelial cells, and epithelial cells. The ability of an IL-9 antagonist, composition, or combination therapy of the invention to modulate the biological activity of immune cells (e.g., T cells, B cells, mast cells, macrophages, neutrophils, and eosinophils), endothelial cells, and epithelial cells can be assessed by: detecting the expression of antigens (e.g., activation of genes by IL-9, such as, but not limited to, mucin genes (e.g., MUC2, MUC5AC, MUC5B, and MUC6) and genes involved in lymphocyte activation (e.g., Lgamma-6A/E)); detecting the proliferation of immune cells, endothelia cells and/or epithelial cells; detecting the activation of signaling molecules (e.g., the phosphorylation of Stat2, the phosphorylation of JAK3, or the phosphorylation of the IL-9R); detecting the effector function of immune cells (e.g., T cells, B cells, mast cells, macrophages, neutrophils, and eosinophils), endothelial cells, and/or epithelial cells; or detecting the differentiation of immune cells, endothelial cells, and/or epithelial cells. Techniques known to those of skill in the art can be used for measuring these activities. For example, cellular proliferation can be assayed by 3H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and FACS analysis. The activation of signaling molecules can be assayed, for example, by kinase assays and electrophoretic shift assays (EMSAs). Mast cell degranulation can be assayed, for example by measuring serotonin (5-HT) release or histamine release with high-performance liquid chromatography (see, e.g., Taylor et al. 1995 Immunology 86(3): 427-433 and Kurosawa et al., 1998 Clin Exp Allergy 28(8): 1007-1012).

The IL-9 antagonists, compositions, or combination therapies of the invention are preferably tested in vitro and then in vivo for the desired therapeutic or prophylactic activity prior to use in humans. For example, assays which can be used to determine whether administration of a specific pharmaceutical composition is indicated include cell culture assays in which a patient tissue sample is grown in culture and exposed to, or otherwise contacted with, a pharmaceutical composition, and the effect of such composition upon the tissue sample is observed. The tissue sample can be obtained by biopsy from the patient. This test allows the identification of the therapeutically most effective therapy (e.g., prophylactic or therapeutic agent) for each individual patient. In various specific embodiments, in vitro assays can be carried out with representative cells of cell types involved a respiratory condition to determine if a pharmaceutical composition of the invention has a desired effect upon such cell types. For example, in vitro asssay can be carried out with cell lines.

The effect of an IL-9 antagonist, a composition, or a combination therapy of the invention on peripheral blood lymphocyte counts can be monitored/assessed using standard techniques known to one of skill in the art. Peripheral blood lymphocytes counts in a subject can be determined by, e.g., obtaining a sample of peripheral blood from said subject, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in subject can be determined by, e.g., separating the lymphocytes from other components of peripheral blood such as plasma using, e.g., a use of Ficoll-Hypaque (Pharmacia) gradient centrifugation, labeling the T-cells with an antibody directed to a T-cell antigen which is conjugated to FITC or phycoerythrin, and measuring the number of T-cells by FACS.

The methods of the invention for treating, managing, preventing, or ameliorating a viral respiratory infection or one or more symptoms thereof can be tested for their ability to inhibit viral replication or reduce viral load in in vitro assays. For example, viral replication can be assayed by a plaque assay such as described, e.g., by Johnson et al., 1997, Journal of Infectious Diseases 176:1215-1224 176:1215-1224. The IL-9 antagonists, compositions, or combination therapies administered according to the methods of the invention can also be assayed for their ability to inhibit or downregulate the expression of viral polypeptides. Techniques known to those of skill in the art, including, but not limited to, western blot analysis, northern blot analysis, and RT-PCR can be used to measure the expression of viral polypeptides.

The methods of the invention for preventing, treating, managing, or ameliorating a respiratory condition or one or more symptoms thereof can be tested for activity against bacteria causing respiratory infections in in vitro assays well-known in the art. In vitro assays known in the art can also be used to test the existence or development of resistance of bacteria to a therapy (e.g., an IL-9 antagonist, other prophylactic or therapeutic agent, a combination thereof, or a composition thereof) of the invention. Such in vitro assays are described in Gales et al., 2002, Diag. Nicrobiol. Infect. Dis. 44(3):301-311; Hicks et al., 2002, Clin. Microbiol. Infect. 8(11):753-757; and Nicholson et al., 2002, Diagn. Microbiol. Infect. Dis. 44(1):101-107.

The therapies (e.g., IL-9 antagonists alone or in combination with prophylactic or therapeutic agents, other than IL-9 antagonists) of the invention for treating, managing, preventing, or ameliorating a respiratory condition or one or more symptoms thereof can be tested for anti-fungal activity against different species of fungus. Any of the standard anti-fungal assays well-known in the art can be used to assess the anti-fungal activity of a therapy. The anti-fungal effect on different species of fungus can be tested. The tests recommended by the National Committee for Clinical Laboratories (NCCLS) (See National Committee for Clinical Laboratories Standards. 1995, Proposed Standard M27T. Villanova, Pa., all of which is incorporated herein by reference in its entirety) and other methods known to those skilled in the art (Pfaller et al., 1993, *Infectious Dis. Clin. N. Am.* 7:435-444) can be used to assess the anti-fungal effect of a therapy. The antifungal properties of a therapy may also be determined from a fungal lysis assay, as well as by other methods, including, inter alia, growth inhibition assays, fluorescence-based fungal viability assays, flow cytometry analyses, and other standard assays known to those skilled in the art.

For example, the anti-fungal activity of a therapy can be tested using macrodilution methods and/or microdilution methods using protocols well-known to those skilled in the art (see, e.g., Clancy et al., 1997 *Journal of Clinical Microbiology,* 35(11):2878-82; Ryder et al., 1998, *Antimicrobial Agents and Chemotherapy,* 42(5):1057-61; U.S. Pat. No. 5,521,153; U.S. Pat. No. 5,883,120, U.S. Pat. No. 5,521,169, all of which are incorporated by reference in their entirety). Briefly, a fungal strain is cultured in an appropriate liquid media, and grown at an appropriate temperature, depending on the particular fungal strain used for a determined amount of time, which is also depends on the particular fungal strain used. An innoculum is then prepared photometrically and the turbidity of the suspension is matched to that of a standard, e.g., a McFarland standard. The effect of a therapy on the turbidity of the inoculum is determined visually or spectrophotometrically. The minimal inhibitory concentration ("MIC") of the therapy is determined, which is defined as the lowest concentration of the lead compound which prevents visible growth of an inoculum as measured by determining the culture turbidity.

The anti-fungal activity of a therapy can also be determined utilizing colorimetric based assays well-known to one of skill in the art. One exemplary calorimetric assay that can be used to assess the anti-fungal activity of a therapy is described by Pfaller et al. (1994, *Journal of Clinical Microbiology*, 32(8): 1993-6, which is incorporated herein by reference in its entirety; also see Tiballi et al., 1995, *Journal of Clinical Microbiology*, 33(4):915-7). This assay employs a colorimetric endpoint using an oxidation-reduction indicator (Alamar Biosciences, Inc., Sacramento Calif.).

The anti-fungal activity of a therapy can also be determined utilizing photometric assays well-known to one of skill in the art (see, e.g., Clancy et al., 1997 *Journal of Clinical Microbiology*, 35(11):2878-82; Jahn et al., 1995, *Journal of Clinical Microbiology*, 33(3):661-667, each of which is incorporated herein by reference in its entirety). This photometric assay is based on quantifying mitochondrial respiration by viable fungi through the reduction of 3-(4,5-dimethyl-2thiazolyl)-2,5,-diphenyl-2H-tetrazolium bromide (MTT) to formazan. MIC's determined by this assay are defined as the highest concentration of the test therapy associated with the first precipitous drop in optical density. In some embodiments, the therapy is assayed for anti-fungal activity using macrodilution, microdilution and MTT assays in parallel.

Further, any in vitro assays known to those skilled in the art can be used to evaluate the prophylactic and/or therapeutic utility of an IL-9 antagonist, a composition, a combination therapy disclosed herein for a respiratory condition or one or more symptoms thereof.

5.6.3 In Vivo Assays

The IL-9 antagonists, compositions, or combination therapies of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapies (e.g., prophylactic and/or therapeutic agents) whether such therapies are administered separately or as an admixture, and the frequency of administration of the therapies.

Animal models can be used to assess the efficacy of the methods of the invention for treating, managing, preventing, or ameliorating a viral respiratory infection or one or more symptom thereof. Animal models for allergies and asthma are known in the art, such as constant-flow inflation with end-inspiratory occlusion described in Ewart et al., 1995 J Appl Physiol 79(2):560-566 and other assays described in, e.g., Komai et al., 2003 Br J Pharmacol 138(5):912-920; Kenyon et al., 2003 Toxicol Appl Pharmacol 186(2):90-100; Path et al., 2002 Am J Resp & Critical Care Med 166(6):818-826; Martins et al., 1990 Crit Care Med 19:515-519; Nicolaides et al., 1997 Proc Natl Acad Sci USA 94:13175-13180; McLane et al., 1998 19:713-720; and Temann et al., 1998 J Exp Med 188(7):1307-1320. Animal models for viral respiratory infections such as, but not limited to, PIV are described by e.g., Shephard et al., 2003 Res Vet Sci 74(2):187-190; Ottolini et al., 2002 J Infect Dis 186(12):1713-1717; and RSV are described by, e.g., Culley et al., 2002 J Exp Med 196(10): 1381-1386; and Curtis et al., 2002 Exp Biol Med 227(9):799-802. In a specific embodiment, cotton rats are administered an IL-9 antagonist, a composition, or a combination therapy according to the methods of the invention, challenged with $10^5$ pfu of RSV, and four or more days later the rats are sacrificed and RSV titer and IL-9 antagonist serum titer is determined. Accordingly, a dosage that results in a 2 log decrease or a 99% reduction in RSV titer in the cotton rat challenged with $10^5$ pfu of RSV relative to the cotton rat challenged with $10^5$ pfu of RSV but not administered the formulation is the dosage of the formulation that can be administered to a human for the treatment, prevention or amelioration of one or more symptoms associated with RSV infection. Further, this embodiment, the tissues (e.g., the lung tissues) from the sacrificed rats can be examined for histological changes.

The administration of IL-9 antagonists, compositions, or combination therapies according to the methods of the invention can be tested for their ability to decrease the time course of a viral respiratory infection by at least 25%, preferably at least 50%, at least 60%, at least 75%, at least 85%, at least 95%, or at least 99%. The IL-9 antagonists, compositions, or combination therapies of the invention can also be tested for their ability to increase the survival period of humans suffering from a viral respiratory infection by at least 25%, preferably at least 50%, at least 60%, at least 75%, at least 85%, at least 95%, or at least 99%. Further, IL-9 antagonists, compositions, or combination therapies of the invention can be tested for their ability reduce the hospitalization period of humans suffering from viral respiratory infection by at least 60%, preferably at least 75%, at least 85%, at least 95%, or at least 99%. Techniques known to those of skill in the art can be used to analyze the function of the IL-9 antagonists, compositions, or combination therapies of the invention in vivo.

Animal models for bacterial infections can also be used to assess the efficacy of the administration of an IL-9 antagonist, a composition, or a combination therapy according to the methods of the invention. Animal models for bacterial infections such as *H. pylori*-infection, genital mycoplasmosis, primary sclerosing cholangitis, cholera, chronic lung infection with *Pseudomonas aeruginosa*, Legionnaires' disease, gastroduodenal ulcer disease, bacterial meningitis, gastric *Helicobacter* infection, pneumococcal otitis media, experimental allergic neuritis, leprous neuropathy, mycobacterial infection, endocarditis, *Aeromonas*-associated enteritis, *Bacteroides fragilis* infection, syphilis, streptococcal endocarditis, acute hematogenous osteomyelitis, human scrub typhus, toxic shock syndrome, anaerobic infections, *Escherichia coli* infections, and *Mycoplasma pneumoniae* infections have been developed (see, e.g., Sugiyama et al., 2002, J. Gastroenterol. 37 suppl 13:6-9; Brown et al., 2001, Am. J. Reprod. Immunol. 46(3):232-41; Vierling, 2001, Best Pract. Res. Clin. Gastroenterol. 15(4):591-610; Klose, 2000, Trends Microbiol. 8(4):189-91; Stotland et al., 2000, Pediatr. Pulmonol. 30(5):413-24; Brieland et al., 2000, Immunopharmacology 48(3):249-52; Lee, 2000, Baillieres Best Pract. Res. Clin. Gastroenterol. 14(1):75-96; Koedel & Pfister, 1999, Infect. Dis. Clin. North. Am. 13(3):549-77; Nedrud, 1999, FEMS Immunol. Med. Microbiol. 24(2):243-50; Prellner et al., 1999, Microb. Drug. Resist. 5(1):73-82; Vriesendorp, 1997, J. Infect. Dis. 176 suppl 2:S164-8; Shetty & Antia, 1996, Indian J. Lepr. 68(1):95-104; Balasubramanian et al., 1994, Immunobiology 191(4-5):395-401; Carbon et al., 1994, Int. J. Biomed. Comput. 36(1-2):59-67; Haberberger et al., 1991, Experientia. 47(5):426-9; Onderdonk et al., 1990, Rev. Infect. Dis. 12 suppl 2:S169-77; Wicher & Wicher, 1989, Crit. Rev. Microbiol. 16(3):181-234; Scheld, 1987, J Antimicrob. Chemother. 20 suppl A:71-85; Emslie & Nade, 1986, Rev. Infect. Dis. 8(6):841-9; Ridgway et al., 1986, Lab Anim. Sci. 36(5):481-5; Quimby & Nguyen, 1985, Crit. Rev. Microbiol. 12(1):1-44; Onderdonk et al., 1979, Rev. Infect. Dis. 1(2):291-301; Smith, 1976, Ciba. Found. Symp. (42):45-72, and Taylor-Robinson, 1976, Infection. 4(1 suppl):4-8).

The IL-9 Antibodies, compositions, or combination therapies of the invention can be tested for their ability to decrease the time course of bacterial respiratory infection by at least 25%, preferably at least 50%, at least 60%, at least 75%, at least 85%, at least 95%, or at least 99%. The IL-9 antagonists, compositions, or combination therapies of the invention can also be tested for their ability to increase the survival period of humans suffering from a bacterial respiratory infection by at least 25%, preferably at least 50%, at least 60%, at least 75%, at least 85%, at least 95%, or at least 99%. Further, IL-9 antagonists, compositions, or combination therapies administered according to the methods of the invention can be tested for their ability reduce the hospitalization period of humans suffering from bacterial respiratory infection by at least 60%, preferably at least 75%, at least 85%, at least 95%, or at least 99%. Techniques known to those of skill in the art can be used to analyze the function of the IL-9 antagonists, compositions, or combination therapies of the invention in vivo.

The efficacy of the IL-9 antagonists, compositions, or combination therapies of the invention for the prevention, management, treatment, or amelioration of a fungal infection can be assessed in animal models for such infections. Animal models for fungal infections such as *Candida albicans, Aspergillus fumigatus*, invasive pulmonary aspergillosis, *Pneumocystis carinii*, pulmonary cryptococcosis, *Pseudomonas aeruginosa, Cunninghamella bertholletia* (see, e.g., Aratani et al., 2002 Med Mycol 40(6):557-563; Bozza et al., 2002 Microbes Infect 4(13):1281-1290; Kurup et al., 2002 Int Arch Allergy Immunol 129(2):129-137; Hori et al., 2002 Eur J Immuno 32(5):1282-1291; Rivera et al., 2002 J Immuno 168(7):3419-3427; Vassallo et al., 2001, Am J Respir Cell Mol Biol 25(2): 203-211; Wilder et al., 2002 Am J Respir Cell Mol Biol 26(3):304-314; Yonezawa et al., 2000 J Infect Chemother 6(3):155-161; Cacciapuoti et al., 2000 Antimicrob Agents Chemother 44(8):2017-2022; and Honda et al., 1998 Mycopathologia 144(3):141-146).

The IL-9 antagonists, compositions, or combination therapies of the invention can be tested for their ability to decrease the time course of fungal respiratory infection by at least 25%, preferably at least 50%, at least 60%, at least 75%, at least 85%, at least 95%, or at least 99%. The IL-9 antagonists, compositions, or combination therapies of the invention can also be tested for their ability to increase the survival period of humans suffering from a fungal respiratory infection by at least 25%, preferably at least 50%, at least 60%, at least 75%, at least 85%, at least 95%, or at least 99%. Further, IL-9 antagonists, compositions, or combination therapies administered according to the methods of the invention can be tested for their ability reduce the hospitalization period of humans suffering from fungal respiratory infection by at least 60%, preferably at least 75%, at least 85%, at least 95%, or at least 99%. Techniques known to those of skill in the art can be used to analyze the function of the IL-9 antagonists, compositions, or combination therapies of the invention in vivo.

Further, any in vivo assays known to those skilled in the art can be used to evaluate the prophylactic and/or therapeutic utility of an IL-9 antagonist, a composition, a combination therapy disclosed herein for a respiratory conditions or one or more symptoms thereof.

5.6.4 Toxicity Assays

The toxicity and/or efficacy of the prophylactic and/or therapeutic protocols of the instant invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.7 Articles of Manufacture

The present invention also encompasses a finished packaged and labeled pharmaceutical product. This article of manufacture includes the appropriate unit dosage form in an appropriate vessel or container such as a glass vial or other container that is hermetically sealed. The pharmaceuctical product may be formulated in single dose vials as a sterile liquid that contains 10 mM histidine buffer at pH 6.0 and 150 mM sodium chloride. Each 1.0 mL of solution may contain 100 mg of protein, 1.6 mg of histidine and 8.9 mg of sodium chloride in water for injection (see U.S. Provisional Application concurrently filed herewith No. 60/561,845, entitled "Anti-IL-9 Antibody Formulations and Uses Thereof, which is incorporated herein by reference in its entirety). During the manufacturing process the pH of the formulation buffer is adjusted to 6.0 using hydrochloric acid. In the case of dosage forms suitable for parenteral administration the active ingredient, e.g., an IL-9 antagonist of the invention that immunospecifically binds to an IL-9 polypeptide, is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, intransal, or topical delivery.

In certain embodiments, the unit dosage form is suitable for intravenous, intramuscular, intranasal, oral, topical, pulmonary, or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the respiratory condition in question. In other words, the article of manufacture includes instruction means indicating or suggesting a dosing regimen and monitoring information including, but not limited to, actual doses, monitoring procedures, total lymphocyte counts, mast cell counts, mast cell degranulation, T cell counts, IgE production, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises an IL-9 antagonist and wherein said packaging material includes instruction means which indicate that said antagonist can be used to treat, prevent, manage, or ameliorate a respiratory condition or one or more symptoms thereof by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises one or more IL-9 antagonists and a second pharmaceutical agent comprises a prophylactic or therapeutic agent, other than an IL-9 antagonist, and wherein said packaging material includes instruction means which indicate that said antagonists can be used to treat, prevent, manage, or ameliorate a respiratory condition or one or more symptoms thereof by administering specific doses and using specific dosing regimens as described herein (see U.S. Provisional Application No. 60/561,845 filed concurrently herewith, entitled "Anti-IL-9 Antibody Formulations and Uses Thereof").

The invention also provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein one pharmaceutical agent comprises an IL-9 antagonist and a prophylactic or therapeutic agent other than an IL-9 antagonist and wherein said packaging material includes instruction means which indicate that said agents can be used to treat, prevent, manage, or ameliorate a respiratory condition or one or more symptoms thereof by administering specific doses and using specific dosing regimens as described herein.

The present invention provides that the adverse effects that may be reduced or avoided by the methods of the invention are indicated in informational material enclosed in an article of manufacture for use in preventing, treating, managing, or ameliorating a respiratory condition or one or more symptoms thereof. Adverse effects that may be reduced or avoided by the methods of the invention include, but are not limited to, vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, and vasodilatation. Since IL-9 antagonists may be immunosuppressive, prolonged immunosuppression may increase the risk of infection, including opportunistic infections. Prolonged and sustained immunosuppression may also result in an increased risk of developing certain types of cancer.

Further, the information material enclosed in an article of manufacture for use in preventing, treating, managing, or ameliorating a respiratory condition or one or more symptoms thereof can indicate that foreign proteins may also result in allergic reactions, including anaphylaxis, or cytosine release syndrome. The information material should indicate that allergic reactions may exhibit only as mild pruritic rashes or they may be severe such as erythroderma, Stevens-Johnson syndrome, vasculitis, or anaphylaxis. The information material should also indicate that anaphylactic reactions (anaphylaxis) are serious and occasionally fatal hypersensitivity reactions. Allergic reactions including anaphylaxis may occur when any foreign protein is injected into the body. They may range from mild manifestations such as urticaria or rash to lethal systemic reactions. Anaphylactic reactions occur soon after exposure, usually within 10 minutes. Patients may experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, or eosinophilia.

5.8 Methods of Producing Peptides, Polypeptides, and Fusion Proteins

Peptides, polypeptides, proteins and fusion proteins can be produced by standard recombinant DNA techniques or by protein synthetic techniques, e.g., by use of a peptide synthesizer. For example, a nucleic acid molecule encoding a peptide, polypeptide, protein or a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing the Fc domain or a fragment thereof such that the bioactive molecule is linked in-frame to the Fc domain or Fc domain fragment.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; International Publication Nos. WO 91/06570, WO 96/04388, WO 96/22024, WO 97/34631, and WO 99/04813; Ashkenazi et al., 1991, Proc. Natl. Acad. Sci. USA 88:10535-10539; Traunecker et al., 1988, Nature, 331:84-86; Zheng et al., 1995, J. Immunol. 154:5590-5600; and Vil et al., 1992, Proc. Natl. Acad. Sci. USA 89:11337-11341, which are incorporated herein by reference in their entireties.

The nucleotide sequences encoding an IL-9 antagonist or another prophylatic or therapeutic agent and an Fc domain or fragment thereof may be an be obtained from any information available to those of skill in the art (i.e., from Genbank, the literature, or by routine cloning). The nucleotide sequences encoding integrin ligands may be obtained from any available information, e.g., from Genbank, the literature or by routine cloning. See, e.g., Xiong et al., Science, 12; 294(5541):339-45 (2001). The nucleotide sequence coding for a polypeptide a fusion protein can be inserted into an appropriate expression vector, i.e., a vector which contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a peptide, polypeptide, protein or a fusion protein may be controlled by any regulatory element, e.g., any promoter or enhancer element, known in the art.

Promoters which may be used to control the expression of the gene encoding fusion protein include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35s RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Corn. 253:818-823); glial fibrillary acidic protein (GFAP) promoter which is active in astrocytes (Gomes et al., 1999, Braz J Med Biol Res 32(5):619-631; Morelli et al., 1999, Gen. Virol. 80:571-83) and gonadotropic releasing hormone gene control region which is active in the hypothalamus (Mason et al., 1986, Science 234:1372-1378).

In a specific embodiment, the expression of a peptide, polypeptide, protein or a fusion protein is regulated by a constitutive promoter. In another embodiment, the expression of a peptide, polypeptide, protein or a fusion protein is regulated by an inducible promoter. In another embodiment, the expression of a peptide, polypeptide, protein or a fusion protein is regulated by a tissue-specific promoter.

In a specific embodiment, a vector is used that comprises a promoter operably linked to a peptide-, polypeptide-, protein- or a fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the polypeptide or fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 81:355-359). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

Expression vectors containing inserts of a gene encoding a peptide, polypeptide, protein or a fusion protein can be identified by three general approaches:(a) nucleic acid hybridization, (b) presence or absence of "marker" gene functions, and (c) expression of inserted sequences. In the first approach, the presence of a gene encoding a peptide, polypeptide, protein or a fusion protein in an expression vector can be detected by nucleic acid hybridization using probes comprising sequences that are homologous to an inserted gene encoding the peptide, polypeptide, protein or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a polypeptide or a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (e.g., fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, J. Natl. Cancer Inst. 73:51-57), SK-N-SH human neuroblastoma (Biochim. Biophys. Acta, 1982, 704:450-460), Daoy human cerebellar medulloblastoma (He et al., 1992, Cancer Res. 52:1144-1148) DBTRG-05MG glioblastoma cells (Kruse et al., 1992, In vitro Cell. Dev. Biol. 28A:609-614), IMR-32 human neuroblastoma (Cancer Res., 1970, 30:2110-2118), 1321N1 human astrocytoma (Proc. Natl. Acad. Sci. USA, 1977, 74:4816), MOG-G-CCM human astrocytoma (Br. J. Cancer, 1984, 49:269), U87MG human glioblastoma-astrocytoma (Acta Pathol. Microbiol. Scand., 1968, 74:465-486), A172 human glioblastoma (Olopade et al., 1992, Cancer Res. 52:2523-2529), C6 Rat glioma cells (Benda et al., 1968, Science 161:370-371), Neuro-2A mouse neuroblastoma (Proc. Natl. Acad. Sci. USA, 1970, 65:129-136), NB41A3 Mouse neuroblastoma (Proc. Natl. Acad. Sci. USA, 1962, 48:1184-1190), SCP sheep choroid plexus (Bolin et al., 1994, J. Virol. Methods 48:211-221), G355-5, PG-4 Cat normal astrocyte (Haapala et al., 1985, J. Virol. 53:827-833), Mpf ferret brain (Trowbridge et al., 1982, In vitro 18:952-960), and normal cell lines such as, for example, CTX TNA2 Rat normal cortex brain (Radany et al., 1992, Proc. Natl. Acad. Sci. USA 89:6467-6471) such as, for example, CRL7030 And Hs578Bst. Furthermore, different vector/host expression systems may effect processing reactions to different extents.

For long-term, high-yield production of recombinant proteins, stable expression is preferred. For example, cell lines which stably express a polypeptide or a fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a polypeptide or a fusion protein that antagonize. Such engineered cell lines may be particularly useful in screening and evaluation of compounds that affect the activity of a peptide, polypeptide or a fusion protein that antagonize IL-9.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Once a peptide, polypeptide, or a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

5.9 Methods of Producing Antibodies

The antibodies that immunospecifically bind to an antigen can be produced by any method known in the art for the synthesis of antibodies, in particular, by chemical synthesis or preferably, by recombinant expression techniques.

Polyclonal antibodies immunospecific for an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies:A Laboratory Manual, (Cold Spring Harbor Laboratory Press, 2nd ed. 1988); Hammerling, et al., in: Monoclonal Antibodies and T Cell Hybridomas 563 681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 Available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 Fragments). F(ab')2 Fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli And the E. coli is infected with helper phage. Phage used in these methods are typically filamentous phage including fd and M13 And the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/O1 134; International publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 And 4,716,111; and International publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65 93. For a detailed discussion of this technology for producing human antibodies and human monoclonal antibodies and protocols for producing such antibodies, see, e.g., International publication Nos. WO 98/24893, WO 96/34096, and WO 96/33735; and U.S. Pat. Nos. 5,413,923, 5,625,126, 5,633, 425, 5,569,825, 5,661,016, 5,545,806, 5,814,318, and 5,939, 598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,311,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', F(ab').sub.2, Fabc, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 Regions of the heavy chain. The humanized antibody can be selected from any class of immunoglobulins, including IgM, IgG, IgD, IgA and IgE, and any isotype, including IgG1, IgG2, IgG3 And IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. A humanized antibody can be produced using variety of techniques known in the art, including but not limited to, CDR-grafting (see e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see e.g., European Patent Nos. EP 592,106 And EP 519,596; Padlan, 1991, Molecular Immunology 28(4/5):489-498; Studnicka et al., 1994, Protein Engineering 7(6):805-814; and Roguska et al., 1994, PNAS 91:969-973, each of which is incorporated herein by its entirety by reference), chain shuffling (see e.g., U.S. Pat. No. 5,565,332, which is incorporated herein in its entirety by reference), and techniques disclosed in, e.g., U.S. Pat. No. 6,407,213, U.S. Pat. No. 5,766,886, International Publication No. WO 9317105, Tan et al., J. Immunol. 169: 1119 25 (2002), Caldas et al., Protein Eng. 13(5):353 60 (2000), Morea et al., Methods 20(3):267 79 (2000), Baca et al., J. Biol. Chem. 272(16):10678 84 (1997), Roguska et al., Protein Eng. 9(10):895 904 (1996), Couto et al., Cancer Res. 55 (23 supp):5973s-5977s (1995), Couto et al., Cancer Res. 55(8):1717 22 (1995), Sandhu J S, Gene 150(2):409 10 (1994), and Pedersen et al., J. Mol. Biol. 235(3):959 73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well known in the art, e.g. by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Further, the antibodies that immunospecifically bind to IL-9 polypeptide or IL-9R or one or more subunits thereof can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8): 2429-2438).

5.9.1 Polynucleotide Sequences Encoding an Antibody

The invention provides polynucleotides comprising a nucleotide sequence encoding an antibody or fragment thereof that immunospecifically binds to an antigen (e.g., an IL-9 polypeptide or IL-9R or one or more subunits thereof). The invention also encompasses polynucleotides that hybridize under high stringency, intermediate or lower stringency hybridization conditions, e.g., as defined supra, to polynucleotides that encode an antibody of the invention.

The polynucleotides may be obtained, and the nucleotide sequence of the polynucleotides determined, by any method known in the art. The nucleotide sequence of antibodies immunospecific for a desired antigen can be obtained, e.g., from the literature or a database such as GenBank. Since the amino acid sequences of, e.g., VITAXIN®, IL-9 antagonists (e.g., I8431-03, I8431-12, I8431-15A, I8431-20A, SC-7923, AF209, BAF209, AB-209, AF409, BAF409, AB-409-NA, ab9632, ab9734, and C212), MED-507, and anti-EphA2 Antibodies are known, nucleotide sequences encoding this antibody or a fragment thereof (e.g., a CDR) can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278:457-479 For a listing of human framework regions). Preferably, the polynucleotide generated by the combination of the framework regions and CDRs encodes an antibody that immunospecifically binds to a particular antigen. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

5.9.2 Recombinant Expression of an Antibody

Recombinant expression of an antibody of the invention, derivative, analog or fragement thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well-known in the art. See, e.g., U.S. Pat. No. 6,331,415, which is incorporated herein by reference in its entirety. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication No. WO 86/05807 And WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* And *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding antibodies which immunospecifically bind to an IL-9 polypeptide or IL-9R or one or more subunits thereof is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT20 And T47D, NS0 (a murine myeloma cell line that does not endogenously produce any immunoglobulin chains), CRL7030 And HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription termina-tors, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szyalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al., (eds.), Current Protocols in Molecular Biology, John Wiley & Sons, NY (1993); Kriegler, Gene Transfer and Expression, A Laboratory Manual, Stockton Press, NY (1990); and in Chapters 12 And 13, Dracopoli et al., (eds), Current Protocols in Human Genetics, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

6. EXAMPLES

Certain embodiments of the invention are illustrated by the following non-limiting examples.

6.1 Example 1

Preparation of IL-9 Antagonist MAb 7F3com-2H2

Anti-human IL-9 Antibody MAb 7F3com-2H2 was prepared using the pMI347 vector. The pMI347 vector coding for the expression of MAb 7F3com-2H2 consists of the following four independent genetic elements:a glutamine synthetase selectable marker expression cassette, the 7F3com-2H2 light chain cDNA expression cassette, the 7F3com-2H2 heavy chain mini-gene expression cassette, and a bacterial origin of replication and antibiotic resistance gene.

The first element, the glutamine synthetase selectable marker expression cassette consists of hamster glutamine synthetase (GS) cDNA under the control of simian virus 40 (SV40) early enhancer and promoter and SV40 early splicing and polyadenylation region for efficient mRNA cleavage and addition of a polyadneylate tail. This element is required for integration, amplification, and stable maintenance of the plasmid in the host cell genome.

Each of the 7F3com-2H2 heavy and light chain expression cassettes consist of the human cytomegalovirus major immediate early (hCMVie) enhancer, promoter, and 5;-untranslaterd region directing the high level transcription of 7F3com-2H2 light cahin cDNA, and athe SV40 early polyadenylation region for efficient polyadenylation. This combination of a strong enhancer/promoter and an efficient polyadenylation region assures high levels of stable 7F3com-2H2 light chain mRNA in the cells. The light and heavy chain expression cassettes are separated by a murine immunoglobulin mu transcription termination region to prevent transcriptional interference of the downstream genes.

The final element of the pMI347 vector is the bacterial origin of replication and antibiotic resistance gene (e.g., beta-lactamase gene) allow for the propagation and selection of the vector E. coli.

The pMI347 vector encoding the anti-IL-9 monoclonal antibody 7F3com-2H2 has been deposited in the form of E. coli (DH5-α) with the American Type Culture Collection (ATCC), located in Manassas, Virginia, under the provisions of the Budapest Treaty on the International Recognition of the Deposit of Microorganisms for the Purposes of Patent Procedure ("Budapest Treaty"), on Apr. 9, 2004, and assigned accession number PTA-5913.

Transient Mammalian Cell Expression of MAb 7F3com-2H2

The expression vector pMI347 was introduced to 293-H cells vial lipid mediated transfection for transient expression. After 72 hours, the cell culture supernatant was harvested and fresh growth medium was added to each plate. The process was repeated after 96 hours. After the third harvest, the cell culture supernatants were pooled and assayed for human IgG content.

Stable Mammalian Cell Expression of MAb 7F3com-2H2

The expression vector pMI347 was linearized with the Sal I restriction enzyme and introduced into NSO cells by electroporation. Cells were selected for integration of the plasmid into the host cell genome in glutamine-free medium. Colonies surviving in the glutamine-free environment were screened for immunoglobulin expression and the highest expressing colonies were expanded. Then, these primary transfectants were cloned by limiting dilution in glutamine-free medium to isolate high producing sub-populations. The clones were screened for specific productivity and growth characteristics. Thos clones that exhibited the most favorable combinations of high productivity and rapid growth were selected for evaluation as production cell lines.

Quantitation of MAb 7F3com-2H2

Cell culture supernatants were screened for 7F3com-2H2 Antibody using a sandwich ELISA. Assay plates coated with goat-anti-human IgG were washed and incubated with cell culture supernatant and human IgG standards. After incubation, the plates were washed to remove non-bound IgG. Then the plates were reacted with horseradish peroxidase-labeled goat-anti-human IgG secondary antibody. After incubation, the plates were again washed. The chromogenic substrate 3, 3', 5,5'-tetramethylbenzidine was added to each well and after fve minutes, 0.1N sulfuric acid was added to terminate the substrate turnover. The substrate turnover was then measured at 450 nm using a microplate reader. The standard curve was plotted as a log-linear relationship and unknown samples were compared to the standard curve to estimate their human IgG content.

6.2 Antibody Purification

The following section describes a method for purifying antibodies to be used in the methods of the invention.

6.2.1 Buffer Components and Equipment

Buffers, process solutions and cleaning solutions are prepared with water for injection (WFI). Buffers are tested for bioburden and endotoxin.

Buffers and Process Solutions
0.1 M citric acid
10 mM sodium citrate, 80 mM NaCl, pH 4.6
25 mM sodium phosphate, pH 6.5
20 mM Tris-HCl, 40 mM NaCl, pH 7.5
0.5 M sodium phosphate, pH 6.5
5 mM sodium phosphate, 40 mM NaCl, pH 6.5
50 mM Glycine-HCl, 30 mM NaCl, pH 2.5
50 mM Glycine-HC, pH 2.35
1.0 M Tris base
Cleaning and Storage Solutions
Water for Injection (WFI)
1.0 N NaOH
0.1 NaOH
20% (v/v) ethanol
0.5 N NaOH, 400 ppm sodium hypochlorite
Formulation Buffers
10 mM Histidine, 150 mM NaCl, pH 6.0
4 M sodium chloride
Equipment (Substitutions with Equivalent Performing Materials are acceptable)
300 kg scale
Conductivity meter Stir plate
pH meter
Vessels: Appropriately sized Stedim™ bags, buffer tanks, PETG Bottles
Watson Marlow 1700 peristaltic pump
Wedgewood UV, pH, conductivity unit
Amersham Pharmacia chromatography controller
Packed POROS HS50 cation exchange gel
Packed Pharmacia rProtein A affinity gel
Packed POROS HQ anion exchange gel
Sterile, depyrogenated silicone tubing
Integritest Filter Integrity Tester II
Sterile Asahi Planova 20 N membrane viral removal filter
Millipore 0.2 Micron Durapore filter
Millipore Multimedia filter
CUNO 60 LP, 10/60 sP filter
CUNO filter housing
Class 100 hood

6.2.2 Purification and Formulation of the Antibodies

The purification process comprises three chromatography steps, a nanofiltration step, a low pH treatment step, and formulation. These steps are designed to remove host cell proteins, DNA and cell culture components such as BSA and transferrin. In addition, the process includes steps to control bioburden and endotoxin and to remove and inactivate viruses.

6.2.2.1 Conditioned Medium (Steps 1 to 6)

Conditioned medium from a single cell culture lot or pooled from multiple cell culture lots is purified as a single lot. The combination of multiple cell culture lots into one purification lot is performed in order to utilize downstream processing steps sized for a single lot size and to decrease the number of purification lots. For example, because the working volumes of 130 L and 250 L cell culture bioreactors are approximately 100 L and 200 L, respectively, these two cell culture lots could be pooled and run as one 300 L purification lot. Process product samples are analyzed for DNA using a PicoGreen or a quantitative PCR assay to detect DNA. Protein concentration is determined either by a Protein A bindable HPLC assay or by UV absorbance at 280 nm. Product-containing process streams are monitored for endotoxin and bioburden. Column effluents are monitored for endotoxin. A description of each step is summarized below.

6.2.2.2 Conditioned Medium Adjustment and Filtration (Step 7)

The conditioned medium is adjusted to pH 4.6±0.2 with 0.1 M citric acid. The adjusted conditioned medium is then filtered using a CUNO filter in-line with a Millipore 0.2 Micron Durapore filter.

6.2.2.3 Cation Exchange Chromatography Step (Step 8)

The adjusted and filtered conditioned medium is loaded onto a cation exchange column that has been equilibrated with 10 mM sodium phosphate, 80 mM sodium chloride, pH 4.6. The bound antibody is washed using the same buffer. The column is then washed with 25 mM sodium phosphate pH 6.5 to remove process impurities, especially BSA. The product is eluted using 20 mM Tris-HCl buffer, 40 mM NaCl, pH 7.5. Following elution of the product, the column is cleaned with 1.0 N NaOH and stored in 0.1 N NaOH at room temperature.

6.2.2.4 rProtein A Chromatograph (Step 9)

The cation exchange product is loaded directly onto a rProtein A column equilibrated with 20 mM Tris-HCl buffer, 40 mM NaCl, pH 7.5. Following loading, the column is washed with the equilibration buffer, and the product is eluted with 50 mM glycine, 30 mM NaCl, pH 3.2. The rProtein A product is neutralized to pH 6.5±0.2 with 1.0 M Tris base. This chromatography step removes additional process-related impurities. At the end of the step, the column is washed with equilibration buffer, cleaned with 0.1 N NaOH, washed with equilibration buffer and stored in 20% (v/v) ethanol at room temperature.

6.2.2.5 Anion Exchange Chromatography (Step 10)

This chromatographic step is the final step designed to remove any trace levels of process-related impurities. The column is equilibrated with 0.5 M sodium phosphate, pH 6.5 Followed by equilibration with 5 mM sodium phosphate, 40 mM sodium chloride, pH 6.5. Under these conditions, the neutralized rProtein A product is loaded onto the equilibrated anion exchange column, and under these conditions, the product is recovered in the non-bound fraction and the process-related impurities are retained in the column. The column is cleaned with 1.0 N NaOH and stored in 0.1 N NaOH at room temperature.

6.2.2.6 Nanofiltration (Step 11)

The anion exchange product is filtered through a sterile Planova™ 20 N membrane (pore size=20 nm) that is prepared by flushing first with WFI and then with 5 mM sodium phosphate, 40 mM sodium chloride pH 6.5. After the product is filtered, the filter is chased with a small volume of 5 mM sodium phosphate, 40 mM sodium chloride, pH 6.5 to maximize product recovery. After filtration the nanofilter is integrity tested.

6.2.2.7 Low pH Treatment (Step 12)

The pH of the nanofiltered product is adjusted to 3.4±0.1 with 50 mM glycine, pH 2.35 And held at this pH for 30±10 minutes. After low pH treatment, the product pH is adjusted to 6.5±0.2 with 1.0 M Tris base.

6.3 Example 2

Relationship Between IL-9 And Airway Hyperresponsiveness

This example demonstrates the relationship between IL-9 And airway hyperresponsiveness as well as the effectiveness of IL-9 Antibodies in reducing airway hyperresponsiveness.

Materials and Methods

Experimental groups of four mice were acclimated to the plethysmography chamber and then exposed to aerosolized saline for two minutes. Penh values were obtained for five minutes after saline aerosol exposure to obtain a Penh baseline value for lung function. Subsequently, methylcholine chloride ("MCh") (Sigma Aldrich, Sigma, Mo.) was introduced to the plethysmography chamber to induce bronchoconstriction in the mice. Penh values were monitored for five minutes after methylcholine chloride exposure. In some studies, 5 μg of recombinant murine IL-9 or BSA was administered once daily for three consecutive days. The mice were acclimated to the plesthymography chamber twenty-four (24) hours after the administration of the last dose of recombinant murine IL-9 or BSA. In other studies, a total of three (3) doses of 200 μg of an anti-IL-9 Antibody, D93, were administered i.p. to mice with each dose being administered every third day. The mice were acclimated to the plesthysmography chamber forty-eight (48) hours after the third dose.

Results

Respiratory dynamics were assessed in conscious, unrestrained mice using a whole-body plethysmography system (Buxco, Troy, N.Y.). Bronchoconstrictive responses of mice to aerosolized challenge agent were measured and expressed as enhanced pause (Penh), a unitless value derived from peak inspiratory and expiratory flows and timing of expiration. The relationship between Penh and airway hyperresponsiveness ("AHR") has been previously established and validated in animal models.

The sensitivity of standard mouse strains, BLB/c, FVB, and C3H/BI6 to MCh challenge at various concentrations were determined using the whole-body plethysmography system. The mean Penh value for BALB/c, FVB, and C3H/BI6 Mice after exposure to 0 mg/ml, 12.5 mg/ml, 25 mg/ml, 50 mg/ml, or 100 mg/ml is shown in FIG. 16. As expected, increasing concentrations of MCh increased the mean Penh value.

IL-9 Increases the Severity of AHR

MCh induced AHR in the standard mouse strain FVB was compared to MCh induced AHR in the mouse strain Tg5 that overexpresses IL-9. As shown in FIG. 17, greater Penh values were obtained for Tg5 strain mice than for FVB strain mice after MCh challenge. These results demonstrate that IL-9 overexpression plays a significant a role in AHR.

To further assess the relationship of IL-9 And AHR, four BALB/c strain mice and four C57BI/6 Mice were locally administered 5 μg of recombinant murine IL-9 or BSA once daily for three consecutive days. As shown in FIG. 18A, the mean Penh values for BALB/c strain mice that were administered IL-9 were greater than the mean Penh values for mice in the control group. As shown in FIG. 18B, the mean Penh values for C57BI/6 strain mice that were administered IL-9 were greater than the mean Penh values for mice in the control group. These results confirm that IL-9 plays a role in increasing the severity of AHR.

Reduction of AHR Following Administration of an IL-9 Antagonist

The effect of an IL-9 Antagonist, in particular, an anti-IL-9 Antibody, on MCh induced AHR was assessed. As shown in FIG. 19, a lower Penh value was obtained in mice that received the anti-IL-9 Antibody D93 compared to the mice that received the BSA control.

6.4 AHR Caused by RSV Exposure

The relationship between exposure to RSV and AHR was studied. Four C57BI/6 Mice were intranasally inoculated with RSV and four other C57BI/6 Mice were intranasally inoculated with PBS. One day after inoculation, the mice were placed in the plethysmography chamber and exposed to aerosolized saline for two minutes. Penh values were obtained for five minutes after saline aerosol exposure to establish a Penh baseline value for lung function. Subsequently 100 mg/ml MCh was introduced to the plethysmography chamber to induce bronchoconstriction in the mice. As shown in FIG. 19, a lower Penh value of mice that were inoculated with RSV compared to the mice that were inoculated with PBS control was obtained. These results demonstrate that RSV exposure results in AHR.

7. Equivalents

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

I claim:

1. A method of treating or ameliorating a respiratory infection, or a symptom thereof, in a human subject suffering therefrom, said method comprising administering to said human subject an effective amount of an antibody or fragment thereof that immunospecifically binds IL-9, wherein the antibody or fragment thereof comprises:
   (a) a VH CDR1 comprising the amino acid sequence of SEQ ID NO:26, a VH CDR2 comprising the amino acid sequence of SEQ ID NO:64, a VH CDR3 comprising the amino acid sequence of SEQ NO:3, a VL CDR1 comprising the amino acid sequence of SEQ ID NO:65, a VL CDR2 comprising the amino acid sequence of SEQ ID NO:66, and a VL CDR3 comprising the amino acid sequence of SEQ ID NO:20; or
   (b) a VH domain comprising the amino acid sequence of SEQ ID NO:27 and a VL domain comprising the amino acid sequence of SEQ ID NO:28.

2. A method of treating or ameliorating wheezing in a human pre-term infant, a human infant or a human child, said method comprising administering to said pre-term infant, infant or child an effective amount of an antibody or fragment thereof that immunospecifically binds IL-9, wherein the antibody or fragment thereof comprises:
   (a) a VH CDR1 comprising the amino acid sequence of SEQ ID NO:26, a VH CDR2 comprising the amino acid sequence of SEQ ID NO:64, a VH CDR3 comprising the amino acid sequence of SEQ ID NO:3, a VL CDR1 comprising the amino acid sequence of SEQ ID NO:65, a VL CDR2 comprising the amino acid sequence of SEQ ID NO:66, and a VL CDR3 comprising the amino acid sequence of SEQ ID NO:20; or
   (b) a VH domain comprising the amino acid sequence of SEQ ID NO:27 and a VL domain comprising the amino acid sequence of SEQ ID NO:28.

3. A method of treating or ameliorating wheezing in a human subject suffering therefrom, said method comprising administering to said human subject:
   an effective amount of an antibody or fragment thereof that immunospecifically binds IL-9, wherein the antibody or fragment thereof comprises:
      (a) a VH CDR1 comprising the amino acid sequence of SEQ ID NO:26, a VH CDR2 comprising the amino acid sequence of SEQ ID NO:64, a VH CDR3 comprising the amino acid sequence of SEQ ID NO:3, a VL CDR1 comprising the amino acid sequence of SEQ ID NO:65, a VL CDR2 comprising the amino acid sequence of SEQ ID NO:66, and a VL CDR3 comprising the amino acid sequence of SEQ ID NO:20; or
      (b) a VH domain comprising the amino acid sequence of SEQ ID NO:27 and a VL domain comprising the amino acid sequence of SEQ ID NO:28, and
   an effective amount of at least one other therapy that is not administration of an IL-9 antagonist.

4. A method of treating or ameliorating asthma or an allergy, or one or more symptoms thereof, in a human subject suffering therefrom, said method comprising administering to said human subject:
   an effective amount of an antibody or fragment thereof that immunospecifically binds IL-9, wherein the antibody or fragment thereof comprises:
      (a) a VH CDR1 comprising the amino acid sequence of SEQ ID NO:26, a VH CDR2 comprising the amino acid sequence of SEQ ID NO:64, a VH CDR3 comprising the amino acid sequence of SEQ ID NO:3, a VL CDR1 comprising the amino acid sequence of SEQ ID NO:65, a VL CDR2 comprising the amino acid sequence of SEQ ID NO:66, and a VL CDR3 comprising the amino acid sequence of SEQ ID NO:20; or
      (b) a VH domain comprising the amino acid sequence of SEQ ID NO:27 and a VL domain comprising the amino acid sequence of SEQ ID NO:28, and
   an effective amount of at least one other asthma or allergy therapy.

5. The method of claim 1 or 2 further comprising administering an effective amount of at least one other therapy that is not administration of an IL-9 antagonist.

6. The method of claim 1, wherein the respiratory infection is a viral infection, a bacterial infection or a fungal infection.

7. The method of claim 6, wherein the viral infection is a parainfluenza virus infection, an influenza virus infection or a metapneumovirus infection.

8. The method of claim 6, wherein the viral infection is a respiratory syncytial virus (RSV) infection.

9. The method of claim 5, wherein the therapy is an immunomodulatory agent, an anti-inflammatory agent, an anti-viral agent, an antibiotic, an antifungal agent or a mast cell modulator.

10. The method of claim 8, further comprising administering to said subject an effective amount of an anti-RSV antigen antibody.

11. The method of claim 10, wherein the anti-RSV antigen antibody is palivizumab.

12. The method of claim 1 or 2 further comprising administering a leukotriene modifier.

13. The method of claim 12, wherein the leukotriene modifier is montelukast, zafirlukast, pranlukast or zileuton.

14. The method of claim 3 or 4, wherein the therapy is an immunomodulatory agent, an anti-inflammatory agent, an anti-viral agent, an antibiotic, an antifungal agent or a mast cell modulator.

15. The method of claim 3 or 4 further comprising administering to said subject a leukotriene modifier, an anti-histamine, an anti-IgE antibody, an anti-IL-4 antibody or a mast cell protease inhibitor.

16. The method of claim 10 further comprising administering a leukotriene modifier.

17. The method of claim 2, 3 or 4, wherein the antibody or fragment thereof is administered parenterally, orally or intranasally.

18. The method of claim 1, wherein the subject is a pre-term infant, an infant, a child or an elderly person.

19. The method of claim 1, wherein the subject has bronchopulmonary dysplasia, congenital heart disease, cystic fibrosis or acquired or congenital immunodeficiency.

20. The method of claim 3 or 4, wherein the subject is a pre-term infant, an infant, a child or an elderly person.

21. The method of claim 3 or 4, wherein the subject has bronchopulmonary dysplasia, congenital heart disease, cystic fibrosis or acquired or congenital immunodeficiency.

22. The method of claim 1 wherein the antibody or fragment thereof is administered parenteraily, orally or intranasally.

* * * * *

UNITED STATES PATENT AND TRADEMARK OFFICE
CERTIFICATE OF CORRECTION

| | | |
|---|---|---|
| PATENT NO. | : 7,582,297 B2 | Page 1 of 1 |
| APPLICATION NO. | : 10/823810 | |
| DATED | : September 1, 2009 | |
| INVENTOR(S) | : Reed | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1054 days.

Signed and Sealed this
Fifteenth Day of February, 2011

David J. Kappos
*Director of the United States Patent and Trademark Office*